(12) United States Patent
D'Aoust et al.

(10) Patent No.: US 11,390,878 B2
(45) Date of Patent: Jul. 19, 2022

(54) INCREASING PROTEIN YIELD IN PLANTS

(71) Applicants: MEDICAGO INC., Quebec (CA); UNIVERSITE LAVAL, Quebec (CA)

(72) Inventors: Marc-Andre D'Aoust, Quebec (CA); Manon Couture, St-Augustin-de-Desmaures (CA); Louis-Philippe Vezina, Neuville (CA); Dominique Michaud, Quebec (CA); Philippe Varennes-Jutras, Montreal (CA); Frank Sainsbury, St. Lucia (AU)

(73) Assignees: MEDICAGO INC., Quebec (CA); UNIVERSITE LAVAL, Quebec (CA)

(*) Notice: Subject to any disclaimer, the term of this patent is extended or adjusted under 35 U.S.C. 154(b) by 462 days.

(21) Appl. No.: 14/605,504

(22) Filed: Jan. 26, 2015

(65) Prior Publication Data

US 2015/0218579 A1   Aug. 6, 2015

Related U.S. Application Data

(63) Continuation-in-part of application No. 14/347,804, filed as application No. PCT/CA2012/050681 on Sep. 28, 2012, now Pat. No. 11,155,581.

(60) Provisional application No. 61/541,780, filed on Sep. 30, 2011.

(51) Int. Cl.
    *C12N 15/82* (2006.01)

(52) U.S. Cl.
    CPC ..... *C12N 15/8258* (2013.01); *C12N 15/8221* (2013.01); *C12N 15/8257* (2013.01); *C12N 2760/16122* (2013.01); *C12N 2760/16151* (2013.01); *C12N 2800/40* (2013.01); *C12N 2820/60* (2013.01); *C12N 2830/60* (2013.01)

(58) Field of Classification Search
    None
    See application file for complete search history.

(56) References Cited

U.S. PATENT DOCUMENTS

| | | | |
|---|---|---|---|
| 4,962,028 A | 10/1990 | Bedbrook et al. | |
| 5,232,833 A | 8/1993 | Sanders et al. | |
| 7,132,291 B2 | 11/2006 | Carduneau et al. | |
| 8,236,529 B2* | 8/2012 | Li | C12Y 302/01132 435/69.7 |
| 8,697,088 B2 | 4/2014 | Smith et al. | |
| 9,056,901 B2 | 6/2015 | Song et al. | |
| 9,505,806 B2 | 11/2016 | Sirko et al. | |
| 9,546,375 B2 | 1/2017 | Couture et al. | |
| 9,555,094 B2 | 1/2017 | Kuroda et al. | |
| 2004/0268442 A1 | 12/2004 | Miller et al. | |
| 2010/0143393 A1 | 6/2010 | Smith et al. | |
| 2012/0207786 A1 | 8/2012 | Smith et al. | |

FOREIGN PATENT DOCUMENTS

| | | | |
|---|---|---|---|
| WO | 00/20557 A2 | 4/2000 | |
| WO | 2007/047831 A2 | 4/2007 | |
| WO | 2007/135480 A1 | 11/2007 | |
| WO | 2008/148104 A1 | 12/2008 | |
| WO | 2009/009876 A1 | 1/2009 | |
| WO | 2009/076778 A1 | 6/2009 | |
| WO | WO 2009076778 A1 * | 6/2009 | ............. C12N 15/82 |
| WO | 2009/087391 A1 | 7/2009 | |
| WO | 2010/003225 A1 | 1/2010 | |
| WO | 2010/003235 A1 | 1/2010 | |
| WO | 2010/006452 A1 | 1/2010 | |
| WO | 2010/025285 A1 | 3/2010 | |
| WO | 2010/148511 A1 | 12/2010 | |
| WO | 2011/011390 A1 | 1/2011 | |
| WO | 2011/035422 A1 | 3/2011 | |
| WO | 2011/102900 A1 | 8/2011 | |
| WO | 2012047941 A2 | 4/2012 | |
| WO | 2012/058762 A1 | 5/2012 | |
| WO | 2012/083445 A1 | 6/2012 | |
| WO | 2012/126123 A8 | 9/2012 | |
| WO | 2013/044390 A1 | 4/2013 | |
| WO | 2014/153674 A1 | 10/2014 | |

(Continued)

OTHER PUBLICATIONS

Betakova (Arch. Virol., 2009, 154:1619-1624).*
Leikina et al. (EMBO, 2002, 21(21):5701-5710).*
Beyer et al. (Archives of Virology, 1986,90: 173-181).*
Robinson et al. (Protoplasma, 2004, 224: 255-260).*
Huang et al. (Biotechnology and Bioengineering, 2009, 103(4): 706-714).*
GenBank AXV41427 (Jan. 2010).*
GenBank FJ766840 (published 2009).*
Reed etal (J. Virol., 2010, 84(3): 1527-1535).*
Banerjee etal (Plos One, 2013, 8(7): e68450).*

(Continued)

*Primary Examiner* — Stephen Uyeno
(74) *Attorney, Agent, or Firm* — J.A. Lindeman & Co., PLLC

(57) ABSTRACT

A method of increasing the yield, stability, or both of an acid sensitive protein in a plant is provided. The method comprises introducing a first nucleic acid and a second nucleic acid into the plant, or portion of the plant. The first nucleic acid comprises a first regulatory region active in the plant and operatively linked to a nucleotide sequence encoding the acid sensitive protein. The second nucleic acid comprises a second regulatory region active in the plant and operatively linked to a nucleotide sequence encoding a channel protein, for example but not limited to a proton channel protein. The plant or portion of the plant is incubated under conditions that permit the expression of the nucleic acids, thereby increasing the yield of the acid sensitive protein when compared to the yield of the acid sensitive protein produced in the plant or portion of the plant produced under the same conditions, and in the absence of the proton channel protein.

10 Claims, 83 Drawing Sheets

Specification includes a Sequence Listing.

(56) References Cited

FOREIGN PATENT DOCUMENTS

WO 2014153674 A1 10/2014

OTHER PUBLICATIONS

Skeiketal (International Journal of Infectious Diseases, 2008, 12: 233-238).*
Chen etal (Advanced Drug Delivery Reviews, 2013, 65: 1357-1369).*
Extended European Search Report in corresponding EP Application No. 14773061.8, dated Nov. 7, 2016.
Patent Examination Report No. 1 in corresponding Australian Application No. 2012315421, dated Oct. 12, 2016.
Translated Third Office Action in corresponding Chinese Application No. 201280047819.2, dated Nov. 8, 2016.
Translated Office Action in corresponding Israeli Application No. 231587, dated Feb. 16, 2017.
Office Action in corresponding Mexican Application No. MX/a/2014/003776, dated Feb. 14, 2017.
Translated Office Action in corresponding Russian Application No. 2014116371, dated Jan. 11, 2017.
Written Opinion and Search Report in corresponding Singapore Application No. 11201507928Q, dated Dec. 15, 2016.
Translated Rejection Decision in corresponding Taiwanese Application No. 101135891, dated Feb. 23, 2017.
NCBI Blast:Protein Sequence, https://blast.ncbi.nlm.nih.gov/Blast.cgi, accessed Oct. 30, 2016.
Binary vector pEAQ-HT-DEST3, complete sequence—Nucleotide, https://www.ncbi.nlm.nih.gov/nucleotide/257196409?report=genbanklog$=nucltop&bl, accessed Oct. 31, 2016.
AXV41427 standard protein, 2010.
FJ766840, Influenza B virus (B/Brisbane/60/2008) segment 4 hemagglutinin (HA) gene 2009; https://www.ncbi.nlm.nih.gov/nuccore/FJ766840?%3Fdb=nucleotide, accessed May 12, 2017.
Office Action in U.S. Appl. No. 14/779,423 dated Nov. 4, 2016.
Office Action in U.S. Appl. No. 14/347,804 dated May 9, 2017.
Restriction Requirement in U.S. Appl. No. 14/347,804 dated Nov. 3, 2016.
Tatiana Betakova & Alan J. Hay "Comparison of the activities of BM2 protein and its H19 and W23 mutants of influenza B virus with activities of M2 protein and its H37 and W41 mutants of influenza A virus", Arch Virol. 2009, 154, pp. 1619-1624.
Hatta et al., "Molecular Basis for High Virulence of Hong Kong H5N1 Influenza A Viruses", Science, 2001, vol. 293, pp. 1840-1842.
Kanagarajan et al., "Transient Expression of Hemagglutinin Antigen from Low Pathogenic Avian Influenza A (H7N7) in Nicotiana benthamiana", PLoS ONE, 2012, vol. 7, Issue 3, e33010, pp. 1-10.
Kang et al., "Influenza vaccines based on virus-like particles", Virus Res. 2009, 143(2), pp. 140-146.
Leikina et al., "Reverblsie stages of the low-pH-triggered conformation change in influenza virus hemagglutinin", The EMBO Journal, vol. 21, No. 21. 2002, pp. 5701-5710.
Robinson et al., "The V-ATPase inhibitors concanamycin A and bafilomycin A lead to Bolgi swelling in tobacco BY-2 cells", Protoplasma, 2004, 224, pp. 255-260.
Song et al., "Protective immunity against H5N1 influenza virus by a single dose vaccination with virus-like particles", Virology, 2010, 405(1), pp. 165-175.
Beyer, W.E.P., et al.: "Influenza Virus Strains with a Fusion Threshold of pH 5.5 or Lower are Inhibited by Amantadine," Archives of Virology, vol. 90, pp. 173-181, 1986.
Bianchi, E., et al.: "Universal Influenza B Vaccine Based on the Maturational Cleavage Site of the Hemagglutinin Precursor," Journal of Virology, vol. 79, No. 12, pp. 7380-7388, Jun. 2005.
Bullough, P., et al.: "Structure of Influenza Haemagglutinin at the pH of Membrane Fusion," Nature, vol. 371, No. 1, pp. 37-43, Sep. 1, 1994.
Chen, J. et al.: "Structure of the Hemagglutinin Precursor Cleavage Site, a Determinant of Influenza Pathogenicity and the Origin of the Labile Conformation," Cell, vol. 95, pp. 409-417, Oct. 30, 1998.
Chiba, M., et al.: "Diverse Suppressors of RNA Silencing Enhance Agroinfection by a Viral Replicon," Virology, vol. 346, pp. 7-14, 2006.
Frugis, G. et al.: "MsJ1, an Alfalfa DnaJ-Like Gene, is Tissue Specific and Transcriptionally Regulated During Cell Cycle," Plant Molecular Biology, vol. 40, pp. 397-408, 1999.
Holsinger, L. et al.: "Influenza Virus M2 Integral Membrane Protein is a Homotetramer Stabilized by Formation of Disulfide Bonds," Virology, vol. 183, pp. 32-43, 1991.
M. Hatta et al.: "Molecular Basis for High Virulence of Hong Jong H5N1 Influenze A Viruses," Science, vol. 293, pp. 1840-1842, Sep. 7, 2001.
Henkel, J.R. et al.: "Influenza Virus M2 Protein Slows Traffic Along the Secretory Pathway: pH Perturbation of Acidified Compartments Affects Early Golgi Transport Steps," Journal of Biological Chemistry, vol. 273, No. 11, pp. 6518-6524, 1998.
Hoffmann, E., et al.,: "Eight-plasmid System for Rapid Generation of Influenza Virus Vaccines," Vaccine, vol. 20, pp. 3165-3170, 2002.
T. Horimoto et al.: "The Development and Characterization of H5 Influenza Virus Vaccines Derived from a 2003 Human Isolate," Vaccine, vol. 24, pp. 3669-3676, 2006.
Huang, et al.: "A DNA Replicon System for Rapid High-Level Production of Virus-Like Particles in Plants," Biotechnology Bioengeering, vol. 103, No. 4, pp. 706-714, Jul. 1, 2009.
Huang, et al. "High-Level Rapid Production of Full-Size Monoclonal Antibodies in Plants by a Single-Vector DNA Replicon System," Biotechnology Bioengeering, vol. 106, No. 1, pp. 9-17, May 1, 2010.
Lamb, Robert A. et al.: "Influenza Virus M2 Protein is an Integral Membrane Protein Expressed on the Infected-Cell Surface," Cell, vol. 40, No. 3, pp. 627-633, 1985.
Latham, T., et al.: "Formation of Wild-type and Chimeric Influenza Virus-like Particles Following Simultaneous Expression of Only Four Structural Proteins," Journal of Virology, vol. 75, No. 13, pp. 6154-6165, Jul. 2001.
Lin et al.: "Genomic Analysis of the Hsp70 Superfamily in Arabidopsis Thaliana," Cell Stress & Chaperones, vol. 6, No. 3, pp. 201-208, 2001.
Liu, L., et al.: "Cowpea Mosaic Virus RNA-1 Acts as an Amplicon Whose Effects can be Counteracted by a RNA-2-Encoded Suppressor of Silencing," Virology vol. 323, pp. 37-48, 2004.
A.J.L. Macario, "Heat-shock Proteins and Molecular Chaperones: Implications for Pathogenesis, Diagnostics and Therapeutics," International Journal of Clinical Laboratory Research, vol. 25, pp. 59-70, 1995.
Neumann, G., et al.: "Plasmid-driven Formation of Influenza Virus-like Particles," Journal of Virology, vol. 74, No. 1, pp. 547-551, Jan. 2000.
Noad, R., et al.: "Virus-like Particles as Immunogens," Trends in Microbiology, vol. 11, No. 9, pp. 438-444, Sep. 2003.
Parsell et al.: "The Function of Heat-shock Proteins in Stress Tolerance: Degradation and Reactivation of Damaged Proteins," Annual Review Genetics, vol. 27, pp. 437-496, 1993.
M. Paul et al.: "Mutational Analysis of the Human Immunodeficiency Virus Type 1 Vpu Transmembrane Domain that Promotes the Enhanced Release of Virus-Like Particles from the Plasma Membrane of Mammalian Cells," Journal of Virology, vol. 72, pp. 1270-1279, 1998.
Reed, M.L., et al.: "The pH of Activation of the Hemagglutinin Protein Regulates H5N1 Influenza Virus Pathogenicity and Transmissability in Ducks," Journal of Virology, vol. 84, No. 3, pp. 1527-1535, Feb. 2010.
Sainsbury, F. et al.: "Expression of Multiple Proteins Using Full-length and Deleted Versions of Cowpea Mosaic Virus RNA-2," Plant Biotechnology Journal, vol. 6, pp. 82-92, 2008.
Sainsbury et al.: "Extremely High-level and Rapid Transient Protein Production in Plants Without the Use of Viral Replication," Plant Physiology, vol. 148, pp. 1212-1218, Nov. 2008.

(56) References Cited

OTHER PUBLICATIONS

Sainsbury, F., et al.: "pEAQ: Versatile Expression Vectors for Easy and Quick Transient Expression of Heterologous Proteins in Plants," Plant Biotechnology Journal, vol. 7, pp. 682-693, 2009.
Skehel, J. et al.: "The Three-dimensional Structure and Antigenic Variation of the Influenza Virus Haemagglutinin," PNAS, pp. 107-111, 1982.
Song, J., et al.: "Influenza Virus-Like Particles Containing M2 Induce Broadly Cross Protective Immunity," PlosS One, vol. 6, No. 1, pp. 1-11, Jan. 2011.
Sugrue, R.J. et al.: "Structural Characteristics of the M2 Protein of Influenza A Viruses: Evidence that it Forms a Tetrameric Channel," Virology, vol. 180, No. 2, pp. 617-624, 1991.
Sugrue, R.J. et al.: "Palmitoylation of the Influenza A Virus M2 Protein," Virology, vol. 179, No. 1, pp. 51-56, 1990.
Szecsi, Judit et al.: "Induction of Neutralising Antibodies by Virus-like Particles Harbouring Surface Proteins from Highly Pathogenic H5N1 and H7N1 Influenza Viruses," Virology Journal, vol. 3, No. 70, pp. 1-7, 2006.
Wakefield L., et al.: "RNA-binding Properties of Influenza A Virus Matrix Protein M1," Nucleic Acid Research, vol. 17, No. 21, 8569-8580, 1989.
Zhang, X. et al.: "Bean Yellow Dwarf Virus Replicons for High-Level Transgene Expression in Transgenic Plants and Cell Cultures," Biotechnology and Bioengineering, vol. 93, No. 2, pp. 271-279, Feb. 5, 2006.
Zebedee, S. et al.: "Influenza A Virus M2 Protein: Monoclonal Antibody Restriction of Virus Growth and Detection of M2 in Virions," Journal of Virology, vol. 62, No. 8, pp. 2762-2772, 1988.
International Search Report from PCT/CA2012/050681 dated Jan. 3, 2013.
International Preliminary Report on Patentability from PCT/CA2012/050681 dated Mar. 31, 2014.
International Search Report from PCT/CA2014/050326 dated Jul. 16, 2014.
M.-A. D'Aoust et al.: "The Production of Hemagglutinin-Based Virus-Like Particles in Plants: A Rapid, Efficient and Safe Response to Pandemic Influenza," Plant Biotechnology Journal, vol. 8, pp. 607-619, 2010.
D'Aoust, M. A. et al.: "Influenza Virus-Like Particles Produced by Transient Expression in Nicotiana Benthamiana Induce a Protective Immune Response Against a Lethal Viral Challenge in Mice," Plant Biotechnology Journal, vol. 6, No. 9, pp. 930-940, Dec. 2008.
Landry, N. et al.: "Preclinical and Clinical Development of Plant-Made Virus-Like Particle Vaccine Against Avian H5N1 Influenza," PLoS One, vol. 5, No. 12, pp. 1-12, Dec. 22, 2010.
Mortimer, E. et al.: "Setting up a Platform for Plant-Based Influenza Virus Vaccine Production in South Africa," BMC Biotechnology, vol. 12, No. 14, pp. 1-10, Apr. 26, 2012.
Shoji, Y. et al.: "A Plant-Produced H1N1 Trimeric Hemagglutinin Protects Mice from a Letha Influenza Virus Challenge," Human Vaccines and Immunotherapeutics, vol. 9, No. 3, pp. 553-560, Mar. 1, 2013.
Gomez-Puertas, P., et al., "Efficient formation of influenza virus-like particles: dependence on the expression level of viral proteins," J. Gen. Virol. (1999) 80 :1635-1645.
Hartl, F. Ulrich, "Molecular chaperones in cellular protein folding," Nature, (1996) vol. 381, Jun. 13, pp. 571-580.
Nemchinov, L.G. et al., "Transient expression of the ectodomain of matrix protein (M2e) of avian influenza A virus in plants," Protein Expression and Purification. (2007) 56:153-159.
Sakaguchi, T., et al., "The Ion Channel Activity of the Influenza Virus M2 Protein Affects Transport through the Golgi Apparatus," J of Cell Bio, vol. 133:4, 1996, pp. 733-747.
Wang, K., et al, "Viral proteins function as ion channels," Biochimica et Biophysica Acta. vol. 1808:2, Feb. 2011, pp. 510-515.
Office Action from related Canadian Application No. 2,850,407, dated Jun. 1, 2015.
English translation of Office Action from related Chinese Application No. 201280047819.2, dated Jun. 24, 2015.
Extended European Search Report from EP 12836545.9, dated May 12, 2015.
First Examination Report from related NZ Application No. 622731, dated Jan. 30, 2015.
Office Action in corresponding Canadian Application No. 2,850,407, dated Jul. 12, 2016.
Translated Second Office Action in corresponding Chinese Application No. 201280047819.2, dated Mar. 2, 2016.
Translated Office Action in corresponding Japanese Application No. 2014-532198, dated Jul. 22, 2016.
Office Action in corresponding Mexican Application No. MX/a/2014/003776, dated Jun. 30, 2016.
New Zealand Letters Patent Np. 622731, issued Aug. 2, 2016.
Translated Office Action in corresponding Russian Application No. 2014116371, dated Jul. 15, 2016.
Translated Office Action in corresponding Taiwanese Application No. 101135891, dated Jul. 15, 2016.
Translated Office Action in corresponding Thailand application No. 1401001699, dated Feb. 22, 2016.
Shoji, Y., et al. A plant-produced H1N1 trimeric hemagglutinin protects mice from a lethal influenza virus challenge. Human Vaccines and Immunotherapeutics, vol. 9, 2013, pp. 553-560.
GenBank Accession AFD32428.2 (2012).
Lu et al., "Insights into Avian influenza virus pathogenicity: the hemagglutinin precursor HAO of subtype H16 has an alpha-Helix structure in its cleavage site with inefficient HA1/HA2 cleavage", Journal of Virology, 2012, vol. 86:23, pp. 12861-12870.
Office Action in corresponding CA Application No. 2,850,407, dated Jul. 4, 2017.
English translation Office Action in corresponding CN Application No. 201280047819.2, dated Jun. 14, 2017.
English translation Office Action in corresponding CN Application No. 201480029001.7, dated Jul. 24, 2017.
Office Action in corresponding EP Application No. 12836545.9, dated Jul. 21, 2017.
English translation of Office Action in corresponding JP Application No. 2014-532198, dated Jun. 28, 2017.
Substantive Examination Adverse Report in corresponding MY Application No. PI 2014700716, dated Nov. 30, 2017.
Office Action in corresponding U.S. Appl. No. 14/779,423, dated Jul. 19, 2017.
English translation in corresponding MX Application No. MX/a/2014/003776, dated Aug. 30, 2017.
Klenk, Hans-Dieter, et al. Host cell proteases controlling virus pathogenicity. Trends in Microbiology, vol. 2:2, 1994, pp. 39-43.
Ito, T., et al. Evolutionary Analysis of the Influenza A Virus M Gene with Comparison of the M1 and M2 Proteins. Journal of Virology, 1991, p. 5491-5498. vol. 65:10.
Redkiewicz, P., et al. Plant Expression systems for production of hemagglutinin as a vaccine against influenza virus. Biochimica Polonica, vol. 61, No. 3/2014, 551-560.
Wiley, D.C., et al. The Structure and Function of the Hemagglutinin Membrane Glycoprotein of Influenza Virus. Annual Review of Biochemistry, vol. 56(1), pp. 365-394, 1987.
Shoji, Yoko et al. Immunogenicity of H1N1 influenza virus-like particles produced in Nicotiana benthamiana. Human Vaccine & Immunotherapeutics 11:1, pp. 118-123, published 2014.
Accession AFN19371, dated Jul. 4, 2012.
GenBank Accession AET122022, dated Nov. 7, 2011.
Kalthoff et al., "Immunization with Plant-Expressed Hemagglutinin Protects Chickens from Lethal Highly Pathogenic Avian Influenza Virus H5N1 Challenge Infection", Journal of Virology, Nov. 2010, vol. 84, No. 22, pp. 12002-12010.
GenBank Accession ABU99194.1, dated Jul. 26, 2016.
GenBank Accession ACN29380.1, dated Feb. 28, 2009.
GenBank Accession ACS71642.1, dated Jun. 29, 2009.
GenBank Accession ACU12738.1, dated Aug. 24, 2017.

\* cited by examiner

A-2X35S/CPMV-HT/H5 Indonesia/NOS (Construct number 489)

Figure 1A

IF-H5A-I-05.s1+3c SEQ ID NO: 2

AAATTTGTCGGGCCCATGGAGAAAATAGTGCTTCTTCTTGC

Figure 1B

IF-H5dTm.r SEQ ID NO: 3

ACTAAAGAAAATAGGCCTTTAAATGCAAATTCTGCATTGTAACGATCCAT

Figure 1C

Schematic representation of construct 1191. SacII and StuI restriction enzyme sites used for plasmid linearization are annotated on the representation.

Figure 1D

Construct 1191 from left to right t-DNA borders (underlined). 2X35S/CPMV-HT/NOS with Plastocyanine-P19-Plastocyanine silencing inhibitor expression cassette (SEQ ID NO: 4)

<u>TGGCAGGATATATTGTGGTGTAAACA</u>AATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGACAAGCTTGCATGCCGGTCAACATGGTGGAGCACGACACACTTGTCT
ACTCCAAAAATATCAAAGATACAGTCTCAGAAGACCAAAGGGCAATTGAGACTTTTCAACAAAGGGTAA
TATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGT
GGTCCCAAAGATGGACCCCCACCCACGAGGAGCATCGTGGAAAAAGAAGACGTTCCAACCACGTCTTCA
AAGCAAGTGGATTGATGTGATAACATGGTGGAGCACGACACACTTGTCTACTCCAAAAATATCAAAGAT
ACAGTCTCAGAAGACCAAAGGGCAATTGAGACTTTTCAACAAAGGGTAATATCCGGAAACCTCCTCGGA
TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCC
CACCCACGAGGAGCATCGTGGAAAAAGAAGACGTTCCAACCACGTCTTCAAAGCAAGTGGATTGATGTG
ATATCTCCACTGACGTAAGGGATGACGCACAATCCCACTATCCTTCGCAAGACCCTTCCTCTATATAAGG
AAGTTCATTTCATTTGGAGAGGTATTAAAATCTTAATAGGTTTTGATAAAAGCGAACGTGGGGAAACCCG
AACCAAACCTTCTTCTAAACTCTCTCTCATCTCTCTTAAAGCAAACTTCTCTCTTGTCTTTCTTGCGTGAGC
GATCTTCAACGTTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTGTCGGTGTGGTCT
TGGGAAAAGAAAGCTTGCTGGAGGCTGCTGTTCAGCCCCATACATTACTTGTTACGATTCTGCTGACTTTC
GGCGGGTGCAATATCTCTACTTCTGCTTGACGAGGTATTGTTGCCTGTACTTCTTTCTTCTTCTTGCTG

Figure 1D continued

```
ATTGGTTCTATAAGAAATCTAGTATTTTCTTTGAAACAGAGTTTTCCCGTGGTTTTCGAACTTGGAGAAAG
ATTGTTAAGCTTCTGTATATTCTGCCCAAATTTGTCGGGCCCGCGGATGGCGAAAAACGTTGCGATTTTCG
GCTTATTGTTTTCTCTTCTTGTGTTGGTTCCTTCTCAGATCTTCGCCTGCAGGCTCCTCAGCCAAAACGACA
CCCCCATCTGTCTATCCACTGGCCCCTGGATCTGCTGCCCAAACTAACTCCATGGTGACCCTGGGATGCCT
GGTCAAGGGCTATTTCCCTGAGCCAGTGACAGTGACCTGGAACTCTGGATCCCTGTCCAGCGGTGTGCAC
ACCTTCCCAGCTGTCCTGCAGTCTGACCTCTACACTCTGAGCAGCTCAGTGACTGTCCCCTCCAGCACCTG
GCCCAGCGAGACCGTCACCTGCAACGTTGCCCACCCGGCCAGCAGCACCAAGGTGGACAAGAAAATTGT
GCCCAGGGATTGTGGTTGTAAGCCTTGCATATGTACAGTCCCAGAAGTATCATCTGTCTTCATCTTCCCCC
CAAAGCCCAAGGATGTGCTCACCATTACTCTGACTCCTAAGGTCACGTGTGTTGTGGTAGACATCAGCAA
GGATGATCCCGAGGTCCAGTTCAGCTGGTTTGTAGATGATGTGGAGGTGCACACAGCTCAGACGCAACCC
CGGGAGGAGCAGTTCAACAGCACTTTCCGCTCAGTCAGTGAACTTCCCATCATGCACCAGGACTGGCTCA
ATGGCAAGGAGCGATCGCTCACCATCACCATCACCATCACCATCACCATTAAAGGCCTATTTTCTTTAGTT
TGAATTTACTGTTATTCGGTGTGCATTTCTATGTTTGGTGAGCGGTTTTCTGTGCTCAGAGTGTGTTTATTT
TATGTAATTTAATTTCTTTGTGAGCTCCTGTTTAGCAGGTCGTCCCTTCAGCAAGGACACAAAAAGATTTT
AATTTTATTAAAAAAAAAAAAAAAAAAGACCGGGAATTCGATATCAAGCTTATCGACCTGCAGATCGTT
CAAACATTTGGCAATAAAGTTTCTTAAGATTGAATCCTGTTGCCGGTCTTGCGATGATTATCATATAATTT
CTGTTGAATTACGTTAAGCATGTAATAATTAACATGTAATGCATGACGTTATTTATGAGATGGGTTTTTAT
GATTAGAGTCCCGCAATTATACATTTAATACGCGATAGAAAACAAAATATAGCGCGCAAACTAGGATAA
ATTATCGCGCGCGGTGTCATCTATGTTACTAGATCTCTAGAGTCTCAAGCTTGGCGCGCCCACGTGACTAG
TGGCACTGGCCGTCGTTTTACAACGTCGTGACTGGGAAAACCCTGGCGTTACCCAACTTAATCGCCTTGC
AGCACATCCCCCTTTCGCCAGCTGGCGTAATAGCGAAGAGGCCCGCACCGATCGCCCTTCCCAACAGTTG
CGCAGCCTGAATGGCGAATGCTAGAGCAGCTTGAGCTTGGATCAGATTGTCGTTTCCCGCCTTCAGTTTA
AACTATCAGTGTTTGACAGGATATATTGGCGGGTAAACCTAAGAGAAAAGAGCGTTTA
```

Figure 1E

Expression cassette number 489 from 2X35S promoter to NOS terminator. H5 from influenza A/Indonesia/5/2005 (H5N1) is underlined. SEQ ID NO: 5

```
GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CATGGAGAAAATAGTGCTTCTTCTTGCAATAGTCAGTCTTGTTAAAAGTGATCAGATTTGCATTGGTTAC
CATGCAAACAATTCAACAGAGCAGGTTGACACAATCATGGAAAAGAACGTTACTGTTACACATGCCCAA
GACATACTGGAAAAGACACACAACGGGAAGCTCTGCGATCTAGATGGAGTGAAGCCTCTAATTTTAAGA
GATTGTAGTGTAGCTGGATGGCTCCTCGGGAACCCAATGTGTGACGAATTCATCAATGTACCGGAATGGT
CTTACATAGTGGAGAAGGCCAATCCAACCAATGACCTCTGTTACCCAGGGAGTTTCAACGACTATGAAGA
```

Figure 1E continued

```
ACTGAAACACCTATTGAGCAGAATAAACCATTTTGAGAAAATTCAAATCATCCCCAAAAGTTCTTGGTCC
GATCATGAAGCCTCATCAGGAGTTAGCTCAGCATGTCCATACCTGGGAAGTCCCTCCTTTTTTAGAAATGT
GGTATGGCTTATCAAAAGAACAGTACATACCCAACAATAAAGAAAAGCTACAATAATACCAACCAAGA
GGATCTTTTGGTACTGTGGGGAATTCACCATCCTAATGATGCGGCAGAGCAGACAAGGCTATATCAAAAC
CCAACCACCTATATTTCCATTGGGACATCAACACTAAACCAGAGATTGGTACCAAAAATAGCTACTAGAT
CCAAAGTAAACGGGCAAAGTGGAAGGATGGAGTTCTTCTGGACAATTTTAAAACCTAATGATGCAATCA
ACTTCGAGAGTAATGGAAATTTCATTGCTCCAGAATATGCATACAAAATTGTCAAGAAAGGGGACTCAGC
AATTATGAAAAGTGAATTGGAATATGGTAACTGCAACACCAAGTGTCAAACTCCAATGGGGGCGATAAA
CTCTAGTATGCCATTCCACAACATACACCCTCTCACCATCGGGGAATGCCCCAAATATGTGAAATCAAAC
AGATTAGTCCTTGCAACAGGGCTCAGAAATAGCCCTCAAAGAGAGAGCAGAAGAAAAAAGAGAGGACT
ATTTGGAGCTATAGCAGGTTTTATAGAGGGAGGATGGCAGGGAATGGTAGATGGTTGGTATGGGTACCA
CCATAGCAATGAGCAGGGGAGTGGGTACGCTGCAGACAAAGAATCCACTCAAAAGGCAATAGATGGAGT
CACCAATAAGGTCAACTCAATCATTGACAAAATGAACACTCAGTTTGAGGCCGTTGGAAGGGAATTTAAT
AACTTAGAAAGGAGAATAGAGAATTTAAACAAGAAGATGGAAGACGGGTTCTAGATGTCTGGACTTAT
AATGCCGAACTTCTGGTTCTCATGGAAAATGAGAGAACTCTAGACTTTCATGACTCAAATGTTAAGAACC
TCTACGACAAGGTCCGACTACAGCTTAGGGATAATGCAAAGGAGCTGGGTAACGGTTGTTTCGAGTTCTA
TCACAAATGTGATAATGAATGTATGGAAAGTATAAGAAACGGAACGTACAACTATCCGCAGTATTCAGA
AGAAGCAAGATTAAAAAGAGAGGAAATAAGTGGGGTAAAATTGGAATCAATAGGAACTTACCAAATAC
TGTCAATTTATTCAACAGTGGCGAGTTCCCTAGCACTGGCAATCATGATGGCTGGTCTATCTTTATGGATG
TGCTCCAATGGATCGTTACAATGCAGAATTTGCATTTAAAGGCCTATTTCTTTAGTTTGAATTTACTGTT
ATTCGGTGTGCATTTCTATGTTTGGTGAGCGGTTTTCTGTGCTCAGAGTGTGTTTATTTTATGTAATTTAAT
TTCTTTGTGAGCTCCTGTTTAGCAGGTCGTCCCTTCAGCAAGGACACAAAAAGATTTTAATTTTATTAAAA
AAAAAAAAAAAAAGACCGGGAATTCGATATCAAGCTTATCGACCTGCAGATCGTTCAAACATTTGGCA
ATAAAGTTTCTTAAGATTGAATCCTGTTGCCGGTCTTGCGATGATTATCATATAATTTCTGTTGAATTACG
TTAAGCATGTAATAATTAACATGTAATGCATGACGTTATTTATGAGATGGGTTTTTATGATTAGAGTCCCG
CAATTATACATTTAATACGCGATAGAAAACAAAATATAGCGCGCAAACTAGGATAAATTATCGCGCGCG
GTGTCATCTATGTTACTAGAT
```

Figure 1F

Amino acid sequence of H5 from influenza A/Indonesia/5/2005 (H5N1) SEQ ID NO: 6

MEKIVLLLAIVSLVKSDQICIGYHANNSTEQVDTIMEKNVTVTHAQDILEKTHNGKLCDL
DGVKPLILRDCSVAGWLLGNPMCDEFINVPEWSYIVEKANPTNDLCYPGSFNDYEELKH
LLSRINHFEKIQIIPKSSWSDHEASSGVSSACPYLGSPSFFRNVVWLIKKNSTYPTIKKSYN
NTNQEDLLVLWGIHHPNDAAEQTRLYQNPTTYISIGTSTLNQRLVPKIATRSKVNGQSGR
MEFFWTILKPNDAINFESNGNFIAPEYAYKIVKKGDSAIMKSELEYGNCNTKCQTPMGAI
NSSMPFHNIHPLTIGECPKYVKSNRLVLATGLRNSPQRESRRKKRGLFGAIAGFIEGGWQ
GMVDGWYGYHHSNEQGSGYAADKESTQKAIDGVTNKVNSIIDKMNTQFEAVGREFNN
LERRIENLNKKMEDGFLDVWTYNAELLVLMENERTLDFHDSNVKNLYDKVRLQLRDN
AKELGNGCFEFYHKCDNECMESIRNGTYNYPQYSEEARLKREEISGVKLESIGTYQILSIY
STVASSLALAIMMAGLSLWMCSNGSLQCRICI

Figure 1G nucleotide sequence encoding H5 from influenza A/Indonesia/5/2005 (H5N1) SEQ ID NO: 42)

ATGGAGAAAATAGTGCTTCTTCTTGCAATAGTCAGTCTTGTTAAAAGTGATCAGATTTGCATTGGTTACCA
TGCAAACAATTCAACAGAGCAGGTTGACACAATCATGGAAAAGAACGTTACTGTTACACATGCCCAAGA
CATACTGGAAAAGACACACAACGGGAAGCTCTGCGATCTAGATGGAGTGAAGCCTCTAATTTTAAGAGA
TTGTAGTGTAGCTGGATGGCTCCTCGGGAACCCAATGTGTGACGAATTCATCAATGTACCGGAATGGTCT
TACATAGTGGAGAAGGCCAATCCAACCAATGACCTCTGTTACCCAGGGAGTTTCAACGACTATGAAGAA
CTGAAACACCTATTGAGCAGAATAAACCATTTTGAGAAAATTCAAATCATCCCCAAAAGTTCTTGGTCCG
ATCATGAAGCCTCATCAGGAGTTAGCTCAGCATGTCCATACCTGGGAAGTCCCTCCTTTTTTAGAAATGTG
GTATGGCTTATCAAAAGAACAGTACATACCCAACAATAAAGAAAAGCTACAATAATACCAACCAAGAG
GATCTTTTGGTACTGTGGGGAATTCACCATCCTAATGATGCGGCAGAGCAGACAAGGCTATATCAAACC
CAACCACCTATATTTCCATTGGGACATCAACACTAAACCAGAGATTGGTACCAAAAATAGCTACTAGATC
CAAAGTAAACGGGCAAAGTGGAAGGATGGAGTTCTTCTGGACAATTTTAAAACCTAATGATGCAATCAA
CTTCGAGAGTAATGGAAATTTCATTGCTCCAGAATATGCATACAAAATTGTCAAGAAAGGGGACTCAGCA
ATTATGAAAAGTGAATTGGAATATGGTAACTGCAACACCAAGTGTCAAACTCCAATGGGGGCGATAAAC
TCTAGTATGCCATTCCACAACATACACCCTCTCACCATCGGGGAATGCCCCAAATATGTGAAATCAAACA
GATTAGTCCTTGCAACAGGGCTCAGAAATAGCCCTCAAAGAGAGAGCAGAAGAAAAAAGAGAGGACTA
TTTGGAGCTATAGCAGGTTTTATAGAGGGAGGATGGCAGGGAATGGTAGATGGTTGGTATGGGTACCAC
CATAGCAATGAGCAGGGGAGTGGGTACGCTGCAGACAAAGAATCCACTCAAAAGGCAATAGATGGAGTC
ACCAATAAGGTCAACTCAATCATTGACAAAATGAACACTCAGTTTGAGGCCGTTGGAAGGGAATTTAATA
ACTTAGAAAGGAGAATAGAGAATTTAAACAAGAAGATGGAAGACGGGTTTCTAGATGTCTGGACTTATA
ATGCCGAACTTCTGGTTCTCATGGAAAATGAGAGAACTCTAGACTTTCATGACTCAAATGTTAAGAACCT
CTACGACAAGGTCCGACTACAGCTTAGGGATAATGCAAAGGAGCTGGGTAACGGTTGTTTCGAGTTCTAT
CACAAATGTGATAATGAATGTATGGAAAGTATAAGAAACGGAACGTACAACTATCCGCAGTATTCAGAA
GAAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGATGT
GCTCCAATGGATCGTTACAATGCAGAATTTGCATTTAA

B-2X35S/CPMV HT/M2 New Caledonia/NOS (Construct number 1261)

TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CC<u>ATGAGTCTTCTAACCGAGGTCGAAACGCCTATCAGAAACGAATGGGGGTGCAGATGCAACGATTCAA</u>
<u>GTGATCCTCTTGTTGTTGCCGCAAGTATAATTGGGATTGTGCACCTGATATTGTGGATTATTGATCGCCTT</u>
<u>TTTTCCAAAAGCATTTATCGTATCTTTAAACACGGTTTAAAAAGAGGGCCTTCTACGGAAGGAGTACCAG</u>
<u>AGTCTATGAGGGAAGAATATCGAGAGGAACAGCAGAATGCTGTGGATGCTGACGATGGTCATTTTGTCA</u>
<u>GCATAGAGCTGGAGTAA</u>AGGCCTATTTTCTTTAGTTTGAATTTACTGTTATTCGGTGTGCATTTCTATGTTT
GGTGAGCGGTTTTCTGTGCTCAGAGTGTGTTTATTTTATGTAATTTAATTTCTTTGTGAGCTCCTGTTTAGC
AGGTCGTCCCTTCAGCAAGGACACAAAAAGATTTTAATTTTATTAAAAAAAAAAAAAAAAAAAGACCGGG
AATTCGATATCAAGCTTATCGACCTGCAGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAATACGCGAT
AGAAAACAAAATATAGCGCGCAAACTAGGATAAATTATCGCGCGCGGTGTCATCTATGTTACTAGAT

Figure 2E

Amino acid sequence of M2 from influenza A/New Caledonia/20/1999 (H1N1) (SEQ ID NO: 11)

MSLLTEVETPIRNEWGCRCNDSSDPLVVAASIIGIVHLILWIIDRLFSKSIYRIFKHGLKRGP
STEGVPESMREEYREEQQNAVDADDGHFVSIELE

C-2X35S/CPMV-HT/M2 Puerto Rico/NOS (Construct number 859)

Figure 3A

Synthesized M2 gene (corresponding to nt 26-51 joined to nt 740-1007 from Genebank accession number EF467824) (SEQ ID NO: 12)

ATGAGTCTTCTAACCGAGGTCGAAACGCCTATCAGAAACGAATGGGGGTGCAGATGCAACGGTTCAAGT
GATCCTCTCACTATTGCCGCAAATATCATTGGGATCTTGCACTTGACATTGTGGATTCTTGATCGTCTTTTT
TTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCA
TAGAGCTGGAGTAA

Figure 3B

Expression cassette number 859 from 2X35S promoter to NOS terminator. M2 from Influenza A/Puerto Rico/8/1934 (H1N1) is underlined. (SEQ ID NO: 13)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAGTCTTCTAACCGAGGTCGAAACGCCTATCAGAAACGAATGGGGGTGCAGATGCAACGGTTCAA
GTGATCCTCTCACTATTGCCGCAAATATCATTGGGATCTTGCACTTGACATTGTGGATTCTTGATCGTCTTT
TTTTCAAATGCATTTACCGTCGCTTTAAATACGGACTGAAAGGAGGGCCTTCTACGGAAGGAGTGCCAAA
GTCTATGAGGGAAGAATATCGAAAGGAACAGCAGAGTGCTGTGGATGCTGACGATGGTCATTTTGTCAG
CATAGAGCTGGAGTAAAGGCCTATTTTCTTTAGTTTGAATTTACTGTTATTCGGTGTGCATTTCTATGTTTG
GTGAGCGGTTTTCTGTGCTCAGAGTGTGTTTATTTTATGTAATTTAATTTCTTTGTGAGCTCCTGTTTAGCA
GGTCGTCCCTTCAGCAAGGACACAAAAAGATTTTAATTTTATTAAAAAAAAAAAAAAAAAAAGACCGGGA
ATTCGATATCAAGCTTATCGACCTGCAGATCGTTCAAACATTTGGCAATAAAGTTTCTTAAGATTGAATCC
TGTTGCCGGTCTTGCGATGATTATCATATAATTTCTGTTGAATTACGTTAAGCATGTAATAATTAACATGT
AATGCATGACGTTATTTATGAGATGGGTTTTTATGATTAGAGTCCCGCAATTATACATTTAATACGCGATA
GAAAACAAAATATAGCGCGCAAACTAGGATAAATTATCGCGCGCGGTGTCATCTATGTTACTAGAT

Figure 3C

Amino acid sequence of M2 from influenza A/Puerto Rico/8/1934 (H1N1) (SEQ ID NO:14)

MSLLTE

D-2X35S/CPMV-HT/PDISP/H1 California/NOS (Construct number 484)

Schematic representation of construct 1192. SacII and StuI restriction enzyme sites used for plasmid linearization are annotated on the representation.

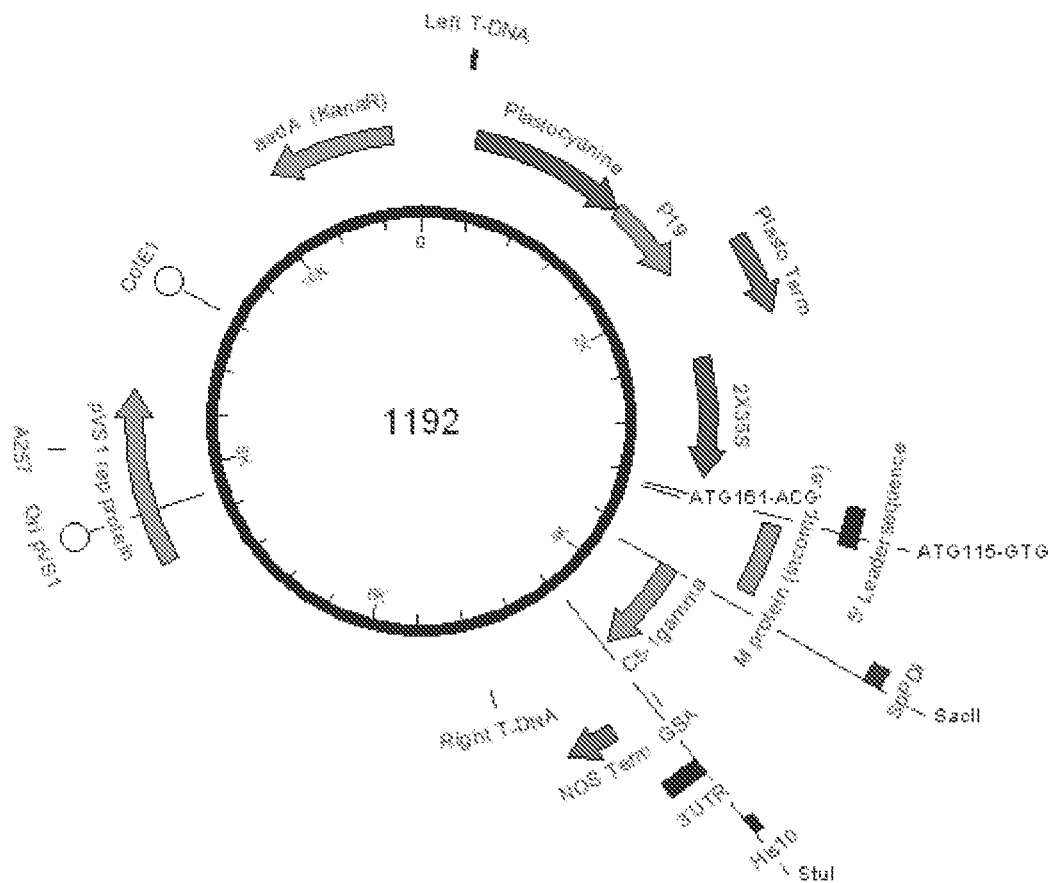

Figure 4E

Construct 1192 from left to right t-DNA borders (underlined). 2X35S/CPMV-HT/PDISP/NOS with Plastocyanine-P19-Plastocyanine silencing inhibitor expression cassette (SEQ ID NO: 18)

<u>TGGCAGGATATATTGTGGTGTAAACA</u>AATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA

Figure 4E continued

ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCTCTCCCCGCGCG
TTGGGAATTACTAGCGCGTGTCGACAAGCTTGCATGCCGGTCAACATGGTGGAGCACGACACACTTGTCT
ACTCCAAAAATATCAAAGATACAGTCTCAGAAGACCAAAGGGCAATTGAGACTTTTCAACAAAGGGTAA
TATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGT
GGTCCCAAAGATGGACCCCCACCCACGAGGAGCATCGTGGAAAAAGAAGACGTTCCAACCACGTCTTCA
AAGCAAGTGGATTGATGTGATAACATGGTGGAGCACGACACACTTGTCTACTCCAAAAATATCAAAGAT
ACAGTCTCAGAAGACCAAAGGGCAATTGAGACTTTTCAACAAAGGGTAATATCCGGAAACCTCCTCGGA
TTCCATTGCCCAGCTATCTGTCACTTTATTGTGAAGATAGTGGAAAAGGAAGGTGGCTCCTACAAATGCC
ATCATTGCGATAAAGGAAAGGCCATCGTTGAAGATGCCTCTGCCGACAGTGGTCCCAAAGATGGACCCC
CACCCACGAGGAGCATCGTGGAAAAAGAAGACGTTCCAACCACGTCTTCAAAGCAAGTGGATTGATGTG
ATATCTCCACTGACGTAAGGGATGACGCACAATCCCACTATCCTTCGCAAGACCCTTCCTCTATATAAGG
AAGTTCATTTCATTTGGAGAGGTATTAAAATCTTAATAGGTTTTGATAAAAGCGAACGTGGGGAAACCCG
AACCAAACCTTCTTCTAAACTCTCTCTCATCTCTCTTAAAGCAAACTTCTCTCTTGTCTTTCTTGCGTGAGC
GATCTTCAACGTTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTGTCGGTGTGGTCT
TGGGAAAAGAAAGCTTGCTGGAGGCTGCTGTTCAGCCCCATACATTACTTGTTACGATTCTGCTGACTTTC
GGCGGGTGCAATATCTCTACTTCTGCTTGACGAGGTATTGTTGCCTGTACTTCTTTCTTCTTCTTGCTG
ATTGGTTCTATAAGAAATCTAGTATTTTCTTTGAAACAGAGTTTTCCCGTGGTTTTCGAACTTGGAGAAAG
ATTGTTAAGCTTCTGTATATTCTGCCCAAATTTGTCGGGCCCATGGCGAAAAACGTTGCGATTTTCGGCTT
ATTGTTTTCTCTTCTTGTGTTGGTTCCTTCTCAGATCTTCGCCGCGGCTCCTCAGCCAAAACGACACCCCA
TCTGTCTATCCACTGGCCCCTGGATCTGCTGCCCAAACTAACTCCATGGTGACCCTGGGATGCCTGGTCAA
GGGCTATTTCCCTGAGCCAGTGACAGTGACCTGGAACTCTGGATCCCTGTCCAGCGGTGTGCACACCTTC
CCAGCTGTCCTGCAGTCTGACCTCTACACTCTGAGCAGCTCAGTGACTGTCCCCTCCAGCACCTGGCCCA
GCGAGACCGTCACCTGCAACGTTGCCCACCCGGCCAGCAGCACCAAGGTGGACAAGAAAATTGTGCCCA
GGGATTGTGGTTGTAAGCCTTGCATATGTACAGTCCCAGAAGTATCATCTGTCTTCATCTTCCCCCCAAAG
CCCAAGGATGTGCTCACCATTACTCTGACTCCTAAGGTCACGTGTGTTGTGGTAGACATCAGCAAGGATG
ATCCCGAGGTCCAGTTCAGCTGGTTTGTAGATGATGTGGAGGTGCACACAGCTCAGACGCAACCCCGGGA
GGAGCAGTTCAACAGCACTTTCCGCTCAGTCAGTGAACTTCCCATCATGCACCAGGACTGGCTCAATGGC
AAGGAGCGATCGCTCACCATCACCATCACCATCACCATCACCATTAAAGGCCTATTTTCTTTAGTTTGAAT
TTACTGTTATTCGGTGTGCATTTCTATGTTTGGTGAGCGGTTTTCTGTGCTCAGAGTGTGTTTATTTTATGT
AATTTAATTTCTTTGTGAGCTCCTGTTTAGCAGGTCGTCCCTTCAGCAAGGACACAAAAGATTTTAATTT
TATTAAAAAAAAAAAAAAAAAGACCGGGAATTCGATATCAAGCTTATCGACCTGCAGATCGTTCAAAC
ATTTGGCAATAAAGTTTCTTAAGATTGAATCCTGTTGCCGGTCTTGCGATGATTATCATATAATTTCTGTT
GAATTACGTTAAGCATGTAATAATTAACATGTAATGCATGACGTTATTTATGAGATGGGTTTTTATGATTA
GAGTCCCGCAATTATACATTTAATACGCGATAGAAAACAAAATATAGCGCGCAAACTAGGATAAATTAT
CGCGCGCGGTGTCATCTATGTTACTAGATCTCTAGAGTCTCAAGCTTGGCGCGCCCACGTGACTAGTGGC

Figure 4E continued

ACTGGCCGTCGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAACAGTTGCGCA
GCCTGAATGGCGAATGCTAGAGCAGCTTGAGCTTGGATCAGATTGTCGTTTCCCGCCTTCAGTTTAAACT
ATCAGTGTTTGACAGGATATATTGGCGGGTAAACCTAAGAGAAAAGAGCGTTTA

Figure 4F

Expression cassette number 484 from 2X35S promoter to NOS terminator. PDISP/H1 from influenza A/California/7/2009 (H1N1) is underlined. (SEQ ID NO: 19)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTCTCTTCTTGTGTTGGTTCCTTCTCAGATCTTCG
CCGACACATTATGTATAGGTTATCATGCGAACAATTCAACAGACACTGTAGACACAGTACTAGAAAAGA
ATGTAACAGTAACACACTCTGTTAACCTTCTAGAAGACAAGCATAACGGGAAACTATGCAAACTAAGAG
GGGTAGCCCCATTGCATTTGGGTAAATGTAACATTGCTGGCTGGATCCTGGGAAATCCAGAGTGTGAATC
ACTCTCCACAGCAAGCTCATGGTCCTACATTGTGGAAACACCTAGTTCAGACAATGGAACGTGTTACCCA
GGAGATTTCATCGATTATGAGGAGCTAAGAGAGCAATTGAGCTCAGTGTCATCATTTGAAAGGTTTGAGA
TATTCCCCAAGACAAGTTCATGGCCCAATCATGACTCGAACAAAGGTGTAACGGCAGCATGTCCTCATGC
TGGAGCAAAAAGCTTCTACAAAAATTTAATATGGCTAGTTAAAAAAGGAAATTCATACCCAAAGCTCAG
CAAATCCTACATTAATGATAAAGGGAAAGAAGTCCTCGTGCTATGGGGCATTCACCATCCATCTACTAGT
GCTGACCAACAAAGTCTCTATCAGAATGCAGATGCATATGTTTTTGTGGGGTCATCAAGATACAGCAAGA
AGTTCAAGCCGGAAATAGCAATAAGACCCAAAGTGAGGGATCAAGAAGGGAGAATGAACTATTACTGG
ACACTAGTAGAGCCGGGAGACAAAATAACATTCGAAGCAACTGGAAATCTAGTGGTACCGAGATATGCA
TTCGCAATGGAAAGAAATGCTGGATCTGGTATTATCATTTCAGATACACCAGTCCACGATTGCAATACAA
CTTGTCAAACACCCAAGGGTGCTATAAACACCAGCCTCCCATTTCAGAATATACATCCGATCACAATTGG
AAAATGTCCAAAATATGTAAAAAGCACAAAATTGAGACTGGCCACAGGATTGAGGAATATCCCGTCTAT
TCAATCTAGAGGCCTATTTGGGGCCATTGCCGGTTTCATTGAAGGGGGGTGGACAGGGATGGTAGATGGA
TGGTACGGTTATCACCATCAAAATGAGCAGGGGTCAGGATATGCAGCCGACCTGAAGAGCACACAGAAT
GCCATTGACGAGATTACTAACAAAGTAAATTCTGTTATTGAAAAGATGAATACACAGTTCACAGCAGTAG
GTAAAGAGTTCAACCACCTGGAAAAAAGAATAGAGAATTTAAATAAAAAAGTTGATGATGGTTTCCTGG
ACATTTGGACTTACAATGCCGAACTGTTGGTTCTATTGGAAAATGAAAGAACTTTGGACTACCACGATTC
AAATGTGAAGAACTTATATGAAAAGGTAAGAAGCCAGCTAAAAAACAATGCCAAGGAAATTGGAAACG
GCTGCTTTGAATTTTACCACAAATGCGATAACACGTGCATGGAAAGTGTCAAAAATGGGACTTATGACTA
CCCAAAATACTCAGAGGAAGCAAAATTAAACAGAGAAGAAATAGATGGGGTAAAGCTGGAATCAACAA
GGATTTACCAGATTTTGGCGATCTATTCAACTGTCGCCAGTTCATTGGTACTGGTAGTCTCCCTGGGGGCA

Figure 4F continued

ATCAGTTTCTGGATGTGCTCTAATGGGTCTCTACAGTGTAGAATATGTATTTAAAGGCCTATTTTCTTTAG
TTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATT
TTAATTTTATTAAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTA
TGATTAGAGTCCCGCAATTATACATTTAATACGCGATAGAAAACAAAATATAGCGCGCAAACTAGGATA
AATTATCGCGCGCGGTGTCATCTATGTTACTAGAT

Figure 4G

Amino acid sequence of PDISP-H1 from influenza A/California/7/2009 (H1N1) (SEQ ID NO: 20)

MAKNVAIFGLLFSLLVLVPSQIFADTLCIGYHANNSTDTVDTVLEKNVTVTHSVNLLEDK
HNGKLCKLRGVAPLHLGKCNIAGWILGNPECESLSTASSWSYIVETPSSDNGTCYPGDFI
DYEELREQLSSVSSFERFEIFPKTSSWPNHDSNKGVTAACPHAGAKSFYKNLIWLVKKGN
SYPKLSKSYINDKGKEVLVLWGIHHPSTSADQQSLYQNADAYVFVGSSRYSKKFKPEIAI
RPKVRDQEGRMNYYWTLVEPGDKITFEATGNLVVPRYAFAMERNAGSGIIISDTPVHDC
NTTCQTPKGAINTSLPFQNIHPITIGKCPKYVKSTKLRLATGLRNIPSIQSRGLFGAIAGFIE
GGWTGMVDGWYGYHHQNEQGSGYAADLKSTQNAIDEITNKVNSVIEKMNTQFTAVGK
EFNHLEKRIENLNKKVDDGFLDIWTYNAELLVLLENERTLDYHDSNVKNLYEKVRSQLK
NNAKEIGNGCFEFYHKCDNTCMESVKNGTYDYPKYSEEAKLNREEIDGVKLESTRIYQIL
AIYSTVASSLVLVVSLGAISFWMCSNGSLQCRICI

E-2X35S/CPMV-HT/PDISP/H3 Perth/NOS (Construct number 1019)

Expression cassette number 1019 from 2X35S promoter to NOS terminator. PDISP/H3 from influenza A/Perth/16/2009 (H3N2) is underlined. (SEQ ID NO: 24)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCTTCG
CCCAAAAACTTCCTGGAAATGACAACAGCACGGCAACGCTGTGCCTTGGGCACCATGCAGTACCAAACG
GAACGATAGTGAAAACAATCACGAATGACCAAATTGAAGTTACTAATGCTACTGAGCTGGTTCAGAGTTC
CTCAACAGGTGAAATATGCGACAGTCCTCATCAGATCCTTGATGGAAAAAACTGCACACTAATAGATGCT
CTATTGGGAGACCCTCAGTGTGATGGCTTCCAAAATAAGAAATGGGACCTTTTTGTTGAACGCAGCAAAG
CCTACAGCAACTGTTACCCTTATGATGTGCCGGATTATGCCTCCCTTAGGTCACTAGTTGCCTCATCCGGC
ACACTGGAGTTTAACAATGAAAGCTTCAATTGGACTGGAGTCACTCAAAACGGAACAAGCTCTGCTTGCA
TAAGGAGATCTAAAAACAGTTTCTTTAGTAGATTGAATTGGTTGACCCACTTAAACTTCAAATACCCAGC
ATTGAACGTGACTATGCCAAACAATGAACAATTTGACAAATTGTACATTTGGGGGGTTCACCACCCGGGT
ACGGACAAAGACCAAATCTTCCTGTATGCTCAAGCATCAGGAAGAATCACAGTCTCTACCAAAAGAAGC
CAACAAACCGTAAGCCCGAATATCGGATCTAGACCCAGAGTAAGGAATATCCCTAGCAGAATAAGCATC
TATTGGACAATAGTAAAACCGGGAGACATACTTTTGATTAACAGCACAGGGAATCTAATTGCTCCTAGGG
GTTACTTCAAAATACGAAGTGGGAAAAGCTCAATAATGAGATCAGATGCACCCATTGGCAAATGCAATT
CTGAATGCATCACTCCAAATGGAAGCATTCCCAATGACAAACCATTCCAAAATGTAAACAGGATCACATA
CGGGGCCTGTCCCAGATATGTTAAGCAAAACACTCTGAAATTGGCAACAGGGATGCGAAATGTACCAGA
GAAACAAACTAGAGGCATATTTGGCGCAATCGCGGGTTTCATAGAAAATGGTTGGGAGGGAATGGTGGA
TGGTTGGTACGGTTTCAGGCATCAAAATTCTGAGGGAAGAGGACAAGCAGCAGATCTCAAAAGCACTCA
AGCAGCAATCGATCAAATCAATGGGAAGCTGAATAGATTGATCGGGAAAACCAACGAGAAATTCCATCA
GATTGAAAAAGAATTCTCAGAAGTCGAAGGGAGAATTCAGGACCTTGAGAAATATGTTGAGGACACTAA
AATAGATCTCTGGTCATACAACGCGGAGCTTCTTGTTGCCCTGGAGAACCAACATACAATTGATCTAACT
GACTCAGAAATGAACAAACTGTTTGAAAAAACAAAGAAGCAACTGAGGGAAAATGCTGAGGATATGGG
CAATGGTTGTTTCAAAATATACCACAAATGTGACAATGCCTGCATAGGATCAATCAGAAATGGAACTTAT
GACCACGATGTATACAGAGATGAAGCATTAAACAACCGGTTTCAGATCAAGGGAGTTGAGCTGAAGTCA
GGGTACAAAGATTGGATCCTATGGATTTCCTTTGCCATATCATGTTTTTTGCTTTGTGTTGCTTTGTTGGGG
TTCATCATGTGGGCCTGCCAAAAAGGCAACATTAGGTGCAACATTTGCATTTGAAGGCCTATTTTCTTTAG
TTTGAATTTACTGTTATTCGGTGTGCATTTCTATGTTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATT
TTAATTTTATTAAAAAAAAAAAAAAAAAAAGACCGGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTA

Figure 5D continued

TGATTAGAGTCCCGCAATTATACATTTAATACGCGATAGAAAACAAAATATAGCGCGCAAACTAGGATA
AATTATCGCGCGCGGTGTCATCTATGTTACTAGAT

Figure 5E

Amino acid sequence of PDISP/H3 from influenza A/Perth/16/2009 (H3N2) (SEQ ID NO: 25)

MAKNVAIFGLLFSLLVLVPSQIFAQKLPGNDNSTATLCLGHHAVPNGTIVKTITNDQIEVT
NATELVQSSSTGEICDSPHQILDGKNCTLIDALLGDPQCDGFQNKKWDLFVERSKAYSNC
YPYDVPDYASLRSLVASSGTLEFNNESFNWTGVTQNGTSSACIRRSKNSFFSRLNWLTHL
NFKYPALNVTMPNNEQFDKLYIWGVHHPGTDKDQIFLYAQASGRITVSTKRSQQTVSPNI
GSRPRVRNIPSRISIYWTIVKPGDILLINSTGNLIAPRGYFKIRSGKSSIMRSDAPIGKCNSEC
ITPNGSIPNDKPFQNVNRITYGACPRYVKQNTLKLATGMRNVPEKQTRGIFGAIAGFIENG
WEGMVDGWYGFRHQNSEGRGQAADLKSTQAAIDQINGKLNRLIGKTNEKFHQIEKEFS
EVEGRIQDLEKYVEDTKIDLWSYNAELLVALENQHTIDLTDSEMNKLFEKTKKQLRENA
EDMGNGCFKIYHKCDNACIGSIRNGTYDHDVYRDEALNNRFQIKGVELKSGYKDWILWI
SFAISCFLLCVALLGFIMWACQKGNIRCNICI

F-2X35S/CPMV-HT/PDISP/HA B Brisbane/NOS (Construct number 1029)

Expression cassette number 1029 from 2X35S promoter to NOS terminator. PDISP/HA from influenza B/Brisbane/60/2008 is underlined. (SEQ ID NO: 29)

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CATGGCGAAAAACGTTGCGATTTTCGGCTTATTGTTTTCTCTTCTTGTGTTGGTTCCTTCTCAGATCTTCG
CCGATCGAATCTGCACTGGAATAACATCGTCAAACTCACCACATGTCGTCAAAACTGCTACTCAAGGGGA
GGTCAATGTGACTGGTGTAATACCACTGACAACAACACCCACCAAATCTCATTTTGCAAATCTCAAAGGA
ACAGAAACCAGGGGGAAACTATGCCCAAAATGCCTCAACTGCACAGATCTGGACGTAGCCTTGGGCAGA
CCAAAATGCACGGGGAAAATACCCTCGGCAAGAGTTTCAATACTCCATGAAGTCAGACCTGTTACATCTG
GGTGCTTTCCTATAATGCACGACAGAACAAAAATTAGACAGCTGCCTAACCTTCTCCGAGGATACGAACA
TATCAGGTTATCAACCCATAACGTTATCAATGCAGAAAATGCACCAGGAGGACCCTACAAAATTGGAAC
CTCAGGGTCTTGCCCTAACATTACCAATGGAAACGGATTTTTCGCAACAATGGCTTGGGCCGTCCCAAAA
AACGACAAAAACAAAACAGCAACAAATCCATTAACAATAGAAGTACCATACATTTGTACAGAAGGAGAA
GACCAAATTACCGTTTGGGGGTTCCACTCTGACAACGAGACCCAAATGGCAAAGCTCTATGGGGACTCAA
AGCCCCAGAAGTTCACCTCATCTGCCAACGGAGTGACCACACATTACGTTTCACAGATTGGTGGCTTCCC
AAATCAAACAGAAGACGGAGGACTACCACAAAGTGGTAGAATTGTTGTTGATTACATGGTGCAAAAATC
TGGGAAAACAGGAACAATTACCTATCAAAGGGGTATTTTATTGCCTCAAAAGGTGTGGTGCGCAAGTGG
CAGGAGCAAGGTAATAAAGGATCCTTGCCTTTAATTGGAGAAGCAGATTGCCTCCACGAAAAATACGG
TGGATTAAACAAAAGCAAGCCTTACTACACAGGGGAACATGCAAAGGCCATAGGAAATTGCCCAATATG
GGTGAAAACACCCTTGAAGCTGGCCAATGGAACCAAATATAGACCTCCTGCAAAACTATTAAAGGAAAG
GGGTTTCTTCGGAGCTATTGCTGGTTTCTTAGAAGGAGGATGGGAAGGAATGATTGCAGGTTGGCACGGA
TACACATCCCATGGGCACATGGAGTAGCGGTGGCAGCAGACCTTAAGAGCACTCAAGAGGCCATAAAC
AAGATAACAAAAAATCTCAACTCTTTGAGTGAGCTGGAAGTAAAGAATCTTCAAAGACTAAGCGGTGCC
ATGGATGAACTCCACAACGAAATACTAGAACTAGATGAGAAAGTGGATGATCTCAGAGCTGATACAATA
AGCTCACAAATAGAACTCGCAGTCCTGCTTTCCAATGAAGGAATAATAAACAGTGAAGATGAACATCTCT
TGGCGCTTGAAAGAAAGCTGAAGAAAATGCTGGGCCCTCTGCTGTAGAGATAGGGAATGGATGCTTTG
AAACCAAACACAAGTGCAACCAGACCTGTCTCGACAGAATAGCTGCTGGTACCTTTGATGCAGGAGAAT
TTTCTCTCCCCACCTTTGATTCACTGAATATTACTGCTGCATCTTTAAATGACGATGGATTGGATAATCAT
ACTATACTGCTTTACTACTCAACTGCTGCCTCCAGTTTGGCTGTAACACTGATGATAGCTATCTTTGTTGTT
TATATGGTCTCCAGAGACAATGTTTCTTGCTCCATCTGTCTATAAAGGCCTATTTTCTTTAGTTTGAATTTA
CTGTTATTCGGTGTGCATTTCTATGTTTGGTGAGCGGTTTTCTGTGCTCAGAGTGTGTTTATTTTATGTAAT
TTAATTTCTTTGTGAGCTCCTGTTTAGCAGGTCGTCCCTTCAGCAAGGACACAAAAAGATTTTAATTTTAT
TAAAAAAAAAAAAAAAAAAGACCGGGAATTCGATATCAAGCTTATCGACCTGCAGATCGTTCAAACATT
TGGCAATAAAGTTTCTTAAGATTGAATCCTGTTGCCGGTCTTGCGATGATTATCATATAATTTCTGTTGAA
TTACGTTAAGCATGTAATAATTAACATGTAATGCATGACGTTATTTATGAGATGGGTTTTTATGATTAGAG

Figure 6D continued

TCCCGCAATTATACATTTAATACGCGATAGAAAACAAAATATAGCGCGCAAACTAGGATAAATTATCGCG
CGCGGTGTCATCTATGTTACTAGAT

Figure 6E,

Amino acid sequence of PDISP/HA from influenza B/Brisbane/60/2008 SEQ ID NO: 30

MAKNVAIFGLLFSLLVLVPSQIFADRICTGITSSNSPHVVKTATQGEVNVTGVIPLTTTPTK
SHFANLKGTETRGKLCPKCLNCTDLDVALGRPKCTGKIPSARVSILHEVRPVTSGCFPIM
HDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCA
SGRSKVIKGSLPLIGEADCLHEKYGGLNKSKPYYTGEHAKAIGNCPIWVKTPLKLANGTK
YRPPAKLLKERGFFGAIAGFLEGGWEGMIAGWHGYTSHGAHGVAVAADLKSTQEAINK
ITKNLNSLSELEVKNLQRLSGAMDELHNEILELDEKVDDLRADTISSQIELAVLLSNEGIIN
SEDEHLLALERKLKKMLGPSAVEIGNGCFETKHKCNQTCLDRIAAGTFDAGEFSLPTFDS
LNITAASLNDDGLDNHTILLYYSTAASSLAVTLMIAIFVVYMVSRDNVSCSICL

G-2X35S/CPMV-HT/PDISP/HA B Brisbane/NOS into BeY

Figure 6G continued

CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGACACGCGTGGCGCGCCCTAGCAGAAGGCATGTTGTTGTGACTCCGAG
GGGTTGCCTCAAACTCTATCTTATAACCGGCGTGGAGGCATGGAGGCAAGGGCATTTTGGTAATTTAAGT
AGTTAGTGGAAAATGACGTCATTTACTTAAAGACGAAGTCTTGCGACAAGGGGGGCCCACGCCGAATTTT
AATATTACCGGCGTGGCCCCACCTTATCGCGAGTGCTTTAGCACGAGCGGTCCAGATTTAAAGTAGAAAA
GTTCCCGCCCACTAGGGTTAAAGGTGTTCACACTATAAAAGCATATACGATGTGATGGTATTTGATAAAG
CGTATATTGTATCAGGTATTTCCGTCGGATACGAATTATTCGTACAAGCTTCTTAAGCCGGTCAACATGGT
GGAGCACGACACACTTGTCTACTCCAAAAATATCAAAGATACAGTCTCAGAAGACCAAAGGGCAATTGA
GACTTTTCAACAAAGGGTAATATCCGGAAACCTCCTCGGATTCCATTGCCCAGCTATCTGTCACTTTATTG
TGAAGATAGTGGAAAAGGAAGGTGGCTCCTACAAATGCCATCATTGCGATAAAGGAAAGGCCATCGTTG
AAGATGCCTCTGCCGACAGTGGTCCCAAAGATGGACCCCCACCCACGAGGAGCATCGTGGAAAAAGAAG
ACGTTCCAACCACGTCTTCAAAGCAAGTGGATTGATGTGATAACATGGTGGAGCACGACACACTTGTCTA
CTCCAAAAATATCAAAGATACAGTCTCAGAAGACCAAAGGGCAATTGAGACTTTTCAACAAAGGGTAAT
ATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAA
AGCAAGTGGATTGATGTGATATCTCCACTGACGTAAGGGATGACGCACAATCCCACTATCCTTCGCAAGA
CCCTTCCTCTATATAAGGAAGTTCATTTCATTTGGAGAGGTATTAAAATCTTAATAGGTTTTGATAAAAGC
GAACGTGGGGAAACCCGAACCAAACCTTCTTCTAAACTCTCTCTCATCTCTCTTAAAGCAAACTTCTCTCT
TGTCTTTCTTGCGTGAGCGATCTTCAACGTTGTCAGATCGTGCTTCGGCACCAGTACAACGTTTTCTTTCA
CTGAAGCGAAATCAAAGATCTCTTTGTGGACACGTAGTGCGGCGCCATTAAATAACGTGTACTTGTCCTA
TTCTTGTCGGTGTGGTCTTGGGAAAAGAAAGCTTGCTGGAGGCTGCTGTTCAGCCCCATACATTACTTGTT
ACGATTCTGCTGACTTTCGGCGGGTGCAATATCTCTACTTCTGCTTGACGAGGTATTGTTGCCTGTACTTC
TTTCTTCTTCTTCTTGCTGATTGGTTCTATAAGAAATCTAGTATTTTCTTTGAAACAGAGTTTTCCCGTGGT
TTTCGAACTTGGAGAAAGATTGTTAAGCTTCTGTATATTCTGCCCAAATTTGTCGGGCCCATGGCGAAAA
ACGTTGCGATTTTCGGCTTATTGTTTTCTCTTCTTGTTGGTTCCTTCTCAGATCTTCGCCGCGGCTCCTC
AGCCAAAACGACACCCCCATCTGTCTATCCACTGGCCCCTGGATCTGCTGCCCAAACTAACTCCATGGTG
ACCCTGGGATGCCTGGTCAAGGGCTATTTCCCTGAGCCAGTGACAGTGACCTGGAACTCTGGATCCCTGT
CCAGCGGTGTGCACACCTTCCCAGCTGTCCTGCAGTCTGACCTCTACACTCTGAGCAGCTCAGTGACTGTC
CCCTCCAGCACCTGGCCCAGCGAGACCGTCACCTGCAACGTTGCCCACCCGGCCAGCAGCACCAAGGTG
GACAAGAAAATTGTGCCCAGGGATTGTGGTTGTAAGCCTTGCATATGTACAGTCCCAGAAGTATCATCTG
TCTTCATCTTCCCCCCAAAGCCCAAGGATGTGCTCACCATTACTCTGACTCCTAAGGTCACGTGTGTTGTG

Figure 6G continued

```
GTAGACATCAGCAAGGATGATCCCGAGGTCCAGTTCAGCTGGTTTGTAGATGATGTGGAGGTGCACACA
GCTCAGACGCAACCCCGGGAGGAGCAGTTCAACAGCACTTTCCGCTCAGTCAGTGAACTTCCCATCATGC
ACCAGGACTGGCTCAATGGCAAGGAAGGCCTATTTTCTTTAGTTTGAATTTACTGTTATTCGGTGTGCATT
TCTATGTTTGGTGAGCGGTTTTCTGTGCTCAGAGTGTGTTTATTTTATGTAATTTAATTTCTTTGTGAGCTC
CTGTTTAGCAGGTCGTCCCTTCAGCAAGGACACAAAAAGATTTTAATTTTATTAAAAAAAAAAAAAAAAA
AGACCGGGAATTCGATATCAAGCTTATCGACCTGCAGATCGTTCAAACATTTGGCAATAAAGTTTCTTAA
GATTGAATCCTGTTGCCGGTCTTGCGATGATTATCATATAATTTCTGTTGAATTACGTTAAGCATGTAATA
ATTAACATGTAATGCATGACGTTATTTATGAGATGGGTTTTTATGATTAGAGTCCCGCAATTATACATTTA
ATACGCGATAGAAAACAAAATATAGCGCGCAAACTAGGATAAATTATCGCGCGCGGTGTCATCTATGTT
ACTAGATCTCTAGAGTCTCAAGCTTGGCGCGGGGTACCGAGCTCGAATTCCGAGTGTACTTCAAGTCAGT
TGGAAATCAATAAAATGATTATTTTATGAATATATTTCATTGTGCAAGTAGATAGAAATTACATATGTTAC
ATAACACACGAAATAAACAAAAAAACACAATCCAAAACAAACACCCCAAACAAAATAACACTATATAT
ATCCTCGTATGAGGAGAGGCACGTTCAGTGACTCGACGATTCCCGAGCAAAAAAAGTCTCCCCGTCACAC
ATATAGTGGGTGACGCAATTATCTTCAAAGTAATCCTTCTGTTGACTTGTCATTGATAACATCCAGTCTTC
GTCAGGATTGCAAAGAATTATAGAAGGGATCCCACCTTTTATTTTCTTCTTTTTTCCATATTTAGGGTTGA
CAGTGAAATCAGACTGGCAACCTATTAATTGCTTCCACAATGGGACGAACTTGAAGGGGATGTCGTCGAT
GATATTATAGGTGGCGTGTTCATCGTAGTTGGTGAAGTCGATGGTCCCGTTCCAGTAGTTGTGTCGCCCGA
GACTTCTAGCCCAGGTGGTCTTTCCGGTACGAGTTGGTCCGCAGATGTAGAGGCTGGGGTGTCTGACCCC
AGTCCTTCCCTCATCCTGGTTAGATCGGCCATCCACTCAAGGTCAGATTGTGCTTGATCGTAGGAGACAG
GATGTATGAAAGTGTAGGCATCGATGCTTACATGATATAGGTGCGTCTCTCTCCAGTTGTGCAGATCTTCG
TGGCAGCGGAGATCTGATTCTGTGAAGGGCGACACGTACTGCTCAGGTTGTGGAGGAAATAATTTGTTGG
CTGAATATTCCAGCCATTGAAGCTTTGTTGCCCATTCATGAGGGAATTCTTCTTTGATCATGTCAAGATAC
TCCTCCTTAGACGTTGCAGTCTGGATAATAGTTCGCCATCGTGCGTCAGATTTGCGAGGAGAGACCTTAT
GATCTCGGAAATCTCCTCTGGTTTTAATATCTCCGTCCTTTGATATGTAATCAAGGACTTGTTTAGAGTTTC
TAGCTGGCTGGATATTAGGGTGATTTCCTTCAAAATCGAAAAAAGAAGGATCCCTAATACAAGGTTTTTT
ATCAAGCTGGATAAGAGCATGATAGTGGGTAGTGCCATCTTGATGAAGCTCAGAAGCAACACCAAGGAA
GAAAATAAGAAAAGGTGTGAGTTTCTCCCAGAGAAACTGGAATAAATCATCTCTTTGAGATGAGCACTTG
GGGTAGGTAAGGAAAACATATTTAGATTGGAGTCTGAAGTTCTTGCTAGCAGAAGGCATGTTGTTGTGAC
TCCGAGGGGTTGCCTCAAACTCTATCTTATAACCGGCGTGGAGGCATGGAGGCAAGGGCATTTTGGTAAT
TTAAGTAGTTAGTGGAAAATGACGTCATTTACTTAAAGACGAAGTCTTGCGACAAGGGGGGCCCACGCC
GAATTTTAATATTACCGGCGTGGCCCCACCTTATCGCGAGTGCTTTAGCACGAGCGGTCCAGATTTAAAG
TAGAAAAGTTCCCGCCCACTAGGGTTAAAGGTGTTCACACTATAAAAGCATATACGATGTGATGGTATTT
GATGGAGCGTATATTGTATCAGGTATTTCCGTCGGATACGAATTATTCGTACGGCCGGCCACTAGTGGCA
CTGGCCGTCGTTTTACAACGTCGTGACTGGGAAAACCCTGGCGTTACCCAACTTAATCGCCTTGCAGCAC
ATCCCCCTTTCGCCAGCTGGCGTAATAGCGAAGAGGCCCGCACCGATCGCCCTTCCCAACAGTTGCGCAG
CCTGAATGGCGAATGCTAGAGCAGCTTGAGCTTGGATCAGATTGTCGTTTCCCGCCTTCAGTTTAAACTAT
CAGTGTTTGACAGGATATATTGGCGGGTAAACCTAAGAGAAAAGAGCGTTTA
```

Figure 6H

Expression cassette number 1008 from BeYDV left LIR to BeYDV right LIR. PDISP/HA from influenza B/Brisbane/60/2008 is underlined. (SEQ ID NO: 32)

```
CTAGCAGAAGGCATGTTGTTGTGACTCCGAGGGGTTGCCTCAAACTCTATCTTATAACCGGCGTGGAGGC
ATGGAGGCAAGGGCATTTTGGTAATTTAAGTAGTTAGTGGAAAATGACGTCATTTACTTAAAGACGAAGT
CTTGCGACAAGGGGGGCCCACGCCGAATTTTAATATTACCGGCGTGGCCCCACCTTATCGCGAGTGCTTT
AGCACGAGCGGTCCAGATTTAAAGTAGAAAAGTTCCCGCCCACTAGGGTTAAAGGTGTTCACACTATAA
AAGCATATACGATGTGATGGTATTTGATAAAGCGTATATTGTATCAGGTATTTCCGTCGGATACGAATTA
TTCGTACAAGCTTCTTAAGCCGGTCAACATGGTGGAGCACGACACACTTGTCTACTCCAAAAATATCAAA
GATACAGTCTCAGAAGACCAAAGGGCAATTGAGACTTTTCAACAAAGGGTAATATCCGGAAACCTCCTC
GGATTCCATTGCCCAGCTATCTGTCACTTTATTGTGAAGATAGTGGAAAAGGAAGGTGGCTCCTACAAAT
GCCATCATTGCGATAAAGGAAAGGCCATCGTTGAAGATGCCTCTGCCGACAGTGGTCCCAAAGATGGAC
```

Figure 6H continued

CCCCACCCACGAGGAGCATCGTGGAAAAGAAGACGTTCCAACCACGTCTTCAAAGCAAGTGGATTGAT
GTGATAACATGGTGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCATTTGGAG
AGGTATTAAAATCTTAATAGGTTTTGATAAAAGCGAACGTGGGGAAACCCGAACCAAACCTTCTTCTAAA
CTCTCTCTCATCTCTCTTAAAGCAAACTTCTCTCTTGTCTTTCTTGCGTGAGCGATCTTCAACGTTGTCAGA
TCGTGCTTCGGCACCAGTACAACGTTTTCTTTCACTGAAGCGAAATCAAAGATCTCTTTGTGGACACGTAG
TGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTTCTTCTTCTTGCTGATTGGTTCTATAAGAAATCT
AGTATTTTCTTTGAAACAGAGTTTTCCCGTGGTTTTCGAACTTGGAGAAAGATTGTTAAGCTTCTGTATAT
TCTGCCCAAATTTGTCGGGCCC<u>ATGGCGAAAAACGTTGCGATTTTCGGCTTATTGTTTCTCTTCTTGTGTT
GGTTCCTTCTCAGATCTTCGCCGATCGAATCTGCACTGGAATAACATCGTCAAACTCACCACATGTCGTCA
AAACTGCTACTCAAGGGGAGGTCAATGTGACTGGTGTAATACCACTGACAACAACACCCACCAAATCTC
ATTTTGCAAATCTCAAAGGAACAGAAACCAGGGGGAAACTATGCCCAAAATGCCTCAACTGCACAGATC
TGGACGTAGCCTTGGGCAGACCAAAATGCACGGGGAAAATACCCTCGGCAAGAGTTTCAATACTCCATG
AAGTCAGACCTGTTACATCTGGGTGCTTTCCTATAATGCACGACAGAACAAAAATTAGACAGCTGCCTAA
CCTTCTCCGAGGATACGAACATATCAGGTTATCAACCCATAACGTTATCAATGCAGAAAATGCACCAGGA
GGACCCTACAAAATTGGAACCTCAGGGTCTTGCCCTAACATTACCAATGGAAACGGATTTTTCGCAACAA
TGGCTTGGGCCGTCCCAAAAAACGACAAAAACAAAACAGCAACAAATCCATTAACAATAGAAGTACCAT
ACATTTGTACAGAAGGAGAAGACCAAATTACCGTTTGGGGGTTCCACTCTGACAACGAGACCCAAATGG
CAAAGCTCTATGGGGACTCAAAGCCCCAGAAGTTCACCTCATCTGCCAACGGAGTGACCACACATTACGT
TTCACAGATTGGTGGCTTCCCAAATCAAACAGAAGACGGAGGACTACCACAAAGTGGTAGAATTGTTGTT
GATTACATGGTGCAAAAATCTGGGAAAACAGGAACAATTACCTATCAAAGGGGTATTTTATTGCCTCAAA
AGGTGTGGTGCGCAAGTGGCAGGAGCAAGGTAATAAAAGGATCCTTGCCTTTAATTGGAGAAGCAGATT
GCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTG
CAAAACTATTAAAGGAAAGGGGTTTCTTCGGAGCTATTGCTGGTTTCTTAGAAGGAGGATGGGAAGGAA
TGATTGCAGGTTGGCACGGATACACATCCCATGGGGCACATGGAGTAGCGGTGGCAGCAGACCTTAAGA
GCACTCAAGAGGCCATAAACAAGATAACAAAAAATCTCAACTCTTTGAGTGAGCTGGAAGTAAAGAATC
TTCAAAGACTAAGCGGTGCCATGGATGAACTCCACAACGAAATACTAGAACTAGATGAGAAAGTGGATG
ATCTCAGAGCTGATACAATAAGCTCACAAATAGAACTCGCAGTCCTGCTTTCCAATGAAGGAATAATAAA
CAGTGAAGATGAACATCTCTTGGCGCTTGAAAGAAAGCTGAAGAAAATGCTGGGCCCCTCTGCTGTAGA
GATAGGGAATGGATGCTTTGAAACCAAACACAAGTGCAACCAGACCTGTCTCGACAGAATAGCTGCTGG
TACCTTTGATGCAGGAGAATTTTCTCTCCCCACCTTTGATTCACTGAATATTACTGCTGCATCTTTAAATG
ACGATGGATTGGATAATCATACTATACTGCTTTACTACTCAACTGCTGCCTCCAGTTTGGCTGTAACACTG
ATGATAGCTATCTTTGTTGTTTATATGGTCTCCAGAGACAATGTTTCTTGCTCCATCTGTCTATAAAGGCCT</u>
ATTTTCTTTAGTTTGAATTTACTGTTATTCGGTGTGCATTTCTATGTTTGGTGAGCGGTTTTCTGTGCTCAG
AGTGTGTTTATTTTATGTAATTTAATTTCTTTGTGAGCTCCTGTTTAGCAGGTCGTCCCTTCAGCAAGGACA
CAAAAAGATTTTAATTTTATTAAAAAAAAAAAAAAAAAAAGACCGGGAATTCGATATCAAGCTTATCGAC
CTGCAGATCGTTCAAACATTTGGCAATAAAGTTTCTTAAGATTGAATCCTGTTGCCGGTCTTGCGATGATT
ATCATATAATTTCTGTTGAATTACGTTAAGCATGTAATAATTAACATGTAATGCATGACGTTATTTATGAG
ATGGGTTTTTATGATTAGAGTCCCGCAATTATACATTTAATACGCGATAGAAAACAAAATATAGCGCGCA
AACTAGGATAAATTATCGCGCGCGGTGTCATCTATGTTACTAGATCTCTAGAGTCTCAAGCTTGGCGCGG
GGTACCGAGCTCGAATTCCGAGTGTACTTCAAGTCAGTTGGAAATCAATAAAATGATTATTTTATGAATA
TATTTCATTGTGCAAGTAGATAGAAATTACATATGTTACATAACACACGAAATAAACAAAAAAACACAAT
CCAAAACAAACACCCCAAACAAAATAACACTATATATATCCTCGTATGAGGAGAGGCACGTTCAGTGAC
TCGACGATTCCCGAGCAAAAAAGTCTCCCCGTCACACATATAGTGGGTGACGCAATTATCTTCAAAGTA
ATCCTTCTGTTGACTTGTCATTGATAACATCCAGTCTTCGTCAGGATTGCAAAGAATTATAGAAGGGATCC
CACCTTTTATTTTCTTCTTTTTTCCATATTTAGGGTTGACAGTGAAATCAGACTGGCAACCTATTAATTGCT
TCCACAATGGGACGAACTTGAAGGGGATGTCGTCGATGATATTATAGGTGGCGTGTTCATCGTAGTTGGT

Figure 6H continued

GAAGTCGATGGTCCCGTTCCAGTAGTTGTGTCGCCCGAGACTTCTAGCCCAGGTGGTCTTTCCGGTACGA
GTTGGTCCGCAGATGTAGAGGCTGGGGTGTCTGACCCCAGTCCTTCCCTCATCCTGGTTAGATCGGCCATC
CACTCAAGGTCAGATTGTGCTTGATCGTAGGAGACAGGATGTATGAAAGTGTAGGCATCGATGCTTACAT
GATATAGGTGCGTCTCTCTCCAGTTGTGCAGATCTTCGTGGCAGCGGAGATCTGATTCTGTGAAGGGCGA
CACGTACTGCTCAGGTTGTGGAGGAAATAATTTGTTGGCTGAATATTCCAGCCATTGAAGCTTTGTTGCCC
ATTCATGAGGGAATTCTTCTTTGATCATGTCAAGATACTCCTCCTTAGACGTTGCAGTCTGGATAATAGTT
CGCCATCGTGCGTCAGATTTGCGAGGAGAGACCTTATGATCTCGGAAATCTCCTCTGGTTTTAATATCTCC
GTCCTTTGATATGTAATCAAGGACTTGTTTAGAGTTTCTAGCTGGCTGGATATTAGGGTGATTTCCTTCAA
AATCGAAAAAGAAGGATCCCTAATACAAGGTTTTTTATCAAGCTGGATAAGAGCATGATAGTGGGTAG
TGCCATCTTGATGAAGCTCAGAAGCAACACCAAGGAAGAAAATAAGAAAAGGTGTGAGTTTCTCCCAGA
GAAACTGGAATAAATCATCTCTTTGAGATGAGCACTTGGGGTAGGTAAGGAAAACATATTTAGATTGGA
GTCTGAAGTTCTTGCTAGCAGAAGGCATGTTGTTGTGACTCCGAGGGGTTGCCTCAAACTCTATCTTATAA
CCGGCGTGGAGGCATGGAGGCAAGGGCATTTTGGTAATTTAAGTAGTTAGTGGAAAATGACGTCATTTAC
TTAAAGACGAAGTCTTGCGACAAGGGGGGCCCACGCCGAATTTTAATATTACCGGCGTGGCCCCACCTTA
TCGCGAGTGCTTTAGCACGAGCGGTCCAGATTTAAAGTAGAAAAGTTCCCGCCCACTAGGGTTAAAGGTG
TTCACACTATAAAAGCATATACGATGTGATGGTATTTGATGGAGCGTATATTGTATCAGGTATTTCCGTCG
GATACGAATTATTCGTAC

H-2X35S/CPMV-HT/PDISP/HA B Brisbane/H5 Indonesia transmembrane domain and cytoplasmic tail (H5Indo TMCT)/NOS into BeYDV+Replicase amplification system (Construct number 1009)

Figure 7A dTmH5I-B Bris.r (SEQ ID NO: 33)

TTGACAGTATTTGGTAATTATCCAATCCATCGTCATTTAAAGATGCAGCA

Figure 7B

B Bris-dTmH5I.c (SEQ ID NO: 34)

CATCTTTAAATGACGATGGATTGGATAATTACCAAATACTGTCAATTTAT

Figure 7C

IF-S1aS4-dTmH5I.r (SEQ ID NO: 35)

ACTAAAGAAAATAGGCCTTTAAATGCAAATTCTGCATTGTAACGATCCAT

Figure 7D,

Expression cassette number 1009 from BeYDV left LIR to BeYDV right LIR. PDISP/HA B Brisbane/H5Indo TMCT is underlined. SEQ ID NO:36

CTAGCAGAAGGCATGTTGTTGTGACTCCGAGGGGTTGCCTCAAACTCTATCTTATAACCGGCGTGGAGGC
ATGGAGGCAAGGGCATTTTGGTAATTTAAGTAGTTAGTGGAAAATGACGTCATTTACTTAAAGACGAAGT
CTTGCGACAAGGGGGGCCCACGCCGAATTTTAATATTACCGGCGTGGCCCCACCTTATCGCGAGTGCTTT
AGCACGAGCGGTCCAGATTTAAAGTAGAAAAGTTCCCGCCCACTAGGGTTAAAGGTGTTCACACTATAA
AAGCATATACGATGTGATGGTATTTGATAAAGCGTATATTGTATCAGGTATTTCCGTCGGATACGAATTA
TTCGTACAAGCTTCTTAAGCCGGTCAACATGGTGGAGCACGACACACTTGTCTACTCCAAAAATATCAAA
GATACAGTCTCAGAAGACCAAAGGGCAATTGAGACTTTTCAACAAAGGGTAATATCCGGAAACCTCCTC
GGATTCCATTGCCCAGCTATCTGTCACTTTATTGTGAAGATAGTGGAAAAGGAAGGTGGCTCCTACAAAT
GCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGAT
GTGATAACATGGTGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCATTTGGAG
AGGTATTAAAATCTTAATAGGTTTTGATAAAAGCGAACGTGGGGAAACCCGAACCAAACCTTCTTCTAAA

Figure 7D continued

CTCTCTCTCATCTCTCTTAAAGCAAACTTCTCTCTTGTCTTTCTTGCGTGAGCGATCTTCAACGTTGTCAGA
TCGTGCTTCGGCACCAGTACAACGTTTTCTTTCACTGAAGCGAAATCAAAGATCTCTTTGTGGACACGTAG
TGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTCTTCTTCTTCTTGCTGATTGGTTCTATAAGAAATCT
AGTATTTTCTTTGAAACAGAGTTTTCCCGTGGTTTTCGAACTTGGAGAAAGATTGTTAAGCTTCTGTATAT
TCTGCCCAAATTTGTCGGGCCC<u>ATGGCGAAAAACGTTGCGATTTTCGGCTTATTGTTTTCTCTTCTTGTGTT</u>
<u>GGTTCCTTCTCAGATCTTCGCCGATCGAATCTGCACTGGAATAACATCGTCAAACTCACCACATGTCGTCA</u>
<u>AAACTGCTACTCAAGGGGAGGTCAATGTGACTGGTGTAATACCACTGACAACAACACCCACCAAATCTC</u>
<u>ATTTTGCAAATCTCAAAGGAACAGAAACCAGGGGGAAACTATGCCCAAAATGCCTCAACTGCACAGATC</u>
<u>TGGACGTAGCCTTGGGCAGACCAAAATGCACGGGGAAAATACCCTCGGCAAGAGTTTCAATACTCCATG</u>
<u>AAGTCAGACCTGTTACATCTGGGTGCTTTCCTATAATGCACGACAGAACAAAAATTAGACAGCTGCCTAA</u>
<u>CCTTCTCCGAGGATACGAACATATCAGGTTATCAACCCATAACGTTATCAATGCAGAAAATGCACCAGGA</u>
<u>GGACCCTACAAAATTGGAACCTCAGGGTCTTGCCCTAACATTACCAATGGAAACGGATTTTTCGCAACAA</u>
<u>TGGCTTGGGCCGTCCCAAAAAACGACAAAAACAAAACAGCAACAAATCCATTAACAATAGAAGTACCAT</u>
<u>ACATTTGTACAGAAGGAGAAGACCAAATTACCGTTTGGGGGTTCCACTCTGACAACGAGACCCAAATGG</u>
<u>CAAAGCTCTATGGGGACTCAAAGCCCCAGAAGTTCACCTCATCTGCCAACGGAGTGACCACACATTACGT</u>
<u>TTCACAGATTGGTGGCTTCCCAAATCAAACAGAAGACGGAGGACTACCACAAAGTGGTAGAATTGTTGTT</u>
<u>GATTACATGGTGCAAAAATCTGGGAAAACAGGAACAATTACCTATCAAAGGGGTATTTTATTGCCCTCAAA</u>
<u>AGGTGTGGTGCGCAAGTGGCAGGAGCAAGGTAATAAAAGGATCCTTGCCTTTAATTGGAGAAGCAGATT</u>
<u>GCCTCCACGAAAAATACGGTGGATTAAACAAAAGCAAGCCTTACTACACAGGGGAACATGCAAAGGCCA</u>
<u>TAGGAAATTGCCCAATATGGGTGAAAACACCCTTGAAGCTGGCCAATGGAACCAAATATAGACCTCCTG</u>
<u>CAAAACTATTAAAGGAAAGGGGTTTCTTCGGAGCTATTGCTGGTTTCTTAGAAGGAGGATGGGAAGGAA</u>
<u>TGATTGCAGGTTGGCACGGATACACATCCCATGGGGCACATGGAGTAGCGGTGGCAGCAGACCTTAAGA</u>
<u>GCACTCAAGAGGCCATAAACAAGATAACAAAAAATCTCAACTCTTTGAGTGAGCTGGAAGTAAAGAATC</u>
<u>TTCAAAGACTAAGCGGTGCCATGGATGAACTCCACAACGAAATACTAGAACTAGATGAGAAAGTGGATG</u>
<u>ATCTCAGAGCTGATACAATAAGCTCACAAATAGAACTCGCAGTCCTGCTTTCCAATGAAGGAATAATAAA</u>
<u>CAGTGAAGATGAACATCTCTTGGCGCTTGAAAGAAAGCTGAAGAAAATGCTGGGCCCCTCTGCTGTAGA</u>
<u>GATAGGGAATGGATGCTTTGAAACCAAACACAAGTGCAACCAGACCTGTCTCGACAGAATAGCTGCTGG</u>
<u>TACCTTTGATGCAGGAGAATTTTCTCTCCCCACCTTTGATTCACTGAATATTACTGCTGCATCTTTAAATG</u>
<u>ACGATGGATTGGATAATTACCAAATACTGTCAATTTATTCAACAGTGGCGAGTTCCCTAGCACTGGCAAT</u>
<u>CATGATGGCTGGTCTATCTTTATGGATGTGCTCCAATGGATCGTTACAATGCAGAATTTGCATTTAAAGGC</u>
CTATTTTCTTTAGTTTGAATTTACTGTTATTCGGTGTGCATTTCTATGTTTGGTGAGCGGTTTTCTGTGCTC
AGAGTGTGTTTATTTTATGTAATTTAATTTCTTTGTGAGCTCCTGTTTAGCAGGTCGTCCCTTCAGCAAGG
ACACAAAAAGATTTTAATTTTATTAAAAAAAAAAAAAAAAAAGACCGGGAATTCGATATCAAGCTTATC
GACCTGCAGATCGTTCAAACATTTGGCAATAAAGTTTCTTAAGATTGAATCCTGTTGCCGGTCTTGCGATG
ATTATCATATAATTTCTGTTGAATTACGTTAAGCATGTAATAATTAACATGTAATGCATGACGTTATTTAT
GAGATGGGTTTTTATGATTAGAGTCCCGCAATTATACATTTAATACGCGATAGAAAACAAAATATAGCGC
GCAAACTAGGATAAATTATCGCGCGCGGTGTCATCTATGTTACTAGATCTCTAGAGTCTCAAGCTTGGCG
CGGGGTACCGAGCTCGAATTCCGAGTGTACTTCAAGTCAGTTGGAAATCAATAAAATGATTATTTATGA
ATATATTTCATTGTGCAAGTAGATAGAAATTACATATGTTACATAACACACGAAATAAACAAAAAACAC
AATCCAAAACAAACACCCCAAACAAAATAACACTATATATATCCTCGTATGAGGAGAGGCACGTTCAGT
GACTCGACGATTCCCGAGCAAAAAAGTCTCCCCGTCACACATATAGTGGGTGACGCAATTATCTTCAAA
GTAATCCTTCTGTTGACTTGTCATTGATAACATCCAGTCTTCGTCAGGATTGCAAAGAATTATAGAAGGG
ATCCCACCTTTTATTTTCTTCTTTTTCCATATTTAGGGTTGACAGTGAAATCAGACTGGCAACCTATTAAT
TGCTTCCACAATGGGACGAACTTGAAGGGGATGTCGTCGATGATATTATAGGTGGCGTGTTCATCGTAGT
TGGTGAAGTCGATGGTCCCGTTCCAGTAGTTGTGTCGCCCGAGACTTCTAGCCCAGGTGGTCTTTCCGGTA
CGAGTTGGTCCGCAGATGTAGAGGCTGGGGTGTCTGACCCCAGTCCTTCCCTCATCCTGGTTAGATCGGC
CATCCACTCAAGGTCAGATTGTGCTTGATCGTAGGAGACAGGATGTATGAAAGTGTAGGCATCGATGCTT
ACATGATATAGGTGCGTCTCTCCAGTTGTGCAGATCTTCGTGGCAGCGGAGATCTGATTCTGTGAAGG
GCGACACGTACTGCTCAGGTTGTGGAGGAAATAATTTGTTGGCTGAATATTCCAGCCATTGAAGCTTTGT
TGCCCATTCATGAGGGAATTCTTCTTTGATCATGTCAAGATACTCCTCCTTAGACGTTGCAGTCTGGATAA
TAGTTCGCCATCGTGCGTCAGATTTGCGAGGAGAGACCTTATGATCTCGGAAATCTCCTCTGGTTTTAATA
TCTCCGTCCTTTGATATGTAATCAAGGACTTGTTTAGAGTTTCTAGCTGGCTGGATATTAGGGTGATTTCC

Figure 7D continued

TTCAAAATCGAAAAAAGAAGGATCCCTAATACAAGGTTTTTTATCAAGCTGGATAAGAGCATGATAGTG
GGTAGTGCCATCTTGATGAAGCTCAGAAGCAACACCAAGGAAGAAAATAAGAAAAGGTGTGAGTTTCTC
CCAGAGAAACTGGAATAAATCATCTCTTTGAGATGAGCACTTGGGGTAGGTAAGGAAAACATATTTAGA
TTGGAGTCTGAAGTTCTTGCTAGCAGAAGGCATGTTGTTGTGACTCCGAGGGGTTGCCTCAAACTCTATCT
TATAACCGGCGTGGAGGCATGGAGGCAAGGGCATTTTGGTAATTTAAGTAGTTAGTGGAAAATGACGTC
ATTTACTTAAAGACGAAGTCTTGCGACAAGGGGGGCCCACGCCGAATTTTAATATTACCGGCGTGGCCCC
ACCTTATCGCGAGTGCTTTAGCACGAGCGGTCCAGATTTAAAGTAGAAAAGTTCCCGCCCACTAGGGTTA
AAGGTGTTCACACTATAAAAGCATATACGATGTGATGGTATTTGATGGAGCGTATATTGTATCAGGTATT
TCCGTCGGATACGAATTATTCGTAC

Figure 7E.

Amino acid sequence of PDISP/HA B Brisbane/H5Indo TMCT (SEQ ID NO: 37)

MAKNVAIFGLLFSLLVLVPSQIFADRICTGITSSNSPHVVKTATQGEVNVTGVIPLTTTPTK
SHFANLKGTETRGKLCPKCLNCTDLDVALGRPKCTGKIPSARVSILHEVRPVTSGCFPIM
HDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCA
SGRSKVIKGSLPLIGEADCLHEKYGGLNKSKPYYTGEHAKAIGNCPIWVKTPLKLANGTK
YRPPAKLLKERGFFGAIAGFLEGGWEGMIAGWHGYTSHGAHGVAVAADLKSTQEAINK
ITKNLNSLSELEVKNLQRLSGAMDELHNEILELDEKVDDLRADTISSQIELAVLLSNEGIIN
SEDEHLLALERKLKKMLGPSAVEIGNGCFETKHKCNQTCLDRIAAGTFDAGEFSLPTFDS
LNITAASLNDDGLDNYQILSIYSTVASSLALAIMMAGLSLWMCSNGSLQCRICI

I-2X35S/CPMV-HT/PDISP/HA B Brisbane with deleted proteolytic loop/NOS into BeYDV+Replicase amplification system (Construct number 1059)

Figure 8A.

1039+1059.r (SEQ ID NO: 38)

CTTCCCATCCTCCACCAGGAGGTCTATATTTGGTTCCATTGGCCAGCTTCAA

Figure 8B

1039+1059.c (SEQ ID NO: 39)

CAAATATAGACCTCCTGGTGGAGGATGGGAAGGAATGATTGCAGGTTGGCAC

Figure 8C.

Expression cassette number 1059 from BeYDV left LIR to BeYDV right LIR. PDISP/HA from influenza B/Brisbane/60/2008 with deleted proteolytic loop is underlined. (SEQ ID NO: 40)

CTAGCAGAAGGCATGTTGTTGTGACTCCGAGGGGTTGCCTCAAACTCTATCTTATAACCGGCGTGGAGGC
ATGGAGGCAAGGGCATTTTGGTAATTTAAGTAGTTAGTGGAAAATGACGTCATTTACTTAAAGACGAAGT
CTTGCGACAAGGGGGGCCCACGCCGAATTTTAATATTACCGGCGTGGCCCCACCTTATCGCGAGTGCTTT
AGCACGAGCGGTCCAGATTTAAAGTAGAAAAGTTCCCGCCCACTAGGGTTAAAGGTGTTCACACTATAA
AAGCATATACGATGTGATGGTATTTGATAAAGCGTATATTGTATCAGGTATTTCCGTCGGATACGAATTA
TTCGTACAAGCTTCTTAAGCCGGTCAACATGGTGGAGCACGACACACTTGTCTACTCCAAAAATATCAAA
GATACAGTCTCAGAAGACCAAAGGGCAATTGAGACTTTTCAACAAAGGGTAATATCCGGAAACCTCCTC
GGATTCCATTGCCCAGCTATCTGTCACTTTATTGTGAAGATAGTGGAAAAGGAAGGTGGCTCCTACAAAT
GCCATCATTGCGATAAAGGAAAGGCCATCGTTGAAGATGCCTCTGCCGACAGTGGTCCCAAAGATGGAC
CCCCACCCACGAGGAGCATCGTGGAAAAGAAGACGTTCCAACCACGTCTTCAAAGCAAGTGGATTGAT
GTGATAACATGGTGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAGAAGACGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGTTCATTTCATTTGGAG
AGGTATTAAAATCTTAATAGGTTTTGATAAAAGCGAACGTGGGGAAACCCGAACCAAACCTTCTTCTAAA
CTCTCTCTCATCTCTCTTAAAGCAAACTTCTCTCTTGTCTTCTTGCGTGAGCGATCTTCAACGTTGTCAGA
TCGTGCTTCGGCACCAGTACAACGTTTTCTTTCACTGAAGCGAAATCAAAGATCTCTTTGTGGACACGTAG
TGCGGCGCCATTAAATAACGTGTACTTGTCCTATTCTTGTCGGTGTGGTCTTGGGAAAAGAAAGCTTGCTG
GAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTCTTCTTCTTCTTGCTGATTGGTTCTATAAGAAATCT
AGTATTTTCTTTGAAACAGAGTTTTCCCGTGGTTTTCGAACTTGGAGAAAGATTGTTAAGCTTCTGTATAT
TCTGCCCAAATTTGTCGGGCCCATGGCGAAAAACGTTGCGATTTTCGGCTTATTGTTTCTCTTCTTGTGTT
GGTTCCTTCTCAGATCTTCGCCGATCGAATCTGCACTGGAATAACATCGTCAAACTCACCACATGTCGTCA
AAACTGCTACTCAAGGGGAGGTCAATGTGACTGGTGTAATACCACTGACAACAACACCCACCAAATCTC
ATTTTGCAAATCTCAAAGGAACAGAAACCAGGGGGAAACTATGCCCAAAATGCCTCAACTGCACAGATC

Figure 8C continued

```
TGGACGTAGCCTTGGGCAGACCAAAATGCACGGGGAAAATACCCTCGGCAAGAGTTTCAATACTCCATG
AAGTCAGACCTGTTACATCTGGGTGCTTTCCTATAATGCACGACAGAACAAAAATTAGACAGCTGCCTAA
CCTTCTCCGAGGATACGAACATATCAGGTTATCAACCCATAACGTTATCAATGCAGAAAATGCACCAGGA
GGACCCTACAAAATTGGAACCTCAGGGTCTTGCCCTAACATTACCAATGGAAACGGATTTTTCGCAACAA
TGGCTTGGGCCGTCCCAAAAAACGACAAAAACAAAACAGCAACAAATCCATTAACAATAGAAGTACCAT
ACATTTGTACAGAAGGAGAAGACCAAATTACCGTTTGGGGGTTCCACTCTGACAACGAGACCCAAATGG
CAAAGCTCTATGGGGACTCAAAGCCCCAGAAGTTCACCTCATCTGCCAACGGAGTGACCACACATTACGT
TTCACAGATTGGTGGCTTCCCAAATCAAACAGAAGACGGAGGACTACCACAAAGTGGTAGAATTGTTGTT
GATTACATGGTGCAAAAATCTGGGAAAACAGGAACAATTACCTATCAAAGGGGTATTTTATTGCCCTCAAA
AGGTGTGGTGCGCAAGTGGCAGGAGCAAGGTAATAAAAGGATCCTTGCCTTTAATTGGAGAAGCAGATT
GCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTG
GTGGAGGATGGGAAGGAATGATTGCAGGTTGGCACGGATACACATCCCATGGGGCACATGGAGTAGCGG
TGGCAGCAGACCTTAAGAGCACTCAAGAGGCCATAAACAAGATAACAAAAAATCTCAACTCTTTGAGTG
AGCTGGAAGTAAAGAATCTTCAAAGACTAAGCGGTGCCATGGATGAACTCCACAACGAAATACTAGAAC
TAGATGAGAAAGTGGATGATCTCAGAGCTGATACAATAAGCTCACAAATAGAACTCGCAGTCCTGCTTTC
CAATGAAGGAATAATAAACAGTGAAGATGAACATCTCTTGGCGCTTGAAAGAAAGCTGAAGAAAATGCT
GGGCCCCTCTGCTGTAGAGATAGGGAATGGATGCTTTGAAACCAAACACAAGTGCAACCAGACCTGTCTC
GACAGAATAGCTGCTGGTACCTTTGATGCAGGAGAATTTTCTCTCCCCACCTTTGATTCACTGAATATTAC
TGCTGCATCTTTAAATGACGATGGATTGGATAATCATACTATACTGCTTTACTACTCAACTGCTGCCTCCA
GTTTGGCTGTAACACTGATGATAGCTATCTTTGTTGTTTATATGGTCTCCAGAGACAATGTTTCTTGCTCC
ATCTGTCTATAAAGGCCTATTTTCTTTAGTTTGAATTTACTGTTATTCGGTGTGCATTTCTATGTTTGGTGA
GCGGTTTTCTGTGCTCAGAGTGTGTTTATTTTATGTAATTTAATTTCTTTGTGAGCTCCTGTTTAGCAGGTC
GTCCCTTCAGCAAGGACACAAAAAGATTTTAATTTTATTAAAAAAAAAAAAAAAAAAGACCGGGAATTC
GATATCAAGCTTATCGACCTGCAGATCGTTCAAACATTTGGCAATAAAGTTTCTTAAGATTGAATCCTGTT
GCCGGTCTTGCGATGATTATCATATAATTTCTGTTGAATTACGTTAAGCATGTAATAATTAACATGTAATG
CATGACGTTATTTATGAGATGGGTTTTTATGATTAGAGTCCCGCAATTATACATTTAATACGCGATAGAAA
ACAAAATATAGCGCGCAAACTAGGATAAATTATCGCGCGCGGTGTCATCTATGTTACTAGATCTCTAGAG
TCTCAAGCTTGGCGCGGGGTACCGAGCTCGAATTCCGAGTGTACTTCAAGTCAGTTGGAAATCAATAAAA
TGATTATTTTATGAATATATTTCATTGTGCAAGTAGATAGAAATTACATATGTTACATAACACACGAAATA
AACAAAAAAACACAATCCAAAACAAACACCCCAAACAAAATAACACTATATATATCCTCGTATGAGGAG
AGGCACGTTCAGTGACTCGACGATTCCCGAGCAAAAAAGTCTCCCCGTCACACATATAGTGGGTGACG
CAATTATCTTCAAAGTAATCCTTCTGTTGACTTGTCATTGATAACATCCAGTCTTCGTCAGGATTGCAAAG
AATTATAGAAGGGATCCCACCTTTTATTTTCTTCTTTTTTCCATATTTAGGGTTGACAGTGAAATCAGACT
GGCAACCTATTAATTGCTTCCACAATGGGACGAACTTGAAGGGGATGTCGTCGATGATATTATAGGTGGC
GTGTTCATCGTAGTTGGTGAAGTCGATGGTCCCGTTCCAGTAGTTGTGTCGCCCGAGACTTCTAGCCCAGG
TGGTCTTTCCGGTACGAGTTGGTCCGCAGATGTAGAGGCTGGGGTGTCTGACCCCAGTCCTTCCCTCATCC
TGGTTAGATCGGCCATCCACTCAAGGTCAGATTGTGCTTGATCGTAGGAGACAGGATGTATGAAAGTGTA
GGCATCGATGCTTACATGATATAGGTGCGTCTCTCCAGTTGTGCAGATCTTCGTGGCAGCGGAGATCT
GATTCTGTGAAGGGCGACACGTACTGCTCAGGTTGTGGAGGAAATAATTTGTTGGCTGAATATTCCAGCC
ATTGAAGCTTTGTTGCCCATTCATGAGGGAATTCTTCTTTGATCATGTCAAGATACTCCTCCTTAGACGTT
GCAGTCTGGATAATAGTTCGCCATCGTGCGTCAGATTTGCGAGGAGAGACCTTATGATCTCGGAAATCTC
CTCTGGTTTTAATATCTCCGTCCTTTGATATGTAATCAAGGACTTGTTTAGAGTTTCTAGCTGGCTGGATAT
TAGGGTGATTTCCTTCAAAATCGAAAAAGAAGGATCCCTAATACAAGGTTTTTATCAAGCTGGATAAG
AGCATGATAGTGGGTAGTGCCATCTTGATGAAGCTCAGAAGCAACACCAAGGAAGAAAATAAGAAAAG
GTGTGAGTTTCTCCCAGAGAAACTGGAATAAATCATCTCTTTGAGATGAGCACTTGGGGTAGGTAAGGAA
AACATATTTAGATTGGAGTCTGAAGTTCTTGCTAGCAGAAGGCATGTTGTTGTGACTCCGAGGGGTTGCC
TCAAACTCTATCTTATAACCGGCGTGGAGGCATGGAGGCAAGGGCATTTTGGTAATTTAAGTAGTTAGTG
GAAAATGACGTCATTTACTTAAAGACGAAGTCTTGCGACAAGGGGGGCCCACGCCGAATTTTAATATTAC
CGGCGTGGCCCCACCTTATCGCGAGTGCTTTAGCACGAGCGGTCCAGATTTAAAGTAGAAAAGTTCCCGC
CCACTAGGGTTAAAGGTGTTCACACTATAAAAGCATATACGATGTGATGGTATTTGATGGAGCGTATATT
GTATCAGGTATTTCCGTCGGATACGAATTATTCGTAC
```

Figure 8D

Amino acid sequence of PDISP/HA from influenza B/Brisbane/60/2008 with deleted proteolytic loop (SEQ ID NO: 41)

MAKNVAIFGLLFSLLVLVPSQIFADRICTGITSSNSPHVVKTATQGEVNVTGVIPLTTTPTK
SHFANLKGTETRGKLCPKCLNCTDLDVALGRPKCTGKIPSARVSILHEVRPVTSGCFPIM
HDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSA
NGVTTHYVSQIGGFPNQTEDGGLPQSGRIVVDYMVQKSGKTGTITYQRGILLPQKVWCA
SGRSKVIKGSLPLIGEADCLHEKYGGLNKSKPYYTGEHAKAIGNCPIWVKTPLKLANGTK
YRPPGGGWEGMIAGWHGYTSHGAHGVAVAADLKSTQEAINKITKNLNSLSELEVKNLQ
RLSGAMDELHNEILELDEKVDDLRADTISSQIELAVLLSNEGIINSEDEHLLALERKLKKM
LGPSAVEIGNGCFETKHKCNQTCLDRIAAGTFDAGEFSLPTFDSLNITAASLNDDGLDNH
TILLYYSTAASSLAVTLMIAIFVVYMVSRDNVSCSICL

Figure 8E nucleotide sequence of PDISP/HA from influenza B/Brisbane/60/2008 with deleted proteolytic loop (SEQ ID NO: 43)

ATGGCGAAAAACGTTGCGATTTTCGGCTTATTGTTTTCTCTTCTTGTGTTGGTTCCTTCTCAGATCTTCGCC
GATCGAATCTGCACTGGAATAACATCGTCAAACTCACCACATGTCGTCAAAACTGCTACTCAAGGGGAGG
TCAATGTGACTGGTGTAATACCACTGACAACAACACCCACCAAATCTCATTTTGCAAATCTCAAAGGAAC
AGAAACCAGGGGGAAACTATGCCCAAAATGCCTCAACTGCACAGATCTGGACGTAGCCTTGGGCAGACC
AAAATGCACGGGGAAAATACCCTCGGCAAGAGTTTCAATACTCCATGAAGTCAGACCTGTTACATCTGGG
TGCTTTCCTATAATGCACGACAGAACAAAAATTAGACAGCTGCCTAACCTTCTCCGAGGATACGAACATA
TCAGGTTATCAACCCATAACGTTATCAATGCAGAAAATGCACCAGGAGGACCCTACAAAATTGGAACCTC
AGGGTCTTGCCCTAACATTACCAATGGAAACGGATTTTTCGCAACAATGGCTTGGGCCGTCCCAAAAAAC
GACAAAAACAAAACAGCAACAAATCCATTAACAATAGAAGTACCATACATTTGTACAGAAGGAGAAGAC
CAAATTACCGTTTGGGGGTTCCACTCTGACAACGAGACCCAAATGGCAAAGCTCTATGGGGACTCAAAGC
CCCAGAAGTTCACCTCATCTGCCAACGGAGTGACCACACATTACGTTTCACAGATTGGTGGCTTCCCAAA
TCAAACAGAAGACGGAGGACTACCACAAAGTGGTAGAATTGTTGTTGATTACATGGTGCAAAAATCTGG
GAAAACAGGAACAATTACCTATCAAAGGGGTATTTTATTGCCTCAAAAGGTGTGGTGCGCAAGTGGCAG
GAGCAAGGTAATAAAAGGATCCTTGCCTTTAATTGGAGAAGCAGATTGCCTCCACGAAAAATACGGTGG
ATTAAACAAAGCAAGCCTTACTACACAGGGGAACATGCAAAGGCCATAGGAAATTGCCCAATATGGGT
GAAAACACCCTTGAAGCTGGCCAATGGAACCAAATATAGACCTCCTGGTGGAGGATGGGAAGGAATGAT
TGCAGGTTGGCACGGATACACATCCATGGGGCACATGGAGTAGCGGTGGCAGCAGACCTTAAGAGCAC
TCAAGAGGCCATAAACAAGATAACAAAAAATCTCAACTCTTTGAGTGAGCTGGAAGTAAAGAATCTTCA
AAGACTAAGCGGTGCCATGGATGAACTCCACAACGAAATACTAGAACTAGATGAGAAAGTGGATGATCT
CAGAGCTGATACAATAAGCTCACAAATAGAACTCGCAGTCCTGCTTTCCAATGAAGGAATAATAAACAG
TGAAGATGAACATCTCTTGGCGCTTGAAAGAAAGCTGAAGAAAATGCTGGGCCCCTCTGCTGTAGAGAT
AGGGAATGGATGCTTTGAAACCAAACACAAGTGCAACCAGACCTGTCTCGACAGAATAGCTGCTGGTAC
CTTTGATGCAGGAGAATTTTCTCTCCCCACCTTTGATTCACTGAATATTACTGCTGCATCTTTAAATGACG
ATGGATTGGATAATCATACTATACTGCTTTACTACTCAACTGCTGCCTCCAGTTTGGCTGTAACACTGATG
ATAGCTATCTTTGTTGTTTATATGGTCTCCAGAGACAATGTTTCTTGCTCCATCTGTCTATAA

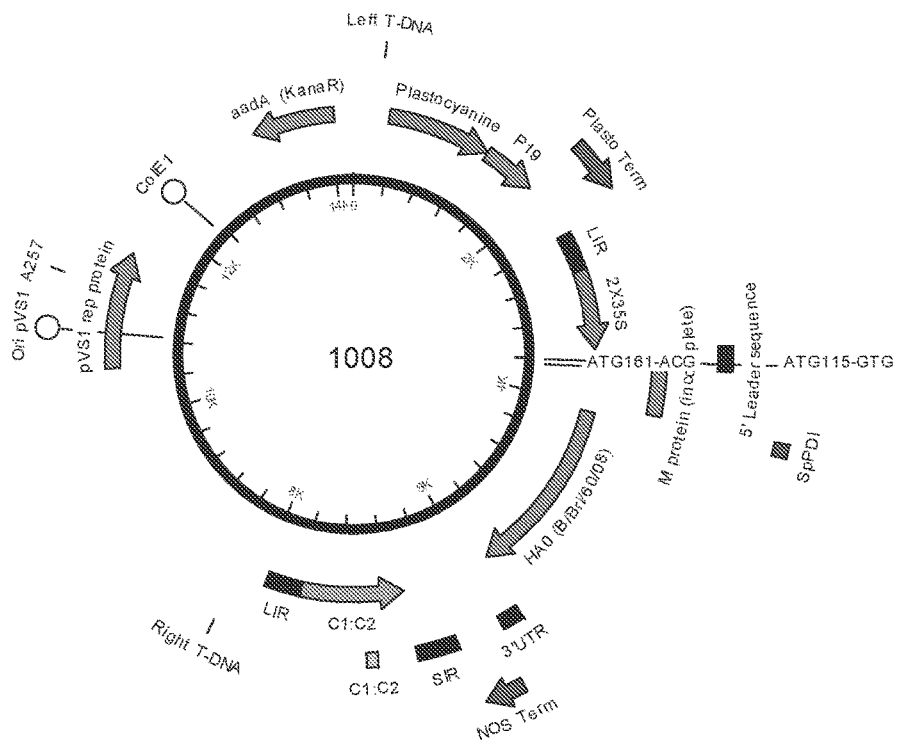
Figure 9
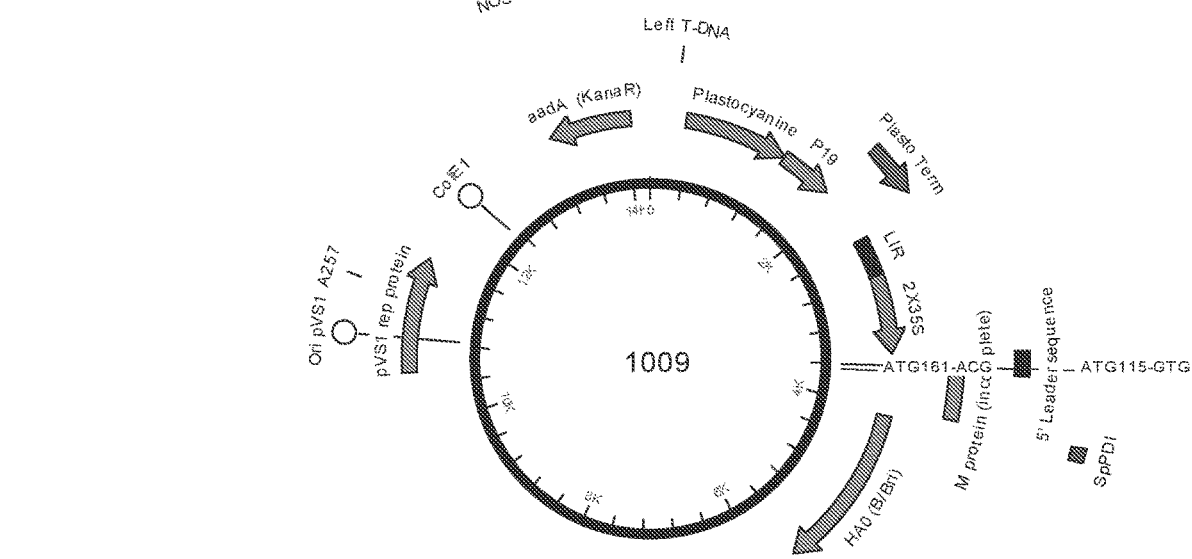
Figure 10
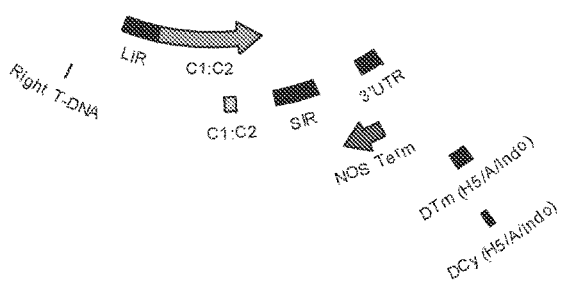

| Construct number | Hemagglutination capacity (HA units / mg protein)[a] |
|---|---|
| 1008 | 533 |
| 1008 + 1261 (4:1) | 3200 |
| 1059 | 4267 |
| 1059 + 1261 (4:1) | 34133 |

[a] Inverse of the smallest amount of total protein required for positive hemagglutination reaction in a final volume of 200 µl.

Figure 24

A-2X35S/CPMV-HT/PDISP/H3 Victoria/NOS (Construct number 1391)

Figure 25A, SEQ ID NO: 44

IF-H3V36111.S2+4c

TCTCAGATCTTCGCCCAAAAACTTCCTGGAAATGACAACAGCACGGCA

Figure 25B, SEQ ID NO: 45

IF-H3V36111.s1-4r

ACTAAAGAAAATAGGCCTTCAAATGCAAATGTTGCACCTAATGTTGCCCTT

Figure 25C, SEQ ID NO: 46

Synthesized H3 gene (corresponding to nt 25 to 1725 from GISAID isolate number EPI_ISL_101506 HA sequence)

ATGAAGACTATCATTGCTTTGAGCCACATTCTATGTCTGGTTTTCGCTCAAAAACTTCCTGGAAATGACAA
CAGCACGGCAACGCTGTGCCTTGGGCACCATGCAGTACCAAACGGAACGATAGTGAAAACAATCACGAA
TGACCAAATTGAAGTTACTAATGCTACTGAGCTGGTTCAGAATTCCTCAATAGGTGAAATATGCGACAGT
CCTCATCAGATCCTTGATGGAGAAAACTGCACACTAATAGATGCTCTATTGGGAGACCCTCAGTGTGATG
GCTTCCAAAATAAGAAATGGGACCTTTTTGTTGAACGAAGCAAAGCCTACAGCAACTGTTACCCTTATGA
TGTGCCGGATTATGCCTCCCTTAGGTCACTAGTTGCCTCATCCGGCACACTGGAGTTTAACAATGAAAGCT
TCAATTGGACTGGAGTCACTCAAAACGGAACAAGTTCTGCTTGCATAAGGAGATCTAATAATAGTTTCTT
TAGTAGATTAAATTGGTTGACCCACTTAAACTTCAAATACCCAGCATTGAACGTGACTATGCCAAACAAT
GAACAATTTGACAAATTGTACATTTGGGGGGTTCACCACCCGGGTACGGACAAGGACCAAATCTTCCTGT
ATGCTCAATCATCAGGAAGAATCACAGTATCTACCAAAAGAAGCCAACAAGCTGTAATCCCGAATATCG
GATCTAGACCCAGAATAAGGAATATCCCTAGCAGAATAAGCATCTATTGGACAATAGTAAAACCGGGAG
ACATACTTTTGATTAACAGCACAGGGAATCTAATTGCTCCTAGGGGTTACTTCAAAATACGAAGTGGGAA
AAGCTCAATAATGAGATCAGATGCACCCATTGGCAAATGCAATTCTGAATGCATCACTCCAAATGGAAGC
ATTCCCAATGACAAACCATTCCAAAATGTAAACAGGATCACATACGGGGCCTGTCCCAGATATGTTAAGC
AAAGCACTCTGAAATTGGCAACAGGAATGCGAAATGTACCAGAGAAACAAACTAGAGGCATATTTGGCG
CAATAGCGGGTTTCATAGAAATGGTTGGGAGGGAATGGTGGATGGTTGGTACGGTTTCAGGCATCAAA
ATTCTGAGGGAAGAGGACAAGCAGCAGATCTCAAAAGCACTCAAGCAGCAATCGATCAAATCAATGGGA
AGCTGAATCGATTGATCGGGAAAACCAACGAGAAATTCCATCAGATTGAAAAAGAATTCTCAGAAGTCG
AAGGGAGAATTCAGGACCTTGAGAAATATGTTGAGGACACTAAAATAGATCTCTGGTCATACAACGCGG
AGCTTCTTGTTGCCCTGGAGAACCAACATACAATTGATCTAACTGACTCAGAAATGAACAAACTGTTTGA
AAAAACAAAGAAGCAACTAAGGGAAAATGCTGAGGATATGGGCAATGGTTGTTTCAAAATATACCACAA
ATGTGACAATGCCTGCATAGGATCAATCAGAAATGGAACTTATGACCACGATGTATACAGAGATGAAGC
ATTAAACAACCGGTTCCAGATCAAGGGAGTTGAGCTGAAGTCAGGGTACAAAGATTGGATCCTATGGAT
TTCCTTTGCCATATCATGTTTTTTGCTTTGTGTTGCTTTGTTGGGGTTCATCATGTGGGCCTGCCAAAAGGG
CAACATTAGGTGCAACATTTGCATTTGA

Figure 25D, SEQ ID NO: 47

Expression cassette number 1391 from 2X35S promoter to NOS terminator. PDISP/H3 from influenza A/Victoria/361/2011 (H3N2) is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTTGGTTCCTTCTCAGATCTTCG
CCCAAAAACTTCCTGGAAATGACAACAGCACGGCAACGCTGTGCCTTGGGCACCATGCAGTACCAAACG
GAACGATAGTGAAAACAATCACGAATGACCAAATTGAAGTTACTAATGCTACTGAGCTGGTTCAGAATTC
CTCAATAGGTGAAATATGCGACAGTCCTCATCAGATCCTTGATGGAGAAAACTGCACACTAATAGATGCT
CTATTGGGAGACCCTCAGTGTGATGGCTTCCAAAATAAGAAATGGGACCTTTTTGTTGAACGAAGCAAAG
CCTACAGCAACTGTTACCCTTATGATGTGCCGGATTATGCCTCCCTTAGGTCACTAGTTGCCTCATCCGGC
ACACTGGAGTTTAACAATGAAAGCTTCAATTGGACTGGAGTCACTCAAAACGGAACAAGTTCTGCTTGCA
TAAGGAGATCTAATAATAGTTTCTTTAGTAGATTAAATTGGTTGACCCACTTAAACTTCAAATACCCAGC
ATTGAACGTGACTATGCCAAACAATGAACAATTTGACAAATTGTACATTTGGGGGGTTCACCACCCGGGT
ACGGACAAGGACCAAATCTTCCTGTATGCTCAATCATCAGGAAGAATCACAGTATCTACCAAAAGAAGC
CAACAAGCTGTAATCCCGAATATCGGATCTAGACCCAGAATAAGGAATATCCCTAGCAGAATAAGCATC
TATTGGACAATAGTAAAACCGGGAGACATACTTTTGATTAACAGCACAGGGAATCTAATTGCTCCTAGGG
GTTACTTCAAAATACGAAGTGGGAAAAGCTCAATAATGAGATCAGATGCACCCATTGGCAAATGCAATT
CTGAATGCATCACTCCAAATGGAAGCATTCCCAATGACAAACCATTCCAAAATGTAAACAGGATCACATA
CGGGGCCTGTCCCAGATATGTTAAGCAAAGCACTCTGAAATTGGCAACAGGAATGCGAAATGTACCAGA
GAAACAAACTAGAGGCATATTTGGCGCAATAGCGGGTTTCATAGAAAATGGTTGGGAGGGAATGGTGGA
TGGTTGGTACGGTTTCAGGCATCAAAATTCTGAGGGAAGAGGACAAGCAGCAGATCTCAAAAGCACTCA
AGCAGCAATCGATCAAATCAATGGGAAGCTGAATCGATTGATCGGGAAAACCAACGAGAAATTCCATCA
GATTGAAAAGAATTCTCAGAAGTCGAAGGGAGAATTCAGGACCTTGAGAAATATGTTGAGGACACTAA
AATAGATCTCTGGTCATACAACGCGGAGCTTCTTGTTGCCCTGGAGAACCAACATACAATTGATCTAACT
GACTCAGAAATGAACAAACTGTTTGAAAAAACAAAGAAGCAACTAAGGGAAAATGCTGAGGATATGGG
CAATGGTTGTTTCAAAATATACCACAAATGTGACAATGCCTGCATAGGATCAATCAGAAATGGAACTTAT
GACCACGATGTATACAGAGATGAAGCATTAAACAACCGGTTCCAGATCAAGGGAGTTGAGCTGAAGTCA
GGGTACAAAGATTGGATCCTATGGATTTCCTTTGCCATATCATGTTTTTTGCTTTGTGTTGCTTTGTTGGGG
TTCATCATGTGGGCCTGCCAAAAGGGCAACATTAGGTGCAACATTTGCATTTGAAGGCCTATTTTCTTTAG
TTTGAATTTACTGTTATTCGGTGTGCATTTCTATGTTGGTGAGCGGTTTTCTGTGCTCAGAGTGTGTTTAT
TTTATGTAATTTAATTTCTTTGTGAGCTCCTGTTTAGCAGGTCGTCCCTTCAGCAAGGACACAAAAAGATT
TTAATTTTATTAAAAAAAAAAAAAAAAAGACCGGAATTCGATATCAAGCTTATCGACCTGCAGATCGT
TCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTA

Figure 25D continued

TGATTAGAGTCCCGCAATTATACATTTAATACGCGATAGAAAACAAAATATAGCGCGCAAACTAGGATA
AATTATCGCGCGCGGTGTCATCTATGTTACTAGAT

Figure 25E, SEQ ID NO: 48

Amino acid sequence of PDISP-H3 from influenza A/ Victoria/361/2011 (H3N2)

MAKNVAIFGLLFSLLVLVPSQIFAQKLPGNDNSTATLCLGHHAVPNGTIVKTITNDQIEVT
NATELVQNSSIGEICDSPHQILDGENCTLIDALLGDPQCDGFQNKKWDLFVERSKAYSNC
YPYDVPDYASLRSLVASSGTLEFNNESFNWTGVTQNGTSSACIRRSNNSFFSRLNWLTHL
NFKYPALNVTMPNNEQFDKLYIWGVHHPGTDKDQIFLYAQSSGRITVSTKRSQQAVIPNI
GSRPRIRNIPSRISIYWTIVKPGDILLINSTGNLIAPRGYFKIRSGKSSIMRSDAPIGKCNSECI
TPNGSIPNDKPFQNVNRITYGACPRYVKQSTLKLATGMRNVPEKQTRGIFGAIAGFIENG
WEGMVDGWYGFRHQNSEGRGQAADLKSTQAAIDQINGKLNRLIGKTNEKFHQIEKEFS
EVEGRIQDLEKYVEDTKIDLWSYNAELLVALENQHTIDLTDSEMNKLFEKTKKQLRENA
EDMGNGCFKIYHKCDNACIGSIRNGTYDHDVYRDEALNNRFQIKGVELKSGYKDWILWI
SFAISCFLLCVALLGFIMWACQKGNIRCNICI*

Figure 25F

Schematic representation of construct number 1391

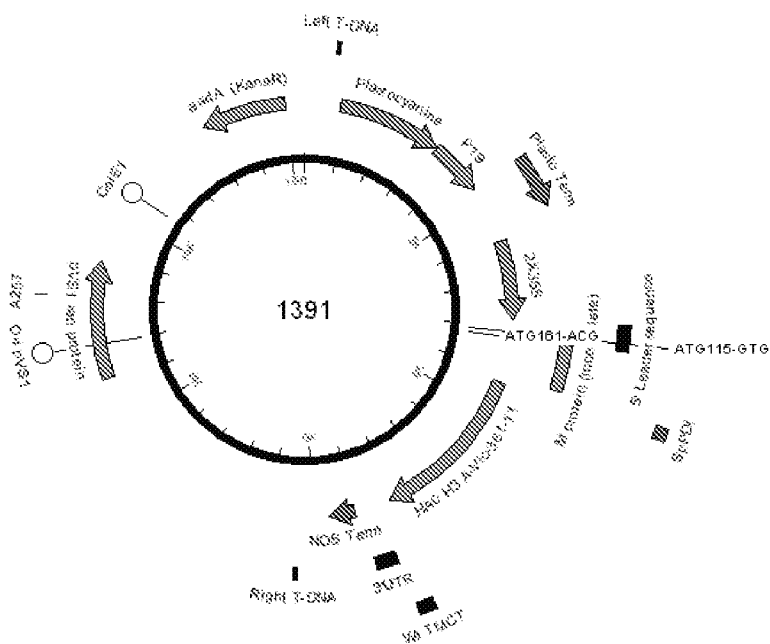

B-2X35S/CPMV-HT/HA B Wisconsin/NOS into BeYDV(m)+Replicase amplification system (Construct number 1462)

Figure 26A, SEQ ID NO: 49

IF-HAB110.S1+3c

AAATTTGTCGGGCCCATGAAGGCAATAATTGTACTACTCATGGTAG

Figure 26B, SEQ ID NO: 50

IF-HAB110.s1-4r

ACTAAAGAAAATAGGCCTTTATAGACAGATGGAGCATGAAACGTTGTCTCTG

Figure 26C, SEQ ID NO: 51

Synthesized HA B Wisconsin (Genbank accession number JN993010)

ATGAAGGCAATAATTGTACTACTCATGGTAGTAACATCCAATGCAGATCGAATCTGCACTGGGATAACAT
CTTCAAACTCACCTCATGTGGTCAAAACAGCTACTCAAGGGGAGGTCAATGTGACTGGCGTGATACCACT
GACAACAACACCAACAAAATCTTATTTTGCAAATCTCAAAGGAACAAGGACCAGAGGGAAACTATGCCC
GGACTGTCTCAACTGTACAGATCTGGATGTGGCCTTGGGCAGGCCAATGTGTGTGGGGACCACACCTTCT
GCTAAAGCTTCAATACTCCACGAGGTCAGACCTGTTACATCCGGGTGCTTTCCTATAATGCACGACAGAA
CAAAAATCAGGCAACTACCCAATCTTCTCAGAGGATATGAAAATATCAGGTTATCAACCCAAAACGTTAT
CGATGCAGAAAAAGCACCAGGAGGACCCTACAGACTTGGAACCTCAGGATCTTGCCCTAACGCTACCAG
TAAAATCGGATTTTTTGCAACAATGGCTTGGGCTGTCCCAAAGGACAACTACAAAAATGCAACGAACCCA
CTAACAGTAGAAGTACCATACATTTGTACAGAAGGGGAAGACCAAATTACTGTTTGGGGGTTCCATTCAG
ATAACAAAACCCAAATGAAGAGCCTCTATGGAGACTCAAATCCTCAAAAGTTCACCTCATCTGCTAATGG
AGTAACCACACATTATGTTTCTCAGATTGGCGACTTCCCAGATCAAACAGAAGACGGAGGACTACCACAA
AGCGGCAGAATTGTTGTTGATTACATGATGCAAAAACCTGGGAAAACAGGAACAATTGTCTATCAAAGA
GGTGTTTTGTTGCCTCAAAAGGTGTGGTGCGCGAGTGGCAGGAGCAAAGTAATAAAAGGGTCATTGCCTT
TAATTGGTGAAGCAGATTGCCTTCATGAAAAATACGGTGGATTAAACAAAAGCAAGCCTTACTACACAG
GAGAACATGCAAAAGCCATAGGAAATTGCCCAATATGGGTAAAAACACCTTTGAAGCTTGCCAATGGAA
CCAAATATAGACCTCCTGCAAAACTATTGAAGGAAAGGGGTTTCTTCGGAGCTATTGCTGGTTTCCTAGA
AGGAGGATGGGAAGGAATGATTGCAGGTTGGCACGGATACACATCTCACGGAGCACATGGAGTGGCAGT
GGCGGCAGACCTTAAGAGTACACAAGAAGCTATAAATAAGATAACAAAAAATCTCAATTCTTTGAGTGA
GCTAGAAGTAAAGAACCTTCAAAGACTAAGTGGTGCCATGGATGAACTCCACAACGAAATACTCGAGCT
GGATGAGAAAGTGGATGATCTCAGAGCTGACACTATAAGCTCACAAATAGAACTTGCAGTCTTGCTTTCC
AACGAAGGAATAATAAACAGTGAAGACGAGCATCTATTGGCACTTGAGAGAAAACTAAAGAAAATGCTG
GGTCCCTCTGCTGTAGACATAGGAAACGGATGCTTCGAAACCAAACACAAATGCAACCAGACCTGCTTA
GACAGGATAGCTGCTGGCACCTTTAATGCAGGAGAATTTTCTCTCCCCACTTTTGATTCATTGAACATTAC
TGCTGCATCTTTAAATGATGATGGATTGGATAACCATACTATACTGCTCTATTACTCAACTGCTGCTTCTA
GTTGGCTGTAACATTAATGCTAGCTATTTTATTGTTTATATGGTCTCCAGAGACAACGTTTCATGCTCC
ATCTGTCTATAA

Figure 26D

Schematic representation of construct 193. SacII and StuI restriction enzyme sites used for plasmid linearization are annotated on the representation.

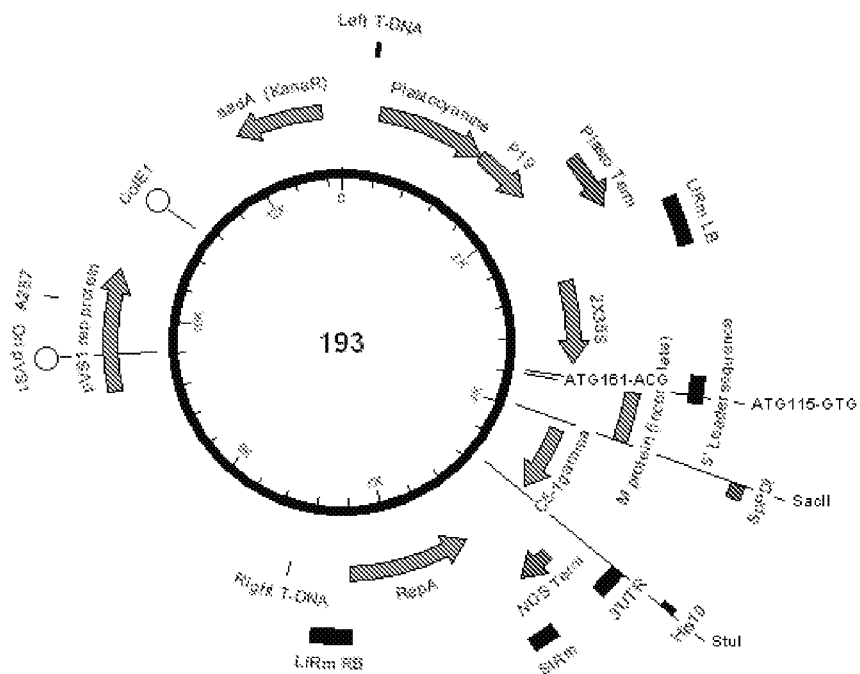

Figure 26E, SEQ ID NO: 52

Construct 193 from left to right t-DNA borders (underlined). 2X35S/CPMV-HT/NOS into BeYDV(m)+Replicase amplification system with Plastocyanine-P19-Plastocyanine silencing inhibitor expression cassette <u>TGGCAGGATATATTGTGGTGTAAACA</u>AATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC

Figure 26E continued

AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGAGACGCGTTGTTGTTGTGACTCCGAGGGGTTGCCTCAAACTCTATCTT
ATAACCGGCGTGGAGGCATGGAGGCAGGGGTATTTGGTCATTTAATAGATAGTGGAAAATGACGTGG
AATTTACTTAAAGACGAAGTCTTTGCGACAAGGGGGGGCCCACGCCGAATTTAATATTACCGGCGTGGCC
CCCCCTTATCGCGAGTGCTTTAGCACGAGCGGTCCAGATTTAAAGTAGAAAATTTCCCGCCCACTAGGGT
TAAAGGTGTTCACACTATAAAAGCATATACGATGTGATGGTATTTGGTCGACAAGCTTGCATGCCGGTCA
ACATGGTGGAGCACGACACACTTGTCTACTCCAAAAATATCAAAGATACAGTCTCAGAAGACCAAAGGG
CAATTGAGACTTTTCAACAAAGGGTAATATCCGGAAACCTCCTCGGATTCCATTGCCCAGCTATCTGTCA
CTTTATTGTGAAGATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAGGAGCATCGTGGA
AAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAA
AGGGTAATATCCGGAAACCTCCTCGGATTCCATTGCCCAGCTATCTGTCACTTTATTGTGAAGATAGTGG
AAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCA
CGTCTTCAAAGCAAGTGGATTGATGTGATATCTCCACTGACGTAAGGGATGACGCACAATCCCACTATCC
TTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCAGTACAACG
TTTTCTTTCACTGAAGCGAAATCAAAGATCTCTTTGTGGACACGTAGTGCGGCGCCATTAAATAACGTGT
ACTTGTCCTATTCTTGTCGGTGTGGTCTTGGGAAAAGAAAGCTTGCTGGAGGCTGCTGTTCAGCCCCATAC
ATTACTTGTTACGATTCTGCTGACTTTCGGCGGGTGCAATATCTCTACTTCTGCTTGACGAGGTATTGTTG
CCTGTACTTCTTTCTTCTTCTTGCTGATTGGTTCTATAAGAAATCTAGTATTTTCTTTGAAACAGAGTT
TTCCCGTGGTTTTCGAACTTGGAGAAAGATTGTTAAGCTTCTGTATATTCTGCCCAAATTTGTCGGGCCCG
CGGATGGCGAAAAACGTTGCGATTTTCGGCTTATTGTTTTCTCTTCTTGTTGGTTCCTTCTCAGATCTTC
GCCTGCAGGCTCCTCAGCCAAAACGACACCCCCATCTGTCTATCCACTGGCCCCTGGATCTGCTGCCCAA
ACTAACTCCATGGTGACCCTGGGATGCCTGGTCAAGGGCTATTTCCCTGAGCCAGTGACAGTGACCTGGA
ACTCTGGATCCCTGTCCAGCGGTGTGCACACCTTCCCAGCTGTCCTGCAGTCTGACCTCTACACTCTGAGC
AGCTCAGTGACTGTCCCCTCCAGCACCTGGCCCAGCGAGACCGTCACCTGCAACGTTGCCCACCCGGCCA
GCAGCACCAAGGTGGACAAGAAAATTGTGCCCAGGGATTGTGGTTGTAAGCCTTGCATATGTACAGTCCC
AGAAGTATCATCTGTCTTCATCTTCCCCCCAAAGCCCAAGGATGTGCTCACCATTACTCTGACTCCTAAGG
TCACGTGTGTTGTGGTAGACATCAGCAAGGATGATCCCGAGGTCCAGTTCAGCTGGTTTGTAGATGATGT
GGAGGTGCACACAGCTCAGACGCAACCCCGGGAGGAGCAGTTCAACAGCACTTTCCGCTCAGTCAGTGA
ACTTCCCATCATGCACCAGGACTGGCTCAATGGCAAGGAGCGATCGCTCACCATCACCATCACCATCACC
ATCACCATTAAAGGCCTATTTTCTTTAGTTTGAATTTACTGTTATTCGGTGTGCATTTCTATGTTTGGTGAG
CGGTTTTCTGTGCTCAGAGTGTGTTTATTTTATGTAATTTAATTTCTTTGTGAGCTCCTGTTTAGCAGGTCG
TCCCTTCAGCAAGGACACAAAAAGATTTTAATTTTATTAAAAAAAAAAAAAAAAAAGACCGGGAATTCG
ATATCAAGCTTATCGACCTGCAGATCGTTCAAACATTTGGCAATAAAGTTTCTTAAGATTGAATCCTGTTG
CCGGTCTTGCGATGATTATCATATAATTTCTGTTGAATTACGTTAAGCATGTAATAATTAACATGTAATGC
ATGACGTTATTTATGAGATGGGTTTTTATGATTAGAGTCCCGCAATTATACATTTAATACGCGATAGAAA
ACAAAATATAGCGCGCAAACTAGGATAAATTATCGCGCGCGGTGTCATCTATGTTACTAGATCTCTAGAG

Figure 26E continued

TCTCAAGCTTGGCGCGCCATAAAATGATTATTTTATGAATATATTTCATTGTGCAAGTAGATAGAAATTAC
ATATGTTACATAACACACGAAATAAACAAAAAAGACAATCCAAAAACAAACACCCCAAAAAAAATAA
TCACTTTAGATAAACTCGTATGAGGAGAGGCACGTTCAGTGACTCGACGATTCCCGAGCAAAAAAAGTCT
CCCCGTCACACATATAGTGGGTGACGCAATTATCTTTAAAGTAATCCTTCTGTTGACTTGTCATTGATAAC
ATCCAGTCTTCGTCAGGATTGCAAAGAATTATAGAAGGGATCCCACCTTTTATTTTCTTCTTTTTTCCATAT
TTAGGGTTGACAGTGAAATCAGACTGGCAACCTATTAATTGCTTCCACAATGGGACGAACTTGAAGGGGA
TGTCGTCGATGATATTATAGGTGGCGTGTTCATCGTAGTTGGTGAAATCGATGGTACCGTTCCAATAGTTG
TGTCGTCCGAGACTTCTAGCCCAGGTGGTCTTTCCGGTACGAGTTGGTCCGCAGATGTAGAGGCTGGGGT
GTCGGATTCCATTCCTTCCATTGTCCTGGTTAAATCGGCCATCCATTCAAGGTCAGATTGAGCTTGTTGGT
ATGAGACAGGATGTATGTAAGTATAAGCGTCTATGCTTACATGGTATAGATGGGTTTCCCTCCAGGAGTG
TAGATCTTCGTGGCAGCGAAGATCTGATTCTGTGAAGGGCGACACATACGGTTCAGGTTGTGGAGGGAAT
AATTTGTTGGCTGAATATTCCAGCCATTGAAGTTTTGTTGCCCATTCATGAGGGAATTCTTCCTTGATCAT
GTCAAGATATTCCTCCTTAGACGTTGCAGTCTGGATAATAGTTCTCCATCGTGCGTCAGATTTGCGAGGAG
AGACCTTATGATCTCGGAAATCTCCTCTGGTTTTAATATCTCCGTCCTTTGATATGTAATCAAGGACTTGT
TTAGAGTTTCTAGCTGGCTGGATATTAGGGTGATTTCCTTCAAAATCGAAAAAAGAAGGATCCCTAATAC
AAGGTTTTTTATCAAGCTGGAGAAGAGCATGATAGTGGGTAGTGCCATCTTGATGAAGCTCAGAAGCAAC
ACCAAGGAAGAAAATAAGAAAAGGTGTGAGTTTCTCCCAGAGAAACTGGAATAAATCATCTCTTTGAGA
TGAGCACTTGGGATAGGTAAGGAAAACATATTTAGATTGGAGTCTGAAGTTCTTACTAGCAGAAGGCATG
TTGTTGTGACTCCGAGGGGTTGCCTCAAACTCTATCTTATAACCGGCGTGGAGGCATGGAGGCAGGGGTA
TTTTGGTCATTTTAATAGATAGTGGAAAATGACGTGGAATTTACTTAAAGACGAAGTCTTTGCGACAAGG
GGGGGCCCACGCCGAATTTAATATTACCGGCGTGGCCCCCCCTTATCGCGAGTGCTTTAGCACGAGCGGT
CCAGATTTAAAGTAGAAAATTTCCCGCCCACTAGGGTTAAAGGTGTTCACACTATAAAAGCATATACGAT
GTGATGGTATTTGACTAGTGGCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGAGGCCCGCACCGAT
CGCCCTTCCCAACAGTTGCGCAGCCTGAATGGCGAATGCTAGAGCAGCTTGAGCTTGGATCAGATTGTCG
TTTCCCGCCTTCAGTTTAAACTATCAGTGTTTGACAGGATATATTGGCGG<u>GTAAACCTAAGAGAAAAGAG
CGTTTA</u>

Figure 26F, SEQ ID NO: 53

Expression cassette number 1462 from 2X35S promoter to NOS terminator. HA from influenza B/Wisconsin/1/2010 is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAAGGCAATAATTGTACTACTCATGGTAGTAACATCCAATGCAGATCGAATCTGCACTGGGATAAC

Figure 26F continued

ATCTTCAAACTCACCTCATGTGGTCAAAACAGCTACTCAAGGGGAGGTCAATGTGACTGGCGTGATACCA
CTGACAACAACACCAACAAAATCTTATTTTGCAAATCTCAAAGGAACAAGGACCAGAGGGAAACTATGC
CCGGACTGTCTCAACTGTACAGATCTGGATGTGGCCTTGGGCAGGCCAATGTGTGTGGGGACCACACCTT
CTGCTAAAGCTTCAATACTCCACGAGGTCAGACCTGTTACATCCGGGTGCTTTCCTATAATGCACGACAG
AACAAAAATCAGGCAACTACCCAATCTTCTCAGAGGATATGAAAATATCAGGTTATCAACCCAAAACGTT
ATCGATGCAGAAAAAGCACCAGGAGGACCCTACAGACTTGGAACCTCAGGATCTTGCCCTAACGCTACC
AGTAAAATCGGATTTTTTGCAACAATGGCTTGGGCTGTCCCAAAGGACAACTACAAAAATGCAACGAAC
CCACTAACAGTAGAAGTACCATACATTTGTACAGAAGGGGAAGACCAAATTACTGTTTGGGGGTTCCATT
CAGATAACAAAACCCAAATGAAGAGCCTCTATGGAGACTCAAATCCTCAAAAGTTCACCTCATCTGCTAA
TGGAGTAACCACACATTATGTTTCTCAGATTGGCGACTTCCCAGATCAAACAGAAGACGGAGGACTACCA
CAAAGCGGCAGAATTGTTGTTGATTACATGATGCAAAAACCTGGGAAAACAGGAACAATTGTCTATCAA
AGAGGTGTTTTGTTGCCTCAAAAGGTGTGGTGCGCGAGTGGCAGGAGCAAAGTAATAAAAGGGTCATTG
CCTTTAATTGGTGAAGCAGATTGCCTTCATGAAAATACGGTGGATTAAACAAAAGCAAGCCTTACTACA
CAGGAGAACATGCAAAAGCCATAGGAAATTGCCCAATATGGGTAAAAACACCTTTGAAGCTTGCCAATG
GAACCAAATATAGACCTCCTGCAAAACTATTGAAGGAAAGGGGTTTCTTCGGAGCTATTGCTGGTTTCCT
AGAAGGAGGATGGAAGGAATGATTGCAGGTTGGCACGGATACACATCTCACGGAGCACATGGAGTGGC
AGTGGCGGCAGACCTTAAGAGTACACAAGAAGCTATAAATAAGATAACAAAAAATCTCAATTCTTTGAG
TGAGCTAGAAGTAAAGAACCTTCAAAGACTAAGTGGTGCCATGGATGAACTCCACAACGAAATACTCGA
GCTGGATGAGAAAGTGGATGATCTCAGAGCTGACACTATAAGCTCACAAATAGAACTTGCAGTCTTGCTT
TCCAACGAAGGAATAATAAACAGTGAAGACGAGCATCTATTGGCACTTGAGAGAAAACTAAAGAAAATG
CTGGGTCCCTCTGCTGTAGACATAGGAAACGGATGCTTCGAAACCAAACACAAATGCAACCAGACCTGC
TTAGACAGGATAGCTGCTGGCACCTTTAATGCAGGAGAATTTTCTCTCCCCACTTTTGATTCATTGAACAT
TACTGCTGCATCTTTAAATGATGATGGATTGGATAACCATACTATACTGCTCTATTACTCAACTGCTGCTT
CTAGTTTGGCTGTAACATTAATGCTAGCTATTTTTATTGTTTATATGGTCTCCAGAGACAACGTTTCATGCT
CCATCTGTCTATAAAGGCCTATTTTCTTTAGTTTGAATTTACTGTTATTCGGTGTGCATTTCTATGTTTGGT
GAGCGGTTTTCTGTGCTCAGAGTGTGTTTATTTTATGTAATTTAATTTCTTTGTGAGCTCCTGTTTAGCAGG
TCGTCCCTTCAGCAAGGACACAAAAAGATTTTAATTTTATTAAAAAAAAAAAAAAAAAAAAAGACCGGGAAT
TCGATATCAAGCTTATCGACCTGCAGATCGTTCAAACATTTGGCAATAAAGTTTCTTAAGATTGAATCCTG
TTGCCGGTCTTGCGATGATTATCATATAATTTCTGTTGAATTACGTTAAGCATGTAATAATTAACATGTAA
TGCATGACGTTATTTATGAGATGGGTTTTTATGATTAGAGTCCCGCAATTATACATTTAATACGCGATAGA
AAACAAAATATAGCGCGCAAACTAGGATAAATTATCGCGCGCGGTGTCATCTATGTTACTAGAT

Figure 26G, SEQ ID NO: 54

Amino acid sequence of HA from influenza B/Wisconsin/1/2010

MKAIIVLLMVVTSNADRICTGITSSNSPHVVKTATQGEVNVTGVIPLTTTPTKSYFANLKGTRTRGKLCPDCLN
CTDLDVALGRPMCVGTTPSAKASILHEVRPVTSGCFPIMHDRTKIRQLPNLLRGYENIRLSTQNVIDAEKAPGG
PYRLGTSGSCPNATSKIGFFATMAWAVPKDNYKNATNPLTVEVPYICTEGEDQITVWGFHSDNKTQMKSLYG
DSNPQKFTSSANGVTTHYVSQIGDFPDQTEDGGLPQSGRIVVDYMMQKPGKTGTIVYQRGVLLPQKVWCASG
RSKVIKGSLPLIGEADCLHEKYGGLNKSKPYYTGEHAKAIGNCPIWVKTPLKLANGTKYRPPAKLLKERGFFG
AIAGFLEGGWEGMIAGWHGYTSHGAHGVAVAADLKSTQEAINKITKNLNSLSELEVKNLQRLSGAMDELHN
EILELDEKVDDLRADTISSQIELAVLLSNEGIINSEDEHLLALERKLKKMLGPSAVDIGNGCFETKHKCNQTCLD
RIAAGTFNAGEFSLPTFDSLNITAASLNDDGLDNHTILLYYSTAASSLAVTLMLAIFIVYMVSRDNVSCSICL*

Figure 26H
Schematic representation of construct number 1462

C-2X35S/CPMV-HT/HA B Wisconsin with deleted proteolytic loop/NOS into BeYDV(m)+Replicase amplification system (Construct number 1467)

Figure 27A, SEQ ID NO: 55

HAB110(PrL-).r

TCCTTCCCATCCTCCACCAGGAGGTCTATATTTGGTTCCATTGGCAAGCTTCAAAG

Figure 27B, SEQ ID NO: 56

HAB110(PrL-).c

ATATAGACCTCCTGGTGGAGGATGGGAAGGAATGATTGCAGGTTGGCACGGA

Figure 27C, SEQ ID NO: 57

Expression cassette number 1467 from 2X35S promoter to NOS terminator. HA from influenza B/Wisconsin/1/2010 with deleted proteolytic loop is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA

Figure 27C continued

AGGCCATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CCATGAAGGCAATAATTGTACTACTCATGGTAGTAACATCCAATGCAGATCGAATCTGCACTGGGATAAC
ATCTTCAAACTCACCTCATGTGGTCAAAACAGCTACTCAAGGGGAGGTCAATGTGACTGGCGTGATACCA
CTGACAACAACACCAACAAAATCTTATTTTGCAAATCTCAAAGGAACAAGGACCAGAGGGAAACTATGC
CCGGACTGTCTCAACTGTACAGATCTGGATGTGGCCTTGGGCAGGCCAATGTGTGTGGGGACCACACCTT
CTGCTAAAGCTTCAATACTCCACGAGGTCAGACCTGTTACATCCGGGTGCTTTCCTATAATGCACGACAG
AACAAAAATCAGGCAACTACCCAATCTTCTCAGAGGATATGAAAATATCAGGTTATCAACCCAAAACGTT
ATCGATGCAGAAAAAGCACCAGGAGGACCCTACAGACTTGGAACCTCAGGATCTTGCCCTAACGCTACC
AGTAAAATCGGATTTTTTGCAACAATGGCTTGGGCTGTCCCAAAGGACAACTACAAAAATGCAACGAAC
CCACTAACAGTAGAAGTACCATACATTTGTACAGAAGGGGAAGACCAAATTACTGTTTGGGGGTTCCATT
CAGATAACAAAACCCAAATGAAGAGCCTCTATGGAGACTCAAATCCTCAAAAGTTCACCTCATCTGCTAA
TGGAGTAACCACACATTATGTTTCTCAGATTGGCGACTTCCCAGATCAAACAGAAGACGGAGGACTACCA
CAAAGCGGCAGAATTGTTGTTGATTACATGATGCAAAAACCTGGGAAAACAGGAACAATTGTCTATCAA
AGAGGTGTTTTGTTGCCTCAAAAGGTGTGGTGCGCGAGTGGCAGGAGCAAAGTAATAAAAGGGTCATTG
CCTTTAATTGGTGAAGCAGATTGCCTTCATGAAAAATACGGTGGATTAAACAAAAGCAAGCCTTACTACA
CAGGAGAACATGCAAAAGCCATAGGAAATTGCCCAATATGGGTAAAAACACCTTTGAAGCTTGCCAATG
GAACCAAATATAGACCTCCTGGTGGAGGATGGGAAGGAATGATTGCAGGTTGGCACGGATACACATCTC
ACGGAGCACATGGAGTGGCAGTGGCGGCAGACCTTAAGAGTACACAAGAAGCTATAAATAAGATAACA
AAAAATCTCAATTCTTTGAGTGAGCTAGAAGTAAAGAACCTTCAAAGACTAAGTGGTGCCATGGATGAA
CTCCACAACGAAATACTCGAGCTGGATGAGAAAGTGGATGATCTCAGAGCTGACACTATAAGCTCACAA
ATAGAACTTGCAGTCTTGCTTTCCAACGAAGGAATAATAAACAGTGAAGACGAGCATCTATTGGCACTTG
AGAGAAAACTAAAGAAAATGCTGGGTCCCTCTGCTGTAGACATAGGAAACGGATGCTTCGAAACCAAAC
ACAAATGCAACCAGACCTGCTTAGACAGGATAGCTGCTGGCACCTTTAATGCAGGAGAATTTTCTCTCCC
CACTTTTGATTCATTGAACATTACTGCTGCATCTTTAAATGATGATGGATTGGATAACCATACTATACTGC
TCTATTACTCAACTGCTGCTTCTAGTTTGGCTGTAACATTAATGCTAGCTATTTTTATTGTTTATATGGTCT
CCAGAGACAACGTTTCATGCTCCATCTGTCTATAAAGGCCTATTTTCTTTAGTTTGAATTTACTGTTATTCG
GTGTGCATTTCTATGTTTGGTGAGCGGTTTTCTGTGCTCAGAGTGTGTTTATTTTATGTAATTTAATTTCTT
TGTGAGCTCCTGTTTAGCAGGTCGTCCCTTCAGCAAGGACACAAAAAGATTTTAATTTTATTAAAAAAAA
AAAAAAAAAAGACCGGGAATTCGATATCAAGCTTATCGACCTGCAGATCGTTCAAACATTTGGCAATAA
AGTTTCTTAAGATTGAATCCTGTTGCCGGTCTTGCGATGATTATCATATAATTTCTGTTGAATTACGTTAA
GCATGTAATAATTAACATGTAATGCATGACGTTATTTATGAGATGGGTTTTTATGATTAGAGTCCCGCAAT
TATACATTTAATACGCGATAGAAAACAAAATATAGCGCGCAAACTAGGATAAATTATCGCGCGCGGTGT
CATCTATGTTACTAGAT

Figure 27D, SEQ ID NO: 58

Amino acid sequence of HA from influenza B/Wisconsin/1/2010 with deleted proteolytic loop

Figure 27D continued

MKAIIVLLMVVTSNADRICTGITSSNSPHVVKTATQGEVNVTGVIPLTTTPTKSYFANLKG
TRTRGKLCPDCLNCTDLDVALGRPMCVGTTPSAKASILHEVRPVTSGCFPIMHDRTKIRQ
LPNLLRGYENIRLSTQNVIDAEKAPGGPYRLGTSGSCPNATSKIGFFATMAWAVPKDNY
KNATNPLTVEVPYICTEGEDQITVWGFHSDNKTQMKSLYGDSNPQKFTSSANGVTTHYV
SQIGDFPDQTEDGGLPQSGRIVVDYMMQKPGKTGTIVYQRGVLLPQKVWCASGRSKVIK
GSLPLIGEADCLHEKYGGLNKSKPYYTGEHAKAIGNCPIWVKTPLKLANGTKYRPPGGG
WEGMIAGWHGYTSHGAHGVAVAADLKSTQEAINKITKNLNSLSELEVKNLQRLSGAMD
ELHNEILELDEKVDDLRADTISSQIELAVLLSNEGIINSEDEHLLALERKLKKMLGPSAVDI
GNGCFETKHKCNQTCLDRIAAGTFNAGEFSLPTFDSLNITAASLNDDGLDNHTILLYYST
AASSLAVTLMLAIFIVYMVSRDNVSCSICL*

Figure 27E

Schematic representation of construct number 1467

D-2X35S/CPMV-HT/PDISP/HA B Malaysia/NOS into BeYDV(m)+Replicase amplification system (Construct number 1631)

Figure 28A, SEQ ID NO: 59

IF-HB-M-04.s2+4c

TCTCAGATCTTCGCCGATCGAATCTGCACTGGGATAACATCGTC

Figure 28B, SEQ ID NO: 60

IF-HB-M-04.s1-4r

ACTAAAGAAAATAGGCCTTTATAGACAGATGGAGCAAGAAACATTG

Figure 28C, SEQ ID NO: 61

Synthesized HA B Malaysia (corresponding to nt 31-1743 from Genbank accession number EU124275). T759C and C888G mutations are underlined.

GATCGAATCTGCACTGGGATAACATCGTCAAACTCACCACATGTTGTCAAAACTGCTACTCAAGGGGAGG
TCAATGTGACTGGTGTAATACCACTGACAACAACACCCACCAAATCTCATTTTGCAAATCTCAAAGGAAC
AGAAACCAGAGGGAAACTATGCCCAAAATGCCTCAACTGCACAGATCTGGACGTGGCCTTGGGCAGACC
AAAATGCACGGGGAACATACCCTCGGCAAGAGTTTCAATACTCCATGAAGTCAGACCTGTTACATCTGGG
TGCTTTCCTATAATGCACGACAGAACAAAAATTAGACAGCTGCCTAAACTTCTCAGAGGATACGAACATA
TCAGGTTATCAACTCATAACGTTATCAATGCAGAAAATGCACCAGGAGGACCCTACAAAATTGGAACCTC
AGGGTCTTGCCCTAACGTTACCAATGGAAACGGATTTTTCGCAACAATGGCTTGGGCCGTCCCAAAAAAC
GACAACAACAAAACAGCAACAAATTCATTAACAATAGAAGTACCATACATTTGTACAGAAGGAGAAGAC
CAAATTACCGTTTGGGGGTTCCACTCTGATAACGAAACCCAAATGGCAAAGCTCTATGGGGACTCAAAGC
CCCAGAAGTTCACCTCATCTGCCAACGGAGTGACCACACATTACGTTTCACAGATTGGTGGCTTCCCAAA
TCAAACAGAAGACGGAGGACTACCACAAAGCGGTAGAATTGTTGTTGATTACATGGTGCAAAAATCTGG
GAAAACAGGAACAATTACCTATCAAAGAGGTATTTTATTGCCTCAAAAAGTGTGGTGCGCAAGTGGCAG
GAGCAAGGTAATAAAAGGATCGTTGCCTTTAATTGGAGAAGCAGATTGCCTCCACGAAAAATACGGTGG
ATTAAACAAAAGCAAGCCTTACTACACAGGGGAACATGCAAAGGCCATAGGAAATTGCCCAATATGGGT
GAAAACACCCTTGAAGCTGGCCAATGGAACCAAATATAGACCTCCTGCAAAACTATTAAAGGAAAGGGG
TTTCTTCGGAGCTATTGCTGGTTTCTTAGAAGGAGGATGGGAAGGAATGATTGCAGGTTGGCACGGATAC
ACATCCCATGGGGCACATGGAGTAGCGGTGGCAGCAGACCTTAAGAGCACTCAAGAGGCCATAAACAAG
ATAACAAAAAATCTCAACTCTTTGAGTGAGCTGGAAGTAAAGAATCTTCAAAGACTAAGCGGTGCCATG
GATGAACTCCACAACGAAATACTAGAACTAGACGAGAAAGTGGATGATCTCAGAGCTGATACAATAAGC
TCACAAATAGAACTCGCAGTCCTGCTTTCCAATGAAGGAATAATAAACAGTGAAGATGAGCATCTCTTGG
CGCTTGAAAGAAAGCTGAAGAAAATGCTGGGCCCCTCTGCTGTAGAGATAGGGAATGGATGCTTTGAAA
CCAAACACAAGTGCAACCAGACCTGTCTCGACAGAATAGCTGCTGGTACCTTTGATGCAGGAGAATTTTC
TCTCCCCACTTTTGATTCACTGAATATTACTGCTGCATCTTTAAATGACGATGGATTGGATAATCATACTA
TACTGCTTTACTACTCAACTGCTGCCTCCAGTTTGGCTGTAACATTGATGATAGCTATCTTTGTTGTTTATA
TGGTCTCCAGAGACAATGTTTCTTGCTCCATCTGTCTATAA

Figure 28D
Schematic representation of construct 194. SacII and StuI restriction enzyme sites used for plasmid linearization are annotated on the representation.

Figure 28E, SEQ ID NO: 62

Construct 194 from left to right t-DNA borders (underlined). 2X35S/CPMV-HT/NOS into BeYDV(m)+Replicase amplification system with Plastocyanine-P19-Plastocyanine silencing inhibitor expression cassette

```
TGGCAGGATATATTGTGGTGTAAACAAATTGACGCTTAGACAACTTAATAACACATTGCGGACGTTTTTA
ATGTACTGAATTAACGCCGAATCCCGGGCTGGTATATTTATATGTTGTCAAATAACTCAAAAACCATAAA
AGTTTAAGTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAATTTTGTTG
CAACATTTGAGAAAATTTTGTTGTTCTCTCTTTTCATTGGTCAAAAACAATAGAGAGAGAAAAAGGAAGA
GGGAGAATAAAAACATAATGTGAGTATGAGAGAGAAAGTTGTACAAAAGTTGTACCAAAATAGTTGTAC
AAATATCATTGAGGAATTTGACAAAAGCTACACAAATAAGGGTTAATTGCTGTAAATAAATAAGGATGA
CGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGT
TGTATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAAA
AAAAAAACGGTATATTTACTAAAAAATCTAAGCCACGTAGGAGGATAACAGGATCCCCGTAGGAGGATA
ACATCCAATCCAACCAATCACAACAATCCTGATGAGATAACCCACTTTAAGCCCACGCATCTGTGGCACA
TCTACATTATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGAGAAGAG
ACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAG
TCCGAGTTGGACTGAGTGGCGGCTACATAACGATGAGACGAATTCGAATCAAGATAATCCCCTTGGTTTC
AAGGAAAGCTGGGGTTTCGGGAAAGTTGTATTTAAGAGATATCTCAGATACGACAGGACGGAAGCTTCA
CTGCACAGAGTCCTTGGATCTTGGACGGGAGATTCGGTTAACTATGCAGCATCTCGATTTTTCGGTTTCGA
CCAGATCGGATGTACCTATAGTATTCGGTTTCGAGGAGTTAGTATCACCGTTTCTGGAGGGTCGCGAACT
CTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAA
TGCTTCTTCGTCTCCTATTTATAATATGGTTTGTTATTGTTAATTTTGTTCTTGTAGAAGAGCTTAATTAAT
CGTTGTTGTTATGAAATACTATTTGTATGAGATGAACTGGTGTAATGTAATTCATTTACATAAGTGGAGTC
```

Figure 28E continued

```
AGAATCAGAATGTTTCCTCCATAACTAACTAGACATGAAGACCTGCCGCGTACAATTGTCTTATATTTGA
ACAACTAAAATTGAACATCTTTTGCCACAACTTTATAAGTGGTTAATATAGCTCAAATATATGGTCAAGTT
CAATAGATTAATAATGGAAATATCAGTTATCGAAATTCATTAACAATCAACTTAACGTTATTAACTACTA
ATTTTATATCATCCCCTTTGATAAATGATAGTACACCAATTAGGAAGGAGCATGCTCGCCTAGGAGATTG
TCGTTTCCCGCCTTCAGTTTGCAAGCTGCTCTAGCCGTGTAGCCAATACGCAAACCGCCTCTCCCCGCGCG
TTGGGAATTACTAGCGCGTGTCGAGACGCGTTGTTGTTGTGACTCCGAGGGGTTGCCTCAAACTCTATCTT
ATAACCGGCGTGGAGGCATGGAGGCAGGGGTATTTTGGTCATTTTAATAGATAGTGGAAAATGACGTGG
AATTTACTTAAAGACGAAGTCTTTGCGACAAGGGGGGGCCCACGCCGAATTTAATATTACCGGCGTGGCC
CCCCCTTATCGCGAGTGCTTTAGCACGAGCGGTCCAGATTTAAAGTAGAAAATTTCCCGCCCACTAGGGT
TAAAGGTGTTCACACTATAAAGCATATACGATGTGATGGTATTTGGTCGACAAGCTTGCATGCCGGTCA
ACATGGTGGAGCACGACACACTTGTCTACTCCAAAAATATCAAAGATACAGTCTCAGAAGACCAAAGGG
CAATTGAGACTTTTCAACAAAGGGTAATATCCGGAAACCTCCTCGGATTCCATTGCCCAGCTATCTGTCA
CTTTATTGTGAAGATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAGGAGCATCGTGGA
AAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAA
AGGGTAATATCCGGAAACCTCCTCGGATTCCATTGCCCAGCTATCTGTCACTTTATTGTGAAGATAGTGG
AAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCA
CGTCTTCAAAGCAAGTGGATTGATGTGATATCTCCACTGACGTAAGGGATGACGCACAATCCCACTATCC
TTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCAGTACAACG
TTTTCTTTCACTGAAGCGAAATCAAAGATCTCTTTGTGGACACGTAGTGCGGCGCCATTAAATAACGTGT
ACTTGTCCTATTCTTGTCGGTGTGGTCTTGGGAAAAGAAAGCTTGCTGGAGGCTGCTGTTCAGCCCCATAC
ATTACTTGTTACGATTCTGCTGACTTTCGGCGGGTGCAATATCTCTACTTCTGCTTGACGAGGTATTGTTG
CCTGTACTTCTTTCTTCTTCTTGCTGATTGGTTCTATAAGAAATCTAGTATTTTCTTTGAAACAGAGTT
TTCCCGTGGTTTTCGAACTTGGAGAAAGATTGTTAAGCTTCTGTATATTCTGCCCAAATTTGTCGGGCCCA
TGGCGAAAAACGTTGCGATTTTCGGCTTATTGTTTTCTCTTCTTGTGTTGGTTCCTTCTCAGATCTTCGCCG
CGGCTCCTCAGCCAAAACGACACCCCCATCTGTCTATCCACTGGCCCCTGGATCTGCTGCCCAAACTAAC
TCCATGGTGACCCTGGGATGCCTGGTCAAGGGCTATTTCCCTGAGCCAGTGACAGTGACCTGGAACTCTG
GATCCCTGTCCAGCGGTGTGCACACCTTCCCAGCTGTCCTGCAGTCTGACCTCTACACTCTGAGCAGCTCA
GTGACTGTCCCCTCCAGCACCTGGCCCAGCGAGACCGTCACCTGCAACGTTGCCCACCCGGCCAGCAGCA
CCAAGGTGGACAAGAAAATTGTGCCCAGGGATTGTGGTTGTAAGCCTTGCATATGTACAGTCCCAGAAGT
ATCATCTGTCTTCATCTTCCCCCCAAAGCCCAAGGATGTGCTCACCATTACTCTGACTCCTAAGGTCACGT
GTGTTGTGGTAGACATCAGCAAGGATGATCCCGAGGTCCAGTTCAGCTGGTTTGTAGATGATGTGGAGGT
GCACACAGCTCAGACGCAACCCCGGGAGGAGCAGTTCAACAGCACTTTCCGCTCAGTCAGTGAACTTCCC
ATCATGCACCAGGACTGGCTCAATGGCAAGGAGCGATCGCTCACCATCACCATCACCATCACCATCACCA
TTAAAGGCCTATTTTCTTTAGTTTGAATTTACTGTTATTCGGTGTGCATTTCTATGTTTGGTGAGCGGTTTT
CTGTGCTCAGAGTGTGTTTATTTTATGTAATTTAATTTCTTTGTGAGCTCCTGTTTAGCAGGTCGTCCCTTC
AGCAAGGACACAAAAAGATTTTAATTTTATTAAAAAAAAAAAAAAAAAAAAGACCGGGAATTCGATATCAA
GCTTATCGACCTGCAGATCGTTCAAACATTTGGCAATAAAGTTTCTTAAGATTGAATCCTGTTGCCGGTCT
TGCGATGATTATCATATAATTTCTGTTGAATTACGTTAAGCATGTAATAATTAACATGTAATGCATGACGT
TATTTATGAGATGGGTTTTTATGATTAGAGTCCCGCAATTATACATTTAATACGCGATAGAAAACAAAAT
ATAGCGCGCAAACTAGGATAAATTATCGCGCGCGGTGTCATCTATGTTACTAGATCTCTAGAGTCTCAAG
CTTGGCGCGCCATAAAATGATTATTTTATGAATATATTTCATTGTGCAAGTAGATAGAAATTACATATGTT
ACATAACACACGAAATAAACAAAAAAGACAATCCAAAAACAAACACCCCAAAAAAAATAATCACTTT
AGATAAACTCGTATGAGGAGAGGCACGTTCAGTGACTCGACGATTCCCGAGCAAAAAAAGTCTCCCCGT
CACACATATAGTGGGTGACGCAATTATCTTTAAAGTAATCCTTCTGTTGACTTGTCATTGATAACATCCAG
TCTTCGTCAGGATTGCAAAGAATTATGAAGGGATCCCACCTTTTATTTTCTTCTTTTTTCCATATTTAGGG
TTGACAGTGAAATCAGACTGGCAACCTATTAATTGCTTCCACAATGGGACGAACTTGAAGGGGATGTCGT
CGATGATATTATAGGTGGCGTGTTCATCGTAGTTGGTGAAATCGATGGTACCGTTCCAATAGTTGTGTCGT
CCGAGACTTCTAGCCCAGGTGGTCTTTCCGGTACGAGTTGGTCCGCAGATGTAGAGGCTGGGGTGTCGGA
TTCCATTCCTTCCATTGTCCTGGTTAAATCGGCCATCCATTCAAGGTCAGATTGAGCTTGTTGGTATGAGA
```

Figure 28E continued

CAGGATGTATGTAAGTATAAGCGTCTATGCTTACATGGTATAGATGGGTTTCCCTCCAGGAGTGTAGATC
TTCGTGGCAGCGAAGATCTGATTCTGTGAAGGGCGACACATACGGTTCAGGTTGTGGAGGGAATAATTTG
TTGGCTGAATATTCCAGCCATTGAAGTTTTGTTGCCCATTCATGAGGGAATTCTTCCTTGATCATGTCAAG
ATATTCCTCCTTAGACGTTGCAGTCTGGATAATAGTTCTCCATCGTGCGTCAGATTTGCGAGGAGAGACCT
TATGATCTCGGAAATCTCCTCTGGTTTTAATATCTCCGTCCTTTGATATGTAATCAAGGACTTGTTTAGAG
TTTCTAGCTGGCTGGATATTAGGGTGATTTCCTTCAAAATCGAAAAAGAAGGATCCCTAATACAAGGTT
TTTTATCAAGCTGGAGAAGAGCATGATAGTGGGTAGTGCCATCTTGATGAAGCTCAGAAGCAACACCAA
GGAAGAAAATAAGAAAAGGTGTGAGTTTCTCCCAGAGAAACTGGAATAAATCATCTCTTTGAGATGAGC
ACTTGGGATAGGTAAGGAAAACATATTTAGATTGGAGTCTGAAGTTCTTACTAGCAGAAGGCATGTTGTT
GTGACTCCGAGGGGTTGCCTCAAACTCTATCTTATAACCGGCGTGGAGGCATGGAGGCAGGGGTATTTTG
GTCATTTTAATAGATAGTGGAAAATGACGTGGAATTTACTTAAAGACGAAGTCTTTGCGACAAGGGGGG
GCCCACGCCGAATTTAATATTACCGGCGTGGCCCCCCCTTATCGCGAGTGCTTTAGCACGAGCGGTCCAG
ATTTAAAGTAGAAAATTTCCCGCCCACTAGGGTTAAAGGTGTTCACACTATAAAAGCATATACGATGTGA
TGGTATTTGACTAGTGGCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGCACCGATCGCC
CTTCCCAACAGTTGCGCAGCCTGAATGGCGAATGCTAGAGCAGCTTGAGCTTGGATCAGATTGTCGTTTC
CCGCCTTCAGTTTAAACTATCAGTGTTTGACAGGATATATTGGCGGGTAAACCTAAGAGAAAGAGCGTT
TA

Figure 28F, SEQ ID NO: 63

Expression cassette number 1631 from 2X35S promoter to NOS terminator. PDISP-HA from influenza B/ Malaysia/2506/2004 is underlined.

GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATAAAGGAA
AGGCCATCGTTGAAGATGCCTCTGCCGACAGTGGTCCCAAAGATGGACCCCCACCCACGAGGAGCATCG
TGGAAAAGAAGACGTTCCAACCACGTCTTCAAAGCAAGTGGATTGATGTGATAACATGGTGGAGCACG
ACACACTTGTCTACTCCAAAAATATCAAAGATACAGTCTCAGAAGACCAAAGGGCAATTGAGACTTTTCA
ACAAAGGGTAATATCCGGAAACCTCCTCGGATTCCATTGCCCAGCTATCTGTCACTTTATTGTGAAGATA
GTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAGAAGACGTTCCA
ACCACGTCTTCAAAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCATCTCTCTTAAAG
CAAACTTCTCTCTTGTCTTTCTTGCGTGAGCGATCTTCAACGTTGTCAGATCGTGCTTCGGCACCAGTACA
ACGTTTTCTTTCACTGAAGCGAAATCAAAGATCTCTTTGTGGACACGTAGTGCGGCGCCATTAAATAACG
TGTACTTGTCCTATTCTTGTCGGTGTGGTCTTGGGAAAAGAAAGCTTGCTGGAGGCTGCTGTTCAGCCCCA
TACATTACTTGTTACGATTCTGCTGACTTTCGGCGGGTGCAATATCTCTACTTCTGCTTGACGAGGTATTG
TTGCCTGTACTTCTTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAATTTGTCGGGC
CATGGCGAAAAACGTTGCGATTTTCGGCTTATTGTTTTCTCTTCTTGTGTTGGTTCCTTCTCAGATCTTCG
CCGATCGAATCTGCACTGGGATAACATCGTCAAACTCACCACATGTTGTCAAAACTGCTACTCAAGGGGA
GGTCAATGTGACTGGTGTAATACCACTGACAACAACACCCACCAAATCTCATTTTGCAAATCTCAAAGGA
ACAGAAACCAGAGGGAAACTATGCCCAAAATGCCTCAACTGCACAGATCTGGACGTGGCCTTGGGCAGA
CCAAAATGCACGGGGAACATACCCTCGGCAAGAGTTTCAATACTCCATGAAGTCAGACCTGTTACATCTG
GGTGCTTTCCTATAATGCACGACAGAACAAAAATTAGACAGCTGCCTAAACTTCTCAGAGGATACGAACA
TATCAGGTTATCAACTCATAACGTTATCAATGCAGAAAATGCACCAGGAGGACCCTACAAAATTGGAACC
TCAGGGTCTTGCCCTAACGTTACCAATGGAAACGGATTTTTCGCAACAATGGCTTGGGCCGTCCCAAAAA
ACGACAACAACAAAACAGCAACAAATTCATTAACAATAGAAGTACCATACATTTGTACAGAAGGAGAAG
ACCAAATTACCGTTTGGGGGTTCCACTCTGATAACGAAACCCAAATGGCAAAGCTCTATGGGGACTCAAA

Figure 28F continued

GCCCCAGAAGTTCACCTCATCTGCCAACGGAGTGACCACACATTACGTTTCACAGATTGGTGGCTTCCCA
AATCAAACAGAAGACGGAGGACTACCACAAAGCGGTAGAATTGTTGTTGATTACATGGTGCAAAAATCT
GGGAAAACAGGAACAATTACCTATCAAAGAGGTATTTTATTGCCTCAAAAAGTGTGGTGCGCAAGTGGC
AGGAGCAAGGTAATAAAAGGATCGTTGCCTTTAATTGGAGAAGCAGATTGCCTCCACGAAAAATACGGT
GGATTAAACAAAAGCAAGCCTTACTACACAGGGGAACATGCAAAGGCCATAGGAAATTGCCCAATATGG
GTGAAAACACCCTTGAAGCTGGCCAATGGAACCAAATATAGACCTCCTGCAAAACTATTAAAGGAAAGG
GGTTTCTTCGGAGCTATTGCTGGTTTCTTAGAAGGAGGATGGGAAGGAATGATTGCAGGTTGGCACGGAT
ACACATCCCATGGGGCACATGGAGTAGCGGTGGCAGCAGACCTTAAGAGCACTCAAGAGGCCATAAACA
AGATAACAAAAAATCTCAACTCTTTGAGTGAGCTGGAAGTAAAGAATCTTCAAAGACTAAGCGGTGCCA
TGGATGAACTCCACAACGAAATACTAGAACTAGACGAGAAAGTGGATGATCTCAGAGCTGATACAATAA
GCTCACAAATAGAACTCGCAGTCCTGCTTTCCAATGAAGGAATAATAAACAGTGAAGATGAGCATCTCTT
GGCGCTTGAAAGAAAGCTGAAGAAAATGCTGGGCCCCTCTGCTGTAGAGATAGGGAATGGATGCTTTGA
AACCAAACACAAGTGCAACCAGACCTGTCTCGACAGAATAGCTGCTGGTACCTTTGATGCAGGAGAATTT
TCTCTCCCCACTTTTGATTCACTGAATATTACTGCTGCATCTTTAAATGACGATGGATTGGATAATCATAC
TATACTGCTTTACTACTCAACTGCTGCCTCCAGTTTGGCTGTAACATTGATGATAGCTATCTTTGTTGTTTA
TATGGTCTCCAGAGACAATGTTTCTTGCTCCATCTGTCTATAAAGGCCTATTTTCTTTAGTTTGAATTTACT
GTTATTCGGTGTGCATTTCTATGTTTGGTGAGCGGTTTTCTGTGCTCAGAGTGTGTTTATTTTATGTAATTT
AATTTCTTTGTGAGCTCCTGTTTAGCAGGTCGTCCCTTCAGCAAGGACACAAAAAGATTTTAATTTTATTA
AAAAAAAAAAAAAAAAAGACCGGGAATTCGATATCAAGCTTATCGACCTGCAGATCGTTCAAACATTTG
GCAATAAAGTTTCTTAAGATTGAATCCTGTTGCCGGTCTTGCGATGATTATCATATAATTTCTGTTGAATT
ACGTTAAGCATGTAATAATTAACATGTAATGCATGACGTTATTTATGAGATGGGTTTTTATGATTAGAGTC
CCGCAATTATACATTTAATACGCGATAGAAAACAAAATATAGCGCGCAAACTAGGATAAATTATCGCGC
GCGGTGTCATCTATGTTACTAGAT

Figure 28G, SEQ ID NO: 64

Amino acid sequence of PDISP-HA from influenza B/Malaysia/2506/2004

MAKNVAIFGLLFSLLVLVPSQIFADRICTGITSSNSPHVVKTATQGEVNVTGVIPLTTTPTKSHFANLKGTETRG
KLCPKCLNCTDLDVALGRPKCTGNIPSARVSILHEVRPVTSGCFPIMHDRTKIRQLPKLLRGYEHIRLSTHNVIN
AENAPGGPYKIGTSGSCPNVTNGNGFFATMAWAVPKNDNNKTATNSLTIEVPYICTEGEDQITVWGFHSDNET
QMAKLYGDSKPQKFTSSANGVTTHYVSQIGGFPNQTEDGGLPQSGRIVVDYMVQKSGKTGTITYQRGILLPQ
KVWCASGRSKVIKGSLPLIGEADCLHEKYGGLNKSKPYYTGEHAKAIGNCPIWVKTPLKLANGTKYRPPAKL
LKERGFFGAIAGFLEGGWEGMIAGWHGYTSHGAHGVAVAADLKSTQEAINKITKNLNSLSELEVKNLQRLSG
AMDELHNEILELDEKVDDLRADTISSQIELAVLLSNEGIINSEDEHLLALERKLKKMLGPSAVEIGNGCFETKH
KCNQTCLDRIAAGTFDAGEFSLPTFDSLNITAASLNDDGLDNHTILLYYSTAASSLAVTLMIAIFVVYMVSRDN
VSCSICL*

Figure 28H

Schematic representation of construct number 1631

| Construct number | Hemagglutination capacity (HA titer)[a] |
|---|---|
| 1462 (0.8) | 136 ± 48 |
| 1467 (0.8) | 2660 ± 384 |
| 1462 + 1261 (0.8:0.2) | 941 ± 192 |
| 1467 + 1261 (0.8:0.2) | 4344 ± 1536 |

[a] Inverse of the highest dilution capable of agglutinating red blood cells.

Figure 32 A
ER retention and secretion
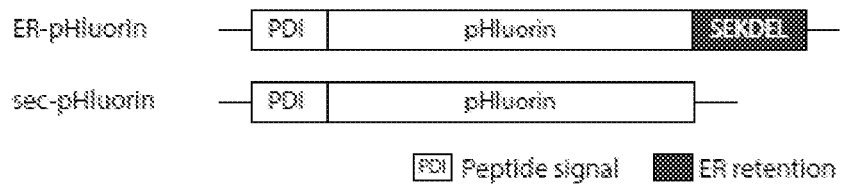
cis-Golgi and trans-Golgi targeting
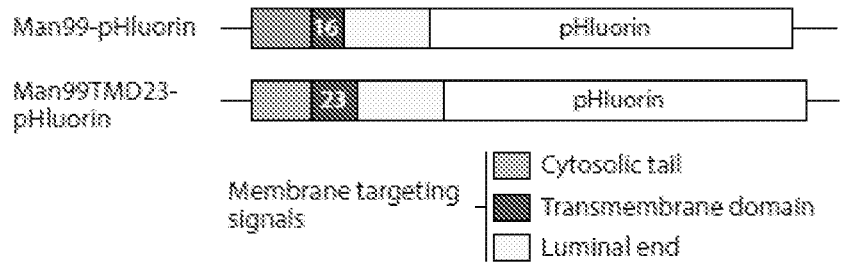
Figure 32 C
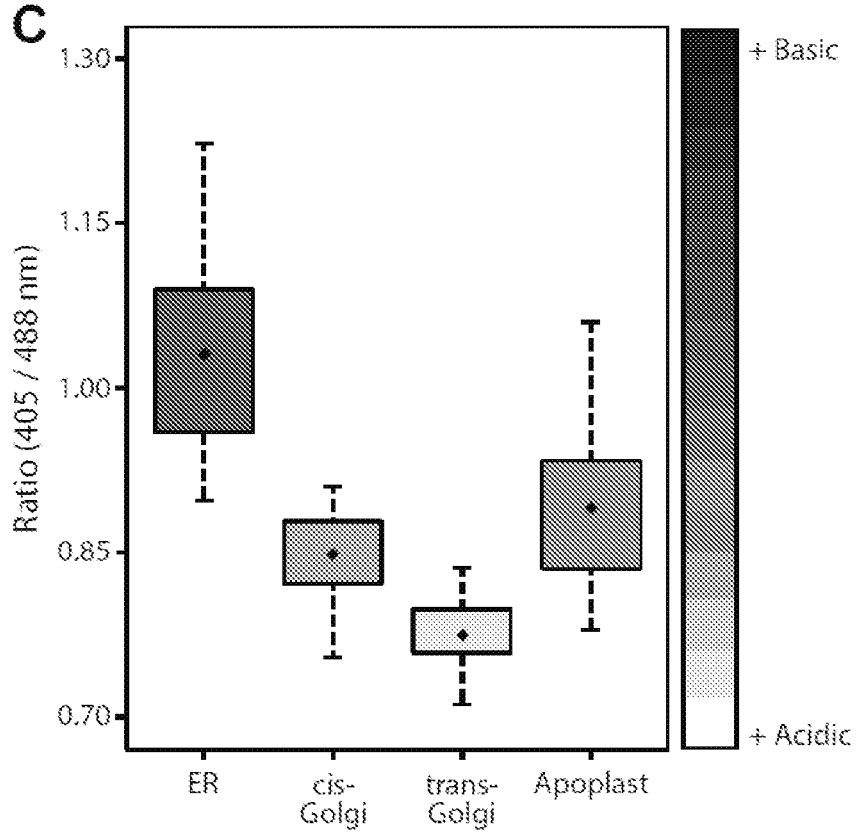

B-2X35S/CPMV-HT/ M2 New Caledonia (A30P)/NOS (Construct number 1210)

Figure 36A, SEQ ID NO:65

M2ANC2099(A30P).r

AATCCCAATTATACTAGGGGCAACAACAAGAGGATCACTTGAATCGT

Figure 36B, SEQ ID NO:66

M2ANC2099(A30P).c

TTGTTGCCCCTAGTATAATTGGGATTGTGCACCTGATATTGTGGATT

Figure 36C, SEQ ID NO:67

Expression cassette number 1210 from 2X35S promoter to NOS terminator. M2 from influenza A/New Caledonia/20/1999 (H1N1) with M2 A30P is underlined.

```
GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACAACGTTTTCTTTCACTG
AAGCGAAATCAAAGATCTCTTTGTGGACACGTAGTGCGGCGCCATTAAATAACGTGTACTTGTCCTATTCT
TGTCGGTGTGGTCTTGGGAAAAGAAAGCTTGCTGGAGGCTGCTGTTCAGCCCCATACATTACTTGTTACGA
TTCTGCTGACTTTCGGCGGGTGCAATATCTCTACTTCTGCTTGACGAGGTATTGTTGCCTGTACTTCTTTC
TTCTTCTTCTTGCTGATTGGTTCTATAAGAAATCTAGTATTTTCTTTGAAACAGAGTTTTCCCGTGGTTTT
CGAACTTGGAGAAAGATTGTTAAGCTTCTGTATATTCTGCCCAAATTTGTCGGGCCCATGAGTCTTCTAAC
CGAGGTCGAAACGCCTATCAGAAACGAATGGGGGTGCAGATGCAACGATTCAAGTGATCCTCTTGTTGTTG
CCCCTAGTATAATTGGGATTGTGCACCTGATATTGTGGATTATTGATCGCCTTTTTTCCAAAAGCATTTAT
CGTATCTTTAAACACGGTTTAAAAAGAGGGCCTTCTACGGAAGGAGTACCAGAGTCTATGAGGGAAGAATA
TCGAGAGGAACAGCAGAATGCTGTGGATGCTGACGATGGTCATTTTGTCAGCATAGAGCTGGAGTAAAGGC
CTATTTTCTTTAGTTTGAATTTACTGTTATTCGGTGTGCATTTCTATGTTTGGTGAGCGGTTTTCTGTGCT
CAGAGTGTGTTTATTTTATGTAATTTAATTTCTTTGTGAGCTCCTGTTTAGCAGGTCGTCCCTTCAGCAAG
GACACAAAAAGATTTTAATTTTATTAAAAAAAAAAAAAAAAAGACCGGGAATTCGATATCAAGCTTATCG
```

Figure 36C continued

```
ACCTGCAGATCGTTCAAACATTTGGCAATAAAGTTTCTTAAGATTGAATCCTGTTGCCGGTCTTGCGATGA
TTATCATATAATTTCTGTTGAATTACGTTAAGCATGTAATAATTAACATGTAATGCATGACGTTATTTATG
AGATGGGTTTTTATGATTAGAGTCCCGCAATTATACATTTAATACGCGATAGAAAACAAAATATAGCGCGC
AAACTAGGATAAATTATCGCGCGCGGTGTCATCTATGTTACTAGAT
```

Figure 36D, SEQ ID NO: 68

Amino acid sequence of M2 from influenza A/New Caledonia/20/1999 (H1N1) with mutation A30P

MSLLTEVETPIRNEWGCRCNDSSDPLVVAPSIIGIVHLILWIIDRLFSKSIYRIFKHGLKRGPSTE

GVPESMREEYREEQQNAVDADDGHFVSIELE

Figure 36E

Schematic representation of construct number 1210

Sec-pHluorin: C-2X35S/CPMV-HT/ PDISP/ pHluorin/NOS (Construct number 1871)

Figure 37A, SEQ ID NO: 69

IF-PDI.S1+3c

AAATTTGTCGGGCCCATGGCGAAAAACGTTGCGATTTTCGGCTTATTG

Figure 37B, SEQ ID NO: 70

IF-pHluorin_primer6.r

ACTAAAGAAAATAGGCCTTTATTTGTATAGTTCATCCATGCCATGTG

Figure 37C, SEQ ID NO: 71

Nucleotide sequence of PDISP/pHluorin

ATGGCGAAAAACGTTGCGATTTTCGGCTTATTGTTTTCTCTTCTTGTGTTGGTTCCTTCTCAGATCTTCGC
CAGTAAAGGAGAAGAACTTTTCACTGGAGTTGTCCCAATTCTTGTTGAATTAGATGGTGATGTTAATGGGC
ACAAATTTTCTGTCAGTGGAGAGGGTGAAGGTGATGCAACATACGGAAAACTTACCCTTAAATTTATTTGC
ACTACTGGAAAACTACCTGTTCCATGGCCAACACTTGTCACTACTTTCTCTTATGGTGTTCAATGCTTTTC
AAGATACCCAGATCATATGAAACGGCATGACTTTTTCAAGAGTGCCATGCCCGAAGGTTATGTACAGGAAA
GAACTATATTTTTCAAAGATGACGGGAACTACAAGACACGTGCTGAAGTCAAGTTTGAAGGTGATACCCTT
GTTAATAGAATCGAGTTAAAAGGTATTGATTTTAAAGATGATGGAAACATTCTTGGACACAAATTGGAATA
CAACTATAACGAGCACTTGGTGTACATCATGGCAGACAAACAAAAGAATGGTACCAAAGCTATCTTTCAAG
TTCACCACAACATTGAAGATGGAGGCGTTCAACTAGCAGACCATTATCAACAAAATACTCCAATTGGCGAT
GGCCCTGTCCTTTTACCAGACAACCATTACCTGCACACACAATCTGCCCTTTCGAAAGATCCCAACGAAAA
GAGAGACCACATGGTCCTTCTTGAGTTTGTAACAGCTGCTGGGATTACACATGGCATGGATGAACTATACA
AATAA

Figure 37D, SEQ ID NO: 72

Expression cassette number 1871 from 2X35S promoter to NOS terminator. PDISP/pHluorin is underlined.

```
GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACAACGTTTTCTTTCACTG
AAGCGAAATCAAAGATCTCTTTGTGGACACGTAGTGCGGCGCCATTAAATAACGTGTACTTGTCCTATTCT
TGTCGGTGTGGTCTTGGGAAAAGAAAGCTTGCTGGAGGCTGCTGTTCAGCCCCATACATTACTTGTTACGA
TTCTGCTGACTTTCGGCGGGTGCAATATCTCTACTTCTGCTTGACGAGGTATTGTTGCCTGTACTTCTTTC
TTCTTCTTCTTGCTGATTGGTTCTATAAGAAATCTAGTATTTTCTTTGAAACAGAGTTTTCCCGTGGTTTT
CGAACTTGGAGAAAGATTGTTAAGCTTCTGTATATTCTGCCCAAATTTGTCGGGCCCATGGCGAAAAACGT
TGCGATTTTCGGCTTATTGTTTTCTCTTCTTGTGTTGGTTCCTTCTCAGATCTTCGCCAGTAAAGGAGAAG
AACTTTTCACTGGAGTTGTCCCAATTCTTGTTGAATTAGATGGTGATGTTAATGGGCACAAATTTTCTGTC
AGTGGAGAGGGTGAAGGTGATGCAACATACGGAAAACTTACCCTTAAATTTATTTGCACTACTGGAAAACT
ACCTGTTCCATGGCCAACACTTGTCACTACTTTCTCTTATGGTGTTCAATGCTTTTCAAGATACCCAGATC
ATATGAAACGGCATGACTTTTTCAAGAGTGCCATGCCCGAAGGTTATGTACAGGAAAGAACTATATTTTTC
AAAGATGACGGGAACTACAAGACACGTGCTGAAGTCAAGTTTGAAGGTGATACCCTTGTTAATAGAATCGA
GTTAAAAGGTATTGATTTTAAAGATGATGGAAACATTCTTGGACACAAATTGGAATACAACTATAACGAGC
ACTTGGTGTACATCATGGCAGACAAACAAAAGAATGGTACCAAAGCTATCTTTCAAGTTCACCACAACATT
GAAGATGGAGGCGTTCAACTAGCAGACCATTATCAACAAAATACTCCAATTGGCGATGGCCCTGTCCTTTT
ACCAGACAACCATTACCTGCACACACAATCTGCCCTTTCGAAAGATCCCAACGAAAAGAGAGACCACATGG
TCCTTCTTGAGTTTGTAACAGCTGCTGGGATTACACATGGCATGGATGAACTATACAAATAAAGGCCTATT
TTCTTTAGTTTGAATTTACTGTTATTCGGTGTGCATTTCTATGTTTGGTGAGCGGTTTTCTGTGCTCAGAG
TGTGTTTATTTTATGTAATTTAATTTCTTTGTGAGCTCCTGTTTAGCAGGTCGTCCCTTCAGCAAGGACAC
AAAAAGATTTTAATTTTATTAAAAAAAAAAAAAAAAAAGACCGGGAATTCGATATCAAGCTTATCGACCTG
CAGATCGTTCAAACATTTGGCAATAAAGTTTCTTAAGATTGAATCCTGTTGCCGGTCTTGCGATGATTATC
ATATAATTTCTGTTGAATTACGTTAAGCATGTAATAATTAACATGTAATGCATGACGTTATTTATGAGATG
GGTTTTTATGATTAGAGTCCCGCAATTATACATTTAATACGCGATAGAAACAAAATATAGCGCGCAAACT
AGGATAAATTATCGCGCGCGGTGTCATCTATGTTACTAGAT
```

Figure 37E, SEQ ID NO: 73

Amino acid sequence of PDISP/pHluorin

MAKNVAIFGLLFSLLVLVPSQIFASKGEELFTGVVPILVELDGDVNGHKFSVSGEGEGDATYGKLTLKFIC
TTGKLPVPWPTLVTTFSYGVQCFSRYPDHMKRHDFFKSAMPEGYVQERTIFFKDDGNYKTRAEVKFEGDTL
VNRIELKGIDFKDDGNILGHKLEYNYNEHLVYIMADKQKNGTKAIFQVHHNIEDGGVQLADHYQQNTPIGD
GPVLLPDNHYLHTQSALSKDPNEKRDHMVLLEFVTAAGITHGMDELYK

Figure 37F

Schematic representation of construct number 1871

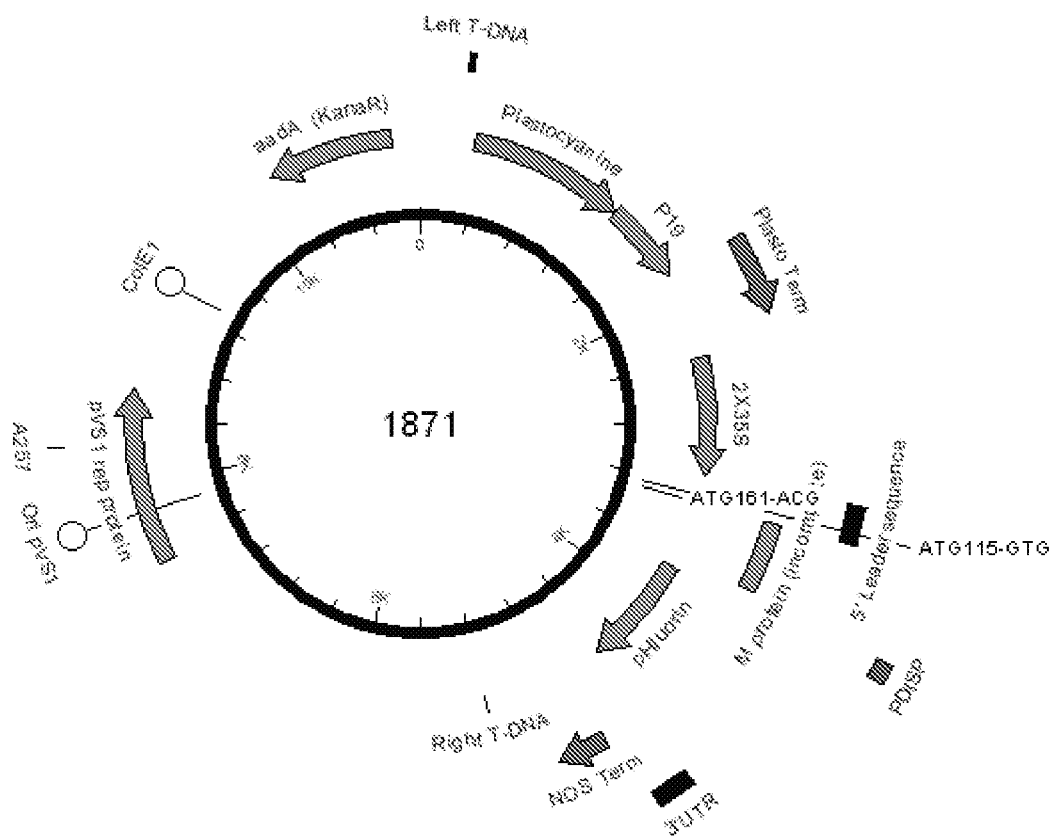

ER-pHluorin: D-2X35S/ CPMV-HT/ PDISP/ pHluorin/ SEKDEL/ NOS (Construct number 1872)

Figure 38A, SEQ ID NO:74

IF-pHluorin_primer2.r

ACTAAAGAAAATAGGCCTTTACAGCTCGTCCTTTTCGCTTTTGTATAGTTCATCCATGCC

Figure 38B, SEQ ID NO:75

Expression cassette number 1872 from 2X35S promoter to NOS terminator. PDISP/pHluorin/SEKDEL is underlined.

GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACAACGTTTTCTTTCACTG
AAGCGAAATCAAAGATCTCTTTGTGGACACGTAGTGCGGCGCCATTAAATAACGTGTACTTGTCCTATTCT
TGTCGGTGTGGTCTTGGGAAAAGAAAGCTTGCTGGAGGCTGCTGTTCAGCCCCATACATTACTTGTTACGA
TTCTGCTGACTTTCGGCGGGTGCAATATCTCTACTTCTGCTTGACGAGGTATTGTTGCCTGTACTTCTTTC
TTCTTCTTCTTGCTGATTGGTTCTATAAGAAATCTAGTATTTTCTTTGAAACAGAGTTTTCCCGTGGTTTT
CGAACTTGGAGAAAGATTGTTAAGCTTCTGTATATTCTGCCCAAATTTGTCGGGCCC<u>ATGGCGAAAAACGT
TGCGATTTTCGGCTTATTGTTTTCTCTTCTTGTGTTGGTTCCTTCTCAGATCTTCGCCAGTAAAGGAGAAG
AACTTTTCACTGGAGTTGTCCCAATTCTTGTTGAATTAGATGGTGATGTTAATGGGCACAAATTTTCTGTC
AGTGGAGAGGGTGAAGGTGATGCAACATACGGAAAACTTACCCTTAAATTTATTTGCACTACTGGAAAACT
ACCTGTTCCATGGCCAACACTTGTCACTACTTTCTCTTATGGTGTTCAATGCTTTTCAAGATACCCAGATC
ATATGAAACGGCATGACTTTTTCAAGAGTGCCATGCCCGAAGGTTATGTACAGGAAAGAACTATATTTTTC
AAAGATGACGGGAACTACAAGACACGTGCTGAAGTCAAGTTTGAAGGTGATACCCTTGTTAATAGAATCGA
GTTAAAGGTATTGATTTTAAAGATGATGGAAACATTCTTGGACACAAATTGGAATACAACTATAACGAGC
ACTTGGTGTACATCATGGCAGACAAACAAAAGAATGGTACCAAAGCTATCTTTCAAGTTCACCACAACATT
GAAGATGGAGGCGTTCAACTAGCAGACCATTATCAACAAAATACTCCAATTGGCGATGGCCCTGTCCTTTT
ACCAGACAACCATTACCTGCACACACAATCTGCCCTTTCGAAAGATCCCAACGAAAAGAGAGACCACATGG
TCCTTCTTGAGTTTGTAACAGCTGCTGGGATTACACATGGCATGGATGAACTATACAAAAGCGAAAAGGAC
GAGCTGTAAAGGCCTATTTTCTTTAGTTTGAATTTACTGTTATTCGGTGTGCATTTCTATGTTTGGTGAGC</u>
GGTTTTCTGTGCTCAGAGTGTGTTTATTTTATGTAATTTAATTTCTTTGTGAGCTCCTGTTTAGCAGGTCG

Figure 38B continued

```
TCCCTTCAGCAAGGACACAAAAAGATTTTAATTTTATTAAAAAAAAAAAAAAAAAAGACCGGGAATTCGAT
ATCAAGCTTATCGACCTGCAGATCGTTCAAACATTTGGCAATAAAGTTTCTTAAGATTGAATCCTGTTGCC
GGTCTTGCGATGATTATCATATAATTTCTGTTGAATTACGTTAAGCATGTAATAATTAACATGTAATGCAT
GACGTTATTTATGAGATGGGTTTTTATGATTAGAGTCCCGCAATTATACATTTAATACGCGATAGAAAACA
AAATATAGCGCGCAAACTAGGATAAATTATCGCGCGCGGTGTCATCTATGTTACTAGAT
```

Figure 38C, SEQ ID NO: 76

Amino acid sequence of PDISP/pHluorin/SEKDEL

```
MAKNVAIFGLLFSLLVLVPSQIFASKGEELFTGVVPILVELDGDVNGHKFSVSGEGEGDATYGKLTLKFIC
TTGKLPVPWPTLVTTFSYGVQCFSRYPDHMKRHDFFKSAMPEGYVQERTIFFKDDGNYKTRAEVKFEGDTL
VNRIELKGIDFKDDGNILGHKLEYNYNEHLVYIMADKQKNGTKAIFQVHHNIEDGGVQLADHYQQNTPIGD
GPVLLPDNHYLHTQSALSKDPNEKRDHMVLLEFVTAAGITHGMDELYKSEKDEL
```

Figure 38D

Schematic representation of construct number 1872

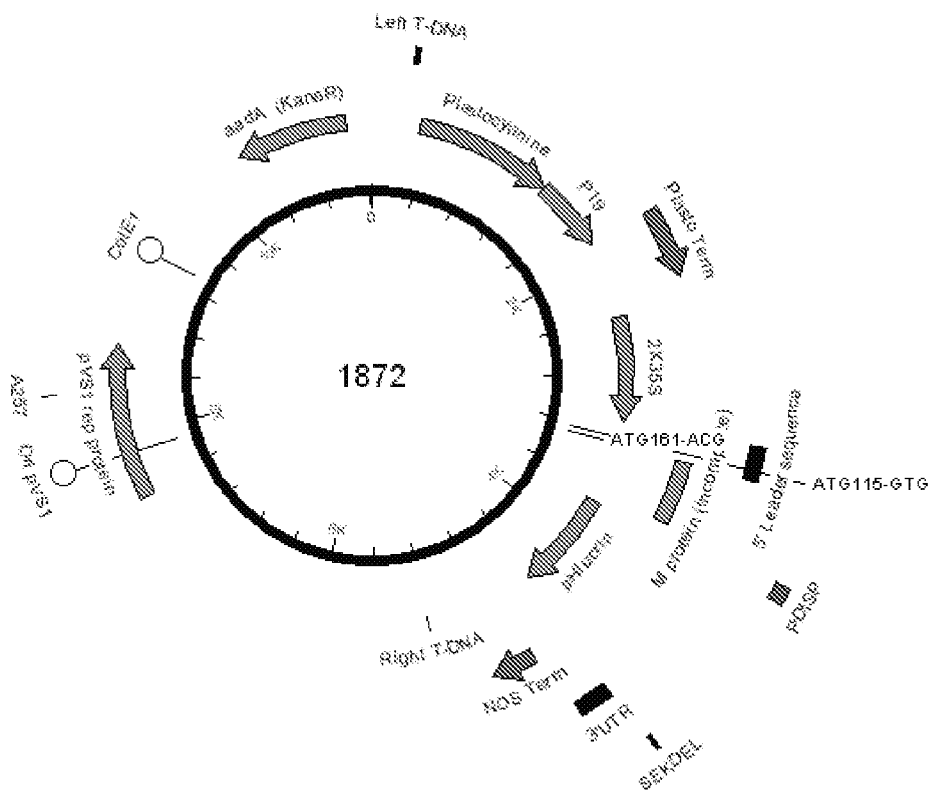

Man99-pHluorin : 2X35S/ CPMV-HT/ Man99/ pHluorin/NOS (Construct number 1873)

Figure 39A, SEQ ID NO:77

IF-pHluorin_primer3.c

AAATTTGTCGGGCCCATGGCGAGAGGGAGCAGATCAGTGGGTA

Figure 39B, SEQ ID NO: 78

Nucleotide sequence of Man99/pHluorin

ATGGCGAGAGGGAGCAGATCAGTGGGTAGCAGCAGCAGCAAATGGAGGTACTGCAACCCTTCCTATTACTT
GAAGCGCCCAAAGCGTCTTGCTCTGCTCTTCATCGTTTTCGTTTGTGTCTCTTTCGTTTTCTGGGACCGTC
AAACTCTCGTCAGAGAGCACCAGGTTGAAATTTCTGAGCTGCAGAAAGAAGTGACTGATTTGAAAAATTTG
GTGGATGATTTAAATAACAAACAAGGTGGTACCTCTGGGAAGACTGACTTGGGGAGAAAAGCTACCAAGTC
CAGTAAAGACGTCAGTAAAGGAGAAGAACTTTTCACTGGAGTTGTCCCAATTCTTGTTGAATTAGATGGTG
ATGTTAATGGGCACAAATTTTCTGTCAGTGGAGAGGGTGAAGGTGATGCAACATACGGAAAACTTACCCTT
AAATTTATTTGCACTACTGGAAAACTACCTGTTCCATGGCCAACACTTGTCACTACTTTCTCTTATGGTGT
TCAATGCTTTTCAAGATACCCAGATCATATGAAACGGCATGACTTTTTCAAGAGTGCCATGCCCGAAGGTT
ATGTACAGGAAAGAACTATATTTTTCAAAGATGACGGGAACTACAAGACACGTGCTGAAGTCAAGTTTGAA
GGTGATACCCTTGTTAATAGAATCGAGTTAAAAGGTATTGATTTTAAAGATGATGGAAACATTCTTGGACA
CAAATTGGAATACAACTATAACGAGCACTTGGTGTACATCATGGCAGACAAACAAAGAATGGTACCAAAG
CTATCTTTCAAGTTCACCACAACATTGAAGATGGAGGCGTTCAACTAGCAGACCATTATCAACAAAATACT
CCAATTGGCGATGGCCCTGTCCTTTTACCAGACAACCATTACCTGCACACACAATCTGCCCTTTCGAAAGA
TCCCAACGAAAAGAGAGACCACATGGTCCTTCTTGAGTTTGTAACAGCTGCTGGGATTACACATGGCATGG
ATGAACTATACAAATAA

Figure 39C, SEQ ID NO:79

Expression cassette number 1873 from 2X35S promoter to NOS terminator. Man99/pHluorin is underlined.

GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA

Figure 39C continued

```
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACAACGTTTTCTTTCACTG
AAGCGAAATCAAAGATCTCTTTGTGGACACGTAGTGCGGCGCCATTAAATAACGTGTACTTGTCCTATTCT
TGTCGGTGTGGTCTTGGGAAAAGAAAGCTTGCTGGAGGCTGCTGTTCAGCCCCATACATTACTTGTTACGA
TTCTGCTGACTTTCGGCGGGTGCAATATCTCTACTTCTGCTTGACGAGGTATTGTTGCCTGTACTTCTTTC
TTCTTCTTCTTGCTGATTGGTTCTATAAGAAATCTAGTATTTTCTTTGAAACAGAGTTTTCCCGTGGTTTT
CGAACTTGGAGAAAGATTGTTAAGCTTCTGTATATTCTGCCCAAATTTGTCGGGCCCATGGCGAGAGGGAG
CAGATCAGTGGGTAGCAGCAGCAGCAAATGGAGGTACTGCAACCCTTCCTATTACTTGAAGCGCCCAAAGC
GTCTTGCTCTGCTCTTCATCGTTTTCGTTTGTGTCTCTTTCGTTTTCTGGGACCGTCAAACTCTCGTCAGA
GAGCACCAGGTTGAAATTTCTGAGCTGCAGAAAGAAGTGACTGATTTGAAAAATTTGGTGGATGATTTAAA
TAACAAACAAGGTGGTACCTCTGGGAAGACTGACTTGGGGAGAAAAGCTACCAAGTCCAGTAAAGACGTCA
GTAAAGGAGAAGAACTTTTCACTGGAGTTGTCCCAATTCTTGTTGAATTAGATGGTGATGTTAATGGGCAC
AAATTTTCTGTCAGTGGAGAGGGTGAAGGTGATGCAACATACGGAAAACTTACCCTTAAATTTATTTGCAC
TACTGGAAAACTACCTGTTCCATGGCCAACACTTGTCACTACTTTCTCTTATGGTGTTCAATGCTTTTCAA
GATACCCAGATCATATGAAACGGCATGACTTTTTCAAGAGTGCCATGCCCGAAGGTTATGTACAGGAAAGA
ACTATATTTTTCAAAGATGACGGGAACTACAAGACACGTGCTGAAGTCAAGTTTGAAGGTGATACCCTTGT
TAATAGAATCGAGTTAAAAGGTATTGATTTTAAAGATGATGGAAACATTCTTGGACACAAATTGGAATACA
ACTATAACGAGCACTTGGTGTACATCATGGCAGACAAACAAAAGAATGGTACCAAAGCTATCTTTCAAGTT
CACCACAACATTGAAGATGGAGGCGTTCAACTAGCAGACCATTATCAACAAAATACTCCAATTGGCGATGG
CCCTGTCCTTTTACCAGACAACCATTACCTGCACACACAATCTGCCCTTTCGAAAGATCCCAACGAAAAGA
GAGACCACATGGTCCTTCTTGAGTTTGTAACAGCTGCTGGGATTACACATGGCATGGATGAACTATACAAA
TAAAGGCCTATTTTCTTTAGTTTGAATTTACTGTTATTCGGTGTGCATTTCTATGTTTGGTGAGCGGTTTT
CTGTGCTCAGAGTGTGTTTATTTTATGTAATTTAATTTCTTTGTGAGCTCCTGTTTAGCAGGTCGTCCCTT
CAGCAAGGACACAAAAAGATTTTAATTTTATTAAAAAAAAAAAAAAAAAGACCGGGAATTCGATATCAAG
CTTATCGACCTGCAGATCGTTCAAACATTTGGCAATAAAGTTTCTTAAGATTGAATCCTGTTGCCGGTCTT
GCGATGATTATCATATAATTTCTGTTGAATTACGTTAAGCATGTAATAATTAACATGTAATGCATGACGTT
ATTTATGAGATGGGTTTTTATGATTAGAGTCCCGCAATTATACATTTAATACGCGATAGAAAACAAAATAT
AGCGCGCAAACTAGGATAAATTATCGCGCGCGGTGTCATCTATGTTACTAGAT
```

Figure 39D, SEQ ID NO:80

Amino acid sequence of Man99/pHluorin

```
MARGSRSVGSSSSKWRYCNPSYYLKRPKRLALLFIVFVCVSFVFWDRQTLVREHQVEISELQKEVTDLKNL
VDDLNNKQGGTSGKTDLGRKATKSSKDVSKGEELFTGVVPILVELDGDVNGHKFSVSGEGEGDATYGKLTL
KFICTTGKLPVPWPTLVTTFSYGVQCFSRYPDHMKRHDFFKSAMPEGYVQERTIFFKDDGNYKTRAEVKFE
GDTLVNRIELKGIDFKDDGNILGHKLEYNYNEHLVYIMADKQKNGTKAIFQVHHNIEDGGVQLADHYQQNT
PIGDGPVLLPDNHYLHTQSALSKDPNEKRDHMVLLEFVTAAGITHGMDELYK
```

Schematic representation of construct number 1873

Man99TMD23-pHluorin: 2X35S/CPMV-HT/ PDISP/ Man99TMD23/ pHluorin/NOS (Construct number 1874)

Figure 40A, SEQ ID NO:81

Nucleotide sequence of Man99TMD23/pHluorin

```
ATGGCGAGAGGGAGCAGATCAGTGGGTAGCAGCAGCAGCAAATGGAGGTACTGCAACCCTTCCTATTACTT
GAAGCGCCCAAAGCGTCTTGCTCTGCTCTTCATCGTTTTCGTTTGTGTCTCTTTCGTTTTCTGGTGTGTCT
CTTTCGTTTTCTGGGACCGTCAAACTCTCGTCAGAGAGCACCAGGTTGAAATTTCTGAGCTGCAGAAAGAA
GTGACTGATTTGAAAAATTTGGTGGATGATTTAAATAACAAACAAGGTGGTACCTCTGGGAAGACTGACTT
GGGGAGAAAAGCTACCAAGTCCAGTAAAGACGTCAGTAAAGGAGAAGAACTTTTCACTGGAGTTGTCCCAA
TTCTTGTTGAATTAGATGGTGATGTTAATGGGCACAAATTTTCTGTCAGTGGAGAGGGTGAAGGTGATGCA
ACATACGGAAAACTTACCCTTAAATTTATTTGCACTACTGGAAAACTACCTGTTCCATGGCCAACACTTGT
CACTACTTTCTCTTATGGTGTTCAATGCTTTTCAAGATACCCAGATCATATGAAACGGCATGACTTTTTCA
AGAGTGCCATGCCCGAAGGTTATGTACAGGAAAGAACTATATTTTTCAAAGATGACGGGAACTACAAGACA
CGTGCTGAAGTCAAGTTTGAAGGTGATACCCTTGTTAATAGAATCGAGTTAAAAGGTATTGATTTTAAAGA
TGATGGAAACATTCTTGGACACAAATTGGAATACAACTATAACGAGCACTTGGTGTACATCATGGCAGACA
AACAAAAGAATGGTACCAAAGCTATCTTTCAAGTTCACCACAACATTGAAGATGGAGGCGTTCAACTAGCA
GACCATTATCAACAAAATACTCCAATTGGCGATGGCCCTGTCCTTTTACCAGACAACCATTACCTGCACAC
ACAATCTGCCCTTTCGAAAGATCCCAACGAAAAGAGAGACCACATGGTCCTTCTTGAGTTTGTAACAGCTG
CTGGGATTACACATGGCATGGATGAACTATACAAATAA
```

Figure 40B, SEQ ID NO:82

Expression cassette number 1874 from 2X35S promoter to NOS terminator. Man99TMD23/pHluorin is underlined.

```
GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACAACGTTTTCTTTCACTG
AAGCGAAATCAAAGATCTCTTTGTGGACACGTAGTGCGGCGCCATTAAATAACGTGTACTTGTCCTATTCT
TGTCGGTGTGGTCTTGGGAAAAGAAAGCTTGCTGGAGGCTGCTGTTCAGCCCCATACATTACTTGTTACGA
```

Figure 40B continued

```
TTCTGCTGACTTTCGGCGGGTGCAATATCTCTACTTCTGCTTGACGAGGTATTGTTGCCTGTACTTCTTTC
TTCTTCTTCTTGCTGATTGGTTCTATAAGAAATCTAGTATTTTCTTTGAAACAGAGTTTTCCCGTGGTTTT
CGAACTTGGAGAAAGATTGTTAAGCTTCTGTATATTCTGCCCAAATTTGTCGGGCCCATGGCGAGAGGGAG
CAGATCAGTGGGTAGCAGCAGCAGCAAATGGAGGTACTGCAACCCTTCCTATTACTTGAAGCGCCCAAAGC
GTCTTGCTCTGCTCTTCATCGTTTTCGTTTGTGTCTCTTTCGTTTTCTGGTGTGTCTCTTTCGTTTTCTGG
GACCGTCAAACTCTCGTCAGAGAGCACCAGGTTGAAATTTCTGAGCTGCAGAAAGAAGTGACTGATTTGAA
AAATTTGGTGGATGATTTAAATAACAAACAAGGTGGTACCTCTGGGAAGACTGACTTGGGGAGAAAAGCTA
CCAAGTCCAGTAAAGACGTCAGTAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTGATGCAACATACGGAAAACT
TACCCTTAAATTTATTTGCACTACTGGAAAACTACCTGTTCCATGGCCAACACTTGTCACTACTTTCTCTT
ATGGTGTTCAATGCTTTTCAAGATACCCAGATCATATGAAACGGCATGACTTTTTCAAGAGTGCCATGCCC
GAAGGTTATGTACAGGAAAGAACTATATTTTTCAAAGATGACGGGAACTACAAGACACGTGCTGAAGTCAA
GTTTGAAGGTGATACCCTTGTTAATAGAATCGAGTTAAAAGGTATTGATTTTAAAGATGATGGAAACATTC
TTGGACACAAATTGGAATACAACTATAACGAGCACTTGGTGTACATCATGGCAGACAAACAAAAGAATGGT
ACCAAAGCTATCTTTCAAGTTCACCACAACATTGAAGATGGAGGCGTTCAACTAGCAGACCATTATCAACA
AAATACTCCAATTGGCGATGGCCCTGTCCTTTTACCAGACAACCATTACCTGCACACACAATCTGCCCTTT
CGAAAGATCCCAACGAAAAGAGAGACCACATGGTCCTTCTTGAGTTTGTAACAGCTGCTGGGATTACACAT
GGCATGGATGAACTATACAAATAAAGGCCTATTTTCTTTAGTTTGAATTTACTGTTATTCGGTGTGCATTT
CTATGTTTGGTGAGCGGTTTTCTGTGCTCAGAGTGTGTTTATTTTATGTAATTTAATTTCTTTGTGAGCTC
CTGTTTAGCAGGTCGTCCCTTCAGCAAGGACACAAAAGATTTTAATTTTATTAAAAAAAAAAAAAAAAAAA
GACCGGGAATTCGATATCAAGCTTATCGACCTGCAGATCGTTCAAACATTTGGCAATAAAGTTTCTTAAGA
TTGAATCCTGTTGCCGGTCTTGCGATGATTATCATATAATTTCTGTTGAATTACGTTAAGCATGTAATAAT
TAACATGTAATGCATGACGTTATTTATGAGATGGGTTTTTATGATTAGAGTCCCGCAATTATACATTTAAT
ACGCGATAGAAAACAAAATATAGCGCGCAAACTAGGATAAATTATCGCGCGCGGTGTCATCTATGTTACTA
GAT
```

Figure 40C, SEQ ID NO:83

Amino acid sequence of Man99TMD23/pHluorin

```
MARGSRSVGSSSSKWRYCNPSYYLKRPKRLALLFIVFVCVSFVFWCVSFVFWDRQTLVREHQVEISELQKE
VTDLKNLVDDLNNKQGGTSGKTDLGRKATKSSKDVSKGEELFTGVVPILVELDGDVNGHKFSVSGEGEGDA
TYGKLTLKFICTTGKLPVPWPTLVTTFSYGVQCFSRYPDHMKRHDFFKSAMPEGYVQERTIFFKDDGNYKT
RAEVKFEGDTLVNRIELKGIDFKDDGNILGHKLEYNYNEHLVYIMADQKNGTKAIFQVHHNIEDGGVQLA
DHYQQNTPIGDGPVLLPDNHYLHTQSALSKDPNEKRDHMVLLEFVTAAGITHGMDELYK
```

Schematic representation of construct number 1874

SEQUENCE LISTING

```
<160> NUMBER OF SEQ ID NOS: 110

<210> SEQ ID NO 1
<211> LENGTH: 5
<212> TYPE: PRT
<213> ORGANISM: Artificial Sequence
<220> FEATURE:
<223> OTHER INFORMATION: proton channel signature sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 1

His Xaa Xaa Xaa Trp
1               5

<210> SEQ ID NO 2
<211> LENGTH: 41
<212> TYPE: DNA
<213> ORGANISM: Artificial Sequence
<220> FEATURE:
<223> OTHER INFORMATION: primer IF-H5A-I-05.s1+3c

<400> SEQUENCE: 2
aaatttgtcg ggcccatgga gaaaatagtg cttcttcttg c                          41

<210> SEQ ID NO 3
<211> LENGTH: 50
<212> TYPE: DNA
<213> ORGANISM: Artificial Sequence
<220> FEATURE:
<223> OTHER INFORMATION: primer IF-H5dTm.r

<400> SEQUENCE: 3
actaaagaaa ataggccttt aaatgcaaat tctgcattgt aacgatccat                 50

<210> SEQ ID NO 4
<211> LENGTH: 4903
<212> TYPE: DNA
```

<213> ORGANISM: Artificial Sequence
<220> FEATURE:
<223> OTHER INFORMATION: Construct 1191

<400> SEQUENCE: 4

```
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacatttta cttgaacaaa      180
aatattcacc tactactgtt ataaatcatt attaaacatt agagtaaaga aatatggatg     240
ataagaacaa gagtagtgat attttgacaa caattttgtt gcaacatttg agaaaatttt     300
gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tatttttaaa attaaagtt gagtcatttg attaaacatg tgattattta     600
atgaattgat gaaagagttg gattaaagtt gtattagtaa ttagaatttg gtgtcaaatt     660
taatttgaca tttgatcttt tcctatatat tgccccatag agtcagttaa ctcattttta     720
tatttcatag atcaaataag agaaataacg gtatattaat ccctccaaaa aaaaaaacg      780
gtatatttac taaaaaatct aagccacgta ggaggataac aggatccccg taggaggata     840
acatccaatc caaccaatca caacaatcct gatgagataa cccactttaa gcccacgcat     900
ctgtggcaca tctacattat ctaaatcaca cattcttcca cacatctgag ccacacaaaa     960
accaatccac atctttatca cccattctat aaaaaatcac actttgtgag tctacacttt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatgaaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct gggggtttcgg gaaagttgta tttaagagat atctcagata cgacaggacg    1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaaggaga    1560
tgccctgaag gtactcaaac cttcgaaaaa gaaagcgagt aagttaaaat gcttcttcgt    1620
ctcctattta taatatggtt tgttattgtt aattttgttc ttgtagaaga gcttaattaa    1680
tcgttgttgt tatgaaatac tatttgtatg agatgaactg gtgtaatgta attcatttac    1740
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
cgacacactt gtctactcca aaaatatcaa agatacagtc tcagaagacc aaagggcaat    2220
```

```
tgagactttt caacaaaggg taatatccgg aaacctcctc ggattccatt gcccagctat    2280
ctgtcacttt attgtgaaga tagtggaaaa ggaaggtggc tcctacaaat gccatcattg    2340
cgataaagga aaggccatcg ttgaagatgc ctctgccgac agtggtccca agatggacc     2400 cccacccacg aggagcatcg tggaaaaaga agacgttcca accacgtctt caaagcaagt    2460
ggattgatgt gataacatgg tggagcacga cacacttgtc tactccaaaa atatcaaaga    2520
tacagtctca gaagaccaaa gggcaattga acttttcaa caagggtaa tatccggaaa      2580 cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atgacccccc acccacgagg agcatcgtgg aaaagaaga    2760 cgttccaacc acgtcttcaa agcaagtgga ttgatgtgat atctccactg acgtaaggga    2820
tgacgcacaa tcccactatc cttcgcaaga cccttcctct ataaaggaa gttcatttca    2880 tttggagagg tattaaaatc ttaataggtt ttgataaaag cgaacgtggg gaaacccgaa    2940
ccaaaccttc ttctaaactc tctctcatct ctcttaaagc aaacttctct cttgtctttc    3000
ttgcgtgagc gatcttcaac gttgtcagat cgtgcttcgg caccagtaca acgttttctt    3060
tcactgaagc gaaatcaaag atctctttgt ggacacgtag tgcggcgcca ttaaataacg    3120
tgtacttgtc ctattcttgt cggtgtggtc ttgggaaaag aaagcttgct ggaggctgct    3180
gttcagcccc atacattact tgttacgatt ctgctgactt tcggcgggtg caatatctct    3240
acttctgctt gacgaggtat tgttgcctgt acttctttct tcttcttctt gctgattggt    3300
tctataagaa atctagtatt ttcttttgaaa cagagttttc ccgtggtttt cgaacttgga    3360
gaaagattgt taagcttctg tatattctgc ccaaatttgt cgggcccgcg gatggcgaaa    3420
aacgttgcga ttttcggctt attgttttct cttcttgtgt tggttccttc tcagatcttc    3480
gcctgcaggc tcctcagcca aaacgacacc cccatctgtc tatccactgg cccctggatc    3540
tgctgcccaa actaactcca tggtgaccct gggatgcctg gtcaagggct atttccctga    3600
gccagtgaca gtgacctgga actctggatc cctgtccagc ggtgtgcaca ccttcccagc    3660
tgtcctgcag tctgacctct acactctgag cagctcagtg actgtcccct ccagcacctg    3720
gcccagcgag accgtcacct gcaacgttgc ccacccggcc agcagcacca aggtggacaa    3780
gaaaattgtg cccagggatt gtggttgtaa gccttgcata tgtacagtcc cagaagtatc    3840
atctgtcttc atcttccccc caaagcccaa ggatgtgctc accattactc tgactcctaa    3900
ggtcacgtgt gttgtggtag acatcagcaa ggatgatccc gaggtccagt tcagctggtt    3960
tgtagatgat gtggaggtgc acacagctca gacgcaaccc cgggaggagc agttcaacag    4020
cactttccgc tcagtcagtg aacttcccat catgcaccag gactggctca atggcaagga    4080
gcgatcgctc accatcacca tcaccatcac catcaccatt aaaggcctat tttctttagt    4140
ttgaatttac tgttattcgg tgtgcatttc tatgtttggt gagcggtttt ctgtgctcag    4200
agtgtgttta ttttatgtaa tttaatttct ttgtgagctc ctgtttagca ggtcgtccct    4260
tcagcaagga cacaaaaaga ttttaatttt attaaaaaaa aaaaaaaaa agaccgggaa     4320 ttcgatatca agcttatcga cctgcagatc gttcaaacat ttggcaataa agtttcttaa    4380
gattgaatcc tgttgccggt cttgcgatga ttatcatata atttctgttg aattacgtta    4440
agcatgtaat aattaacatg taatgcatga cgttatttat gagatgggtt tttatgatta    4500
gagtcccgca attatacatt taatacgcga tagaaaacaa aatatagcgc gcaaactagg    4560
```

| | |
|---|---|
| ataaattatc gcgcgcggtg tcatctatgt tactagatct ctagagtctc aagcttggcg | 4620 |
| cgcccacgtg actagtggca ctggccgtcg ttttacaacg tcgtgactgg gaaaaccctg | 4680 |
| gcgttaccca acttaatcgc cttgcagcac atccccttt cgccagctgg cgtaatagcg | 4740 |
| aagaggcccg caccgatcgc ccttcccaac agttgcgcag cctgaatggc gaatgctaga | 4800 |
| gcagcttgag cttggatcag attgtcgttt cccgccttca gtttaaacta tcagtgtttg | 4860 |
| acaggatata ttggcgggta aacctaagag aaaagagcgt tta | 4903 |

<210> SEQ ID NO 5
<211> LENGTH: 3447
<212> TYPE: DNA
<213> ORGANISM: Artificial Sequence
<220> FEATURE:
<223> OTHER INFORMATION: Expression cassette number 489

<400> SEQUENCE: 5

| | |
|---|---|
| gtcaacatgg tggagcacga cacacttgtc tactccaaaa atatcaaaga tacagtctca | 60 |
| gaagaccaaa gggcaattga acttttcaa caaagggtaa tatccggaaa cctcctcgga | 120 |
| ttccattgcc cagctatctg tcactttatt gtgaagatag tggaaaagga aggtggctcc | 180 |
| tacaaatgcc atcattgcga taaggaaag gccatcgttg aagatgcctc tgccgacagt | 240 |
| ggtcccaaag atggaccccc acccacgagg agcatcgtgg aaaaagaaga cgttccaacc | 300 |
| acgtcttcaa gcaagtggga ttgatgtgat aacatggtgg agcacgacac acttgtctac | 360 |
| tccaaaaata tcaaagatac agtctcagaa gaccaaaggg caattgagac ttttcaacaa | 420 |
| agggtaatat ccgaaaacct cctcggattc cattgcccag ctatctgtca ctttattgtg | 480 |
| aagatagtgg aaaggaagg tggctcctac aaatgccatc attgcgataa aggaaaggcc | 540 |
| atcgttgaag atgcctctgc cgacagtggt cccaaagatg gaccccccacc cacgaggagc | 600 |
| atcgtggaaa aagaagacgt tccaaccacg tcttcaaagc aagtggattg atgtgatatc | 660 |
| tccactgacg taagggatga cgcacaatcc cactatcctt cgcaagaccc ttcctctata | 720 |
| taaggaagtt catttcattt ggagaggtat taaaatctta ataggttttg ataaaagcga | 780 |
| acgtggggaa acccgaacca aaccttcttc taaactctct ctcatctctc ttaaagcaaa | 840 |
| cttctctctt gtctttcttg cgtgagcgat cttcaacgtt gtcagatcgt gcttcggcac | 900 |
| cagtacaacg ttttctttca ctgaagcgaa atcaaagatc tctttgtgga cacgtagtgc | 960 |
| ggcgccatta ataacgtgt acttgtccta ttcttgtcgg tgtggtcttg ggaaaagaaa | 1020 |
| gcttgctgga ggctgctgtt cagccccata cattacttgt tacgattctg ctgactttcg | 1080 |
| gcgggtgcaa tatctctact tctgcttgac gaggtattgt tgcctgtact tctttcttct | 1140 |
| tcttcttgct gattggttct ataagaaatc tagtattttc tttgaaacag agttttcccg | 1200 |
| tggttttcga acttggagaa agattgttaa gcttctgtat attctgccca aatttgtcgg | 1260 |
| gcccatggag aaaatagtgc ttcttcttgc aatagtcagt cttgttaaaa gtgatcagat | 1320 |
| ttgcattggt taccatgcaa acaattcaac agagcaggtt gacacaatca tggaaaagaa | 1380 |
| cgttactgtt acacatgccc aagacatact ggaaaagaca cacacggga agctctgcga | 1440 |
| tctagatgga gtgaagcctc aattttaag agattgtagt gtagctggat ggctcctcgg | 1500 |
| gaacccaatg tgtgacgaat tcatcaatgt accggaatgg tcttacatag tggagaaggc | 1560 |
| caatccaacc aatgacctct gttacccagg gagtttcaac gactatgaag aactgaaaca | 1620 |
| cctattgagc agaataaacc attttgagaa aattcaaatc atccccaaaa gttcttggtc | 1680 |
| cgatcatgaa gcctcatcag gagttagctc agcatgtcca tacctgggaa gtccctcctt | 1740 |

```
ttttagaaat gtggtatggc ttatcaaaaa gaacagtaca tacccaacaa taaagaaaag    1800
ctacaataat accaaccaag aggatctttt ggtactgtgg ggaattcacc atcctaatga    1860
tgcggcagag cagacaaggc tatatcaaaa cccaaccacc tatatttcca ttgggacatc    1920
aacactaaac cagagattgg taccaaaaat agctactaga tccaaagtaa acgggcaaag    1980
tggaaggatg gagttcttct ggacaatttt aaaacctaat gatgcaatca acttcgagag    2040
taatggaaat ttcattgctc cagaatatgc atacaaaatt gtcaagaaag ggactcagc     2100 aattatgaaa agtgaattgg aatatggtaa ctgcaacacc aagtgtcaaa ctccaatggg    2160
ggcgataaac tctagtatgc cattccacaa catacaccct ctcaccatcg ggaatgccc     2220 caaatatgtg aaatcaaaca gattagtcct tgcaacaggg ctcagaaata gccctcaaag    2280
agagagcaga agaaaaaaga gaggactatt tggagctata gcaggttta tagagggagg    2340 atggcaggga atggtagatg gttggtatgg gtaccaccat agcaatgagc aggggagtgg    2400
gtacgctgca gacaaagaat ccactcaaaa ggcaatagat ggagtcacca ataaggtcaa    2460
ctcaatcatt gacaaaatga acactcagtt tgaggccgtt ggaagggaat taataacttt    2520
agaaaggaga atagagaatt aaacaagaa gatggaagac gggtttctag atgtctggac    2580
ttataatgcc gaacttctgg ttctcatgga aaatgagaga actctagact tcatgactc     2640 aaatgttaag aacctctacg acaaggtccg actacagctt agggataatg caaaggagct    2700
gggtaacggt tgtttcgagt tctatcacaa atgtgataat aatgtatgg aaagtataag    2760 aaacggaacg tacaactatc cgcagtattc agaagaagca agattaaaaa gagaggaaat    2820
aagtggggta aaattggaat caataggaac ttaccaaata ctgtcaattt attcaacagt    2880
ggcgagttcc ctagcactgg caatcatgat ggctggtcta tctttatgga tgtgctccaa    2940
tggatcgtta caatgcagaa tttgcattta aaggcctatt ttctttagtt tgaatttact    3000
gttattcggt gtgcatttct atgtttggtg agcggttttc tgtgctcaga gtgtgtttat    3060
tttatgtaat ttaatttctt tgtgagctcc tgtttagcag gtcgtccctt cagcaaggac    3120
acaaaaagat tttaatttta ttaaaaaaaa aaaaaaaaa gaccgggaat tcgatatcaa    3180
gcttatcgac ctgcagatcg ttcaaacatt tggcaataaa gtttcttaag attgaatcct    3240
gttgccggtc ttgcgatgat tatcatataa tttctgttga attacgttaa gcatgtaata    3300
attaacatgt aatgcatgac gttatttatg agatgggttt ttatgattag agtcccgcaa    3360
ttatacattt aatacgcgat agaaaacaaa atatagcgcg caaactagga taaattatcg    3420
cgcgcggtgt catctatgtt actagat                                        3447
```

<210> SEQ ID NO 6
<211> LENGTH: 568
<212> TYPE: PRT
<213> ORGANISM: Influenza virus

<400> SEQUENCE: 6

```
Met Glu Lys Ile Val Leu Leu Ala Ile Val Ser Leu Val Lys Ser
 1               5                  10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
        50                  55                  60
```

```
Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
             85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
```

```
                    485                 490                 495
Ser Ile Arg Asn Gly Thr Tyr Asn Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 7
<211> LENGTH: 42
<212> TYPE: DNA
<213> ORGANISM: Artificial Sequence
<220> FEATURE:
<223> OTHER INFORMATION: primer IF-S1-M1+M2ANC.c

<400> SEQUENCE: 7

```
aaatttgtcg ggcccatgag tcttctaacc gaggtcgaaa cg                42
```

<210> SEQ ID NO 8
<211> LENGTH: 43
<212> TYPE: DNA
<213> ORGANISM: Artificial Sequence
<220> FEATURE:
<223> OTHER INFORMATION: primer IF-S1-4-M2ANC.r

<400> SEQUENCE: 8

```
actaaagaaa ataggccttt actccagctc tatgctgaca aaa               43
```

<210> SEQ ID NO 9
<211> LENGTH: 294
<212> TYPE: DNA
<213> ORGANISM: Artificial Sequence
<220> FEATURE:
<223> OTHER INFORMATION: nucleotide sequence of synthesized M2 gene
      (DQ508860)

<400> SEQUENCE: 9

```
atgagtcttc taaccgaggt cgaaacgcct atcagaaacg aatggggtg cagatgcaac      60 gattcaagtg atcctcttgt tgttgccgca agtataattg ggattgtgca cctgatattg    120
tggattattg atcgcctttt ttccaaaagc atttatcgta tctttaaaca cggtttaaaa    180
agagggcctt ctacggaagg agtaccagag tctatgaggg aagaatatcg agaggaacag    240
cagaatgctg tggatgctga cgatggtcat tttgtcagca tagagctgga gtaa           294
```

<210> SEQ ID NO 10
<211> LENGTH: 2034
<212> TYPE: DNA
<213> ORGANISM: Artificial Sequence
<220> FEATURE:
<223> OTHER INFORMATION: Expression cassette number 1261

<400> SEQUENCE: 10

```
gtcaacatgg tggagcacga cacacttgtc tactccaaaa atatcaaaga tacagtctca      60
gaagaccaaa gggcaattga cttttcaa caaagggtaa tatccggaaa cctcctcgga      120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
```

```
ggtcccaaag atggacccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaggaagg tggctcctac aaatgccatc attgcgataa aggaaaggcc    540
atcgttgaag atgcctctgc cgacagtggt cccaaagatg acccccacc acgaggagc     600
atcgtggaaa agaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta ataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatgagt cttctaaccg aggtcgaaac gcctatcaga aacgaatggg ggtgcagatg   1320
caacgattca agtgatcctc ttgttgttgc cgcaagtata attgggattg tgcacctgat   1380
attgtggatt attgatcgcc ttttttccaa aagcatttat cgtatcttta aacacggttt   1440
aaaaagaggg ccttctacgg aaggagtacc agagtctatg agggaagaat atcgagagga   1500
acagcagaat gctgtggatg ctgacgatgg tcattttgtc agcatagagc tggagtaaag   1560
gcctattttc tttagtttga atttactgtt attcggtgtg catttctatg tttggtgagc   1620
ggttttctgt gctcagagtg tgtttatttt atgtaattta atttctttgt gagctcctgt   1680
ttagcaggtc gtccccttcag caaggacaca aaagattt aatttattat aaaaaaaaa    1740
aaaaaaagac cgggaattcg atatcaagct tatcgacctg cagatcgttc aaacatttgg   1800
caataaagtt tcttaagatt gaatcctgtt gccggtcttg cgatgattat catataattt   1860
ctgttgaatt acgttaagca tgtaataatt aacatgtaat gcatgacgtt atttatgaga   1920
tgggttttta tgattagagt cccgcaatta tacatttaat acgcgataga aaacaaaata   1980
tagcgcgcaa actaggataa attatcgcgc gcggtgtcat ctatgttact agat          2034
```

<210> SEQ ID NO 11
<211> LENGTH: 97
<212> TYPE: PRT
<213> ORGANISM: Influenza virus

<400> SEQUENCE: 11

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Val His Leu Ile Leu Trp Ile Ile Asp Arg Leu Phe Ser
35 40 45

Lys Ser Ile Tyr Arg Ile Phe Lys His Gly Leu Lys Arg Gly Pro Ser

| | 50 | | 55 | | | 60 | | | | | |
|---|---|---|---|---|---|---|---|---|---|---|---|
Thr Glu Gly Val Pro Glu Ser Met Arg Glu Glu Tyr Arg Glu Glu Gln
65                      70                      75                      80

Gln Asn Ala Val Asp Ala Asp Asp Gly His Phe Val Ser Ile Glu Leu
                  85                      90                      95

Glu

<210> SEQ ID NO 12
<211> LENGTH: 294
<212> TYPE: DNA
<213> ORGANISM: Artificial Sequence
<220> FEATURE:
<223> OTHER INFORMATION: nucleotide sequence of synthesized M2 gene

<400> SEQUENCE: 12

```
atgagtcttc taaccgaggt cgaaacgcct atcagaaacg aatgggggtg cagatgcaac      60
ggttcaagtg atcctctcac tattgccgca aatatcattg gatcttgca cttgacattg     120 tggattcttg atcgtctttt tttcaaatgc atttaccgtc gctttaaata cggactgaaa     180
ggagggcctt ctacggaagg agtgccaaag tctatgaggg aagaatatcg aaaggaacag     240
cagagtgctg tggatgctga cgatggtcat tttgtcagca tagagctgga gtaa           294
```

<210> SEQ ID NO 13
<211> LENGTH: 2034
<212> TYPE: DNA
<213> ORGANISM: Artificial Sequence
<220> FEATURE:
<223> OTHER INFORMATION: Expression cassette number 859

<400> SEQUENCE: 13

```
gtcaacatgg tggagcacga cacacttgtc tactccaaaa atatcaaaga tacagtctca      60
gaagaccaaa gggcaattga acttttcaa caaagggtaa tatccggaaa cctcctcgga     120
ttccattgcc cagctatctg tcactttatt gtgaagatag tggaaaagga aggtggctcc     180
tacaaatgcc atcattgcga taaggaaag gccatcgttg aagatgcctc tgccgacagt     240
ggtcccaaag atggaccccc acccacgagg agcatcgtgg aaaaagaaga cgttccaacc     300
acgtcttcaa gcaagtgga ttgatgtgat aacatggtgg agcacgacac acttgtctac     360
tccaaaaata tcaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa ggaaaggcc     540 atcgttgaag atgcctctgc cgacagtggt cccaaagatg gacccccacc cacgaggagc     600
atcgtggaaa aagaagacgt tccaaccacg tcttcaaagc aagtggattg atgtgatatc     660
tccactgacg taagggatga cgcacaatcc cactatcctt cgcaagaccc ttcctctata     720
taaggaagtt catttcattt ggagaggtat aaaatctta ataggttttg ataaaagcga     780
acgtggggaa acccgaacca aaccttcttc taaactctct ctcatctctc ttaaagcaaa     840
cttctctctt gtcttctctt gcgtgagcgat cttcaacgtt gtcagatcgt gcttcggcac     900
cagtacaacg ttttctttca ctgaagcgaa atcaaagatc tctttgtgga cacgtagtgc     960
ggcgccatta ataacgtgt acttgtccta ttcttgtcgg tgtggtcttg ggaaaagaaa    1020
gcttgctgga ggctgctgtt cagccccata cattacttgt tacgattctg ctgactttcg    1080
gcgggtgcaa tatctctact tctgcttgac gaggtattgt tgcctgtact ctttcttct    1140 tcttcttgct gattggttct ataagaaatc tagtatttc tttgaaacag agttttcccg    1200
```

```
tggttttcga acttggagaa agattgttaa gcttctgtat attctgccca aatttgtcgg    1260
gcccatgagt cttctaaccg aggtcgaaac gcctatcaga aacgaatggg ggtgcagatg    1320
caacggttca agtgatcctc tcactattgc cgcaaatatc attgggatct gcacttgac    1380 attgtggatt cttgatcgtc ttttttttcaa atgcatttac cgtcgcttta atacggact    1440 gaaaggaggg ccttctacgg aaggagtgcc aaagtctatg agggaagaat atcgaaagga    1500
acagcagagt gctgtggatg ctgacgatgg tcattttgtc agcatagagc tggagtaaag    1560
gcctattttc tttagtttga atttactgtt attcggtgtg catttctatg tttggtgagc    1620
ggttttctgt gctcagagtg tgtttatttt atgtaattta atttctttgt gagctcctgt    1680
ttagcaggtc gtcccttcag caaggacaca aaaagatttt aatttttatta aaaaaaaaa    1740 aaaaaaagac cgggaattcg atatcaagct tatcgacctg cagatcgttc aaacatttgg    1800
caataaagtt tcttaagatt gaatcctgtt gccggtcttg cgatgattat catataattt    1860
ctgttgaatt acgttaagca tgtaataatt aacatgtaat gcatgacgtt atttatgaga    1920
tgggttttta tgattagagt cccgcaatta tacatttaat acgcgataga aaacaaaata    1980
tagcgcgcaa actaggataa attatcgcgc gcggtgtcat ctatgttact agat          2034
```

<210> SEQ ID NO 14
<211> LENGTH: 97
<212> TYPE: PRT
<213> ORGANISM: Influenza virus

<400> SEQUENCE: 14

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 15
<211> LENGTH: 46
<212> TYPE: DNA
<213> ORGANISM: Artificial Sequence
<220> FEATURE:
<223> OTHER INFORMATION: primer IF-H1A-C-09.s2+4c

<400> SEQUENCE: 15
tctcagatct tcgccgacac attatgtata ggttatcatg cgaaca                46

<210> SEQ ID NO 16
<211> LENGTH: 49
<212> TYPE: DNA
<213> ORGANISM: Artificial Sequence
<220> FEATURE:
<223> OTHER INFORMATION: primer IF-H1A-C-09.s1-4r

<400> SEQUENCE: 16

```
actaaagaaa ataggccttt aaatacatat tctacactgt agagaccca         49
```

```
<210> SEQ ID NO 17
<211> LENGTH: 1701
<212> TYPE: DNA
<213> ORGANISM: Artificial Sequence
<220> FEATURE:
<223> OTHER INFORMATION: nucleotide sequence of synthesized H1 gene

<400> SEQUENCE: 17
atgaaggcaa tactagtagt tctgctatat acatttgcaa ccgcaaatgc agacacatta    60
tgtataggtt atcatgcgaa caattcaaca gacactgtag acacagtact agaaaagaat   120
gtaacagtaa cacactctgt taaccttcta gaagacaagc ataacgggaa actatgcaaa   180
ctaagagggg tagccccatt gcatttgggt aaatgtaaca ttgctggctg gatcctggga   240
aatccagagt gtgaatcact ctccacagca agctcatggt cctacattgt ggaaacacct   300
agttcagaca tggaacgtg ttacccagga gatttcatcg attatgagga gctaagagag   360
caattgagct cagtgtcatc atttgaaagg tttgagatat cccccaagac aagttcatgg   420
cccaatcatg actcgaacaa aggtgtaacg gcagcatgtc ctcatgctgg agcaaaaagc   480
ttctacaaaa atttaatatg gctagttaaa aaggaaatt cataccaaa gctcagcaaa   540
tcctacatta atgataaagg gaagaagtc ctcgtgctat ggggcattca ccatccatct   600
actagtgctg accaacaaag tctctatcag aatgcagatg catatgtttt tgtggggtca   660
tcaagataca gcaagaagtt caagccggaa atagcaataa gacccaaagt gagggatcaa   720
gaagggagaa tgaactatta ctggacacta gtagagccgg gagacaaaat aacattcgaa   780
gcaactggaa atctagtggt accgagatat gcattcgcaa tggaaagaaa tgctggatct   840
ggtattatca tttcagatac accagtccac gattgcaata aacttgtca acacccaag   900
ggtgctataa acaccagcct cccattcag aatatacatc cgatcacaat tggaaaatgt   960
ccaaatatg taaaaagcac aaaattgaga ctggccacag gattgaggaa tatcccgtct  1020
attcaatcta gaggcctatt tgggccatt gccggtttca ttgaaggggg gtggacaggg  1080
atggtagatg gatggtacgg ttatcaccat caaaatgagc aggggtcagg atatgcagcc  1140
gacctgaaga gcacacagaa tgccattgac gagattacta acaaagtaaa ttctgttatt  1200
gaaaagatga atacacagtt cacagcagta ggtaaagagt tcaaccacct ggaaaaaga  1260
atagagaatt taaataaaaa agttgatgat ggtttcctgg acatttggac ttacaatgcc  1320
gaactgttgg ttctattgga aaatgaaaga actttggact accacgattc aaatgtgaag  1380
aacttatatg aaaaggtaag aagccagcta aaaaacaatg ccaaggaaat tggaaacggc  1440
tgctttgaat tttaccacaa atgcgataac acgtgcatgg aaagtgtcaa aaatgggact  1500
tatgactacc caaaatactc agaggaagca aaattaaaca gagaagaaat gatgggta   1560
aagctggaat caacaaggat ttaccagatt tggcgatct attcaactgt cgccagttca  1620
ttggtactgg tagtctccct gggggcaatc agtttctgga tgtgctctaa tgggtctcta  1680
cagtgtagaa tatgtattta a                                           1701
```

```
<210> SEQ ID NO 18
<211> LENGTH: 4897
<212> TYPE: DNA
<213> ORGANISM: Artificial Sequence
<220> FEATURE:
<223> OTHER INFORMATION: Construct 1192

<400> SEQUENCE: 18
```

```
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacattttta cttgaacaaa     180
aatattcacc tactactgtt ataaatcatt attaaacatt agagtaaaga aatatggatg     240
ataagaacaa gagtagtgat attttgacaa caattttgtt gcaacatttg agaaaatttt     300
gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tattttttaaa attaaaagtt gagtcatttg attaaacatg tgattattta     600
atgaattgat gaaagagttg gattaaagtt gtattagtaa ttagaatttg gtgtcaaatt     660
taatttgaca tttgatcttt tcctatatat tgccccatag agtcagttaa ctcatttta      720 tatttcatag atcaaataag agaaataacg gtatattaat ccctccaaaa aaaaaaacg      780 gtatatttac taaaaaatct aagccacgta ggaggataac aggatccccg taggaggata     840
acatccaatc caaccaatca caacaatcct gatgagataa cccactttaa gcccacgcat     900
ctgtggcaca tctacattat ctaaatcaca cattcttcca cacatctgag ccacacaaaa     960
accaatccac atctttatca cccattctat aaaaaatcac actttgtgag tctacacttt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatggaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct ggggtttcgg gaaagttgta tttaagagat atctcagata cgacaggacg    1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaagagga    1560
tgccctgaag gtactcaaac cttcgaaaaa gaaagcgagt aagttaaaat gcttcttcgt    1620
ctcctattta taatatggtt tgttattgtt aattttgttc ttgtagaaga gcttaattaa    1680
tcgttgttgt tatgaaatac tatttgtatg agatgaactg gtgtaatgta attcatttac    1740
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
cgacacactt gtctactcca aaaatatcaa agatacagtc tcagaagacc aaagggcaat    2220
tgagactttt caacaaaggg taatatccgg aaacctcctc ggattccatt gcccagctat    2280
ctgtcacttt attgtgaaga tagtggaaaa ggaaggtggc tcctacaaat gccatcattg    2340
```

```
cgataaagga aaggccatcg ttgaagatgc ctctgccgac agtggtccca aagatggacc    2400
cccacccacg aggagcatcg tggaaaaaga agacgttcca accacgtctt caaagcaagt    2460
ggattgatgt gataacatgg tggagcacga cacacttgtc tactccaaaa atatcaaaga    2520
tacagtctca gaagaccaaa gggcaattga gacttttcaa caaagggtaa tatccggaaa    2580
cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atggaccccc acccacgagg agcatcgtgg aaaaagaaga    2760
cgttccaacc acgtcttcaa agcaagtgga ttgatgtgat atctccactg acgtaaggga    2820
tgacgcacaa tcccactatc cttcgcaaga cccttcctct atataaggaa gttcatttca    2880
tttggagagg tattaaaatc ttaataggtt ttgataaaag cgaacgtggg gaaacccgaa    2940
ccaaaccttc ttctaaactc tctctcatct ctcttaaagc aaacttctct cttgtctttc    3000
ttgcgtgagc gatcttcaac gttgtcagat cgtgcttcgg caccagtaca acgttttctt    3060
tcactgaagc gaaatcaaag atctctttgt ggacacgtag tgcggcgcca ttaaataacg    3120
tgtacttgtc ctattcttgt cggtgtggtc ttgggaaaag aaagcttgct ggaggctgct    3180
gttcagcccc atacattact tgttacgatt ctgctgactt tcggcgggtg caatatctct    3240
acttctgctt gacgaggtat tgttgcctgt acttctttct tcttcttctt gctgattggt    3300
tctataagaa atctagtatt ttcttgaaa cagagttttc ccgtggtttt cgaacttgga    3360
gaaagattgt taagcttctg tatattctgc ccaaatttgt cgggcccatg gcgaaaaacg    3420
ttgcgatttt cggcttattg ttttctcttc ttgtgttggt tccttctcag atcttcgccg    3480
cggctcctca gccaaaacga caccccatc tgtctatcca ctggcccctg gatctgctgc    3540
ccaaactaac tccatggtga ccctgggatg cctggtcaag ggctatttcc ctgagccagt    3600
gacagtgacc tggaactctg gatccctgtc cagcggtgtg cacaccttcc cagctgtcct    3660
gcagtctgac ctctacactc tgagcagctc agtgactgtc ccctccagca cctggcccag    3720
cgagaccgtc acctgcaacg ttgcccaccc ggccagcagc accaaggtgg acaagaaaat    3780
tgtgcccagg gattgtggtt gtaagccttg catatgtaca gtcccagaag tatcatctgt    3840
cttcatcttc cccccaaagc ccaaggatgt gctcaccatt actctgactc ctaaggtcac    3900
gtgtgttgtg gtagacatca gcaaggatga tcccgaggtc cagttcagct ggtttgtaga    3960
tgatgtggag gtgcacacag ctcagacgca accccgggag gagcagttca acagcacttt    4020
ccgctcagtc agtgaacttc ccatcatgca ccaggactgg ctcaatggca aggagcgatc    4080
gctcaccatc accatcacca tcaccatcac cattaaaggc ctattttctt tagtttgaat    4140
ttactgttat tcggtgtgca tttctatgtt tggtgagcgg ttttctgtgc tcagagtgtg    4200 tttatttttat gtaatttaat ttcttttgtga gctcctgttt agcaggtcgt cccttcagca    4260
aggacacaaa aagattttaa ttttattaaa aaaaaaaaaa aaaagaccg ggaattcgat    4320 atcaagctta tcgacctgca gatcgttcaa acatttggca ataaagtttc ttaagattga    4380
atcctgttgc cggtcttgcg atgattatca tataatttct gttgaattac gttaagcatg    4440
taataattaa catgtaatgc atgacgttat ttatgagatg gtttttatg attagagtcc    4500 cgcaattata catttaatac gcgatagaaa acaaaatata gcgcgcaaac taggataaat    4560
tatcgcgcgc ggtgtcatct atgttactag atctctagag tctcaagctt ggcgcgccca    4620
cgtgactagt ggcactggcc gtcgttttac aacgtcgtga ctgggaaaac cctggcgtta    4680
cccaacttaa tcgccttgca gcacatcccc ctttcgccag ctggcgtaat agcgaagagg    4740
```

```
cccgcaccga tcgcccttcc caacagttgc gcagcctgaa tggcgaatgc tagagcagct    4800
tgagcttgga tcagattgtc gtttcccgcc ttcagtttaa actatcagtg tttgacagga    4860
tatattggcg ggtaaaccta agagaaaaga gcgttta                             4897

<210> SEQ ID NO 19
<211> LENGTH: 3462
<212> TYPE: DNA
<213> ORGANISM: Artificial Sequence
<220> FEATURE:
<223> OTHER INFORMATION: Expression cassette number 484

<400> SEQUENCE: 19
gtcaacatgg tggagcacga cacacttgtc tactccaaaa atatcaaaga tacagtctca      60
gaagaccaaa gggcaattga acttttcaa caaagggtaa tatccggaaa cctcctcgga     120
ttccattgcc cagctatctg tcactttatt gtgaagatag tggaaaagga aggtggctcc     180
tacaaatgcc atcattgcga taaggaaag gccatcgttg aagatgcctc tgccgacagt     240
ggtcccaaag atggaccccc acccacgagg agcatcgtgg aaaaagaaga cgttccaacc     300
acgtcttcaa agcaagtgga ttgatgtgat aacatggtgg agcacgacac acttgtctac     360
tccaaaaata tcaaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa ggaaaggcc     540 atcgttgaag atgcctctgc cgacagtggt cccaaagatg gaccccacc acgaggagc     600 atcgtggaaa agaagacgt tccaaccacg tcttcaaagc aagtggattg atgtgatatc     660
tccactgacg taagggatga cgcacaatcc cactatcctt cgcaagaccc ttcctctata     720
taaggaagtt catttcattt ggagaggtat taaaatctta ataggttttg ataaaagcga     780
acgtggggaa acccgaacca aaccttcttc taaactctct ctcatctctc ttaaagcaaa     840
cttctctctt gtctttcttg cgtgagcgat cttcaacgtt gtcagatcgt gcttcggcac     900
cagtacaacg ttttctttca ctgaagcgaa atcaaagatc tctttgtgga cacgtagtgc     960
ggcgccatta ataacgtgt acttgtccta ttcttgtcgg tgtggtcttg ggaaaagaaa    1020
gcttgctgga ggctgctgtt cagccccata cattacttgt tacgattctg ctgactttcg    1080
gcgggtgcaa tatctctact tctgcttgac gaggtattgt tgcctgtact tctttcttct    1140
tcttcttgct gattggttct ataagaaatc tagtattttc tttgaaacag agttttcccg    1200
tggttttcga acttggagaa agattgttaa gcttctgtat attctgccca aatttgtcgg    1260
gcccatggcg aaaaacgttg cgattttcgg cttattgttt tctcttcttg tgttggttcc    1320
ttctcagatc ttcgccgaca cattatgtat aggttatcat gcgaacaatt caacagacac    1380
tgtagacaca gtactagaaa agaatgtaac agtaacacac tctgttaacc ttctagaaga    1440
caagcataac gggaaactat gcaaactaag aggggtagcc ccattgcatt tgggtaaatg    1500
taacattgct ggctggatcc tgggaaatcc agagtgtgaa tcactctcca cagcaagctc    1560
atggtcctac attgtggaaa cacctagttc agacaatgga acgtgttacc caggagattt    1620
catcgattat gaggagctaa gagagcaatt gagctcagtg tcatcatttg aaaggtttga    1680
gatattcccc aagacaagtt catggcccaa tcatgactcg aacaaaggtg taacggcagc    1740
atgtcctcat gctggagcaa aaagcttcta caaaaattta atatggctag ttaaaaaagg    1800
aaattcatac ccaaagctca gcaaatccta cattaatgat aaagggaaag aagtcctcgt    1860
```

| | |
|---|---|
| gctatggggc attcaccatc catctactag tgctgaccaa caaagtctct atcagaatgc | 1920 |
| agatgcatat gttttgtgg ggtcatcaag atacagcaag aagttcaagc cggaaatagc | 1980 |
| aataagaccc aaagtgaggg atcaagaagg gagaatgaac tattactgga cactagtaga | 2040 |
| gccgggagag aaaataacat tcgaagcaac tggaaatcta gtggtaccga gatatgcatt | 2100 |
| cgcaatggaa agaaatgctg gatctggtat tatcatttca gatacaccag tccacgattg | 2160 |
| caatacaact tgtcaaacac ccaagggtgc tataaacacc agcctcccat ttcagaatat | 2220 |
| acatccgatc acaattggaa aatgtccaaa atatgtaaaa agcacaaaat tgagactggc | 2280 |
| cacaggattg aggaatatcc cgtctattca atctagaggc ctatttgggg ccattgccgg | 2340 |
| tttcattgaa gggggtgga cagggatggt agatggatgg tacggttatc accatcaaaa | 2400 |
| tgagcagggg tcaggatatg cagccgacct gaagagcaca cagaatgcca ttgacgagat | 2460 |
| tactaacaaa gtaaattctg ttattgaaaa gatgaataca cagttcacag cagtaggtaa | 2520 |
| agagttcaac cacctggaaa aagaataga gaatttaaat aaaaaagttg atgatggttt | 2580 |
| cctggacatt tggacttaca atgccgaact gttggttcta ttggaaaatg aaagaacttt | 2640 |
| ggactaccac gattcaaatg tgaagaactt atatgaaaag gtaagaagcc agctaaaaaa | 2700 |
| caatgccaag gaaattggaa acggctgctt tgaattttac cacaaatgcg ataacacgtg | 2760 |
| catggaaagt gtcaaaaatg ggacttatga ctacccaaaa tactcagagg aagcaaaatt | 2820 |
| aaacagagaa gaaatagatg gggtaaagct ggaatcaaca aggatttacc agattttggc | 2880 |
| gatctattca actgtcgcca gttcattggt actggtagtc tccctggggg caatcagttt | 2940 |
| ctggatgtgc tctaatgggt ctctacagtg tagaatatgt atttaaaggc ctattttctt | 3000 |
| tagtttgaat ttactgttat tcggtgtgca tttctatgtt tggtgagcgg tttctgtgc | 3060 |
| tcagagtgtg tttattttat gtaatttaat ttctttgtga gctcctgttt agcaggtcgt | 3120 |
| cccttcagca aggacacaaa aagatttaa ttttattaaa aaaaaaaaaa aaaagaccg | 3180 |
| ggaattcgat atcaagctta tcgacctgca gatcgttcaa acatttggca ataaagtttc | 3240 |
| ttaagattga atcctgttgc cggtcttgcg atgattatca tataatttct gttgaattac | 3300 |
| gttaagcatg taataattaa catgtaatgc atgacgttat ttatgagatg gttttatg | 3360 |
| attagagtcc cgcaattata catttaatac gcgatagaaa acaaaatata gcgcgcaaac | 3420 |
| taggataaat tatcgcgcgc ggtgtcatct atgttactag at | 3462 |

<210> SEQ ID NO 20
<211> LENGTH: 573
<212> TYPE: PRT
<213> ORGANISM: Influenza virus

<400> SEQUENCE: 20

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

```
Ala Ser Ser Trp Ser Tyr Ile Val Glu Thr Pro Ser Ser Asp Asn Gly
                100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
                180                 185                 190

Lys Gly Lys Glu Val Leu Val Leu Trp Gly Ile His His Pro Ser Thr
                195                 200                 205

Ser Ala Asp Gln Gln Ser Leu Tyr Gln Asn Ala Asp Ala Tyr Val Phe
                210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Ala Met Glu Arg Asn Ala Gly Ser Gly
                275                 280                 285

Ile Ile Ile Ser Asp Thr Pro Val His Asp Cys Asn Thr Thr Cys Gln
                290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
                435                 440                 445

Leu Leu Val Leu Leu Glu Asn Glu Arg Thr Leu Asp Tyr His Asp Ser
                450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
                500                 505                 510
```

```
Tyr Ser Glu Glu Ala Lys Leu Asn Arg Glu Glu Ile Asp Gly Val Lys
            515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

```
<210> SEQ ID NO 21
<211> LENGTH: 40
<212> TYPE: DNA
<213> ORGANISM: Artificial Sequence
<220> FEATURE:
<223> OTHER INFORMATION: primer IF-S2+S4-H3 Per.c

<400> SEQUENCE: 21
tctcagatct tcgcccaaaa acttcctgga aatgacaaca                   40

<210> SEQ ID NO 22
<211> LENGTH: 45
<212> TYPE: DNA
<213> ORGANISM: Artificial Sequence
<220> FEATURE:
<223> OTHER INFORMATION: primer IF-S1a4-H3 Per.r

<400> SEQUENCE: 22
actaaagaaa ataggccttc aaatgcaaat gttgcaccta atgtt            45

<210> SEQ ID NO 23
<211> LENGTH: 1701
<212> TYPE: DNA
<213> ORGANISM: Artificial Sequence
<220> FEATURE:
<223> OTHER INFORMATION: nucleotide sequence of synthesized H3 gene

<400> SEQUENCE: 23
atgaagacta tcattgcttt gagctacatt ctatgtctgg ttttcgctca aaaacttcct     60
ggaaatgaca cagcacggc aacgctgtgc cttgggcacc atgcagtacc aaacggaacg    120
atagtgaaaa caatcacgaa tgaccaaatt gaagttacta atgctactga gctggttcag    180
agttcctcaa caggtgaaat atgcgacagt cctcatcaga tccttgatgg aaaaaactgc    240
acactaatag atgctctatt gggagaccct cagtgtgatg gcttccaaaa taagaaatgg    300
gacctttttg ttgaacgcag caaagcctac agcaactgtt acccttatga tgtgccggat    360
tatgcctccc ttaggtcact agttgcctca tccggcacac tggagtttaa caatgaaagc    420
ttcaattgga ctggagtcac tcaaaacgga acaagctctg cttgcataag agatctaaa     480 aacagtttct ttagtagatt gaattggttg acccacttaa acttcaaata cccagcattg    540
aacgtgacta tgccaaacaa tgaacaattt gacaaattgt acatttgggg ggttcaccac    600
ccgggtacgg acaaagacca aatcttcctg tatgctcaag catcaggaag aatcacagtc    660
tctaccaaaa gaagccaaca aaccgtaagc ccgaatatcg gatctagacc cagagtaagg    720
aatatcccta gcagaataag catctattgg acaatagtaa accgggaga catactttg     780 attaacagca caggaatct aattgctcct agggggttact tcaaaatacg aagtgggaaa    840
agctcaataa tgagatcaga tgcacccatt ggcaaatgca attctgaatg catcactcca    900
aatggaagca ttcccaatga caaaccattc caaaatgtaa acaggatcac atacgggcc     960 tgtcccagat atgttaagca aaacactctg aaattggcaa cagggatgcg aaatgtacca    1020
```

```
gagaaacaaa ctagaggcat atttggcgca atcgcgggtt tcatagaaaa tggttgggag    1080
ggaatggtgg atggttggta cggtttcagg catcaaaatt ctgagggaag aggacaagca    1140
gcagatctca aaagcactca agcagcaatc gatcaaatca atgggaagct gaatagattg    1200
atcgggaaaa ccaacgagaa attccatcag attgaaaaag aattctcaga agtcgaaggg    1260
agaattcagg accttgagaa atatgttgag gacactaaaa tagatctctg gtcatacaac    1320
gcggagcttc ttgttgccct ggagaaccaa catacaattg atctaactga ctcagaaatg    1380
aacaaactgt ttgaaaaaac aaagaagcaa ctgagggaaa atgctgagga tatgggcaat    1440
ggttgtttca aaatatacca caaatgtgac aatgcctgca taggatcaat cagaaatgga    1500
acttatgacc acgatgtata cagagatgaa gcattaaaca accggtttca gatcaaggga    1560
gttgagctga gtcagggta caaagattgg atccctatgga tttcctttgc catatcatgt    1620 ttttttgcttt gtgttgcttt gttggggttc atcatgtggg cctgccaaaa aggcaacatt    1680
aggtgcaaca tttgcatttg a                                               1701
```

<210> SEQ ID NO 24
<211> LENGTH: 3465
<212> TYPE: DNA
<213> ORGANISM: Artificial Sequence
<220> FEATURE:
<223> OTHER INFORMATION: Expression cassette number 1019

<400> SEQUENCE: 24

```
gtcaacatgg tggagcacga cacacttgtc tactccaaaa atatcaaaga tacagtctca      60
gaagaccaaa gggcaattga acttttcaa caaagggtaa tatccggaaa cctcctcgga     120
ttccattgcc cagctatctg tcactttatt gtgaagatag tggaaaagga aggtggctcc     180
tacaaatgcc atcattgcga taaggaaag gccatcgttg aagatgcctc tgccgacagt     240
ggtcccaaag atggacccc acccacgagg agcatcgtgg aaaagaaga cgttccaacc     300 acgtcttcaa agcaagtgga ttgatgtgat aacatggtgg agcacgacac acttgtctac     360
tccaaaaata tcaaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa aggaaaggcc     540
atcgttgaag atgcctctgc cgacagtggt cccaaagatg gacccccacc cacgaggagc     600
atcgtggaaa agaagacgt tccaaccacg tcttcaaagc aagtggattg atgtgatatc     660
tccactgacg taagggatga cgcacaatcc cactatcctt cgcaagaccc ttcctctata     720
taaggaagtt catttcattt ggagaggtat aaaatctta ataggttttg ataaaagcga     780
acgtggggaa acccgaacca aaccttcttc taaactctct ctcatctctc ttaaagcaaa     840
cttctctctt gtcttttcttg cgtgagcgat cttcaacgtt gtcagatcgt gcttcggcac     900
cagtacaacg ttttctttca ctgaagcgaa atcaaagatc tctttgtgga cacgtagtgc     960
ggcgccatta aataacgtgt acttgtccta ttcttgtcgg tgtggtcttg ggaaaagaaa    1020
gcttgctgga ggctgctgtt cagccccata cattacttgt tacgattctg ctgactttcg    1080
gcgggtgcaa tatctctact tctgcttgac gaggtattgt tgcctgtact tctttcttct    1140
tcttcttgct gattggttct ataagaaatc tagtattttc tttgaaacag agttttcccg    1200
tggttttcga acttggagaa agattgttaa gcttctgtat attctgccca aatttgtcgg    1260
gcccatggcg aaaaacgttg cgattttcgg cttattgttt tctcttcttg tgttggttcc    1320
```

| | |
|---|---|
| ttctcagatc ttcgcccaaa aacttcctgg aaatgacaac agcacggcaa cgctgtgcct | 1380 |
| tgggcaccat gcagtaccaa acggaacgat agtgaaaaca atcacgaatg accaaattga | 1440 |
| agttactaat gctactgagc tggttcagag ttcctcaaca ggtgaaatat gcgacagtcc | 1500 |
| tcatcagatc cttgatggaa aaaactgcac actaatagat gctctattgg agaccctca | 1560 |
| gtgtgatggc ttccaaaata gaaatggga ccttttttgtt gaacgcagca aagcctacag | 1620 |
| caactgttac cctatgatg tgccggatta tgcctcccctt aggtcactag ttgcctcatc | 1680 |
| cggcacactg gagtttaaca atgaaagctt caattggact ggagtcactc aaaacggaac | 1740 |
| aagctctgct tgcataagga gatctaaaaa cagtttcttt agtagattga attggttgac | 1800 |
| ccacttaaac ttcaaatacc cagcattgaa cgtgactatg ccaaacaatg aacaatttga | 1860 |
| caaattgtac atttgggggg ttcaccaccc gggtacggac aaagaccaaa tcttcctgta | 1920 |
| tgctcaagca tcaggaagaa tcacagtctc taccaaaaga agccaacaaa ccgtaagccc | 1980 |
| gaatatcgga tctagaccca gagtaaggaa tatccctagc agaataagca tctattggac | 2040 |
| aatagtaaaa ccgggagaca tactttttgat taacagcaca gggaatctaa ttgctcctag | 2100 |
| gggttacttc aaaatacgaa gtgggaaaag ctcaataatg agatcagatg cacccattgg | 2160 |
| caaatgcaat tctgaatgca tcactccaaa tggaagcatt cccaatgaca aaccattcca | 2220 |
| aaatgtaaac aggatcacat acggggcctg tcccagatat gttaagcaaa acactctgaa | 2280 |
| attggcaaca gggatgcgaa atgtaccaga gaaacaaact agaggcatat ttggcgcaat | 2340 |
| cgcgggtttc atagaaaatg gttgggaggg aatggtggat ggttggtacg gtttcaggca | 2400 |
| tcaaaattct gagggaagag gacaagcagc agatctcaaa agcactcaag cagcaatcga | 2460 |
| tcaaatcaat gggaagctga atagattgat cgggaaaacc aacgagaaat tccatcagat | 2520 |
| tgaaaaagaa ttctcagaag tcgaagggag aattcaggac cttgagaaat atgttgagga | 2580 |
| cactaaaata gatctctggt catacaacgc ggagcttctt gttgccctgg agaaccaaca | 2640 |
| tacaattgat ctaactgact cagaaatgaa caaactgttt gaaaaaacaa gaagcaact | 2700 |
| gagggaaaat gctgaggata tgggcaatgg ttgtttcaaa atataccaca atgtgacaa | 2760 |
| tgcctgcata ggatcaatca gaatggaac ttatgaccac gatgtataca gagatgaagc | 2820 |
| attaaacaac cggtttcaga tcaagggagt tgagctgaag tcagggtaca agattggat | 2880 |
| cctatggatt tccttgccca tatcatgttt tttgctttgt gttgctttgt tggggttcat | 2940 |
| catgtgggcc tgccaaaaag gcaacattag gtgcaacatt tgcatttgaa ggcctatttt | 3000 |
| ctttagtttg aatttactgt tattcggtgt gcatttctat gtttggtgag cggttttctg | 3060 |
| tgctcagagt gtgtttattt tatgtaattt aatttcttttg tgagctcctg tttagcaggt | 3120 |
| cgtcccttca gcaaggacac aaaaagattt taattttatt aaaaaaaaaa aaaaaaaga | 3180 |
| ccgggaattc gatatcaagc ttatcgacct gcagatcgtt caaacatttg gcaataaagt | 3240 |
| ttcttaagat tgaatcctgt tgccggtctt gcgatgatta tcatataatt tctgttgaat | 3300 |
| tacgttaagc atgtaataat taacatgtaa tgcatgacgt tatttatgag atgggttttt | 3360 |
| atgattagag tcccgcaatt atacatttaa tacgcgatag aaaacaaaat atagcgcgca | 3420 |
| aactaggata aattatcgcg cgcggtgtca tctatgttac tagat | 3465 |

<210> SEQ ID NO 25
<211> LENGTH: 574
<212> TYPE: PRT
<213> ORGANISM: Influenza virus
<400> SEQUENCE: 25

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
50                  55                  60

Glu Leu Val Gln Ser Ser Ser Thr Gly Glu Ile Cys Asp Ser Pro His
65                  70                  75                  80

Gln Ile Leu Asp Gly Lys Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
130                 135                 140

Asn Asn Glu Ser Phe Asn Trp Thr Gly Val Thr Gln Asn Gly Thr Ser
145                 150                 155                 160

Ser Ala Cys Ile Arg Arg Ser Lys Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ala Ser Gly
210                 215                 220

Arg Ile Thr Val Ser Thr Lys Arg Ser Gln Gln Thr Val Ser Pro Asn
225                 230                 235                 240

Ile Gly Ser Arg Pro Arg Val Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Asn
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415
```

```
His Gln Ile Glu Lys Glu Phe Ser Glu Val Gly Arg Ile Gln Asp
                420                 425                 430

Leu Glu Lys Tyr Val Glu Asp Thr Lys Ile Asp Leu Trp Ser Tyr Asn
            435                 440                 445

Ala Glu Leu Leu Val Ala Leu Glu Asn Gln His Thr Ile Asp Leu Thr
        450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

```
<210> SEQ ID NO 26
<211> LENGTH: 40
<212> TYPE: DNA
<213> ORGANISM: Artificial Sequence
<220> FEATURE:
<223> OTHER INFORMATION: primer IF-S2+S4-B Bris.c

<400> SEQUENCE: 26
tctcagatct tcgccgatcg aatctgcact ggaataacat                40

<210> SEQ ID NO 27
<211> LENGTH: 43
<212> TYPE: DNA
<213> ORGANISM: Artificial Sequence
<220> FEATURE:
<223> OTHER INFORMATION: primer IF-S1a4-B Bris.r

<400> SEQUENCE: 27
actaaagaaa ataggccttt atagacagat ggagcaagaa aca            43

<210> SEQ ID NO 28
<211> LENGTH: 1758
<212> TYPE: DNA
<213> ORGANISM: Artificial Sequence
<220> FEATURE:
<223> OTHER INFORMATION: nucleotide sequence of synthesized HA B
      Brisbane gene

<400> SEQUENCE: 28
atgaaggcaa taattgtact actcatggta gtaacatcca atgcagatcg aatctgcact    60
ggaataacat cgtcaaactc accacatgtc gtcaaaactg ctactcaagg ggaggtcaat   120
gtgactggtg taataccact gacaacaaca cccaccaaat ctcatttgc aaatctcaaa    180 ggaacagaaa ccagggggaa actatgccca aaatgcctca actgcacaga tctggacgta   240 gcccttgggca gaccaaaatg cacggggaaa ataccctcgg caagagtttc aatactccat   300
gaagtcagac tgttacatc tgggtgcttt cctataatgc acgacagaac aaaaattaga    360
cagctgccta accttctccg aggatacgaa catatcaggt tatcaaccca taacgttatc   420
```

```
aatgcagaaa atgcaccagg aggaccctac aaaattggaa cctcagggtc ttgccctaac    480
attaccaatg gaaacggatt tttcgcaaca atggcttggg ccgtcccaaa aaacgacaaa    540
aacaaaacag caacaaatcc attaacaata gaagtaccat acatttgtac agaaggagaa    600
gaccaaatta ccgtttgggg gttccactct gacaacgaga cccaaatggc aaagctctat    660
ggggactcaa agccccagaa gttcacctca tctgccaacg gagtgaccac acattacgtt    720
tcacagattg tgggcttccc aaatcaaaca gaagacggag gactaccaca aagtggtaga    780
attgttgttg attacatggt gcaaaaatct gggaaaacag gaacaattac ctatcaaagg    840
ggtattttat tgcctcaaaa ggtgtggtgc gcaagtggca ggagcaaggt aataaaagga    900
tccttgcctt taattggaga agcagattgc ctccacgaaa aatacggtgg attaaacaaa    960
agcaagcctt actacacagg gaacatgca  aaggccatag gaaattgccc aatatgggtg   1020
aaaacaccct tgaagctggc caatggaacc aaatatagac ctcctgcaaa actattaaag   1080
gaaaggggtt tcttcggagc tattgctggt ttcttagaag gaggatggga aggaatgatt   1140
gcaggttggc acggatacac atcccatggg gcacatgag  tagcggtggc agcagaccett   1200 aagagcactc aagaggccat aaacaagata caaaaaaatc tcaactcttt gagtgagctg   1260
gaagtaaaga atcttcaaag actaagcggt gccatggatg aactccacaa cgaaatacta   1320
gaactagatg agaaagtgga tgatctcaga gctgatacaa taagctcaca aatagaactc   1380
gcagtcctgc tttccaatga aggaataata acagtgaag  atgaacatct cttggcgctt   1440
gaaagaaagc tgaagaaaat gctgggcccc tctgctgtag agatagggaa tggatgcttt   1500
gaaaccaaac acagtgcaa  ccagacctgt ctcgacagaa tagctgctgg tacctttgat   1560
gcaggagaat tttctctccc cacctttgat tcactgaata ttactgctgc atctttaaat   1620
gacgatggat tggataatca tactatactg ctttactact caactgctgc ctccagtttg   1680
gctgtaacac tgatgatagc tatctttgtt gtttatatgg tctccagaga caatgtttct   1740
tgctccatct gtctataa                                                 1758

<210> SEQ ID NO 29
<211> LENGTH: 3525
<212> TYPE: DNA
<213> ORGANISM: Artificial Sequence
<220> FEATURE:
<223> OTHER INFORMATION: Expression cassette number 1029

<400> SEQUENCE: 29
gtcaacatgg tggagcacga cacacttgtc tactccaaaa atatcaaaga tacagtctca     60
gaagaccaaa gggcaattga acttttcaa  caaagggtaa tatccggaaa cctcctcgga    120
ttccattgcc cagctatctg tcactttatt gtgaagatag tggaaaagga aggtggctcc    180
tacaaatgcc atcattgcga taaggaaag  gccatcgttg aagatgcctc tgccgacagt    240
ggtcccaaag atggaccccc acccacgagg agcatcgtgg aaaagaagga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa ggaaaggcc    540 atcgttgaag atgcctctgc cgacagtggt cccaaagatg gaccccccac  cacgaggagc    600
atcgtggaaa agaagacgt  tccaaccacg tcttcaaagc aagtggattg atgtgatatc    660
tccactgacg taagggatga cgcacaatcc cactatcctt cgcaagaccc ttcctctata    720
```

-continued

```
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgccgatc gaatctgcac tggaataaca tcgtcaaact caccacatgt   1380
cgtcaaaact gctactcaag gggaggtcaa tgtgactggt gtaataccac tgacaacaac   1440
acccaccaaa tctcattttg caaatctcaa aggaacagaa accaggggga aactatgccc   1500
aaaatgcctc aactgcacag atctggacgt agccttgggc agaccaaaat gcacggggaa   1560
aataccctcg gcaagagttt caatactcca tgaagtcaga cctgttacat ctgggtgctt   1620
tcctataatg cacgacagaa caaaaattag acagctgcct aaccttctcc gaggatacga   1680
acatatcagg ttatcaaccc ataacgttat caatgcagaa aatgcaccag gaggaccccta  1740 caaaattgga acctcaggt cttgccctaa cattaccaat ggaaacggat ttttcgcaac   1800
aatggcttgg gccgtcccaa aaaacgacaa aaacaaaaca gcaacaaatc cattaacaat   1860
agaagtacca tacatttgta cagaaggaga agaccaaatt accgtttggg ggttccactc   1920
tgacaacgag acccaaatgg caaagctcta tggggactca aagccccaga agttcacctc   1980
atctgccaac ggagtgacca cacattacgt ttcacagatt ggtggcttcc caaatcaaac   2040
agaagacgga ggactaccac aaagtggtag aattgttgtt gattacatgg tgcaaaaatc   2100
tgggaaaaca ggaacaatta cctatcaaag gggtatttta ttgcctcaaa aggtgtggtg   2160
cgcaagtggc aggagcaagg taataaaagg atccttgcct ttaattggag aagcagattg   2220
cctccacgaa aaatacggtg gattaaacaa aagcaagcct tactacacag gggaacatgc   2280
aaaggccata ggaaattgcc caatatgggt gaaaacaccc ttgaagctgg ccaatggaac   2340
caaatataga cctcctgcaa aactattaaa ggaaaggggt ttcttcggag ctattgctgg   2400
tttcttagaa ggaggatggg aaggaatgat tgcaggttgg cacggataca catcccatgg   2460
ggcacatgga gtagcggtgg cagcagacct taagagcact caagaggcca taaacaagat   2520
aacaaaaaat ctcaactctt tgagtgagct ggaagtaaag aatcttcaaa gactaagcgg   2580
tgccatggat gaactccaca cgaaatact agaactagat gagaaagtgg atgatctcag   2640
agctgataca ataagctcac aaatagaact cgcagtcctg ctttccaatg aaggaataat   2700
aaacagtgaa gatgaacatc tcttggcgct tgaaagaaag ctgaagaaaa tgctgggccc   2760
ctctgctgta gagataggga atggatgctt tgaaaccaaa cacaagtgca accagacctg   2820
tctcgacaga atagctgctg gtaccttga tgcaggagaa ttttctctcc ccacctttga   2880
ttcactgaat attactgctg catctttaaa tgacgatgga ttggataatc atactatact   2940
gctttactac tcaactgctg cctccagttt ggctgtaaca ctgatgatag ctatctttgt   3000
tgtttatatg gtctccagag acaatgtttc ttgctccatc tgtctataaa ggcctatttt   3060
```

-continued

```
ctttagtttg aatttactgt tattcggtgt gcatttctat gtttggtgag cggttttctg    3120
tgctcagagt gtgtttattt tatgtaattt aatttctttg tgagctcctg tttagcaggt    3180
cgtcccttca gcaaggacac aaaaagattt taatttttatt aaaaaaaaaa aaaaaaaga    3240 ccgggaattc gatatcaagc ttatcgacct gcagatcgtt caaacatttg gcaataaagt    3300
ttcttaagat tgaatcctgt tgccggtctt gcgatgatta tcatataatt tctgttgaat    3360
tacgttaagc atgtaataat taacatgtaa tgcatgacgt tatttatgag atgggttttt    3420
atgattagag tcccgcaatt atacatttaa tacgcgatag aaaacaaaat atagcgcgca    3480
aactaggata aattatcgcg cgcggtgtca tctatgttac tagat                    3525
```

<210> SEQ ID NO 30
<211> LENGTH: 594
<212> TYPE: PRT
<213> ORGANISM: Influenza virus

<400> SEQUENCE: 30

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
```

Lys Val Ile Lys Gly Ser Leu Pro Leu Ile Gly Glu Ala Asp Cys Leu
305             310                 315                 320

His Glu Lys Tyr Gly Gly Leu Asn Lys Ser Lys Pro Tyr Tyr Thr Gly
            325                 330                 335

Glu His Ala Lys Ala Ile Gly Asn Cys Pro Ile Trp Val Lys Thr Pro
                340                 345                 350

Leu Lys Leu Ala Asn Gly Thr Lys Tyr Arg Pro Pro Ala Lys Leu Leu
            355                 360                 365

Lys Glu Arg Gly Phe Phe Gly Ala Ile Ala Gly Phe Leu Glu Gly Gly
370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
            435                 440                 445

Leu Glu Leu Asp Glu Lys Val Asp Asp Leu Arg Ala Asp Thr Ile Ser
450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
            515                 520                 525

Asp Ala Gly Glu Phe Ser Leu Pro Thr Phe Asp Ser Leu Asn Ile Thr
530                 535                 540

Ala Ala Ser Leu Asn Asp Asp Gly Leu Asp Asn His Thr Ile Leu Leu
545                 550                 555                 560

Tyr Tyr Ser Thr Ala Ala Ser Ser Leu Ala Val Thr Leu Met Ile Ala
                565                 570                 575

Ile Phe Val Val Tyr Met Val Ser Arg Asp Asn Val Ser Cys Ser Ile
            580                 585                 590

Cys Leu

<210> SEQ ID NO 31
<211> LENGTH: 6861
<212> TYPE: DNA
<213> ORGANISM: Artificial Sequence
<220> FEATURE:
<223> OTHER INFORMATION: Construct 1194

<400> SEQUENCE: 31
tggcaggata tattgtggtg taaacaaatt gacgcttaga caacttaata acacattgcg     60
gacgttttta atgtactgaa ttaacgccga atcccgggct ggtatattta tatgttgtca    120
aataactcaa aaaccataaa agtttaagtt agcaagtgtg tacattttta cttgaacaaa    180
aatattcacc tactactgtt ataaatcatt attaaacatt agagtaaaga aatatggatg    240
ataagaacaa gagtagtgat attttgacaa caatttttgtt gcaacatttg agaaaatttt    300
gttgttctct cttttcattg gtcaaaaaca atagagagag aaaaaggaag agggagaata    360

```
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tattttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140 gatgggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca cgcgtggcgc gccctagcag aaggcatgtt   2160
gttgtgactc cgaggggttg cctcaaactc tatcttataa ccggcgtgga ggcatggagg   2220
caagggcatt ttggtaattt aagtagttag tggaaaatga cgtcatttac ttaaagacga   2280
agtcttgcga caaggggggc ccacgccgaa ttttaatatt accggcgtgg ccccacctta   2340
tcgcgagtgc tttagcacga gcggtccaga tttaaagtag aaaagttccc gcccactagg   2400
gttaaaggtg ttcacactat aaaagcatat acgatgtgat ggtatttgat aaagcgtata   2460
ttgtatcagg tatttccgtc ggatacgaat tattcgtaca agcttcttaa gccggtcaac   2520
atggtggagc acgacacact tgtctactcc aaaaatatca aagatacagt ctcagaagac   2580
caaagggcaa ttgagacttt tcaacaaagg gtaaatatccg gaaacctcct cggattccat   2640
tgcccagcta tctgtcactt tattgtgaag atagtggaaa aggaaggtgg ctcctacaaa   2700
```

```
tgccatcatt gcgataaagg aaaggccatc gttgaagatg cctctgccga cagtggtccc    2760
aaagatggac ccccacccac gaggagcatc gtggaaaaag aagacgttcc aaccacgtct    2820
tcaaagcaag tggattgatg tgataacatg gtggagcacg acacacttgt ctactccaaa    2880
aatatcaaag atacagtctc agaagaccaa agggcaattg agacttttca acaaagggta    2940
atatccggaa acctcctcgg attccattgc ccagctatct gtcactttat tgtgaagata    3000
gtggaaaagg aaggtggctc ctacaaatgc catcattgcg ataaaggaaa ggccatcgtt    3060
gaagatgcct ctgccgacag tggtcccaaa gatggacccc acccacgag gagcatcgtg     3120 gaaaagaag acgttccaac cacgtcttca aagcaagtgg attgatgtga tatctccact     3180
gacgtaaggg atgacgcaca atcccactat ccttcgcaag acccttcctc tatataagga    3240
agttcatttc atttggagag gtattaaaat cttaataggt tttgataaaa gcgaacgtgg    3300
ggaaacccga accaaacctt cttctaaact ctctctcatc tctcttaaag caaacttctc    3360
tcttgtcttt cttgcgtgag cgatcttcaa cgttgtcaga tcgtgcttcg gcaccagtac    3420
aacgttttct ttcactgaag cgaaatcaaa gatctctttg tggacacgta gtgcggcgcc    3480
attaaataac gtgtacttgt cctattcttg tcggtgtggt cttgggaaaa gaaagcttgc    3540
tggaggctgc tgttcagccc catacattac ttgttacgat tctgctgact tcggcgggt    3600 gcaatatctc tacttctgct tgacgaggta ttgttgcctg tacttctttc ttcttcttct    3660
tgctgattgg ttctataaga aatctagtat tttctttgaa acagagtttt cccgtggttt    3720
tcgaacttgg agaaagattg ttaagcttct gtatattctg cccaaatttg tcgggcccat    3780
ggcgaaaaac gttgcgattt tcggcttatt gttttctctt cttgtgttgg ttccttctca    3840
gatcttcgcc gcggctcctc agccaaaacg acaccccccat ctgtctatcc actggcccct   3900
ggatctgctg cccaaactaa ctccatggtg accctgggat gcctggtcaa gggctatttc    3960
cctgagccag tgacagtgac ctggaactct ggatccctgt ccagcggtgt gcacaccttc    4020
ccagctgtcc tgcagtctga cctctacact ctgagcagct cagtgactgt cccctccagc    4080
acctggccca gcgagaccgt cacctgcaac gttgcccacc cggccagcag caccaaggtg    4140
gacaagaaaa ttgtgcccag ggattgtggt tgtaagcctt gcatatgtac agtcccagaa    4200
gtatcatctg tcttcatctt ccccccaaag cccaaggatg tgctcaccat tactctgact    4260
cctaaggtca cgtgtgttgt ggtagacatc agcaaggatg atcccgaggt ccagttcagc    4320
tggtttgtag atgatgtgga ggtgcacaca gctcagacgc aaccccggga ggagcagttc    4380
aacagcactt tccgctcagt cagtgaactt cccatcatgc accaggactg gctcaatggc    4440
aaggaaggcc tatttctttt agtttgaatt tactgttatt cggtgtgcat ttctatgttt    4500
ggtgagcggt tttctgtgct cagagtgtgt ttattttatg taatttaatt tctttgtgag    4560
ctcctgttta gcaggtcgtc ccttcagcaa ggacacaaaa agatttttaat tttattaaaa    4620 aaaaaaaaa aaaagaccgg gaattcgata tcaagcttat cgacctgcag atcgttcaaa     4680
catttggcaa taaagtttct taagattgaa tcctgttgcc ggtcttgcga tgattatcat    4740
ataatttctg ttgaattacg ttaagcatgt aataattaac atgtaatgca tgacgttatt    4800
tatgagatgg gttttttatga ttagagtccc gcaattatac atttaatacg cgatagaaaa   4860
caaaatatag cgcgcaaact aggataaatt atcgcgcgcg gtgtcatcta tgttactaga    4920
tctctagagt ctcaagcttg gcgcggggta ccgagctcga attccgagtg tacttcaagt    4980
cagttggaaa tcaataaaat gattattta tgaatatatt tcattgtgca agtagataga    5040
aattacatat gttacataac acacgaaata aacaaaaaa cacaatccaa aacaaacacc    5100
```

-continued

| | | | | | |
|---|---|---|---|---|---|
| ccaaacaaaa | taacactata | tatatcctcg | tatgaggaga | ggcacgttca | gtgactcgac | 5160 |
| gattcccgag | caaaaaaagt | ctccccgtca | cacatatagt | gggtgacgca | attatcttca | 5220 |
| aagtaatcct | tctgttgact | tgtcattgat | aacatccagt | cttcgtcagg | attgcaaaga | 5280 |
| attatagaag | ggatcccacc | tttatttc | ttcttttttc | catatttagg | gttgacagtg | 5340 |
| aaatcagact | ggcaacctat | taattgcttc | cacaatggga | cgaacttgaa | ggggatgtcg | 5400 |
| tcgatgatat | tataggtggc | gtgttcatcg | tagttggtga | agtcgatggt | cccgttccag | 5460 |
| tagttgtgtc | gcccgagact | tctagcccag | gtggtctttc | cggtacgagt | tggtccgcag | 5520 |
| atgtagaggc | tggggtgtct | gaccccagtc | cttccctcat | cctggttaga | tcggccatcc | 5580 |
| actcaaggtc | agattgtgct | tgatcgtagg | agacaggatg | tatgaaagtg | taggcatcga | 5640 |
| tgcttacatg | ataggtgc | gtctctctcc | agttgtgcag | atcttcgtgg | cagcggagat | 5700 |
| ctgattctgt | gaagggcgac | acgtactgct | caggttgtgg | aggaaataat | ttgttggctg | 5760 |
| aatattccag | ccattgaagc | tttgttgccc | attcatgagg | gaattcttct | ttgatcatgt | 5820 |
| caagatactc | ctccttagac | gttgcagtct | ggataatagt | tcgccatcgt | gcgtcagatt | 5880 |
| tgcgaggaga | gaccttatga | tctcggaaat | ctcctctggt | tttaatatct | ccgtcctttg | 5940 |
| atatgtaatc | aaggacttgt | ttagagtttc | tagctggctg | gatattaggg | tgatttcctt | 6000 |
| caaaatcgaa | aaaagaagga | tccctaatac | aaggtttttt | atcaagctgg | ataagagcat | 6060 |
| gatagtgggt | agtgccatct | tgatgaagct | cagaagcaac | accaaggaag | aaaataagaa | 6120 |
| aaggtgtgag | tttctcccag | agaaactgga | ataaatcatc | tctttgagat | gagcacttgg | 6180 |
| ggtaggtaag | gaaaacatat | ttagattgga | gtctgaagtt | cttgctagca | gaaggcatgt | 6240 |
| tgttgtgact | ccgaggggtt | gcctcaaact | ctatcttata | accggcgtgg | aggcatggag | 6300 |
| gcaagggcat | tttggtaatt | taagtagtta | gtggaaaatg | acgtcattta | cttaaagacg | 6360 |
| aagtcttgcg | acaaggggggg | cccacgccga | attttaatat | taccggcgtg | gccccacctt | 6420 |
| atcgcgagtg | ctttagcacg | agcggtccag | atttaaagta | gaaaagttcc | cgcccactag | 6480 |
| ggttaaaggt | gttcacacta | taaaagcata | tacgatgtga | tggtatttga | tggagcgtat | 6540 |
| attgtatcag | gtatttccgt | cggatacgaa | ttattcgtac | ggccggccac | tagtggcact | 6600 |
| ggccgtcgtt | ttacaacgtc | gtgactggga | aaaccctggc | gttacccaac | ttaatcgcct | 6660 |
| tgcagcacat | cccccttcg | ccagctggcg | taatagcgaa | gaggcccgca | ccgatcgccc | 6720 |
| ttcccaacag | ttgcgcagcc | tgaatggcga | atgctagagc | agcttgagct | tggatcagat | 6780 |
| tgtcgtttcc | cgccttcagt | ttaaactatc | agtgtttgac | aggatatatt | ggcgggtaaa | 6840 |
| cctaagagaa | aagagcgttt | a | | | | 6861 |

<210> SEQ ID NO 32
<211> LENGTH: 5555
<212> TYPE: DNA
<213> ORGANISM: Artificial Sequence
<220> FEATURE:
<223> OTHER INFORMATION: Expression cassette number 1008

<400> SEQUENCE: 32

| | | | | | |
|---|---|---|---|---|---|
| ctagcagaag | gcatgttgtt | gtgactccga | ggggttgcct | caaactctat | cttataaccg | 60 |
| gcgtggaggc | atggaggcaa | gggcattttg | gtaatttaag | tagttagtgg | aaaatgacgt | 120 |
| catttactta | aagacgaagt | cttgcgacaa | gggggggccca | cgccgaattt | taatattacc | 180 |
| ggcgtggccc | caccttatcg | cgagtgcttt | agcacgagcg | gtccagattt | aaagtagaaa | 240 |

```
agttcccgcc cactagggtt aaaggtgttc acactataaa agcatatacg atgtgatggt    300
atttgataaa gcgtatattg tatcaggtat ttccgtcgga tacgaattat tcgtacaagc    360
ttcttaagcc ggtcaacatg gtggagcacg acacacttgt ctactccaaa aatatcaaag    420
atacagtctc agaagaccaa agggcaattg agacttttca acaagggta atatccggaa     480 acctcctcgg attccattgc ccagctatct gtcactttat tgtgaagata gtggaaaagg    540
aaggtggctc ctacaaatgc catcattgcg ataaaggaaa ggccatcgtt gaagatgcct    600
ctgccgacag tggtcccaaa gatggacccc cacccacgag gagcatcgtg gaaaagaag     660 acgttccaac cacgtcttca aagcaagtgg attgatgtga taacatggtg gagcacgaca    720
cacttgtcta ctccaaaaat atcaaagata cagtctcaga agaccaaagg gcaattgaga    780
cttttcaaca aagggtaata tccggaaacc tcctcggatt ccattgccca gctatctgtc    840
actttattgt gaagatagtg aaaaggaag gtggctccta caaatgccat cattgcgata    900
aaggaaaggc catcgttgaa gatgcctctg ccgacagtgg tcccaaagat ggaccccac    960 ccacgaggag catcgtggaa aagaagacg ttccaaccac gtcttcaaag caagtggatt    1020
gatgtgatat ctccactgac gtaagggatg acgcacaatc ccactatcct tcgcaagacc    1080
cttcctctat ataaggaagt tcatttcatt tggagaggta ttaaaatctt aataggtttt    1140
gataaaagcg aacgtgggga aacccgaacc aaaccttctt ctaaactctc tctcatctct    1200
cttaaagcaa acttctctct tgtctttctt gcgtgagcga tcttcaacgt tgtcagatcg    1260
tgcttcggca ccagtacaac gttttctttc actgaagcga aatcaaagat ctctttgtgg    1320
acacgtagtg cggcgccatt aaataacgtg tacttgtcct attcttgtcg gtgtggtctt    1380
gggaaaagaa agcttgctgg aggctgctgt tcagccccat acattacttg ttacgattct    1440
gctgactttc ggcgggtgca atatctctac ttctgcttga cgaggtattg ttgcctgtac    1500
ttctttcttc ttcttcttgc tgattggttc tataagaaat ctagtatttt ctttgaaaca    1560
gagttttccc gtggttttcg aacttggaga aagattgtta agcttctgta tattctgccc    1620
aaatttgtcg ggcccatggc gaaaaacgtt gcgattttcg gcttattgtt ttctcttctt    1680
gtgttggttc cttctcagat cttcgccgat cgaatctgca ctggaataac atcgtcaaac    1740
tcaccacatg tcgtcaaaac tgctactcaa ggggaggtca atgtgactgg tgtaatacca    1800
ctgacaacaa cacccaccaa atctcatttt gcaaatctca aggaacaga aaccaggggg     1860 aaactatgcc caaaatgcct caactgcaca gatctggacg tagccttggg cagaccaaaa    1920
tgcacgggga aaatacctc ggcaagagtt tcaatactcc atgaagtcag acctgttaca    1980
tctgggtgct ttcctataat gcacgacaga acaaaaatta gacagctgcc taaccttctc    2040
cgaggatacg aacatatcag gttatcaacc cataacgtta tcaatgcaga aaatgccacca    2100 ggaggaccct acaaaattgg aacctcaggg tcttgcccta acattaccaa tggaaacgga    2160 ttttcgcaa caatggcttg gccgtccca aaaaacgaca aaaacaaaac agcaacaaat     2220
ccattaacaa tagaagtacc atacatttgt acagaaggag aagaccaaat taccgtttgg    2280
gggttccact ctgacaacga acccaaatg gcaaagctct atgggactc aaagccccag     2340 aagttcacct catctgccaa cggagtgacc acacattacg tttcacagat tggtggcttc    2400
ccaaatcaaa cagaagacgg aggactacca caaagtggta gaattgttgt tgattacatg    2460
gtgcaaaaat ctgggaaaac aggaacaatt acctatcaaa ggggtatttt attgcctcaa    2520
aaggtgtggg cgcaagtggg caggagcaag gtaataaaag gatccttgcc tttaattgga    2580
gaagcagatt gcctccacga aaatacggt ggattaaaca aaagcaagcc ttactacaca    2640
```

```
ggggaacatg caaaggccat aggaaattgc ccaatatggg tgaaaacacc cttgaagctg    2700
gccaatggaa ccaaatatag acctcctgca aaactattaa aggaaagggg tttcttcgga    2760
gctattgctg gtttcttaga aggaggatgg gaaggaatga ttgcaggttg gcacggatac    2820
acatcccatg gggcacatgg agtagcggtg gcagcagacc ttaagagcac tcaagaggcc    2880
ataaacaaga taacaaaaaa tctcaactct ttgagtgagc tggaagtaaa gaatcttcaa    2940
agactaagcg gtgccatgga tgaactccac aacgaaatac tagaactaga tgagaaagtg    3000
gatgatctca gagctgatac aataagctca caaatagaac tcgcagtcct gctttccaat    3060
gaaggaataa taaacagtga agatgaacat ctcttggcgc ttgaaagaaa gctgaagaaa    3120
atgctgggcc cctctgctgt agagataggg aatggatgct tgaaaccaa acacaagtgc    3180 aaccagacct gtctcgacag aatagctgct ggtaccttg atgcaggaga attttctctc    3240
cccacctttg attcactgaa tattactgct gcatctttaa atgacgatgg attggataat    3300
catactatac tgctttacta ctcaactgct gcctccagtt tggctgtaac actgatgata    3360
gctatctttg ttgtttatat ggtctccaga gacaatgttt cttgctccat ctgtctataa    3420
aggcctattt tctttagttt gaatttactg ttattcggtg tgcatttcta tgtttggtga    3480
gcggttttct gtgctcagag tgtgtttatt ttatgtaatt taatttcttt gtgagctcct    3540
gtttagcagg tcgtccccttc agcaaggaca caaaaagatt ttaattttat taaaaaaaaa    3600
aaaaaaaaag accgggaatt cgatatcaag cttatcgacc tgcagatcgt tcaaacattt    3660
ggcaataaag tttcttaaga ttgaatcctg ttgccggtct tgcgatgatt atcatataat    3720
ttctgttgaa ttacgttaag catgtaataa ttaacatgta atgcatgacg ttatttatga    3780
gatgggtttt tatgattaga gtcccgcaat tatacattta atacgcgata gaaaacaaaa    3840
tatagcgcgc aaactaggat aaattatcgc gcgcggtgtc atctatgtta ctagatctct    3900
agagtctcaa gcttggcgcg gggtaccgag ctcgaattcc gagtgtactt caagtcagtt    3960
ggaaatcaat aaaatgatta ttttatgaat atatttcatt gtgcaagtag atagaaatta    4020
catatgttac ataacacacg aaataaacaa aaaaacacaa tccaaaacaa acaccccaaa    4080
caaaataaca ctatatatat cctcgtatga ggagaggcac gttcagtgac tcgacgattc    4140
ccgagcaaaa aaagtctccc cgtcacacat atagtgggtg acgcaattat cttcaaagta    4200
atccttctgt tgacttgtca ttgataacat ccagtcttcg tcaggattgc aaagaattat    4260
agaagggatc ccaccttta ttttcttctt ttttccatat ttagggttga cagtgaaatc    4320
agactggcaa cctattaatt gcttccacaa tgggacgaac ttgaagggga tgtcgtcgat    4380
gatattatag gtggcgtgtt catcgtagtt ggtgaagtcg atggtcccgt tccagtagtt    4440
gtgtcgcccg agacttctag cccaggtggt ctttccggta cgagttggtc cgcagatgta    4500
gaggctgggg tgtctgaccc cagtccttcc ctcatcctgg ttagatcggc catccactca    4560
aggtcagatt gtgcttgatc gtaggagaca ggatgtgatga aagtgtaggc atcgatgctt    4620
acatgatata ggtgcgtctc tctccagttg tgcagatctt cgtggcagcg gagatctgat    4680
tctgtgaagg gcgacacgta ctgctcaggt tgtggaggaa ataatttgtt ggctgaatat    4740
tccagccatt gaagctttgt tgcccattca tgagggaatt cttctttgat catgtcaaga    4800
tactcctcct tagacgttgc agtctggata atagttcgcc atcgtgcgtc agatttgcga    4860
ggagagacct tatgatctcg gaatctcct ctggttttaa tatctccgtc ctttgatatg    4920
taatcaagga cttgtttaga gtttctagct ggctggatat taggggtgatt tccttcaaaa    4980
```

```
tcgaaaaaag aaggatccct aatacaaggt tttttatcaa gctggataag agcatgatag    5040
tgggtagtgc catcttgatg aagctcagaa gcaacaccaa ggaagaaaat aagaaaaggt    5100
gtgagtttct cccagagaaa ctggaataaa tcatctcttt gagatgagca cttggggtag    5160
gtaaggaaaa catatttaga ttggagtctg aagttcttgc tagcagaagg catgttgttg    5220
tgactccgag ggggttgcctc aaactctatc ttataaccgg cgtggaggca tggaggcaag    5280
ggcattttgg taatttaagt agttagtgga aaatgacgtc atttacttaa agacgaagtc    5340
ttgcgacaag gggggcccac gccgaatttt aatattaccg gcgtggcccc accttatcgc    5400
gagtgcttta gcacgagcgg tccagattta aagtagaaaa gttcccgccc actagggtta    5460
aaggtgttca cactataaaa gcatatacga tgtgatggta tttgatggag cgtatattgt    5520
atcaggtatt tccgtcggat acgaattatt cgtac                              5555
```

```
<210> SEQ ID NO 33
<211> LENGTH: 50
<212> TYPE: DNA
<213> ORGANISM: Artificial Sequence
<220> FEATURE:
<223> OTHER INFORMATION: primer dTmH5I-B Bris.r

<400> SEQUENCE: 33
ttgacagtat ttggtaatta tccaatccat cgtcatttaa agatgcagca                50

<210> SEQ ID NO 34
<211> LENGTH: 50
<212> TYPE: DNA
<213> ORGANISM: Artificial Sequence
<220> FEATURE:
<223> OTHER INFORMATION: primer B Bris-dTmH5I.c

<400> SEQUENCE: 34
catctttaaa tgacgatgga ttggataatt accaaatact gtcaatttat                50

<210> SEQ ID NO 35
<211> LENGTH: 50
<212> TYPE: DNA
<213> ORGANISM: Artificial Sequence
<220> FEATURE:
<223> OTHER INFORMATION: primer IF-S1aS4-dTmH5I.r

<400> SEQUENCE: 35
actaaagaaa ataggccttt aaatgcaaat tctgcattgt aacgatccat                50

<210> SEQ ID NO 36
<211> LENGTH: 5555
<212> TYPE: DNA
<213> ORGANISM: Artificial Sequence
<220> FEATURE:
<223> OTHER INFORMATION: Expression cassette number 1009

<400> SEQUENCE: 36
ctagcagaag gcatgttgtt gtgactccga ggggttgcct caaactctat cttataaccg     60
gcgtggaggc atggaggcaa gggcattttg gtaatttaag tagttagtgg aaaatgacgt    120
catttactta aagacgaagt cttgcgacaa gggggggccca cgccgaattt taatattacc    180
ggcgtggccc caccttatcg cgagtgcttt agcacgagcg gtccagattt aaagtagaaa    240
agttcccgcc cactagggtt aaaggtgttc acactataaa agcatatacg atgtgatggt    300
atttgataaa gcgtatattg tatcaggtat ttccgtcgga tacgaattat tcgtacaagc    360
ttcttaagcc ggtcaacatg gtggagcacg acacacttgt ctactccaaa aatatcaaag    420
```

```
atacagtctc agaagaccaa agggcaattg agacttttca acaaagggta atatccggaa    480
acctcctcgg attccattgc ccagctatct gtcactttat tgtgaagata gtggaaaagg    540
aaggtggctc ctacaaatgc catcattgcg ataaaggaaa ggccatcgtt gaagatgcct    600
ctgccgacag tggtcccaaa gatggacccc cacccacgag gagcatcgtg gaaaagaag     660 acgttccaac cacgtcttca aagcaagtgg attgatgtga acatggtg gagcacgaca      720 cacttgtcta ctccaaaaat atcaaagata cagtctcaga agaccaaagg gcaattgaga    780
cttttcaaca aagggtaata tccggaaacc tcctcggatt ccattgccca gctatctgtc    840
actttattgt gaagatagtg gaaaggaag gtggctccta caaatgccat cattgcgata     900
aaggaaaggc catcgttgaa gatgcctctg ccgacagtgg tcccaaagat ggaccccac    960 ccacgaggag catcgtggaa aagaagacg ttcaaccac gtcttcaaag caagtggatt      1020
gatgtgatat ctccactgac gtaagggatg acgcacaatc ccactatcct cgcaagacc    1080 cttcctctat ataaggaagt tcatttcatt tggagaggta ttaaaatctt aataggtttt    1140
gataaaagcg aacgtgggga aacccgaacc aaaccttctt ctaaactctc tctcatctct    1200
cttaaagcaa acttctctct tgtctttctt gcgtgagcga tcttcaacgt tgtcagatcg    1260
tgcttcggca ccagtacaac gttttctttc actgaagcga atcaaagat ctctttgtgg     1320 acacgtagtg cggcgccatt aaataacgtg tacttgtcct attcttgtcg gtgtggtctt    1380
gggaaaagaa agcttgctgg aggctgctgt tcagccccat acattacttg ttacgattct    1440
gctgactttc ggcgggtgca atatctctac ttctgcttga cgaggtattg ttgcctgtac    1500
ttctttcttc ttcttcttgc tgattggttc tataagaaat ctagtatttt ctttgaaaca    1560
gagttttccc gtggttttcg aacttggaga aagattgtta agcttctgta tattctgccc    1620
aaatttgtcg ggcccatggc gaaaaacgtt gcgattttcg gcttattgtt ttctcttctt    1680
gtgttggttc cttctcagat cttcgccgat cgaatctgca ctggaataac atcgtcaaac    1740
tcaccacatg tcgtcaaaac tgctactcaa ggggaggtca atgtgactgg tgtaatacca    1800
ctgacaacaa cacccaccaa atctcatttt gcaaatctca aggaacaga accaggggg     1860 aaactatgcc caaaatgcct caactgcaca gatctggacg tagccttggg cagaccaaaa    1920
tgcacgggga aaatacccct ggcaagagtt caatactcc atgaagtcag acctgttaca     1980
tctgggtgct ttcctataat gcacgacaga acaaaaatta gacagctgcc taaccttctc    2040
cgaggatacg aacatatcag gttatcaacc cataacgtta tcaatgcaga aaatgcacca    2100
ggaggaccct acaaaattgg aacctcaggg tcttgcccta acattaccaa tggaaacgga    2160 ttttcgcaa caatggcttg ggccgtccca aaaaacgaca aaaacaaaac agcaacaaat    2220
ccattaacaa tagaagtacc atacatttgt acagaaggag aagaccaaat taccgtttgg    2280
gggttccact ctgacaacga acccaaatg gcaaagctct atgggactc aaagcccag     2340 aagttcacct catctgccaa cggagtgacc acacattacg tttcacagat tggtggcttc    2400
ccaaatcaaa cagaagacgg aggactacca caaagtggta gaattgttgt tgattacatg    2460
gtgcaaaaat ctgggaaaac aggaacaatt acctatcaaa ggggtatttt attgcctcaa    2520
aaggtgtggt gcgcaagtgg caggagcaag gtaataaaag gatccttgcc tttaattgga    2580
gaagcagatt gcctccacga aaaatacgt ggattaaaca aaagcaagcc ttactacaca    2640
ggggaacatg caaaggccat aggaaattgc ccaatatggg tgaaaacacc cttgaagctg    2700
gccaatggaa ccaaatatag acctcctgca aaactattaa aggaagggg tttcttcgga    2760
```

```
gctattgctg gtttcttaga aggaggatgg gaaggaatga ttgcaggttg gcacggatac    2820
acatcccatg gggcacatgg agtagcggtg gcagcagacc ttaagagcac tcaagaggcc    2880
ataaacaaga taacaaaaaa tctcaactct ttgagtgagc tggaagtaaa gaatcttcaa    2940
agactaagcg gtgccatgga tgaactccac aacgaaatac tagaactaga tgagaaagtg    3000
gatgatctca gagctgatac aataagctca caaatagaac tcgcagtcct gctttccaat    3060
gaaggaataa taaacagtga agatgaacat ctcttggcgc ttgaaagaaa gctgaagaaa    3120
atgctgggcc cctctgctgt agagataggg aatggatgct ttgaaaccaa acacaagtgc    3180
aaccagacct gtctcgacag aatagctgct ggtacctttg atgcaggaga attttctctc    3240
cccacctttg attcactgaa tattactgct gcatctttaa atgacgatgg attggataat    3300
taccaaatac tgtcaatttta ttcaacagtg gcgagttccc tagcactggc aatcatgatg    3360
gctggtctat ctttatggat gtgctccaat ggatcgttac aatgcagaat ttgcatttaa    3420
aggcctattt tctttagttt gaatttactg ttattcggtg tgcatttcta tgtttggtga    3480
gcggttttct gtgctcagag tgtgtttatt ttatgtaatt taatttcttt gtgagctcct    3540
gtttagcagg tcgtcccttc agcaaggaca caaaaagatt ttaattttat taaaaaaaaa    3600
aaaaaaaaag accgggaatt cgatatcaag cttatcgacc tgcagatcgt tcaaacattt    3660
ggcaataaag tttcttaaga ttgaatcctg ttgccggtct tgcgatgatt atcatataat    3720
ttctgttgaa ttacgttaag catgtaataa ttaacatgta atgcatgacg ttatttatga    3780
gatgggtttt tatgattaga gtcccgcaat tatacattta atacgcgata gaaaacaaaa    3840
tatagcgcgc aaactaggat aaattatcgc gcgcggtgtc atctatgtta ctagatctct    3900
agagtctcaa gcttggcgcg gggtaccgag ctcgaattcc gagtgtactt caagtcagtt    3960
ggaaatcaat aaaatgatta ttttatgaat atatttcatt gtgcaagtag atagaaatta    4020
catatgttac ataacacacg aaataaacaa aaaacacaa tccaaaacaa acaccccaaa    4080
caaaataaca ctatatatat cctcgtatga ggagaggcac gttcagtgac tcgacgattc    4140
ccgagcaaaa aaagtctccc cgtcacacat atagtgggtg acgcaattat cttcaaagta    4200
atccttctgt tgacttgtca ttgataacat ccagtcttcg tcaggattgc aaagaattat    4260
agaagggatc ccacctttta ttttcttctt ttttccatat ttagggttga cagtgaaatc    4320
agactggcaa cctattaatt gcttccacaa tgggacgaac ttgaagggga tgtcgtcgat    4380
gatattatag gtggcgtgtt catcgtagtt ggtgaagtcg atggtcccgt tccagtagtt    4440
gtgtcgcccg agacttctag cccaggtggt ctttccggta cgagttggtc cgcagatgta    4500
gaggctgggg tgtctgaccc cagtccttcc ctcatcctgg ttagatcggc catccactca    4560
aggtcagatt gtgcttgatc gtaggagaca ggatgtatga aagtgtaggc atcgatgctt    4620
acatgatata ggtgcgtctc tctccagttg tgcagatctt cgtggcagcg gagatctgat    4680
tctgtgaagg gcgacacgta ctgctcaggt tgtggaggaa ataatttgtt ggctgaatat    4740
tccagccatt gaagctttgt tgcccattca tgagggaatt cttctttgat catgtcaaga    4800
tactcctcct tagacgttgc agtctggata atagttcgcc atcgtgcgtc agatttgcga    4860
ggagagacct tatgatctcg gaaatctcct ctggttttaa tatctccgtc ctttgatatg    4920
taatcaagga cttgtttaga gtttctagct ggctggatat tagggtgatt tccttcaaaa    4980
tcgaaaaaag aaggatccct aatacaaggt ttttatcaa gctggataag agcatgatag    5040
tgggtagtgc catcttgatg aagctcagaa gcaacaccaa ggaagaaaat aagaaaaggt    5100
gtgagtttct cccagagaaa ctggaataaa tcatctcttt gagatgagca cttggggtag    5160
```

```
gtaaggaaaa catatttaga ttggagtctg aagttcttgc tagcagaagg catgttgttg    5220
tgactccgag gggttgcctc aaactctatc ttataaccgg cgtggaggca tggaggcaag    5280
ggcattttgg taatttaagt agttagtgga aaatgacgtc atttacttaa agacgaagtc    5340
ttgcgacaag gggggcccac gccgaatttt aatattaccg gcgtggcccc accttatcgc    5400
gagtgcttta gcacgagcgg tccagattta aagtagaaaa gttcccgccc actagggtta    5460
aaggtgttca cactataaaa gcatatacga tgtgatggta tttgatggag cgtatattgt    5520
atcaggtatt tccgtcggat acgaattatt cgtac                              5555
```

<210> SEQ ID NO 37
<211> LENGTH: 594
<212> TYPE: PRT
<213> ORGANISM: Influenza virus

<400> SEQUENCE: 37

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300
```

```
Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
                355                 360                 365

Lys Glu Arg Gly Phe Phe Gly Ala Ile Ala Gly Phe Leu Glu Gly Gly
370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
            405                 410                 415

Asn Lys Ile Thr Lys Asn Leu Asn Ser Leu Ser Glu Leu Glu Val Lys
                420                 425                 430

Asn Leu Gln Arg Leu Ser Gly Ala Met Asp Glu Leu His Asn Glu Ile
            435                 440                 445

Leu Glu Leu Asp Glu Lys Val Asp Asp Leu Arg Ala Asp Thr Ile Ser
450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
            485                 490                 495

Leu Gly Pro Ser Ala Val Glu Ile Gly Asn Gly Cys Phe Glu Thr Lys
                500                 505                 510

His Lys Cys Asn Gln Thr Cys Leu Asp Arg Ile Ala Ala Gly Thr Phe
            515                 520                 525

Asp Ala Gly Glu Phe Ser Leu Pro Thr Phe Asp Ser Leu Asn Ile Thr
530                 535                 540

Ala Ala Ser Leu Asn Asp Asp Gly Leu Asp Asn Tyr Gln Ile Leu Ser
545                 550                 555                 560

Ile Tyr Ser Thr Val Ala Ser Ser Leu Ala Leu Ala Ile Met Met Ala
            565                 570                 575

Gly Leu Ser Leu Trp Met Cys Ser Asn Gly Ser Leu Gln Cys Arg Ile
                580                 585                 590

Cys Ile

<210> SEQ ID NO 38
<211> LENGTH: 52
<212> TYPE: DNA
<213> ORGANISM: Artificial Sequence
<220> FEATURE:
<223> OTHER INFORMATION: primer 1039+1059.r

<400> SEQUENCE: 38
cttcccatcc tccaccagga ggtctatatt tggttccatt ggccagcttc aa          52

<210> SEQ ID NO 39
<211> LENGTH: 52
<212> TYPE: DNA
<213> ORGANISM: Artificial Sequence
<220> FEATURE:
<223> OTHER INFORMATION: primer 1039+1059.c

<400> SEQUENCE: 39
```

```
caaatataga cctcctggtg gaggatggga aggaatgatt gcaggttggc ac              52
```

<210> SEQ ID NO 40
<211> LENGTH: 5504
<212> TYPE: DNA
<213> ORGANISM: Artificial Sequence
<220> FEATURE:
<223> OTHER INFORMATION: Expression cassette number 1059 from BeYDV left
      LIR to BeYDV right LIR. PDISP/HA from influenza B/Brisbane/60/2008
      with deleted proteolytic loop

<400> SEQUENCE: 40

```
ctagcagaag gcatgttgtt gtgactccga ggggttgcct caaactctat cttataaccg      60
gcgtggaggc atggaggcaa gggcattttg gtaatttaag tagttagtgg aaaatgacgt     120
catttactta aagacgaagt cttgcgacaa ggggggccca cgccgaattt taatattacc     180
ggcgtggccc caccttatcg cgagtgcttt agcacgagcg gtccagattt aaagtagaaa     240
agttcccgcc cactagggtt aaaggtgttc acactataaa agcatatacg atgtgatggt     300
atttgataaa gcgtatattg tatcaggtat ttccgtcgga tacgaattat tcgtacaagc     360
ttcttaagcc ggtcaacatg gtggagcacg acacacttgt ctactccaaa aatatcaaag     420
atacagtctc agaagaccaa agggcaattg agacttttca acaagggta atatccggaa     480
acctcctcgg attccattgc ccagctatct gtcactttat tgtgaagata gtggaaaagg     540
aaggtggctc ctacaaatgc catcattgcg ataaaggaaa ggccatcgtt gaagatgcct     600
ctgccgacag tggtcccaaa gatggacccc cacccacgag gagcatcgtg gaaaagaag     660
acgttccaac cacgtcttca aagcaagtgg attgatgtga taacatggtg gagcacgaca     720
cacttgtcta ctccaaaaat atcaaagata cagtctcaga gaccaaaggg caattgaga    780
cttttcaaca aagggtaata tccggaaacc tcctcggatt ccattgccca gctatctgtc     840
actttattgt gaagatagtg gaaaggaag gtggctccta caaatgccat cattgcgata     900
aaggaaaggc catcgttgaa gatgcctctg ccgacagtgg tcccaaagat gaccccccac     960
ccacgaggag catcgtggaa aagaagacg ttccaaccac gtcttcaaag caagtggatt    1020
gatgtgatat ctccactgac gtaagggatg acgcacaatc ccactatcct tcgcaagacc    1080
cttcctctat ataaggaagt tcatttcatt tggagaggta ttaaaatctt aataggtttt    1140
gataaaagcg aacgtgggga aacccgaacc aaaccttctt ctaaactctc tctcatctct    1200
cttaaagcaa acttctctct tgtctttctt gcgtgagcga tcttcaacgt tgtcagatcg    1260
tgcttcggca ccagtacaac gttttctttc actgaagcga atcaaagat ctctttgtgg    1320
acacgtagtg cggcgccatt aaataacgtg tacttgtcct attcttgtcg gtgtggtctt    1380
gggaaaagaa agcttgctgg aggctgctgt tcagccccat acattacttg ttacgattct    1440
gctgactttc ggcgggtgca atatctctac ttctgcttga cgaggtattg ttgcctgtac    1500
ttctttcttc ttcttcttgc tgattggttc tataagaaat ctagtatttt ctttgaaaca    1560
gagttttccc gtggttttcg aacttggaga aagattgtta agcttctgta tattctgccc    1620
aaatttgtcg ggcccatggc gaaaacgttt gcgattttcg gcttattgtt ttctcttctt    1680
gtgttggttc cttctcagat cttcgccgat cgaatctgca ctggaataac atcgtcaaac    1740
tcaccacatg tcgtcaaaac tgctactcaa ggggaggtca atgtgactgg tgtaatacca    1800
ctgacaacaa cacccaccaa atctcatttt gcaaatctca aaggaacaga accaggggg    1860
aaactatgcc caaaatgcct caactgcaca gatctggacg tagccttggg cagaccaaaa    1920
tgcacgggga aaatacccct cggcaagagt tcaatactcc atgaagtcag acctgttaca    1980
```

```
tctgggtgct ttcctataat gcacgacaga acaaaaatta gacagctgcc taaccttctc    2040
cgaggatacg aacatatcag gttatcaacc cataacgtta tcaatgcaga aaatgcacca    2100
ggaggaccct acaaaattgg aacctcaggg tcttgcccta acattaccaa tggaaacgga    2160
tttttcgcaa caatggcttg ggccgtccca aaaaacgaca aaaacaaaac agcaacaaat    2220
ccattaacaa tagaagtacc atacatttgt acagaaggag aagaccaaat taccgtttgg    2280
gggttccact ctgacaacga gacccaaatg gcaaagctct atggggactc aaagccccag    2340
aagttcacct catctgccaa cggagtgacc acacattacg tttcacagat tggtggcttc    2400
ccaaatcaaa cagaagacgg aggactacca caaagtggta gaattgttgt tgattacatg    2460
gtgcaaaaat ctgggaaaac aggaacaatt acctatcaaa ggggtatttt attgcctcaa    2520
aaggtgtggt gcgcaagtgg caggagcaag gtaataaaag gatccttgcc tttaattgga    2580
gaagcagatt gcctccacga aaaatacggt ggattaaaca aaagcaagcc ttactacaca    2640
ggggaacatg caaaggccat aggaaattgc ccaatatggg tgaaaacacc cttgaagctg    2700
gccaatggaa ccaaatatag acctcctggt ggaggatggg aaggaatgat tgcaggttgg    2760
cacggataca catcccatgg ggcacatgga gtagcggtgg cagcagacct taagagcact    2820
caagaggcca taaacaagat aacaaaaaat ctcaactctt tgagtgagct ggaagtaaag    2880
aatcttcaaa gactaagcgg tgccatggat gaactccaca acgaaatact agaactagat    2940
gagaaagtgg atgatctcag agctgataca ataagctcac aaatagaact cgcagtcctg    3000 cttccaatg aaggaataat aaacagtgaa gatgaacatc tcttggcgct tgaaagaaag    3060
ctgaagaaaa tgctgggccc ctctgctgta gagatag gga atggatgctt tgaaaccaaa    3120
cacaagtgca accagacctg tctcgacaga atagctgctg gtacctttga tgcaggagaa    3180
ttttctctcc ccacctttga ttcactgaat attactgctg catctttaaa tgacgatgga    3240
ttggataatc atactatact gctttactac tcaactgctg cctccagttt ggctgtaaca    3300
ctgatgatag ctatctttgt tgtttatatg gtctccagag acaatgtttc ttgctccatc    3360
tgtctataaa ggcctatttt ctttagtttg aatttactgt tattcggtgt gcatttctat    3420
gtttggtgag cggttttctg tgctcagagt gtgtttattt tatgtaattt aatttctttg    3480
tgagctcctg tttagcaggt cgtcccttca gcaaggacac aaaaagattt taattttatt    3540
aaaaaaaaaa aaaaaaaga ccgggaattc gatatcaagc ttatcgacct gcagatcgtt    3600
caaacatttg gcaataaagt ttcttaagat tgaatcctgt tgccggtctt gcgatgatta    3660
tcatataatt tctgttgaat tacgttaagc atgtaataat taacatgtaa tgcatgacgt    3720
tatttatgag atgggttttt atgattagag tcccgcaatt atacatttaa tacgcgatag    3780
aaaacaaaat atagcgcgca aactaggata aattatcgcg cgcggtgtca tctatgttac    3840
tagatctcta gagtctcaag cttggcgcgg ggtaccgagc tcgaattccg agtgtacttc    3900
aagtcagttg gaaatcaata aaatgattat tttatgaata tatttcattg tgcaagtaga    3960
tagaaattac atatgttaca taacacacga aataaacaaa aaacacaat ccaaaacaaa    4020 cacccaaac aaaataacac tatatatatc ctcgtatgag gagaggcacg ttcagtgact    4080
cgacgattcc cgagcaaaaa aagtctcccc gtcacacata tagtgggtga cgcaattatc    4140
ttcaaagtaa tccttctgtt gacttgtcat tgataacatc cagtcttcgt caggattgca    4200
aagaattata gaagggatcc cacctttat tttcttcttt tttccatatt tagggttgac    4260
agtgaaatca gactggcaac ctattaattg cttccacaat gggacgaact tgaaggggat    4320
```

-continued

```
gtcgtcgatg atattatagg tggcgtgttc atcgtagttg gtgaagtcga tggtcccgtt    4380
ccagtagttg tgtcgcccga gacttctagc ccaggtggtc tttccggtac gagttggtcc    4440
gcagatgtag aggctggggt gtctgacccc agtccttccc tcatcctggt tagatcggcc    4500
atccactcaa ggtcagattg tgcttgatcg taggagacag gatgtatgaa agtgtaggca    4560
tcgatgctta catgatatag gtgcgtctct ctccagttgt gcagatcttc gtggcagcgg    4620
agatctgatt ctgtgaaggg cgacacgtac tgctcaggtt gtggaggaaa taatttgttg    4680
gctgaatatt ccagccattg aagctttgtt gcccattcat gagggaattc ttctttgatc    4740
atgtcaagat actcctcctt agacgttgca gtctggataa tagttcgcca tcgtgcgtca    4800
gatttgcgag gagagacctt atgatctcgg aaatctcctc tggttttaat atctccgtcc    4860
tttgatatgt aatcaaggac ttgtttagag tttctagctg gctggatatt agggtgattt    4920
ccttcaaaat cgaaaaaaga aggatcccta atacaaggtt ttttatcaag ctggataaga    4980
gcatgatagt gggtagtgcc atcttgatga agctcagaag caacaccaag gaagaaaata    5040
agaaaaggtg tgagtttctc ccagagaaac tggaataaat catctctttg agatgagcac    5100
ttggggtagg taaggaaaac atatttagat tggagtctga agttcttgct agcagaaggc    5160
atgttgttgt gactccgagg ggttgcctca aactctatct tataaccggc gtggaggcat    5220
ggaggcaagg gcattttggt aatttaagta gttagtggaa aatgacgtca tttacttaaa    5280
gacgaagtct tgcgacaagg ggggcccacg ccgaattta atattaccgg cgtggcccca    5340
ccttatcgcg agtgctttag cacgagcggt ccagatttaa agtagaaaag ttcccgccca    5400
ctagggttaa aggtgttcac actataaaag catatacgat gtgatggtat ttgatggagc    5460
gtatattgta tcaggtattt ccgtcggata cgaattattc gtac                      5504
```

<210> SEQ ID NO 41
<211> LENGTH: 577
<212> TYPE: PRT
<213> ORGANISM: Influenza virus

<400> SEQUENCE: 41

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
```

```
              165                 170                 175
Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
            195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
            275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
            355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
            435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
            515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
                565                 570                 575

Leu
```

<210> SEQ ID NO 42
<211> LENGTH: 1707
<212> TYPE: DNA
<213> ORGANISM: Influenza virus

<400> SEQUENCE: 42

| | | | | | |
|---|---|---|---|---|---|
| atggagaaaa | tagtgcttct | tcttgcaata | gtcagtcttg | ttaaaagtga | tcagatttgc | 60 |
| attggttacc | atgcaaacaa | ttcaacagag | caggttgaca | caatcatgga | aaagaacgtt | 120 |
| actgttacac | atgcccaaga | catactggaa | agacacaca | acgggaagct | ctgcgatcta | 180 |
| gatggagtga | agcctctaat | tttaagagat | tgtagtgtag | ctggatggct | cctcgggaac | 240 |
| ccaatgtgtg | acgaattcat | caatgtaccg | gaatggtctt | acatagtgga | aaggccaat | 300 |
| ccaaccaatg | acctctgtta | cccagggagt | ttcaacgact | atgaagaact | gaaacaccta | 360 |
| ttgagcagaa | taaaccattt | tgagaaaatt | caaatcatcc | ccaaaagttc | ttggtccgat | 420 |
| catgaagcct | catcaggagt | tagctcagca | tgtccatacc | tgggaagtcc | ctcctttttt | 480 |
| agaaatgtgg | tatggcttat | caaaaagaac | agtacatacc | caacaataaa | gaaagctac | 540 |
| aataatacca | accaagagga | tctttttggta | ctgtggggaa | ttcaccatcc | taatgatgcg | 600 |
| gcagagcaga | caaggctata | tcaaaaccca | accacctata | tttccattgg | gacatcaaca | 660 |
| ctaaaccaga | gattggtacc | aaaaatagct | actagatcca | agtaaacgg | caaagtgga | 720 |
| aggatggagt | tcttctggac | aattttaaaa | cctaatgatg | caatcaactt | cgagagtaat | 780 |
| ggaaatttca | ttgctccaga | atatgcatac | aaaattgtca | agaaggga | ctcagcaatt | 840 |
| atgaaaagtg | aattggaata | tggtaactgc | aacaccaagt | gtcaaactcc | aatgggggcg | 900 |
| ataaactcta | gtatgccatt | ccacaacata | caccctctca | ccatcgggga | atgccccaaa | 960 |
| tatgtgaaat | caaacagatt | agtccttgca | acagggctca | gaaatagccc | tcaaagagag | 1020 |
| agcagaagaa | aaaagagagg | actatttgga | gctatagcag | ttttataga | gggaggatgg | 1080 |
| cagggaatgg | tagatggttg | gtatgggtac | caccatagca | atgagcaggg | gagtgggtac | 1140 |
| gctgcagaca | aagaatccac | tcaaaaggca | atagatggag | tcaccaataa | ggtcaactca | 1200 |
| atcattgaca | aaatgaacac | tcagtttgag | gccgttggaa | gggaatttaa | taacttagaa | 1260 |
| aggagaatag | agaatttaaa | caagaagatg | gaagacgggt | ttctagatgt | ctggacttat | 1320 |
| aatgccgaac | ttctggttct | catggaaaat | gagagaactc | tagactttca | tgactcaaat | 1380 |
| gttaagaacc | tctacgacaa | ggtccgacta | cagcttaggg | ataatgcaaa | ggagctgggt | 1440 |
| aacggttgtt | tcgagttcta | tcacaaatgt | gataatgaat | gtatgaaag | tataagaaac | 1500 |
| ggaacgtaca | actatccgca | gtattcagaa | gaagcaagat | taaaagaga | ggaaataagt | 1560 |
| ggggtaaaat | tggaatcaat | aggaacttac | caaatactgt | caatttattc | aacagtggcg | 1620 |
| agttccctag | cactggcaat | catgatggct | ggtctatctt | tatggatgtg | ctccaatgga | 1680 |
| tcgttacaat | gcagaatttg | catttaa | | | | 1707 |

<210> SEQ ID NO 43
<211> LENGTH: 1734
<212> TYPE: DNA
<213> ORGANISM: Influenza virus

<400> SEQUENCE: 43

| | | | | | |
|---|---|---|---|---|---|
| atggcgaaaa | acgttgcgat | tttcggctta | ttgtttttctc | ttcttgtgtt | ggttccttct | 60 |
| cagatcttcg | ccgatcgaat | ctgcactgga | ataacatcgt | caaactcacc | acatgtcgtc | 120 |
| aaaactgcta | ctcaagggga | ggtcaatgtg | actggtgtaa | taccactgac | aacaacaccc | 180 |

```
accaaatctc attttgcaaa tctcaaagga acagaaacca gggggaaact atgcccaaaa      240
tgcctcaact gcacagatct ggacgtagcc ttgggcagac caaaatgcac ggggaaaata      300
ccctcggcaa gagtttcaat actccatgaa gtcagacctg ttacatctgg gtgctttcct      360
ataatgcacg acagaacaaa aattagacag ctgcctaacc ttctccgagg atacgaacat      420
atcaggttat caacccataa cgttatcaat gcagaaaatg caccaggagg accctacaaa      480
attggaacct cagggtcttg ccctaacatt accaatggaa acggattttt cgcaacaatg      540
gcttgggccg tcccaaaaaa cgacaaaaac aaaacagcaa caaatccatt aacaatagaa      600
gtaccataca tttgtacaga aggagaagac caaattaccg tttgggggtt ccactctgac      660
aacgagaccc aaatggcaaa gctctatggg gactcaaagc cccagaagtt cacctcatct      720
gccaacggag tgaccacaca ttacgtttca cagattggtg gcttcccaaa tcaaacagaa      780
gacggaggac taccacaaag tggtagaatt gttgttgatt acatggtgca aaaatctggg      840
aaaacaggaa caattaccta tcaagggggt attttattgc ctcaaaaggt gtggtgcgca      900
agtggcagga gcaaggtaat aaaaggatcc ttgccttttaa ttggagaagc agattgcctc      960
cacgaaaaat acggtggatt aaacaaaagc aagccttact acacagggga acatgcaaag     1020
gccataggaa attgcccaat atgggtgaaa acacccttga agctggccaa tggaaccaaa     1080
tatagacctc ctggtggagg atgggaagga atgattgcag gttggcacgg atacacatcc     1140 catgggcac atggagtagc ggtggcagca gaccttaaga gcactcaaga ggccataaac     1200
aagataacaa aaaatctcaa ctctttgagt gagctggaag taagaatct tcaaagacta     1260 agcggtgcca tggatgaact ccacaacgaa atactagaac tagatgagaa agtggatgat     1320
ctcagagctg atacaataag ctcacaaata gaactcgcag tcctgctttc caatgaagga     1380
ataataaaca gtgaagatga acatctcttg gcgcttgaaa gaaagctgaa gaaaatgctg     1440
ggcccctctg ctgtagagat agggaatgga tgctttgaaa ccaaacacaa gtgcaaccag     1500
acctgtctcg acagaatagc tgctggtacc tttgatgcag gagaattttc tctccccacc     1560
tttgattcac tgaatattac tgctgcatct ttaaatgacg atggattgga taatcatact     1620
atactgcttt actactcaac tgctgcctcc agtttggctg taacactgat gatagctatc     1680
tttgttgttt atatggtctc cagagacaat gtttcttgct ccatctgtct ataa            1734
```

<210> SEQ ID NO 44  
<211> LENGTH: 48  
<212> TYPE: DNA  
<213> ORGANISM: Artificial Sequence  
<220> FEATURE:  
<223> OTHER INFORMATION: primer IF-H3V36111.S2+4c

<400> SEQUENCE: 44

```
tctcagatct tcgcccaaaa acttcctgga aatgacaaca gcacggca                    48
```

<210> SEQ ID NO 45  
<211> LENGTH: 51  
<212> TYPE: DNA  
<213> ORGANISM: Artificial Sequence  
<220> FEATURE:  
<223> OTHER INFORMATION: primer IF-H3V36111.s1-4r

<400> SEQUENCE: 45

```
actaaagaaa ataggccttc aaatgcaaat gttgcaccta atgttgccct t                51
```

<210> SEQ ID NO 46

<211> LENGTH: 1701
<212> TYPE: DNA
<213> ORGANISM: Artificial Sequence
<220> FEATURE:
<223> OTHER INFORMATION: nucleotide sequence of synthesized H3 gene

<400> SEQUENCE: 46

| | | | | | |
|---|---|---|---|---|---|
| atgaagacta | tcattgcttt | gagccacatt | ctatgtctgg | ttttcgctca | aaaacttcct | 60 |
| ggaaatgaca | acagcacggc | aacgctgtgc | cttgggcacc | atgcagtacc | aaacggaacg | 120 |
| atagtgaaaa | caatcacgaa | tgaccaaatt | gaagttacta | atgctactga | gctggttcag | 180 |
| aattcctcaa | taggtgaaat | atgcgacagt | cctcatcaga | tccttgatgg | agaaaactgc | 240 |
| acactaatag | atgctctatt | gggagaccct | cagtgtgatg | gcttccaaaa | taagaaatgg | 300 |
| gacctttttg | ttgaacgaag | caaagcctac | agcaactgtt | acccttatga | tgtgccggat | 360 |
| tatgcctccc | ttaggtcact | agttgcctca | tccggcacac | tggagtttaa | caatgaaagc | 420 |
| ttcaattgga | ctggagtcac | tcaaaacgga | acaagttctg | cttgcataag | gagatctaat | 480 |
| aatagtttct | ttagtagatt | aaattggttg | acccacttaa | acttcaaata | cccagcattg | 540 |
| aacgtgacta | tgccaaacaa | tgaacaattt | gacaaattgt | acatttgggg | ggttcaccac | 600 |
| ccgggtacgg | acaaggacca | aatcttcctg | tatgctcaat | catcaggaag | aatcacagta | 660 |
| tctaccaaaa | gaagccaaca | agctgtaatc | ccgaatatcg | gatctagacc | cagaataagg | 720 |
| aatatcccta | gcagaataag | catctattgg | acaatagtaa | aaccgggaga | catacttttg | 780 |
| attaacagca | cagggaatct | aattgctcct | aggggttact | tcaaaatacg | aagtgggaaa | 840 |
| agctcaataa | tgagatcaga | tgcacccatt | ggcaaatgca | attctgaatg | catcactcca | 900 |
| aatggaagca | ttcccaatga | caaaccattc | caaaatgtaa | acaggatcac | atacggggcc | 960 |
| tgtcccagat | atgttaagca | aagcactctg | aaattggcaa | caggaatgcg | aaatgtacca | 1020 |
| gagaaacaaa | ctagaggcat | atttggcgca | atagcgggtt | tcatagaaaa | tggttgggag | 1080 |
| ggaatggtgg | atggttggta | cggtttcagg | catcaaaatt | ctgagggaag | aggacaagca | 1140 |
| gcagatctca | aaagcactca | agcagcaatc | gatcaaatca | atgggaagct | gaatcgattg | 1200 |
| atcgggaaaa | ccaacgagaa | attccatcag | attgaaaaag | aattctcaga | agtcgaaggg | 1260 |
| agaattcagg | accttgagaa | atatgttgag | gacactaaaa | tagatctctg | gtcatacaac | 1320 |
| gcggagcttc | ttgttgccct | ggagaaccaa | catacaattg | atctaactga | ctcagaaatg | 1380 |
| aacaaactgt | ttgaaaaaac | aaagaagcaa | ctaagggaaa | atgctgagga | tatgggcaat | 1440 |
| ggttgtttca | aaatatacca | caaatgtgac | aatgcctgca | taggatcaat | cagaaatgga | 1500 |
| acttatgacc | acgatgtata | cagagatgaa | gcattaaaca | accggttcca | gatcaaggga | 1560 |
| gttgagctga | agtcagggta | caaagattgg | atcctatgga | tttcctttgc | catatcatgt | 1620 |
| tttttgcttt | gtgttgcttt | gttggggttc | atcatgtggg | cctgccaaaa | gggcaacatt | 1680 |
| aggtgcaaca | tttgcatttg | a | | | | 1701 |

<210> SEQ ID NO 47
<211> LENGTH: 3465
<212> TYPE: DNA
<213> ORGANISM: Artificial Sequence
<220> FEATURE:
<223> OTHER INFORMATION: expression cassette number 1391

<400> SEQUENCE: 47

| | | | | | |
|---|---|---|---|---|---|
| gtcaacatgg | tggagcacga | cacacttgtc | tactccaaaa | atatcaaaga | tacagtctca | 60 |
| gaagaccaaa | gggcaattga | gacttttcaa | caaagggtaa | tatccggaaa | cctcctcgga | 120 |

-continued

| | |
|---|---|
| ttccattgcc cagctatctg tcactttatt gtgaagatag tggaaaagga aggtggctcc | 180 |
| tacaaatgcc atcattgcga taaaggaaag gccatcgttg aagatgcctc tgccgacagt | 240 |
| ggtcccaaag atggacccc acccacgagg agcatcgtgg aaaagaaga cgttccaacc | 300 |
| acgtcttcaa agcaagtgga ttgatgtgat aacatggtgg agcacgacac acttgtctac | 360 |
| tccaaaaata tcaaagatac agtctcagaa gaccaaaggg caattgagac ttttcaacaa | 420 |
| agggtaatat ccgaaaacct cctcggattc cattgcccag ctatctgtca ctttattgtg | 480 |
| aagatagtgg aaaggaagg tggctcctac aaatgccatc attgcgataa aggaaaggcc | 540 |
| atcgttgaag atgcctctgc cgacagtggt cccaaagatg acccccacc cacgaggagc | 600 |
| atcgtggaaa aagaagacgt tccaaccacg tcttcaaagc aagtggattg atgtgatatc | 660 |
| tccactgacg taagggatga cgcacaatcc cactatcctt cgcaagaccc ttcctctata | 720 |
| taaggaagtt catttcattt ggagaggtat taaaatctta ataggttttg ataaaagcga | 780 |
| acgtggggaa acccgaacca aaccttcttc taaactctct ctcatctctc ttaaagcaaa | 840 |
| cttctctctt gtctttcttg cgtgagcgat cttcaacgtt gtcagatcgt gcttcggcac | 900 |
| cagtacaacg ttttctttca ctgaagcgaa atcaaagatc tctttgtgga cacgtagtgc | 960 |
| ggcgccatta ataacgtgt acttgtccta ttcttgtcgg tgtggtcttg ggaaaagaaa | 1020 |
| gcttgctgga ggctgctgtt cagccccata cattacttgt tacgattctg ctgactttcg | 1080 |
| gcgggtgcaa tatctctact tctgcttgac gaggtattgt tgcctgtact tctttcttct | 1140 |
| tcttcttgct gattggttct ataagaaatc tagtatttc tttgaaacag agttttcccg | 1200 |
| tggttttcga acttggagaa agattgttaa gcttctgtat attctgccca aatttgtcgg | 1260 |
| gcccatggcg aaaaacgttg cgattttcgg cttattgttt tctcttcttg tgttggttcc | 1320 |
| ttctcagatc ttcgcccaaa aacttcctgg aaatgacaac agcacggcaa cgctgtgcct | 1380 |
| tgggcaccat gcagtaccaa acggaacgat agtgaaaaca atcacgaatg accaaattga | 1440 |
| agttactaat gctactgagc tggttcagaa ttcctcaata ggtgaaatat gcgacagtcc | 1500 |
| tcatcagatc cttgatggag aaaactgcac actaatagat gctctattgg gagaccctca | 1560 |
| gtgtgatggc ttccaaaata gaaatggga ccttttgtt gaacgaagca aagcctacag | 1620 |
| caactgttac ccttatgatg tgccggatta tgcctccctt aggtcactag ttgcctcatc | 1680 |
| cggcacactg gagtttaaca atgaaagctt caattggact ggagtcactc aaaacggaac | 1740 |
| aagttctgct tgcataagga gatctaataa tagtttcttt agtagattaa attggttgac | 1800 |
| ccacttaaac ttcaaatacc cagcattgaa cgtgactatg ccaaacaatg aacaatttga | 1860 |
| caaattgtac atttgggggg ttcaccaccc gggtacggac aaggaccaaa tcttcctgta | 1920 |
| tgctcaatca tcaggaagaa tcacagtatc taccaaaaga agccaacaag ctgtaatccc | 1980 |
| gaatatcgga tctagaccca gaataaggaa tatccctagc agaataagca tctattggac | 2040 |
| aatagtaaaa ccgggagaca tacttttgat taacagcaca gggaatctaa ttgctcctag | 2100 |
| gggttacttc aaaatacgaa gtgggaaaag ctcaataatg agatcagatg cacccattgg | 2160 |
| caaatgcaat tctgaatgca tcactccaaa tggaagcatt cccaatgaca aaccattcca | 2220 |
| aaatgtaaac aggatcacat acgggccctg tcccagatat gttaagcaaa gcactctgaa | 2280 |
| attggcaaca ggaatgcgaa atgtaccaga gaaacaaact agaggcatat ttggcgcaat | 2340 |
| agcgggtttc atagaaaatg gttgggaggg aatggtggat ggttggtacg gtttcaggca | 2400 |
| tcaaaattct gagggaagag gacaagcagc agatctcaaa agcactcaag cagcaatcga | 2460 |

-continued

```
tcaaatcaat gggaagctga atcgattgat cgggaaaacc aacgagaaat ccatcagat      2520 tgaaaaagaa ttctcagaag tcgaagggag aattcaggac cttgagaaat atgttgagga      2580
cactaaaata gatctctggt catacaacgc ggagcttctt gttgccctgg agaaccaaca      2640
tacaattgat ctaactgact cagaaatgaa caaactgttt gaaaaaacaa agaagcaact      2700
aagggaaaat gctgaggata tgggcaatgg ttgtttcaaa atataccaca aatgtgacaa      2760
tgcctgcata ggatcaatca gaaatggaac ttatgaccac gatgtataca gagatgaagc      2820
attaaacaac cggttccaga tcaagggagt tgagctgaag tcagggtaca agattggat       2880 cctatggatt tcctttgcca tatcatgttt tttgctttgt gttgctttgt tggggttcat      2940
catgtgggcc tgccaaaagg gcaacattag gtgcaacatt tgcatttgaa ggcctatttt      3000
ctttagtttg aatttactgt tattcggtgt gcatttctat gtttggtgag cggttttctg      3060
tgctcagagt gtgtttattt tatgtaattt aatttctttg tgagctcctg tttagcaggt      3120
cgtcccttca gcaaggacac aaaaagattt taatttttatt aaaaaaaaaa aaaaaaaga      3180 ccgggaattc gatatcaagc ttatcgacct gcagatcgtt caaacatttg gcaataaagt      3240
ttcttaagat tgaatcctgt tgccggtctt gcgatgatta tcatataatt tctgttgaat      3300
tacgttaagc atgtaataat taacatgtaa tgcatgacgt tatttatgag atgggttttt      3360
atgattagag tcccgcaatt atacatttaa tacgcgatag aaaacaaaat atagcgcgca      3420
aactaggata aattatcgcg cgcggtgtca tctatgttac tagat                      3465
```

<210> SEQ ID NO 48
<211> LENGTH: 574
<212> TYPE: PRT
<213> ORGANISM: Influenza virus

<400> SEQUENCE: 48

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Asn Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
```

```
              195                 200                 205
Pro Gly Thr Asp Lys Asp Gln Ile Phe Leu Tyr Ala Gln Ser Ser Gly
210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
                260                 265                 270

Gly Asn Leu Ile Ala Pro Arg Gly Tyr Phe Lys Ile Arg Ser Gly Lys
                275                 280                 285

Ser Ser Ile Met Arg Ser Asp Ala Pro Ile Gly Lys Cys Asn Ser Glu
290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
                340                 345                 350

Arg Gly Ile Phe Gly Ala Ile Ala Gly Phe Ile Glu Asn Gly Trp Glu
                355                 360                 365

Gly Met Val Asp Gly Trp Tyr Gly Phe Arg His Gln Asn Ser Glu Gly
370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
                420                 425                 430

Leu Glu Lys Tyr Val Glu Asp Thr Lys Ile Asp Leu Trp Ser Tyr Asn
                435                 440                 445

Ala Glu Leu Leu Val Ala Leu Glu Asn Gln His Thr Ile Asp Leu Thr
450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
                500                 505                 510

Asp Val Tyr Arg Asp Glu Ala Leu Asn Asn Arg Phe Gln Ile Lys Gly
                515                 520                 525

Val Glu Leu Lys Ser Gly Tyr Lys Asp Trp Ile Leu Trp Ile Ser Phe
530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
                565                 570
```

<210> SEQ ID NO 49
<211> LENGTH: 46
<212> TYPE: DNA
<213> ORGANISM: Artificial Sequence
<220> FEATURE:
<223> OTHER INFORMATION: primer IF-HAB110.S1+3c

<400> SEQUENCE: 49

```
aaatttgtcg ggcccatgaa ggcaataatt gtactactca tggtag            46
```

<210> SEQ ID NO 50
<211> LENGTH: 52
<212> TYPE: DNA
<213> ORGANISM: Artificial Sequence
<220> FEATURE:
<223> OTHER INFORMATION: primer IF-HAB110.s1-4r

<400> SEQUENCE: 50

```
actaaagaaa ataggccttt atagacagat ggagcatgaa acgttgtctc tg      52
```

<210> SEQ ID NO 51
<211> LENGTH: 1755
<212> TYPE: DNA
<213> ORGANISM: Artificial Sequence
<220> FEATURE:
<223> OTHER INFORMATION: nucleotide sequence of synthesized HA
      B/Wisconin (JN993010)

<400> SEQUENCE: 51

```
atgaaggcaa taattgtact actcatggta gtaacatcca atgcagatcg aatctgcact    60
gggataacat cttcaaactc acctcatgtg gtcaaaacag ctactcaagg ggaggtcaat   120
gtgactggcg tgataccact gacaacaaca ccaacaaaat cttattttgc aaatctcaaa   180
ggaacaagga ccagagggaa actatgcccg gactgtctca actgtacaga tctggatgtg   240
gccttgggca ggccaatgtg tgtggggacc acaccttctg ctaaagcttc aatactccac   300
gaggtcagac tgttacatc cgggtgcttt cctataatgc acgacagaac aaaaatcagg   360
caactaccca tcttctcag aggatatgaa aatatcaggt tatcaaccca aaacgttatc   420
gatgcagaaa aagcaccagg aggaccctac agacttggaa cctcaggatc ttgccctaac   480
gctaccagta aaatcggatt ttttgcaaca atggcttggg ctgtcccaaa ggacaactac   540
aaaaatgcaa cgaacccact aacagtagaa gtaccataca tttgtacaga aggggaagac   600
caaattactg tttggggggtt ccattcagat aacaaaaccc aaatgaagag cctctatgga   660
gactcaaatc ctcaaaagtt cacctcatct gctaatggag taaccacaca ttatgtttct   720
cagattggcg acttcccaga tcaaacagaa gacggaggac taccacaaag cggcagaatt   780
gttgttgatt acatgatgca aaaacctggg aaaacaggaa caattgtcta tcaaagaggt   840
gttttgttgc ctcaaaaggt gtggtgcgcg agtggcagga gcaaagtaat aaaagggtca   900
ttgcctttaa ttggtgaagc agattgcctt catgaaaaat acggtggatt aaacaaaagc   960
aagccttact acacaggaga acatgcaaaa gccataggaa attgcccaat atgggtaaaa  1020
acacctttga agcttgccaa tggaaccaaa tatagacctc ctgcaaaact attgaaggaa  1080
aggggtttct tcggagctat tgctggtttc ctagaaggag gatgggaagg aatgattgca  1140
ggttggcacg gatacacatc tcacggagca catgagtgg cagtggcggc agaccttaag  1200
agtacacaag aagctataaa taagataaca aaaaatctca attctttgag tgagctagaa  1260
gtaaagaacc ttcaaagact aagtggtgcc atggatgaac tccacaacga atactcgag  1320
ctggatgaga aagtggatga tctcagagct gacactataa gctcacaaat agaacttgca  1380
gtcttgcttt ccaacgaagg aataataaac agtgaagacg agcatctatt ggcacttgag  1440
agaaaactaa agaaaatgct gggtcccctct gctgtagaca taggaaacgg atgcttcgaa  1500
accaaacaca aatgcaacca gacctgctta gacaggatag ctgctggcac ctttaatgca  1560
```

```
ggagaattttt ctctccccac tttttgattca ttgaacatta ctgctgcatc tttaaatgat    1620
gatggattgg ataaccatac tatactgctc tattactcaa ctgctgcttc tagtttggct    1680
gtaacattaa tgctagctat ttttattgtt tatatggtct ccagagacaa cgtttcatgc    1740
tccatctgtc tataa                                                      1755

<210> SEQ ID NO 52
<211> LENGTH: 6745
<212> TYPE: DNA
<213> ORGANISM: Artificial Sequence
<220> FEATURE:
<223> OTHER INFORMATION: Construct 193

<400> SEQUENCE: 52
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacatttta cttgaacaaa      180 aatattcacc tactactgtt ataaatcatt attaaacatt agagtaaaga aatatggatg     240
ataagaacaa gagtagtgat attttgacaa cattttgtt gcaacatttg agaaaatttt      300
gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tatttttaaa attaaagtt gagtcatttg attaaacatg tgattattta     600
atgaattgat gaaagagttg gattaaagtt gtattagtaa ttagaatttg gtgtcaaatt     660
taatttgaca tttgatcttt tcctatatat tgccccatag agtcagttaa ctcatttta      720 tatttcatag atcaaataag agaataacg gtatattaat ccctccaaaa aaaaaaaacg     780
gtatatttac taaaaaatct aagccacgta ggaggataac aggatccccg taggaggata     840
acatccaatc caaccaatca caacaatcct gatgagataa cccactttaa gcccacgcat     900
ctgtggcaca tctacattat ctaaatcaca cattcttcca cacatctgag ccacacaaaa     960
accaatccac atctttatca cccattctat aaaaaatcac actttgtgag tctacacttt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatggaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct ggggtttcgg gaagttgta tttaagagat atctcagata cgacaggacg     1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaagagga    1560
tgccctgaag gtactcaaac cttcgaaaaa gaaagcgagt aagttaaaat gcttcttcgt    1620 ctcctatttta taatatggtt tgttattgtt aattttgttc ttgtagaaga gcttaattaa    1680
tcgttgttgt tatgaaatac tatttgtatg agatgaactg gtgtaatgta attcatttac    1740
ataagtggag tcagaatcag aatgtttcct ccataactaa ctagacatga agacctgccg    1800
cgtacaattg tcttatattt gaacaactaa aattgaacat cttttgccac aactttataa    1860
```

```
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaga cgcgttgttg ttgtgactcc gaggggttgc    2160
ctcaaactct atcttataac cggcgtggag gcatggaggc aggggtattt tggtcatttt    2220
aatagatagt ggaaaatgac gtggaattta cttaaagacg aagtctttgc gacaaggggg    2280
ggcccacgcc gaatttaata ttaccggcgt ggccccccct tatcgcgagt gctttagcac    2340
gagcggtcca gatttaaagt agaaaatttc ccgcccacta gggttaaagg tgttcacact    2400
ataaaagcat atacgatgtg atggtatttg gtcgacaagc ttgcatgccg gtcaacatgg    2460
tggagcacga cacacttgtc tactccaaaa atatcaaaga tacagtctca gaagaccaaa    2520
gggcaattga gacttttcaa caagggtaa tatccggaaa cctcctcgga ttccattgcc     2580
cagctatctg tcactttatt gtgaagatag tggaaaagga aggtggctcc tacaaatgcc    2640
atcattgcga taaggaaag gccatcgttg aagatgcctc tgccgacagt ggtcccaaag      2700 atggacccc acccacgagg agcatcgtgg aaaaagaaga cgttccaacc acgtcttcaa      2760
agcaagtgga ttgatgtgat aacatggtgg agcacgacac acttgtctac tccaaaaata    2820
tcaaagatac agtctcagaa gaccaaaggg caattgagac ttttcaacaa agggtaatat    2880
ccggaaacct cctcggattc cattgcccag ctatctgtca ctttattgtg aagatagtgg    2940
aaaaggaagg tggctcctac aaatgccatc attgcgataa aggaaaggcc atcgttgaag    3000
atgcctctgc cgacagtggt cccaaagatg gaccccacc cacgaggagc atcgtggaaa     3060
aagaagacgt tccaaccacg tcttcaaagc aagtggattg atgtgatatc tccactgacg    3120
taagggatga cgcacaatcc cactatcctt cgcaagaccc ttcctctata taaggaagtt    3180
catttcattt ggagaggtat taaaatctta ataggttttg ataaaagcga acgtggggaa    3240
acccgaacca aaccttcttc taaactctct ctcatctctc ttaaagcaaa cttctctctt    3300
gtctttcttg cgtgagcgat cttcaacgtt gtcagatcgt gcttcggcac cagtacaacg    3360
ttttctttca ctgaagcgaa atcaaagatc tctttgtgga cacgtagtgc ggcgccatta    3420
aataacgtgt acttgtccta ttcttgtcgg tgtggtcttg ggaaaagaaa gcttgctgga    3480
ggctgctgtt cagccccata cattacttgt tacgattctg ctgactttcg gcgggtgcaa    3540
tatctctact tctgcttgac gaggtattgt tgcctgtact tctttcttct tcttcttgct    3600
gattggttct ataagaaatc tagtattttc tttgaaacag agttttcccg tggttttcga    3660
acttggagaa agattgttaa gcttctgtat attctgccca aatttgtcgg gcccgcggat    3720
ggcgaaaaac gttgcgattt tcggcttatt gttttctctt cttgtgttgg ttccttctca    3780
gatcttcgcc tgcaggctcc tcagccaaaa cgacaccccc atctgtctat ccactggccc    3840
ctggatctgc tgcccaaact aactccatgg tgaccctggg atgcctggtc aagggctatt    3900
tccctgagcc agtgacagtg acctggaact ctggatccct gtccagcggt gtgcacacct    3960
tcccagctgt cctgcagtct gacctctaca ctctgagcag ctcagtgact gtcccctcca    4020
gcacctggcc cagcgagacc gtcacctgca acgttgccca cccggccagc agcaccaagg    4080
tggacaagaa aattgtgccc agggattgtg gttgtaagcc ttgcatatgt acagtcccag    4140
aagtatcatc tgtcttcatc ttccccccaa agcccaagga tgtgctcacc attactctga    4200
```

```
ctcctaaggt cacgtgtgtt gtggtagaca tcagcaagga tgatcccgag gtccagttca   4260
gctggtttgt agatgatgtg gaggtgcaca cagctcagac gcaacccgg gaggagcagt    4320
tcaacagcac tttccgctca gtcagtgaac ttcccatcat gcaccaggac tggctcaatg   4380
gcaaggagcg atcgctcacc atcaccatca ccatcaccat caccattaaa ggcctatttt   4440
ctttagtttg aatttactgt tattcggtgt gcatttctat gtttggtgag cggttttctg   4500
tgctcagagt gtgtttattt tatgtaattt aatttctttg tgagctcctg tttagcaggt   4560
cgtcccttca gcaaggacac aaaaagattt taatttattt aaaaaaaaaa aaaaaaaga    4620
ccgggaattc gatatcaagc ttatcgacct gcagatcgtt caaacatttg gcaataaagt   4680
ttcttaagat tgaatcctgt tgccggtctt gcgatgatta tcatataatt tctgttgaat   4740
tacgttaagc atgtaataat taacatgtaa tgcatgacgt tatttatgag atgggttttt   4800
atgattagag tcccgcaatt atacatttaa tacgcgatag aaaacaaaat atagcgcgca   4860
aactaggata attatcgcg cgcggtgtca tctatgttac tagatctcta gagtctcaag   4920
cttgcgcgc cataaaatga ttattttatg aatatatttc attgtgcaag tagatagaaa    4980
ttacatatgt tacataacac acgaaataaa caaaaaaga caatccaaaa acaaacaccc    5040
caaaaaaaat aatcacttta gataaactcg tatgaggaga ggcacgttca gtgactcgac   5100
gattcccgag caaaaaaagt ctccccgtca cacatatagt gggtgacgca attatcttta   5160
aagtaatcct tctgttgact tgtcattgat aacatccagt cttcgtcagg attgcaaaga   5220
attatagaag ggatcccacc ttttattttc ttcttttttc catatttagg gttgacagtg   5280
aaatcagact ggcaacctat taattgcttc cacaatggga cgaacttgaa ggggatgtcg   5340
tcgatgatat tataggtggc gtgttcatcg tagttggtga atcgatggt accgttccaa    5400
tagttgtgtc gtccgagact tctagcccag gtggtctttc cggtacgagt tggtccgcag   5460
atgtagaggc tgggtgtcg gattccattc cttccattgt cctggttaaa tcggccatcc    5520
attcaaggtc agattgagct tgttggtatg agacaggatg tatgtaagta taagcgtcta   5580
tgcttacatg gtatagatgg gttttccctcc aggagtgtag atcttcgtgg cagcgaagat   5640
ctgattctgt gaagggcgac acatacggtt caggttgtgg agggaataat tgttggctg    5700
aatattccag ccattgaagt tttgttgccc attcatgagg gaattcttcc ttgatcatgt   5760
caagatattc ctccttagac gttgcagtct ggataatagt tctccatcgt gcgtcagatt   5820
tgcgaggaga gaccttatga tctcggaaat ctcctctggt tttaatatct ccgtcctttg   5880
atatgtaatc aaggacttgt ttagagtttc tagctggctg gatattaggg tgatttcctt   5940
caaaatcgaa aaagaagga tccctaatac aaggttttt atcaagctgg agaagagcat     6000
gatagtgggt agtgccatct tgatgaagct cagaagcaac accaaggaag aaataagaa    6060
aaggtgtgag tttctcccag agaaactgga ataaatcatc tctttgagat gagcacttgg   6120
gataggtaag gaaacatat ttagattgga gtctgaagtt cttactagca gaaggcatgt    6180
tgttgtgact ccgaggggtt gcctcaaact ctatcttata accggcgtgg aggcatggag   6240
gcaggggtat tttggtcatt ttaatagata gtggaaaatg acgtggaatt tacttaaaga   6300
cgaagtcttt gcgacaaggg ggggcccacg ccgaatttaa tattaccggc gtggccccc    6360
cttatcgcga gtgctttagc acgagcggtc cagatttaaa gtagaaaatt tcccgcccac   6420
tagggttaaa ggtgttcaca ctataaaagc atatacgatg tgatggtatt tgactagtgg   6480
cactggccgt cgttttacaa cgtcgtgact gggaaaaccc tggcgttacc caacttaatc   6540
gccttgcagc acatccccct ttcgccagct ggcgtaatag cgaagaggcc cgcaccgatc   6600
```

<210> SEQ ID NO 53
<211> LENGTH: 3495
<212> TYPE: DNA
<213> ORGANISM: Artificial Sequence
<220> FEATURE:
<223> OTHER INFORMATION: Expression cassette number 1462

<400> SEQUENCE: 53

```
gcccttccca acagttgcgc agcctgaatg gcgaatgcta gagcagcttg agcttggatc      6660
agattgtcgt ttcccgcctt cagtttaaac tatcagtgtt tgacaggata tattggcggg      6720
taaacctaag agaaaagagc gttta                                            6745
```

```
gtcaacatgg tggagcacga cacacttgtc tactccaaaa atatcaaaga tacagtctca        60
gaagaccaaa gggcaattga acttttcaa caaagggtaa tatccggaaa cctcctcgga        120
ttccattgcc cagctatctg tcactttatt gtgaagatag tggaaaagga aggtggctcc       180
tacaaatgcc atcattgcga taaggaaag gccatcgttg aagatgcctc tgccgacagt        240
ggtcccaaag atggaccccc acccacgagg agcatcgtgg aaaagaaga cgttccaacc        300 acgtcttcaa agcaagtgga ttgatgtgat aacatggtgg agcacgacac acttgtctac       360
tccaaaaata tcaaagatac agtctcagaa gaccaaaggg caattgagac ttttcaacaa       420
agggtaatat ccgaaaacct cctcggattc cattgcccag ctatctgtca ctttattgtg       480
aagatagtgg aaaaggaagg tggctcctac aaatgccatc attgcgataa ggaaaggcc       540 atcgttgaag atgcctctgc cgacagtggt cccaaagatg gaccccccacc acgaggagc       600 atcgtggaaa agaagacgt tccaaccacg tcttcaaagc aagtggattg atgtgatatc       660
tccactgacg taagggatga cgcacaatcc cactatcctt cgcaagaccc ttcctctata       720
taaggaagtt catttcattt ggagaggtat taaaatctta ataggttttg ataaaagcga       780
acgtggggaa acccgaacca aaccttcttc taaactctct ctcatctctc ttaaagcaaa       840
cttctctctt gtctttcttg cgtgagcgat cttcaacgtt gtcagatcgt gcttcggcac       900
cagtacaacg ttttctttca ctgaagcgaa atcaaagatc tctttgtgga cacgtagtgc       960
ggcgccatta ataacgtgt acttgtccta ttcttgtcgg tgtggtcttg ggaaaagaaa       1020
gcttgctgga ggctgctgtt cagccccata cattacttgt tacgattctg ctgactttcg      1080
gcgggtgcaa tatctctact tctgcttgac gaggtattgt tgcctgtact tctttcttct      1140
tcttcttgct gattggttct ataagaaatc tagtattttc tttgaaacag agttttcccg      1200
tggttttcga acttggagaa agattgttaa gcttctgtat attctgccca aatttgtcgg      1260
gcccatgaag gcaataattg tactactcat ggtagtaaca tccaatgcag atcgaatctg      1320
cactgggata acatcttcaa actcacctca tgtggtcaaa acagctactc aaggggaggt      1380
caatgtgact ggcgtgatac cactgacaac aacaccaaca aaatcttatt ttgcaaatct      1440
caaaggaaca aggaccagag ggaaactatg cccggactgt ctcaactgta cagatctgga      1500
tgtggccttg gcaggccaa tgtgtgtggg gaccacacct tctgctaaag cttcaatact       1560
ccacgaggtc agacctgtta catccgggtg cttttcctata atgcacgaca gaacaaaaat      1620
caggcaacta cccaatcttc tcagaggata tgaaaatatc aggttatcaa cccaaaacgt      1680
tatcgatgca gaaaaagcac caggaggacc ctacagactt ggaacctcag gatcttgccc      1740
taacgctacc agtaaaatcg gattttttgc aacaatggct tgggctgtcc caaaggacaa      1800
ctacaaaaat gcaacgaacc cactaacagt agaagtacca tacatttgta cagaaggaga      1860
```

```
agaccaaatt actgtttggg ggttccattc agataacaaa acccaaatga agagcctcta    1920
tggagactca aatcctcaaa agttcacctc atctgctaat ggagtaacca cacattatgt    1980
ttctcagatt ggcgacttcc cagatcaaac agaagacgga ggactaccac aaagcggcag    2040
aattgttgtt gattacatga tgcaaaaacc tgggaaaaca ggaacaattg tctatcaaag    2100
aggtgttttg ttgcctcaaa aggtgtggtg cgcgagtggc aggagcaaag taataaaagg    2160
gtcattgcct ttaattggtg aagcagattg ccttcatgaa aaatacggtg gattaaacaa    2220
aagcaagcct tactacacag gagaacatgc aaaagccata ggaaattgcc caatatgggt    2280
aaaaacacct ttgaagcttg ccaatggaac caaatataga cctcctgcaa aactattgaa    2340
ggaaaggggt ttcttcggag ctattgctgg tttcctagaa ggaggatggg aaggaatgat    2400
tgcaggttgg cacggataca catctcacgg agcacatgga gtggcagtgg cggcagacct    2460
taagagtaca caagaagcta taaataagat aacaaaaaat ctcaattctt tgagtgagct    2520
agaagtaaag aaccttcaaa gactaagtgg tgccatggat gaactccaca acgaaatact    2580
cgagctggat gagaaagtgg atgatctcag agctgacact ataagctcac aaatagaact    2640
tgcagtcttg ctttccaacg aaggaataat aaacagtgaa gacgagcatc tattggcact    2700
tgagagaaaa ctaaagaaaa tgctgggtcc ctctgctgta gacataggaa acggatgctt    2760
cgaaaccaaa cacaaatgca accagacctg cttagacagg atagctgctg cacctttaa    2820 tgcaggagaa ttttctctcc ccactttga ttcattgaac attactgctg catctttaaa    2880
tgatgatgga ttggataacc atactatact gctctattac tcaactgctg cttctagttt    2940
ggctgtaaca ttaatgctag ctatttttat tgtttatatg gtctccagag acaacgtttc    3000
atgctccatc tgtctataaa ggcctatttt ctttagtttg aatttactgt tattcggtgt    3060
gcatttctat gtttggtgag cggttttctg tgctcagagt gtgtttattt tatgtaattt    3120
aatttctttg tgagctcctg tttagcaggt cgtcccttca gcaaggacac aaaaagattt    3180 taatttatt aaaaaaaaaa aaaaaaaga ccgggaattc gatatcaagc ttatcgacct    3240
gcagatcgtt caaacatttg gcaataaagt ttcttaagat tgaatcctgt tgccggtctt    3300
gcgatgatta tcatataatt tctgttgaat tacgttaagc atgtaataat taacatgtaa    3360
tgcatgacgt tatttatgag atgggttttt atgattagag tcccgcaatt atacatttaa    3420
tacgcgatag aaaacaaaat atagcgcgca aactaggata aattatcgcg cgcggtgtca    3480
tctatgttac tagat                                                    3495
```

<210> SEQ ID NO 54
<211> LENGTH: 584
<212> TYPE: PRT
<213> ORGANISM: Influenza virus

<400> SEQUENCE: 54

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80
```

-continued

```
Ala Leu Gly Arg Pro Met Cys Val Gly Thr Thr Pro Ser Ala Lys Ala
                 85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
```

```
              500             505             510
Ile Ala Ala Gly Thr Phe Asn Ala Gly Glu Phe Ser Leu Pro Thr Phe
            515                 520             525

Asp Ser Leu Asn Ile Thr Ala Ala Ser Leu Asn Asp Asp Gly Leu Asp
    530                 535             540

Asn His Thr Ile Leu Leu Tyr Tyr Ser Thr Ala Ala Ser Ser Leu Ala
545                 550             555                 560

Val Thr Leu Met Leu Ala Ile Phe Ile Val Tyr Met Val Ser Arg Asp
                565             570             575

Asn Val Ser Cys Ser Ile Cys Leu
            580

<210> SEQ ID NO 55
<211> LENGTH: 56
<212> TYPE: DNA
<213> ORGANISM: Artificial Sequence
<220> FEATURE:
<223> OTHER INFORMATION: primer HAB110(PrL-).r

<400> SEQUENCE: 55
tccttcccat cctccaccag gaggtctata tttggttcca ttggcaagct tcaaag      56

<210> SEQ ID NO 56
<211> LENGTH: 52
<212> TYPE: DNA
<213> ORGANISM: Artificial Sequence
<220> FEATURE:
<223> OTHER INFORMATION: primer HAB110(PrL-).c

<400> SEQUENCE: 56
atatagacct cctggtggag gatgggaagg aatgattgca ggttggcacg ga          52

<210> SEQ ID NO 57
<211> LENGTH: 3444
<212> TYPE: DNA
<213> ORGANISM: Artificial Sequence
<220> FEATURE:
<223> OTHER INFORMATION: Expression cassette number 1467

<400> SEQUENCE: 57
gtcaacatgg tggagcacga cacacttgtc tactccaaaa atatcaaaga tacagtctca    60
gaagaccaaa gggcaattga acttttcaa caaagggtaa tatccggaaa cctcctcgga    120
ttccattgcc cagctatctg tcactttatt gtgaagatag tggaaaagga aggtggctcc    180
tacaaatgcc atcattgcga taaggaaag gccatcgttg aagatgcctc tgccgacagt    240
ggtcccaaag atggaccccc acccacgagg agcatcgtgg aaaaagaaga cgttccaacc    300
acgtcttcaa gcaagtggga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa ggaaaggcc    540 atcgttgaag atgcctctgc cgacagtggt cccaaagatg gaccccacc cacgaggagc    600 atcgtggaaa agaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaagcga    780 acgtggggaa acccgaacca aaccttcttc taaactctct ctcatctctc ttaaagcaaa    840
```

```
cttctctctt gtctttcttg cgtgagcgat cttcaacgtt gtcagatcgt gcttcggcac      900
cagtacaacg ttttctttca ctgaagcgaa atcaaagatc tctttgtgga cacgtagtgc      960
ggcgccatta ataacgtgt acttgtccta ttcttgtcgg tgtggtcttg ggaaaagaaa      1020
gcttgctgga ggctgctgtt cagccccata cattacttgt tacgattctg ctgactttcg     1080
gcgggtgcaa tatctctact tctgcttgac gaggtattgt tgcctgtact tctttcttct     1140
tcttcttgct gattggttct ataagaaatc tagtattttc tttgaaacag agttttcccg     1200
tggttttcga acttggagaa agattgttaa gcttctgtat attctgccca aatttgtcgg     1260
gcccatgaag gcaataattg tactactcat ggtagtaaca tccaatgcag atcgaatctg     1320
cactgggata acatcttcaa actcacctca tgtggtcaaa acagctactc aaggggaggt     1380
caatgtgact ggcgtgatac cactgacaac aacaccaaca aaatcttatt ttgcaaatct     1440
caaaggaaca aggaccagag ggaaactatg cccggactgt ctcaactgta cagatctgga     1500
tgtggccttg gcaggccaa tgtgtgtggg gaccacacct tctgctaaag cttcaatact     1560
ccacgaggtc agacctgtta catccgggtg ctttcctata atgcacgaca gaacaaaaat     1620
caggcaacta cccaatcttc tcagaggata tgaaaatatc aggttatcaa cccaaaacgt     1680
tatcgatgca gaaaaagcac caggaggacc ctacagactt ggaacctcag gatcttgccc     1740
taacgctacc agtaaaatcg attttttttgc aacaatggct tgggctgtcc caaaggacaa     1800
ctacaaaaat gcaacgaacc cactaacagt agaagtacca tacatttgta cagaagggga     1860
agaccaaatt actgtttggg ggttccattc agataacaaa acccaaatga agagcctcta     1920
tggagactca aatcctcaaa agttcacctc atctgctaat ggagtaacca cacattatgt     1980
ttctcagatt ggcgacttcc cagatcaaac agaagacgga ggactaccac aaagcggcag     2040
aattgttgtt gattacatga tgcaaaaacc tgggaaaaca ggaacaattg tctatcaaag     2100
aggtgttttg ttgcctcaaa aggtgtggtg cgcgagtggc aggagcaaag taataaaagg     2160
gtcattgcct ttaattggtg aagcagattg ccttcatgaa aaatacggtg gattaaacaa     2220
aagcaagcct tactacacag gagaacatgc aaaagccata ggaaattgcc caatatgggt     2280
aaaaacacct tgaagcttg ccaatggaac caaatatagga cctcctggtg gaggatggga     2340
aggaatgatt gcaggttggc acggatacac atctcacgga gcacatggag tggcagtggc     2400
ggcagacctt aagagtacac aagaagctat aaataagata caaaaaatc tcaattcttt     2460 gagtgagcta gaagtaaaga accttcaaag actaagtggt gccatggatg aactccacaa     2520
cgaaatactc gagctggatg agaaagtgga tgatctcaga gctgacacta taagctcaca     2580
aatagaactt gcagtcttgc tttccaacga aggaataata aacagtgaag acgagcatct     2640
attggcactt gagagaaaac taagaaaat gctgggtccc tctgctgtag acataggaaa     2700
cggatgcttc gaaaccaaac acaaatgcaa ccagacctgc ttagacagga tagctgctgg     2760
cacctttaat gcaggagaat tttctctccc cactttttgat tcattgaaca ttactgctgc     2820
atctttaaat gatgatggat tggataacca tactatactg ctctattact caactgctgc     2880
ttctagtttg gctgtaacat taatgctagc tatttttatt gtttatatgg tctccagaga     2940
caacgtttca tgctccatct gtctataaag gcctatttc tttagtttga atttactgtt     3000
attcggtgtg catttctatg tttggtgagc ggttttctgt gctcagagtg tgtttatttt     3060
atgtaattta atttctttgt gagctcctgt ttagcaggtc gtcccttcag caaggacaca     3120
aaaagatttt aatttattta aaaaaaaaaa aaaaaagac cgggaattcg atatcaagct     3180
tatcgacctg cagatcgttc aaacatttgg caataaagtt tcttaagatt gaatcctgtt     3240
```

```
gccggtcttg cgatgattat catataattt ctgttgaatt acgttaagca tgtaataatt    3300
aacatgtaat gcatgacgtt atttatgaga tgggttttta tgattagagt cccgcaatta    3360
tacatttaat acgcgataga aaacaaaata tagcgcgcaa actaggataa attatcgcgc    3420
gcggtgtcat ctatgttact agat                                           3444
```

<210> SEQ ID NO 58
<211> LENGTH: 567
<212> TYPE: PRT
<213> ORGANISM: Influenza virus

<400> SEQUENCE: 58

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335
```

-continued

```
Ile Trp Val Lys Thr Pro Leu Lys Leu Ala Asn Gly Thr Lys Tyr Arg
            340                 345                 350
Pro Pro Gly Gly Trp Glu Gly Met Ile Ala Gly Trp His Gly Tyr
        355                 360                 365
Thr Ser His Gly Ala His Gly Val Ala Val Ala Ala Asp Leu Lys Ser
    370                 375                 380
Thr Gln Glu Ala Ile Asn Lys Ile Thr Lys Asn Leu Asn Ser Leu Ser
385                 390                 395                 400
Glu Leu Glu Val Lys Asn Leu Gln Arg Leu Ser Gly Ala Met Asp Glu
                405                 410                 415
Leu His Asn Glu Ile Leu Glu Leu Asp Glu Lys Val Asp Asp Leu Arg
            420                 425                 430
Ala Asp Thr Ile Ser Ser Gln Ile Glu Leu Ala Val Leu Leu Ser Asn
        435                 440                 445
Glu Gly Ile Ile Asn Ser Glu Asp Glu His Leu Leu Ala Leu Glu Arg
    450                 455                 460
Lys Leu Lys Lys Met Leu Gly Pro Ser Ala Val Asp Ile Gly Asn Gly
465                 470                 475                 480
Cys Phe Glu Thr Lys His Lys Cys Asn Gln Thr Cys Leu Asp Arg Ile
                485                 490                 495
Ala Ala Gly Thr Phe Asn Ala Gly Glu Phe Ser Leu Pro Thr Phe Asp
            500                 505                 510
Ser Leu Asn Ile Thr Ala Ala Ser Leu Asn Asp Asp Gly Leu Asp Asn
        515                 520                 525
His Thr Ile Leu Leu Tyr Tyr Ser Thr Ala Ala Ser Ser Leu Ala Val
    530                 535                 540
Thr Leu Met Leu Ala Ile Phe Ile Val Tyr Met Val Ser Arg Asp Asn
545                 550                 555                 560
Val Ser Cys Ser Ile Cys Leu
                565
```

<210> SEQ ID NO 59
<211> LENGTH: 44
<212> TYPE: DNA
<213> ORGANISM: Artificial Sequence
<220> FEATURE:
<223> OTHER INFORMATION: primer IF-HB-M-04.s2+4c

<400> SEQUENCE: 59
tctcagatct tcgccgatcg aatctgcact gggataacat cgtc        44

<210> SEQ ID NO 60
<211> LENGTH: 46
<212> TYPE: DNA
<213> ORGANISM: Artificial Sequence
<220> FEATURE:
<223> OTHER INFORMATION: primer IF-HB-M-04.s1-4r

<400> SEQUENCE: 60
actaaagaaa ataggccttt atagacagat ggagcaagaa acattg      46

<210> SEQ ID NO 61
<211> LENGTH: 1713
<212> TYPE: DNA
<213> ORGANISM: Artificial Sequence
<220> FEATURE:
<223> OTHER INFORMATION: nucleotide sequence of synthesized HA B
      Malaysia

<400> SEQUENCE: 61

```
gatcgaatct gcactgggat aacatcgtca aactcaccac atgttgtcaa aactgctact      60
caagggagg  tcaatgtgac tggtgtaata ccactgacaa caacacccac caaatctcat     120
tttgcaaatc tcaaaggaac agaaaccaga gggaaactat gcccaaaatg cctcaactgc     180
acagatctgg acgtggcctt gggcagacca aaatgcacgg gaacatacc  ctcggcaaga    240
gtttcaatac tccatgaagt cagacctgtt acatctgggt gctttcctat aatgcacgac    300
agaacaaaaa ttagacagct gcctaaactt ctcagaggat acgaacatat caggttatca    360
actcataacg ttatcaatgc agaaaatgca ccaggaggac cctacaaaat tggaacctca    420
gggtcttgcc ctaacgttac caatggaaac ggatttttcg caacaatggc ttgggccgtc    480
ccaaaaaacg acaacaacaa aacagcaaca aattcattaa caatagaagt accatacatt    540
tgtacagaag gagaagacca aattaccgtt tgggggttcc actctgataa cgaaacccaa    600
atggcaaagc tctatgggga ctcaaagccc cagaagttca cctcatctgc caacggagtg    660
accacacatt acgtttcaca gattggtggc ttcccaaatc aaacagaaga cggaggacta    720
ccacaaagcg gtagaattgt tgttgattac atggtgcaaa atctgggaa  acaggaaca    780
attacctatc aaagaggtat tttattgcct caaaaagtgt ggtgcgcaag tggcaggagc    840
aaggtaataa aaggatcgtt gcctttaatt ggagaagcag attgcctcca cgaaaaatac    900
ggtggattaa acaaaagcaa gccttactac acaggggaac atgcaaaggc cataggaaat    960
tgcccaatat gggtgaaaac acccttgaag ctggccaatg gaaccaaata tagacctcct   1020
gcaaaactat taaaggaaag gggtttcttc ggagctattg ctggtttctt agaaggagga   1080
tgggaaggaa tgattgcagg ttggcacgga tacacatccc atgggcaca  tggagtagcg   1140
gtggcagcag accttaagag cactcaagag gccataaaca agataacaaa aaatctcaac   1200
tctttgagtg agctggaagt aaagaatctt caaagactaa gcggtgccat ggatgaactc   1260
cacaacgaaa tactagaact agacgagaaa gtggatgatc tcagagctga tacaataagc   1320
tcacaaatag aactcgcagt cctgctttcc aatgaaggaa taataaacag tgaagatgag   1380
catctcttgg cgcttgaaag aaagctgaag aaaatgctgg gccctctgc  tgtagagata   1440
gggaatggat gctttgaaac caaacacaag tgcaaccaga cctgtctcga cagaatagct   1500
gctggtacct ttgatgcagg agaattttct ctccccactt ttgattcact gaatattact   1560
gctgcatctt taaatgacga tggattggat aatcatacta tactgctta  ctactcaact   1620
gctgcctcca gtttggctgt aacattgatg atagctatct tgttgtttta tatggtctcc   1680
agagacaatg tttcttgctc catctgtcta taa                                1713
```

<210> SEQ ID NO 62
<211> LENGTH: 6739
<212> TYPE: DNA
<213> ORGANISM: Artificial Sequence
<220> FEATURE:
<223> OTHER INFORMATION: Construct 194

<400> SEQUENCE: 62

```
tggcaggata tattgtggtg taaacaaatt gacgcttaga caacttaata acacattgcg     60
gacgttttta atgtactgaa ttaacgccga atcccgggct ggtatattta tatgttgtca    120
aataactcaa aaaccataaa agtttaagtt agcaagtgtg tacatttta  cttgaacaaa    180
atatattcacc tactactgtt ataaatcatt attaaacatt agagtaaaga aatatggat   240
ataagaacaa gagtagtgat attttgacaa caatttttgtt gcaacatttg agaaaatttt    300
```

```
gttgttctct cttttcattg gtcaaaaaca atagagagag aaaaggaag agggagaata    360
aaaacataat gtgagtatga gagagaaagt tgtacaaaag ttgtaccaaa atagttgtac   420
aaatatcatt gaggaatttg acaaaagcta cacaaataag ggttaattgc tgtaaataaa   480
taaggatgac gcattagaga gatgtaccat tagagaattt ttggcaagtc attaaaaaga   540
aagaataaat tatttttaaa attaaaagtt gagtcatttg attaaacatg tgattattta   600
atgaattgat gaaagagttg gattaaagtt gtattagtaa ttagaatttg gtgtcaaatt   660
taatttgaca tttgatcttt tcctatatat tgccccatag agtcagttaa ctcattttta   720
tatttcatag atcaaataag agaaataacg gtatattaat ccctccaaaa aaaaaaaacg   780
gtatatttac taaaaaatct aagccacgta ggaggataac aggatccccg taggaggata   840
acatccaatc caaccaatca caacaatcct gatgagataa cccactttaa gcccacgcat   900
ctgtggcaca tctacattat ctaaatcaca cattcttcca cacatctgag ccacacaaaa   960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctatttta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaga cgcgttgttg ttgtgactcc gaggggttgc   2160
ctcaaactct atcttataac cggcgtggag gcatggaggc aggggtattt tggtcatttt   2220
aatagatagt ggaaaatgac gtggaattta cttaaagacg aagtctttgc gacaagggg    2280
ggcccacgcc gaatttaata ttaccggcgt ggccccccct tatcgcgagt gctttagcac   2340
gagcggtcca gatttaaagt agaaaatttc ccgcccacta gggttaaagg tgttcacact   2400
ataaaagcat atacgatgtg atggtatttg gtcgacaagc ttgcatgccg gtcaacatgg   2460
tggagcacga cacacttgtc tactccaaaa atatcaaaga tacagtctca gaagaccaaa   2520
gggcaattga gacttttcaa caaagggtaa tatccgaaaa cctcctcgga ttccattgcc   2580
cagctatctg tcactttatt gtgaagatag tggaaaagga aggtggctcc tacaaatgcc   2640
```

```
atcattgcga taaaggaaag gccatcgttg aagatgcctc tgccgacagt ggtcccaaag    2700
atggacccc  acccacgagg agcatcgtgg aaaaagaaga cgttccaacc acgtcttcaa    2760
agcaagtgga ttgatgtgat aacatggtgg agcacgacac acttgtctac tccaaaaata    2820
tcaaagatac agtctcagaa gaccaaaggg caattgagac ttttcaacaa agggtaatat    2880
ccggaaacct cctcggattc cattgcccag ctatctgtca ctttattgtg aagatagtgg    2940
aaaaggaagg tggctcctac aaatgccatc attgcgataa aggaaaggcc atcgttgaag    3000
atgcctctgc cgacagtggt cccaaagatg acccccacc  cacgaggagc atcgtggaaa    3060
aagaagacgt tccaaccacg tcttcaaagc aagtggattg atgtgatatc tccactgacg    3120
taagggatga cgcacaatcc cactatcctt cgcaagaccc ttcctctata taggaagtt     3180
catttcattt ggagaggtat taaaatctta ataggtttg  ataaaagcga acgtggggaa    3240
acccgaacca aaccttcttc taaactctct ctcatctctc ttaaagcaaa cttctctctt    3300
gtctttcttg cgtgagcgat cttcaacgtt gtcagatcgt gcttcggcac cagtacaacg    3360
ttttctttca ctgaagcgaa atcaaagatc tctttgtgga cacgtagtgc ggcgccatta    3420
aataacgtgt acttgtccta ttcttgtcgg tgtggtcttg ggaaaagaaa gcttgctgga    3480
ggctgctgtt cagcccata  cattacttgt tacgattctg ctgactttcg gcgggtgcaa    3540
tatctctact tctgcttgac gaggtattgt tgcctgtact tctttcttct tcttcttgct    3600
gattggttct ataagaaatc tagtatttc  tttgaaacag agttttcccg tggttttcga    3660
acttggagaa agattgttaa gcttctgtat attctgccca aatttgtcgg gcccatggcg    3720
aaaaacgttg cgattttcgg cttattgttt tctcttcttg tgttggttcc ttctcagatc    3780
ttcgccgcgg ctcctcagcc aaaacgacac ccccatctgt ctatccactg gcccctggat    3840
ctgctgccca aactaactcc atggtgaccc tgggatgcct ggtcaagggc tatttccctg    3900
agccagtgac agtgacctgg aactctggat ccctgtccag cggtgtgcac accttcccag    3960
ctgtcctgca gtctgacctc tacactctga gcagctcagt gactgtcccc tccagcacct    4020
ggcccagcga gaccgtcacc tgcaacgttg cccacccggc cagcagcacc aaggtggaca    4080
agaaaattgt gcccagggat tgtggttgta agccttgcat atgtacagtc ccagaagtat    4140
catctgtctt catcttcccc ccaaagccca aggatgtgct caccattact ctgactccta    4200
aggtcacgtg tgttgtggta gacatcagca aggatgatcc cgaggtccag ttcagctggt    4260
ttgtagatga tgtggaggtg cacacagctc agacgcaacc ccgggaggag cagttcaaca    4320
gcactttccg ctcagtcagt gaacttccca tcatgcacca ggactggctc aatggcaagg    4380
agcgatcgct caccatcacc atcaccatca ccatcaccat taaaggccta ttttctttag    4440
tttgaattta ctgttattcg gtgtgcattt ctatgtttgg tgagcggttt tctgtgctca    4500
gagtgtgttt attttatgta atttaatttc tttgtgagct cctgtttagc aggtcgtccc    4560
ttcagcaagg acacaaaaag atttaatttt tattaaaaaa aaaaaaaaaa aagaccggga    4620
attcgatatc aagcttatcg acctgcagat cgttcaaaca tttggcaata agtttcttaa    4680
gattgaatc  ctgttgccgg tcttgcgatg attatcatat aatttctgtt gaattacgtt    4740
aagcatgtaa taattaacat gtaatgcatg acgttattta tgagatgggt ttttatgatt    4800
agagtcccgc aattatacat ttaatacgcg atagaaaaca aaatatagcg cgcaaactag    4860
gataaattat cgcgcgcggt gtcatctatg ttactagatc tctagagtct caagcttggc    4920
gcgccataaa atgattattt tatgaatata tttcattgtg caagtagata gaaattacat    4980
atgttacata acacacgaaa taaacaaaaa aagcaatcc  aaaaacaaac ccccaaaaa     5040
```

| | |
|---|---|
| aaataatcac tttagataaa ctcgtatgag gagaggcacg ttcagtgact cgacgattcc | 5100 |
| cgagcaaaaa aagtctcccc gtcacacata tagtgggtga cgcaattatc tttaaagtaa | 5160 |
| tccttctgtt gacttgtcat tgataacatc cagtcttcgt caggattgca aagaattata | 5220 |
| gaagggatcc caccttttat tttcttcttt tttccatatt tagggttgac agtgaaatca | 5280 |
| gactggcaac ctattaattg cttccacaat gggacgaact tgaaggggat gtcgtcgatg | 5340 |
| atattatagg tggcgtgttc atcgtagttg gtgaaatcga tggtaccgtt ccaatagttg | 5400 |
| tgtcgtccga gacttctagc ccaggtggtc tttccggtac gagttggtcc gcagatgtag | 5460 |
| aggctggggt gtcggattcc attccttcca ttgtcctggt aaatcggcc atccattcaa | 5520 |
| ggtcagattg agcttgttgg tatgagacag gatgtatgta agtataagcg tctatgctta | 5580 |
| catggtatag atgggtttcc ctccaggagt gtagatcttc gtggcagcga agatctgatt | 5640 |
| ctgtgaaggg cgacacatac ggttcaggtt gtggagggaa taatttgttg gctgaatatt | 5700 |
| ccagccattg aagttttgtt gcccattcat gagggaattc ttccttgatc atgtcaagat | 5760 |
| attcctcctt agacgttgca gtctggataa tagttctcca tcgtgcgtca gatttgcgag | 5820 |
| gagagacctt atgatctcgg aaatctcctc tggttttaat atctccgtcc tttgatatgt | 5880 |
| aatcaaggac ttgtttagag tttctagctg gctggatatt agggtgattt ccttcaaaat | 5940 |
| cgaaaaaga aggatcccta atacaaggtt ttttatcaag ctggagaaga gcatgatagt | 6000 |
| gggtagtgcc atcttgatga agctcagaag caacaccaag gaagaaaata agaaaaggtg | 6060 |
| tgagtttctc ccagagaaac tggaataaat catctctttg agatgagcac ttgggatagg | 6120 |
| taaggaaaac atatttagat tggagtctga agttcttact agcagaaggc atgttgttgt | 6180 |
| gactccgagg ggttgcctca aactctatct tataaccggc gtggaggcat ggaggcaggg | 6240 |
| gtattttggt cattttaata gatagtggaa aatgacgtgg aatttactta aagacgaagt | 6300 |
| ctttgcgaca agggggggcc cacgccgaat ttaatattac cggcgtggcc cccccttatc | 6360 |
| gcgagtgctt tagcacgagc ggtccagatt taaagtagaa aatttcccgc ccactagggt | 6420 |
| taaaggtgtt cacactataa aagcatatac gatgtgatgg tatttgacta gtggcactgg | 6480 |
| ccgtcgtttt acaacgtcgt gactgggaaa accctggcgt tacccaactt aatcgccttg | 6540 |
| cagcacatcc cccttttcgcc agctggcgta atagcgaaga ggcccgcacc gatcgccctt | 6600 |
| cccaacagtt gcgcagcctg aatggcgaat gctagagcag cttgagcttg gatcagattg | 6660 |
| tcgtttcccg ccttcagttt aaactatcag tgtttgacag gatatattgg cgggtaaacc | 6720 |
| taagagaaaa gagcgttta | 6739 |

<210> SEQ ID NO 63
<211> LENGTH: 3525
<212> TYPE: DNA
<213> ORGANISM: Artificial Sequence
<220> FEATURE:
<223> OTHER INFORMATION: Expression cassette number 1631

<400> SEQUENCE: 63

| | |
|---|---|
| gtcaacatgg tggagcacga cacacttgtc tactccaaaa atatcaaaga tacagtctca | 60 |
| gaagaccaaa gggcaattga gacttttcaa caaagggtaa tatccggaaa cctcctcgga | 120 |
| ttccattgcc cagctatctg tcactttatt gtgaagatag tggaaaagga aggtggctcc | 180 |
| tacaaatgcc atcattgcga taaaggaaag gccatcgttg aagatgcctc tgccgacagt | 240 |
| ggtcccaaag atggaccccc acccacgagg agcatcgtgg aaaaagaaga cgttccaacc | 300 |

```
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg acccccacc cacgaggagc     600
atcgtggaaa agaagacgt tccaaccacg tcttcaaagc aagtggattg atgtgatatc     660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgccgatc gaatctgcac tgggataaca tcgtcaaact caccacatgt   1380
tgtcaaaact gctactcaag gggaggtcaa tgtgactggt gtaataccac tgacaacaac   1440
acccaccaaa tctcattttg caaatctcaa aggaacagaa accagaggga aactatgccc   1500
aaaatgcctc aactgcacag atctggacgt ggccttgggc agaccaaaat gcacggggaa   1560
catacccteg gcaagagttt caatactcca tgaagtcaga cctgttacat ctgggtgctt   1620
tcctataatg cacgacagaa caaaaattag acagctgcct aaacttctca gaggatacga   1680
acatatcagg ttatcaactc ataacgttat caatgcagaa aatgcaccag gaggacccta   1740
caaaattgga acctcagggt cttgccctaa cgttaccaat ggaaacggat ttttcgcaac   1800
aatggcttgg gccgtcccaa aaaacgacaa caacaaaaca gcaacaaatt cattaacaat   1860
agaagtacca tacatttgta cagaaggaga agaccaaatt accgtttggg ggttccactc   1920
tgataacgaa acccaaatgg caaagctcta tggggactca aagccccaga agttcacctc   1980
atctgccaac ggagtgacca cacattacgt ttcacagatt ggtggcttcc caaatcaaac   2040
agaagacgga ggactaccac aaagcggtag aattgttgtt gattacatgg tgcaaaaatc   2100
tgggaaaaca ggaacaatta cctatcaaag aggtatttta ttgcctcaaa agtgtggtg    2160
cgcaagtggc aggagcaagg taataaaagg atcgttgcct ttaattggag aagcagattg   2220
cctccacgaa aaatacggtg gattaaacaa aagcaagcct tactacacag gggaacatgc   2280
aaaggccata ggaaattgcc caatatgggt gaaaacaccc ttgaagctgg ccaatggaac   2340
caaatataga cctcctgcaa aactattaaa ggaaagggt tcttcggag ctattgctgg    2400
tttcttagaa ggaggatggg aaggaatgat tgcaggttgg cacggataca catcccatgg   2460
ggcacatgga gtagcggtgg cagcagacct taagagcact caagaggcca taaacaagat   2520
aacaaaaaat ctcaactctt tgagtgagct ggaagtaaag aatcttcaaa gactaagcgg   2580
tgccatggat gaactccaca acgaaatact agaactagag agaaagtgg atgatctcag    2640
agctgataca ataagctcac aaatagaact cgcagtcctg cttttccaatg aaggaataat   2700
```

-continued

```
aaacagtgaa gatgagcatc tcttggcgct tgaaagaaag ctgaagaaaa tgctgggccc    2760
ctctgctgta gagataggga atggatgctt tgaaaccaaa cacaagtgca accagacctg    2820
tctcgacaga atagctgctg gtacctttga tgcaggagaa ttttctctcc ccactttttga   2880 ttcactgaat attactgctg catctttaaa tgacgatgga ttggataatc atactatact    2940
gctttactac tcaactgctg cctccagttt ggctgtaaca ttgatgatag ctatctttgt    3000
tgtttatatg gtctccagag acaatgtttc ttgctccatc tgtctataaa ggcctatttt    3060
ctttagtttg aatttactgt tattcggtgt gcatttctat gtttggtgag cggttttctg    3120
tgctcagagt gtgtttatttt tatgtaattt aatttctttg tgagctcctg tttagcaggt    3180
cgtcccttca gcaaggacac aaaaagattt taattttatt aaaaaaaaaa aaaaaaaga    3240 ccgggaattc gatatcaagc ttatcgacct gcagatcgtt caaacatttg gcaataaagt    3300
ttcttaagat tgaatcctgt tgccggtctt gcgatgatta tcatataatt tctgttgaat    3360
tacgttaagc atgtaataat taacatgtaa tgcatgacgt tatttatgag atgggttttt    3420
atgattagag tcccgcaatt atacatttaa tacgcgatag aaaacaaaat atagcgcgca    3480
aactaggata aattatcgcg cgcggtgtca tctatgttac tagat                    3525
```

<210> SEQ ID NO 64
<211> LENGTH: 594
<212> TYPE: PRT
<213> ORGANISM: Influenza virus

<400> SEQUENCE: 64

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Asn Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Lys Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Val Thr Asn Gly Asn Gly Phe
                165                 170                 175

Phe Ala Thr Met Ala Trp Ala Val Pro Lys Asn Asp Asn Asn Lys Thr
            180                 185                 190

Ala Thr Asn Ser Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220
```

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
            245                 250                 255

Asn Gln Thr Glu Asp Gly Gly Leu Pro Gln Ser Gly Arg Ile Val Val
        260                 265                 270

Asp Tyr Met Val Gln Lys Ser Gly Lys Thr Gly Thr Ile Thr Tyr Gln
    275                 280                 285

Arg Gly Ile Leu Leu Pro Gln Lys Val Trp Cys Ala Ser Gly Arg Ser
290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Ala Lys Leu Leu
        355                 360                 365

Lys Glu Arg Gly Phe Phe Gly Ala Ile Ala Gly Phe Leu Glu Gly Gly
    370                 375                 380

Trp Glu Gly Met Ile Ala Gly Trp His Gly Tyr Thr Ser His Gly Ala
385                 390                 395                 400

His Gly Val Ala Val Ala Ala Asp Leu Lys Ser Thr Gln Glu Ala Ile
                405                 410                 415

Asn Lys Ile Thr Lys Asn Leu Asn Ser Leu Ser Glu Leu Glu Val Lys
            420                 425                 430

Asn Leu Gln Arg Leu Ser Gly Ala Met Asp Glu Leu His Asn Glu Ile
        435                 440                 445

Leu Glu Leu Asp Glu Lys Val Asp Asp Leu Arg Ala Asp Thr Ile Ser
    450                 455                 460

Ser Gln Ile Glu Leu Ala Val Leu Leu Ser Asn Glu Gly Ile Ile Asn
465                 470                 475                 480

Ser Glu Asp Glu His Leu Leu Ala Leu Glu Arg Lys Leu Lys Lys Met
                485                 490                 495

Leu Gly Pro Ser Ala Val Glu Ile Gly Asn Gly Cys Phe Glu Thr Lys
            500                 505                 510

His Lys Cys Asn Gln Thr Cys Leu Asp Arg Ile Ala Ala Gly Thr Phe
        515                 520                 525

Asp Ala Gly Glu Phe Ser Leu Pro Thr Phe Asp Ser Leu Asn Ile Thr
    530                 535                 540

Ala Ala Ser Leu Asn Asp Asp Gly Leu Asp Asn His Thr Ile Leu Leu
545                 550                 555                 560

Tyr Tyr Ser Thr Ala Ala Ser Ser Leu Ala Val Thr Leu Met Ile Ala
                565                 570                 575

Ile Phe Val Val Tyr Met Val Ser Arg Asp Asn Val Ser Cys Ser Ile
            580                 585                 590

Cys Leu

<210> SEQ ID NO 65
<211> LENGTH: 47
<212> TYPE: DNA
<213> ORGANISM: Artificial Sequence
<220> FEATURE:
<223> OTHER INFORMATION: M2ANC2099(A30P).r

<400> SEQUENCE: 65
aatcccaatt atactagggg caacaacaag aggatcactt gaatcgt         47

<210> SEQ ID NO 66
<211> LENGTH: 47
<212> TYPE: DNA
<213> ORGANISM: Artificial Sequence
<220> FEATURE:
<223> OTHER INFORMATION: Primer M2ANC2099(A30P).c

<400> SEQUENCE: 66
ttgttgcccc tagtataatt gggattgtgc acctgatatt gtggatt         47

<210> SEQ ID NO 67
<211> LENGTH: 2034
<212> TYPE: DNA
<213> ORGANISM: Artificial Sequence
<220> FEATURE:
<223> OTHER INFORMATION: Expression cassette number 1210

<400> SEQUENCE: 67
gtcaacatgg tggagcacga cacacttgtc tactccaaaa atatcaaaga tacagtctca    60
gaagaccaaa gggcaattga acttttcaa caaagggtaa tatccggaaa cctcctcgga   120
ttccattgcc cagctatctg tcactttatt gtgaagatag tggaaaagga aggtggctcc   180
tacaaatgcc atcattgcga taaggaaag gccatcgttg aagatgcctc tgccgacagt   240
ggtcccaaag atggaccccc acccacgagg agcatcgtgg aaaaagaaga cgttccaacc   300
acgtcttcaa gcaagtggga ttgatgtgat aacatggtgg agcacgacac acttgtctac   360
tccaaaaata tcaaagatac agtctcagaa gaccaaaggg caattgagac ttttcaacaa   420
agggtaatat ccggaaacct cctcggattc cattgcccag ctatctgtca ctttattgtg   480
aagatagtgg aaaaggaagg tggctcctac aaatgccatc attgcgataa ggaaaggcc   540
atcgttgaag atgcctctgc cgacagtggt cccaaagatg gaccccace acgaggagc   600
atcgtggaaa agaagacgt tccaaccacg tcttcaaagc aagtggattg atgtgatatc   660
tccactgacg taagggatga cgcacaatcc cactatcctt gcaagaccc ttcctctata   720
taaggaagtt catttcattt ggagaggtat aaaatctta ataggttttg ataaaagcga   780
acgtggggaa acccgaacca aaccttcttc taaactctct ctcatctctc ttaaagcaaa   840
cttctctctt gtctttcttg cgtgagcgat cttcaacgtt gtcagatcgt gcttcggcac   900
cagtacaacg ttttctttca ctgaagcgaa atcaaagatc tctttgtgga cacgtagtgc   960
ggcgccatta ataacgtgt acttgtccta ttcttgtcgg tgtggtcttg ggaaaagaaa  1020
gcttgctgga ggctgctgtt cagccccata cattacttgt tacgattctg ctgactttcg  1080
gcgggtgcaa tatctctact tctgcttgac gaggtattgt tgcctgtact tctttcttct  1140
tcttcttgct gattggttct ataagaaatc tagtattttc tttgaaacag agttttcccg  1200
tggttttcga acttggagaa agattgttaa gcttctgtat attctgccca aatttgtcgg  1260
gcccatgagt cttctaaccg aggtcgaaac gcctatcaga acgaatggg ggtgcagatg  1320
caacgattca agtgatcctc ttgttgttgc ccctagtata attgggattg tgcacctgat  1380
attgtggatt attgatcgcc ttttttccaa aagcatttat cgtatcttta aacacggttt  1440
aaaaagaggg ccttctacgg aaggagtacc agagtctatg agggaagaat atcgagagga  1500
acagcagaat gctgtggatg ctgacgatgg tcattttgtc agcatagagc tggagtaaag  1560
gcctatttc tttagtttga atttactgtt attcggtgtg catttctatg tttggtgagc  1620

```
ggttttctgt gctcagagtg tgtttatttt atgtaattta atttctttgt gagctcctgt    1680
ttagcaggtc gtcccttcag caaggacaca aaaagatttt aatttatta aaaaaaaaaa    1740 aaaaaaagac cgggaattcg atatcaagct tatcgacctg cagatcgttc aaacatttgg    1800
caataaagtt tcttaagatt gaatcctgtt gccggtcttg cgatgattat catataattt    1860
ctgttgaatt acgttaagca tgtaataatt aacatgtaat gcatgacgtt atttatgaga    1920
tgggttttta tgattagagt cccgcaatta tacatttaat acgcgataga aaacaaaata    1980
tagcgcgcaa actaggataa attatcgcgc gcggtgtcat ctatgttact agat           2034
```

<210> SEQ ID NO 68
<211> LENGTH: 97
<212> TYPE: PRT
<213> ORGANISM: Influenza

<400> SEQUENCE: 68

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Pro Ser Ile
            20                  25                  30

Ile Gly Ile Val His Leu Ile Leu Trp Ile Ile Asp Arg Leu Phe Ser
        35                  40                  45

Lys Ser Ile Tyr Arg Ile Phe Lys His Gly Leu Lys Arg Gly Pro Ser
    50                  55                  60

Thr Glu Gly Val Pro Glu Ser Met Arg Glu Glu Tyr Arg Glu Glu Gln
65                  70                  75                  80

Gln Asn Ala Val Asp Ala Asp Asp Gly His Phe Val Ser Ile Glu Leu
                85                  90                  95

Glu

<210> SEQ ID NO 69
<211> LENGTH: 48
<212> TYPE: DNA
<213> ORGANISM: Artificial Sequence
<220> FEATURE:
<223> OTHER INFORMATION: IF-PDI.S1+3c

<400> SEQUENCE: 69
aaatttgtcg ggcccatggc gaaaaacgtt gcgattttcg gcttattg                  48

<210> SEQ ID NO 70
<211> LENGTH: 47
<212> TYPE: DNA
<213> ORGANISM: Artificial Sequence
<220> FEATURE:
<223> OTHER INFORMATION: IF-pHluorin_primer6.r

<400> SEQUENCE: 70
actaaagaaa ataggccttt atttgtatag ttcatccatg ccatgtg                   47

<210> SEQ ID NO 71
<211> LENGTH: 786
<212> TYPE: DNA
<213> ORGANISM: Artificial Sequence
<220> FEATURE:
<223> OTHER INFORMATION: Nucleotide sequence of PDISP/pHluorin

<400> SEQUENCE: 71
atggcgaaaa acgttgcgat tttcggctta ttgttttctc ttcttgtgtt ggttccttct    60

| | |
|---|---:|
| cagatcttcg ccagtaaagg agaagaactt ttcactggag ttgtcccaat tcttgttgaa | 120 |
| ttagatggtg atgttaatgg gcacaaattt tctgtcagtg gagagggtga aggtgatgca | 180 |
| acatacggaa aacttaccct taaatttatt tgcactactg gaaaactacc tgttccatgg | 240 |
| ccaacacttg tcactacttt ctcttatggt gttcaatgct tttcaagata cccagatcat | 300 |
| atgaaacggc atgactttt caagagtgcc atgcccgaag ttatgtaca ggaaagaact | 360 |
| atatttttca aagatgacgg aactacaag acacgtgctg aagtcaagtt tgaaggtgat | 420 |
| acccttgtta atagaatcga gttaaaaggt attgatttta aagatgatgg aaacattctt | 480 |
| ggacacaaat tggaatacaa ctataacgag cacttggtgt acatcatggc agacaaacaa | 540 |
| aagaatggta ccaaagctat ctttcaagtt caccacaaca ttgaagatgg aggcgttcaa | 600 |
| ctagcagacc attatcaaca aaatactcca attggcgatg gccctgtcct tttaccagac | 660 |
| aaccattacc tgcacacaca atctgccctt tcgaaagatc ccaacgaaaa gagagaccac | 720 |
| atggtccttc ttgagtttgt aacagctgct gggattacac atggcatgga tgaactatac | 780 |
| aaataa | 786 |

<210> SEQ ID NO 72
<211> LENGTH: 2526
<212> TYPE: DNA
<213> ORGANISM: Artificial Sequence
<220> FEATURE:
<223> OTHER INFORMATION: Expression cassette number 1871

<400> SEQUENCE: 72

| | |
|---|---:|
| gtcaacatgg tggagcacga cacacttgtc tactccaaaa atatcaaaga tacagtctca | 60 |
| gaagaccaaa gggcaattga gactttcaa caaagggtaa tatccggaaa cctcctcgga | 120 |
| ttccattgcc cagctatctg tcactttatt gtgaagatag tggaaaagga aggtggctcc | 180 |
| tacaaatgcc atcattgcga taaggaaag gccatcgttg aagatgcctc tgccgacagt | 240 |
| ggtcccaaag atgacccccc acccacgagg agcatcgtgg aaaaagaaga cgttccaacc | 300 |
| acgtcttcaa agcaagtgga ttgatgtgat aacatggtgg agcacgacac acttgtctac | 360 |
| tccaaaaata tcaaagatac agtctcagaa gaccaaaggg caattgagac ttttcaacaa | 420 |
| agggtaatat ccggaaacct cctcggattc cattgcccag ctatctgtca ctttattgtg | 480 |
| aagatagtgg aaaaggaagg tggctcctac aaatgccatc attgcgataa ggaaaggcc | 540 |
| atcgttgaag atgcctctgc cgacagtggt cccaaagatg acccccacc cacgaggagc | 600 |
| atcgtggaaa agaagacgt tccaaccacg tcttcaaagc aagtggattg atgtgatatc | 660 |
| tccactgacg taagggatga cgcacaatcc cactatcctt cgcaagaccc ttcctctata | 720 |
| taaggaagtt catttcattt ggagaggtat taaaatctta ataggttttg ataaaagcga | 780 |
| acgtggggaa acccgaacca aaccttcttc taaactctct ctcatctctc ttaaagcaaa | 840 |
| cttctctctt gtctttcttg cgtgagcgat cttcaacgtt gtcagatcgt gcttcggcac | 900 |
| cagtacaacg ttttctttca ctgaagcgaa atcaaagatc tctttgtgga cacgtagtgc | 960 |
| ggcgccatta ataacgtgt acttgtccta ttcttgtcgg tgtggtcttg ggaaaagaaa | 1020 |
| gcttgctgga ggctgctgtt cagccccata cattacttgt tacgattctg ctgactttcg | 1080 |
| gcgggtgcaa tatctctact tctgcttgac gaggtattgt tgcctgtact tctttcttct | 1140 |
| tcttcttgct gattggttct ataagaaatc tagtattttc tttgaaacag agttttcccg | 1200 |
| tggttttcga acttggagaa agattgttaa gcttctgtat attctgccca aatttgtcgg | 1260 |
| gcccatggcg aaaaacgttg cgattttcgg cttattgttt tctcttcttg tgttggttcc | 1320 |

```
ttctcagatc ttcgccagta aaggagaaga acttttcact ggagttgtcc caattcttgt    1380
tgaattagat ggtgatgtta atgggcacaa attttctgtc agtggagagg gtgaaggtga    1440
tgcaacatac ggaaaactta cccttaaatt tatttgcact actggaaaac tacctgttcc    1500
atggccaaca cttgtcacta ctttctctta tggtgttcaa tgcttttcaa gatacccaga    1560
tcatatgaaa cggcatgact ttttcaagag tgccatgccc gaaggttatg tacaggaaag    1620
aactatattt ttcaaagatg acgggaacta caagacacgt gctgaagtca agtttgaagg    1680
tgataccctt gttaatagaa tcgagttaaa aggtattgat tttaaagatg atggaaacat    1740
tcttggacac aaaattggaa taactataa cgagcacttg gtgtacatca tggcagacaa    1800
acaaaagaat ggtaccaaag ctatctttca agttcaccac aacattgaag atggaggcgt    1860
tcaactagca gaccattatc aacaaaatac tccaattggc gatggccctg tccttttacc    1920
agacaaccat tacctgcaca cacaatctgc cctttcgaaa gatcccaacg aaaagagaga    1980
ccacatggtc cttcttgagt ttgtaacagc tgctgggatt acacatggca tggatgaact    2040
atacaaataa aggcctattt tctttagttt gaatttactg ttattcggtg tgcatttcta    2100
tgtttggtga gcggttttct gtgctcagag tgtgtttatt ttatgtaatt taatttcttt    2160
gtgagctcct gtttagcagg tcgtcccttc agcaaggaca caaaagatt ttaattttat    2220 taaaaaaaaa aaaaaaaaag accgggaatt cgatatcaag cttatcgacc tgcagatcgt    2280
tcaaacattt ggcaataaag tttcttaaga ttgaatcctg ttgccggtct tgcgatgatt    2340
atcatataat ttctgttgaa ttacgttaag catgtaataa ttaacatgta atgcatgacg    2400
ttatttatga gatgggtttt tatgattaga gtcccgcaat tatacattta atacgcgata    2460
gaaaacaaaa tatagcgcgc aaactaggat aaattatcgc gcgcggtgtc atctatgtta    2520
ctagat                                                              2526
```

<210> SEQ ID NO 73
<211> LENGTH: 261
<212> TYPE: PRT
<213> ORGANISM: Artificial Sequence
<220> FEATURE:
<223> OTHER INFORMATION: Amino acid sequence of PDISP/pHluorin

<400> SEQUENCE: 73

Met Ala Lys Asn Val Ala Ile Phe Gly Leu Leu Phe Ser Leu Leu Val
1               5                   10                  15

Leu Val Pro Ser Gln Ile Phe Ala Ser Lys Gly Glu Glu Leu Phe Thr
            20                  25                  30

Gly Val Val Pro Ile Leu Val Glu Leu Asp Gly Asp Val Asn Gly His
        35                  40                  45

Lys Phe Ser Val Ser Gly Glu Gly Glu Gly Asp Ala Thr Tyr Gly Lys
    50                  55                  60

Leu Thr Leu Lys Phe Ile Cys Thr Thr Gly Lys Leu Pro Val Pro Trp
65                  70                  75                  80

Pro Thr Leu Val Thr Thr Phe Ser Tyr Gly Val Gln Cys Phe Ser Arg
                85                  90                  95

Tyr Pro Asp His Met Lys Arg His Asp Phe Phe Lys Ser Ala Met Pro
            100                 105                 110

Glu Gly Tyr Val Gln Glu Arg Thr Ile Phe Phe Lys Asp Asp Gly Asn
        115                 120                 125

Tyr Lys Thr Arg Ala Glu Val Lys Phe Glu Gly Asp Thr Leu Val Asn
    130                 135                 140

```
Arg Ile Glu Leu Lys Gly Ile Asp Phe Lys Asp Asp Gly Asn Ile Leu
145                 150                 155                 160

Gly His Lys Leu Glu Tyr Asn Tyr Asn Glu His Leu Val Tyr Ile Met
                165                 170                 175

Ala Asp Lys Gln Lys Asn Gly Thr Lys Ala Ile Phe Gln Val His His
            180                 185                 190

Asn Ile Glu Asp Gly Gly Val Gln Leu Ala Asp His Tyr Gln Gln Asn
        195                 200                 205

Thr Pro Ile Gly Asp Gly Pro Val Leu Leu Pro Asp Asn His Tyr Leu
    210                 215                 220

His Thr Gln Ser Ala Leu Ser Lys Asp Pro Asn Glu Lys Arg Asp His
225                 230                 235                 240

Met Val Leu Leu Glu Phe Val Thr Ala Ala Gly Ile Thr His Gly Met
                245                 250                 255

Asp Glu Leu Tyr Lys
            260

<210> SEQ ID NO 74
<211> LENGTH: 60
<212> TYPE: DNA
<213> ORGANISM: Artificial Sequence
<220> FEATURE:
<223> OTHER INFORMATION: IF-pHluorin_primer2.r

<400> SEQUENCE: 74
actaaagaaa ataggccttt acagctcgtc cttttcgctt tgtatagtt catccatgcc    60

<210> SEQ ID NO 75
<211> LENGTH: 2544
<212> TYPE: DNA
<213> ORGANISM: Artificial Sequence
<220> FEATURE:
<223> OTHER INFORMATION: Expression cassette number 1872

<400> SEQUENCE: 75
gtcaacatgg tggagcacga cacacttgtc tactccaaaa atatcaaaga tacagtctca    60
gaagaccaaa gggcaattga dacttttcaa caaagggtaa tatccggaaa cctcctcgga   120
ttccattgcc cagctatctg tcactttatt gtgaagatag tggaaaagga aggtggctcc   180
tacaaatgcc atcattgcga taaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa ggaaaggcc    540 atcgttgaag atgcctctgc cgacagtggt cccaaagatg gaccccc acc acgaggagc    600 atcgtggaaa agaagacgt tccaaccacg tcttcaaagc aagtggattg atgtgatatc    660
tccactgacg taaggatga cgcacaatcc cactatcctt gcaagaccc ttcctctata    720 taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtcttttcttg cgtgagcgat cttcaacgtt gtcagatcgt gcttcggcac    900
cagtacaacg ttttctttca ctgaagcgaa atcaaagatc tctttgtgga cacgtagtgc    960
```

```
ggcgccatta aataacgtgt acttgtccta ttcttgtcgg tgtggtcttg ggaaaagaaa    1020
gcttgctgga ggctgctgtt cagccccata cattacttgt tacgattctg ctgactttcg    1080
gcgggtgcaa tatctctact tctgcttgac gaggtattgt tgcctgtact tctttcttct    1140
tcttcttgct gattggttct ataagaaatc tagtattttc tttgaaacag agttttcccg    1200
tggttttcga acttggagaa agattgttaa gcttctgtat attctgccca aatttgtcgg    1260
gcccatggcg aaaaacgttg cgattttcgg cttattgttt tctcttcttg tgttggttcc    1320
ttctcagatc ttcgccagta aaggagaaga acttttcact ggagttgtcc caattcttgt    1380
tgaattagat ggtgatgtta atgggcacaa atttctgtc agtggagagg gtgaaggtga    1440
tgcaacatac ggaaaactta cccttaaatt tatttgcact actggaaaac tacctgttcc    1500
atggccaaca cttgtcacta ctttctctta tggtgttcaa tgcttttcaa gatacccaga    1560
tcatatgaaa cggcatgact ttttcaagag tgccatgccc gaaggttatg tacaggaaag    1620
aactatattt ttcaaagatg acgggaacta caagacacgt gctgaagtca agtttgaagg    1680
tgataccctt gttaatagaa tcgagttaaa aggtattgat tttaaagatg atggaaacat    1740
tcttggacac aaattggaat acaactataa cgagcacttg gtgtacatca tggcagacaa    1800
acaaaagaat ggtaccaaag ctatctttca agttcaccac aacattgaag atggaggcgt    1860
tcaactagca gaccattatc aacaaaatac tccaattggc gatggccctg tccttttacc    1920
agacaaccat tacctgcaca cacaatctgc cctttcgaaa gatcccaacg aaaagagaga    1980
ccacatggtc cttcttgagt ttgtaacagc tgctgggatt acacatggca tggatgaact    2040
atacaaaagc gaaaaggacg agctgtaaag gcctattttc tttagtttga atttactgtt    2100
attcggtgtg catttctatg tttggtgagc ggttttctgt gctcagagtg tgtttatttt    2160
atgtaattta atttctttgt gagctcctgt ttagcaggtc gtcccttcag caaggacaca    2220
aaaagatttt aatttttatta aaaaaaaaaa aaaaaaagac cgggaattcg atatcaagct    2280
tatcgacctg cagatcgttc aaacatttgg caataaagtt tcttaagatt gaatcctgtt    2340
gccggtcttg cgatgattat catataattt ctgttgaatt acgttaagca tgtaataatt    2400
aacatgtaat gcatgacgtt atttatgaga tgggttttta tgattagagt cccgcaatta    2460
tacatttaat acgcgataga aaacaaaata tagcgcgcaa actaggataa attatcgcgc    2520
gcggtgtcat ctatgttact agat                                           2544
```

<210> SEQ ID NO 76
<211> LENGTH: 267
<212> TYPE: PRT
<213> ORGANISM: Artificial Sequence
<220> FEATURE:
<223> OTHER INFORMATION: Amino acid sequence of PDISP/pHluorin/SEKDEL

<400> SEQUENCE: 76

```
Met Ala Lys Asn Val Ala Ile Phe Gly Leu Leu Phe Ser Leu Leu Val
1               5                   10                  15

Leu Val Pro Ser Gln Ile Phe Ala Ser Lys Gly Glu Glu Leu Phe Thr
            20                  25                  30

Gly Val Val Pro Ile Leu Val Glu Leu Asp Gly Asp Val Asn Gly His
        35                  40                  45

Lys Phe Ser Val Ser Gly Glu Gly Glu Gly Asp Ala Thr Tyr Gly Lys
    50                  55                  60

Leu Thr Leu Lys Phe Ile Cys Thr Thr Gly Lys Leu Pro Val Pro Trp
65                  70                  75                  80
```

Pro Thr Leu Val Thr Thr Phe Ser Tyr Gly Val Gln Cys Phe Ser Arg
            85                  90                  95

Tyr Pro Asp His Met Lys Arg His Asp Phe Phe Lys Ser Ala Met Pro
        100                 105                 110

Glu Gly Tyr Val Gln Glu Arg Thr Ile Phe Phe Lys Asp Asp Gly Asn
        115                 120                 125

Tyr Lys Thr Arg Ala Glu Val Lys Phe Glu Gly Asp Thr Leu Val Asn
130                 135                 140

Arg Ile Glu Leu Lys Gly Ile Asp Phe Lys Asp Asp Gly Asn Ile Leu
145                 150                 155                 160

Gly His Lys Leu Glu Tyr Asn Tyr Asn Glu His Leu Val Tyr Ile Met
            165                 170                 175

Ala Asp Lys Gln Lys Asn Gly Thr Lys Ala Ile Phe Gln Val His His
            180                 185                 190

Asn Ile Glu Asp Gly Gly Val Gln Leu Ala Asp His Tyr Gln Gln Asn
        195                 200                 205

Thr Pro Ile Gly Asp Gly Pro Val Leu Leu Pro Asp Asn His Tyr Leu
        210                 215                 220

His Thr Gln Ser Ala Leu Ser Lys Asp Pro Asn Glu Lys Arg Asp His
225                 230                 235                 240

Met Val Leu Leu Glu Phe Val Thr Ala Ala Gly Ile Thr His Gly Met
            245                 250                 255

Asp Glu Leu Tyr Lys Ser Glu Lys Asp Glu Leu
            260                 265

<210> SEQ ID NO 77
<211> LENGTH: 43
<212> TYPE: DNA
<213> ORGANISM: Artificial Sequence
<220> FEATURE:
<223> OTHER INFORMATION: IF-pHluorin_primer3.c

<400> SEQUENCE: 77
aaatttgtcg ggcccatggc gagagggagc agatcagtgg gta                43

<210> SEQ ID NO 78
<211> LENGTH: 1011
<212> TYPE: DNA
<213> ORGANISM: Artificial Sequence
<220> FEATURE:
<223> OTHER INFORMATION: Nucleotide sequence of Man99/pHluorin

<400> SEQUENCE: 78
atggcgagag ggagcagatc agtgggtagc agcagcagca aatggaggta ctgcaaccct    60
tcctattact tgaagcgccc aaagcgtctt gctctgctct tcatcgtttt cgtttgtgtc   120
tctttcgttt tctgggaccg tcaaactctc gtcagagagc accaggttga aatttctgag   180
ctgcagaaag aagtgactga tttgaaaaat tggtggatg atttaaataa caaacaaggt    240
ggtacctctg ggaagactga cttggggaga aaagctacca agtccagtaa agacgtcagt   300
aaaggagaag aacttttcac tggagttgtc ccaattcttg ttgaattaga tggtgatgtt   360
aatgggcaca atttttctgt cagtggagag ggtgaaggtg atgcaacata cggaaaactt   420
acccttaaat ttatttgcac tactggaaaa ctacctgttc catggccaac acttgtcact   480
actttctctt atggtgttca atgcttttca agatacccag atcatatgaa acggcatgac   540 ttttcaaga gtgccatgcc cgaaggttat gtacaggaaa gaactatatt tttcaaagat   600
gacgggaact acaagacacg tgctgaagtc aagtttgaag gtgataccct tgttaataga   660

```
atcgagttaa aaggtattga tttaaagat gatggaaaca ttcttggaca caaattggaa      720
tacaactata acgagcactt ggtgtacatc atggcagaca aacaaaagaa tggtaccaaa      780
gctatctttc aagttcacca caacattgaa gatggaggcg ttcaactagc agaccattat      840
caacaaaata ctccaattgg cgatggccct gtccttttac cagacaacca ttacctgcac      900
acacaatctg cccttcgaa agatcccaac gaaagagag accacatggt ccttcttgag      960
tttgtaacag ctgctgggat tacacatggc atggatgaac tatacaaata a              1011
```

<210> SEQ ID NO 79
<211> LENGTH: 2751
<212> TYPE: DNA
<213> ORGANISM: Artificial Sequence
<220> FEATURE:
<223> OTHER INFORMATION: Expression cassette number 1873

<400> SEQUENCE: 79

```
gtcaacatgg tggagcacga cacacttgtc tactccaaaa atatcaaaga tacagtctca       60
gaagaccaaa gggcaattga acttttcaa caaagggtaa tatccggaaa cctcctcgga      120
ttccattgcc cagctatctg tcactttatt gtgaagatag tggaaaagga aggtggctcc      180
tacaaatgcc atcattgcga taaggaaag gccatcgttg aagatgcctc tgccgacagt      240
ggtcccaaag atgaccccc acccacgagg agcatcgtgg aaaagaaga cgttccaacc      300 acgtcttcaa agcaagtgga ttgatgtgat aacatggtgg agcacgacac acttgtctac      360
tccaaaaata tcaaagatac agtctcagaa gaccaaaggg caattgagac ttttcaacaa      420
agggtaatat ccggaaacct cctcggattc cattgcccag ctatctgtca ctttattgtg      480
aagatagtgg aaaaggaagg tggctcctac aaatgccatc attgcgataa aggaaaggcc      540
atcgttgaag atgcctctgc cgacagtggt cccaaagatg accccccacc cacgaggagc      600
atcgtggaaa agaagacgt tccaaccacg tcttcaaagc aagtggattg atgtgatatc      660
tccactgacg taagggatga cgcacaatcc cactatcctt cgcaagaccc ttcctctata      720
taaggaagtt catttcattt ggagaggtat taaaatctta ataggttttg ataaaagcga      780
acgtggggaa acccgaacca aaccttcttc taaactctct ctcatctctc ttaaagcaaa      840
cttctctctt gtcttcttg cgtgagcgat cttcaacgtt gtcagatcgt gcttcggcac      900
cagtacaacg ttttctttca ctgaagcgaa atcaaagatc tctttgtgga cacgtagtgc      960
ggcgccatta aataacgtgt acttgtccta ttcttgtcgg tgtggtcttg ggaaaagaaa     1020
gcttgctgga ggctgctgtt cagccccata cattacttgt tacgattctg ctgactttcg     1080
gcgggtgcaa tatctctact tctgcttgac gaggtattgt tgcctgtact tcttctcttct     1140 tcttcttgct gattggttct ataagaaatc tagtattttc tttgaaacag agttttcccg     1200
tggttttcga acttggagaa agattgttaa gcttctgtat attctgccca aatttgtcgg     1260
gcccatggcg agagggagca gatcagtggg tagcagcagc agcaaatgga ggtactgcaa     1320
cccttcctat tacttgaagc gcccaaagcg tcttgctctg ctcttcatcg ttttcgtttg     1380
tgtctctttc gttttctggg accgtcaaac tctcgtcaga gagcaccagg ttgaaatttc     1440
tgagctgcag aaagaagtga ctgatttgaa aaatttggtg gatgatttaa ataacaaaca     1500
aggtggtacc tctgggaaga ctgacttggg gagaaaagct accaagtcca gtaaagacgt     1560
cagtaaagga gaagaacttt tcactggagt tgtcccaatt cttgttgaat tagatggtga     1620
tgttaatggg cacaaatttt ctgtcagtgg agagggtgaa ggtgatgcaa catacggaaa     1680
```

```
acttacccctt aaatttatttt gcactactgg aaaactacct gttccatggc caacacttgt   1740
cactactttc tcttatggtg ttcaatgctt ttcaagatac ccagatcata tgaaacggca   1800 tgacttttc aagagtgcca tgcccgaagg ttatgtacag gaaagaacta tattttcaa    1860 agatgacggg aactacaaga cacgtgctga agtcaagttt gaaggtgata cccttgttaa   1920
tagaatcgag ttaaaaggta ttgattttaa agatgatgga acattcttg gacacaaatt    1980 ggaatacaac tataacgagc acttggtgta catcatggca gacaaacaaa gaatggtac    2040 caaagctatc tttcaagttc accacaacat tgaagatgga ggcgttcaac tagcagacca   2100
ttatcaacaa aatactccaa ttggcgatgg ccctgtcctt ttaccagaca accattacct   2160
gcacacacaa tctgcccttt cgaaagatcc caacgaaaag agagaccaca tggtccttct   2220
tgagtttgta acagctgctg ggattacaca tggcatggat gaactataca aataaaggcc   2280
tatttctttt agtttgaatt tactgttatt cggtgtgcat ttctatgttt ggtgagcggt   2340
tttctgtgct cagagtgtgt ttattttatg taatttaatt tctttgtgag ctcctgttta   2400
gcaggtcgtc ccttcagcaa ggacacaaaa agattttaat tttattaaaa aaaaaaaaa   2460 aaaagaccgg gaattcgata tcaagcttat cgacctgcag atcgttcaaa catttggcaa   2520
taaagtttct taagattgaa tcctgttgcc ggtcttgcga tgattatcat ataatttctg   2580
ttgaattacg ttaagcatgt aataattaac atgtaatgca tgacgttatt tatgagatgg   2640
gtttttatga ttagagtccc gcaattatac atttaatacg cgatagaaaa caaaatatag   2700
cgcgcaaact aggataaaat atcgcgcgcg gtgtcatcta tgttactaga t           2751
```

<210> SEQ ID NO 80
<211> LENGTH: 336
<212> TYPE: PRT
<213> ORGANISM: Artificial Sequence
<220> FEATURE:
<223> OTHER INFORMATION: Amino acid sequence of Man99/pHluorin

<400> SEQUENCE: 80

```
Met Ala Arg Gly Ser Arg Ser Val Gly Ser Ser Ser Lys Trp Arg
1               5                   10                  15

Tyr Cys Asn Pro Ser Tyr Tyr Leu Lys Arg Pro Lys Arg Leu Ala Leu
                20                  25                  30

Leu Phe Ile Val Phe Val Cys Val Ser Phe Val Phe Trp Asp Arg Gln
            35                  40                  45

Thr Leu Val Arg Glu His Gln Val Glu Ile Ser Glu Leu Gln Lys Glu
        50                  55                  60

Val Thr Asp Leu Lys Asn Leu Val Asp Asp Leu Asn Asn Lys Gln Gly
65                  70                  75                  80

Gly Thr Ser Gly Lys Thr Asp Leu Gly Arg Lys Ala Thr Lys Ser Ser
                85                  90                  95

Lys Asp Val Ser Lys Gly Glu Glu Leu Phe Thr Gly Val Val Pro Ile
            100                 105                 110

Leu Val Glu Leu Asp Gly Asp Val Asn Gly His Lys Phe Ser Val Ser
        115                 120                 125

Gly Glu Gly Glu Gly Asp Ala Thr Tyr Gly Lys Leu Thr Leu Lys Phe
    130                 135                 140

Ile Cys Thr Thr Gly Lys Leu Pro Val Pro Trp Pro Thr Leu Val Thr
145                 150                 155                 160

Thr Phe Ser Tyr Gly Val Gln Cys Phe Ser Arg Tyr Pro Asp His Met
                165                 170                 175
```

Lys Arg His Asp Phe Phe Lys Ser Ala Met Pro Glu Gly Tyr Val Gln
            180                 185                 190

Glu Arg Thr Ile Phe Phe Lys Asp Asp Gly Asn Tyr Lys Thr Arg Ala
        195                 200                 205

Glu Val Lys Phe Glu Gly Asp Thr Leu Val Asn Arg Ile Glu Leu Lys
    210                 215                 220

Gly Ile Asp Phe Lys Asp Asp Gly Asn Ile Leu Gly His Lys Leu Glu
225                 230                 235                 240

Tyr Asn Tyr Asn Glu His Leu Val Tyr Ile Met Ala Asp Lys Gln Lys
                245                 250                 255

Asn Gly Thr Lys Ala Ile Phe Gln Val His His Asn Ile Glu Asp Gly
            260                 265                 270

Gly Val Gln Leu Ala Asp His Tyr Gln Gln Asn Thr Pro Ile Gly Asp
        275                 280                 285

Gly Pro Val Leu Leu Pro Asp Asn His Tyr Leu His Thr Gln Ser Ala
    290                 295                 300

Leu Ser Lys Asp Pro Asn Glu Lys Arg Asp His Met Val Leu Leu Glu
305                 310                 315                 320

Phe Val Thr Ala Ala Gly Ile Thr His Gly Met Asp Glu Leu Tyr Lys
                325                 330                 335

<210> SEQ ID NO 81
<211> LENGTH: 1032
<212> TYPE: DNA
<213> ORGANISM: Artificial Sequence
<220> FEATURE:
<223> OTHER INFORMATION: Nucleotide sequence of Man99TMD23/pHluorin

<400> SEQUENCE: 81
atggcgagag ggagcagatc agtgggtagc agcagcagca aatggaggta ctgcaaccct      60
tcctattact tgaagcgccc aaagcgtctt gctctgctct tcatcgtttt cgtttgtgtc     120
tctttcgttt tctggtgtgt ctcttttcgtt ttctgggacc gtcaaactct cgtcagagag     180
caccaggttg aaattctga gctgcagaaa gaagtgactg atttgaaaaa tttggtggat      240
gatttaaata caaacaagg tggtacctct gggaagactg acttggggag aaaagctacc      300
aagtccagta agacgtcag taaaggagaa gaacttttca ctggagttgt cccaattctt      360
gttgaattag atggtgatgt taatgggcac aaattttctg tcagtggaga gggtgaaggt      420
gatgcaacat acggaaaact tacccttaaa tttatttgca ctactggaaa actacctgtt      480
ccatggccaa cacttgtcac tactttctct tatggtgttc aatgcttttc aagataccca      540
gatcatatga acggcatga cttttttcaag agtgccatgc ccgaaggtta tgtacaggaa      600
agaactatat ttttcaaaga tgacgggaac tacaagacac gtgctgaagt caagtttgaa      660
ggtgataccc ttgttaatag aatcgagtta aaaggtattg attttaaaga tgatggaaac      720
attcttggac acaaattgga atacaactat aacgagcact tggtgtacat catggcagac      780
aaacaaaaga atggtaccaa agctatcttt caagttcacc acaacattga agatggaggc      840
gttcaactag cagaccatta tcaacaaaat actccaattg gcgatggccc tgtccttttta      900 ccagacaacc attacctgca cacacaatct gccctttcga agatcccaa cgaaaagaga      960 gaccacatgg tccttcttga gtttgtaaca gctgctggga ttacacatgg catggatgaa     1020
ctatacaaat aa                                                         1032

<210> SEQ ID NO 82
<211> LENGTH: 2772

<212> TYPE: DNA
<213> ORGANISM: Artificial Sequence
<220> FEATURE:
<223> OTHER INFORMATION: Expression cassette number 1874

<400> SEQUENCE: 82

```
gtcaacatgg tggagcacga cacacttgtc tactccaaaa atatcaaaga tacagtctca    60
gaagaccaaa gggcaattga acttttcaa caaagggtaa tatccggaaa cctcctcgga   120
ttccattgcc cagctatctg tcactttatt gtgaagatag tggaaaagga aggtggctcc   180
tacaaatgcc atcattgcga taaggaaag gccatcgttg aagatgcctc tgccgacagt    240
ggtcccaaag atggaccccc acccacgagg agcatcgtgg aaaagaaga cgttccaacc    300
acgtcttcaa agcaagtgga ttgatgtgat aacatggtgg agcacgacac acttgtctac   360
tccaaaaata tcaaagatac agtctcagaa gaccaaaggg caattgagac ttttcaacaa   420
agggtaatat ccggaaacct cctcggattc cattgcccag ctatctgtca ctttattgtg   480
aagatagtgg aaaaggaagg tggctcctac aaatgccatc attgcgataa ggaaaggcc    540
atcgttgaag atgcctctgc cgacagtggt cccaagatg gacccccacc cacgaggagc    600
atcgtggaaa agaagacgt tccaaccacg tcttcaaagc aagtggattg atgtgatatc    660
tccactgacg taagggatga cgcacaatcc cactatcctt cgcaagaccc ttcctctata   720
taaggaagtt catttcattt ggagaggtat taaaatctta ataggttttg ataaaagcga   780
acgtggggaa acccgaacca aaccttcttc taaactctct ctcatctctc ttaaagcaaa   840
cttctctctt gtctttcttg cgtgagcgat cttcaacgtt gtcagatcgt gcttcggcac   900
cagtacaacg ttttctttca ctgaagcgaa atcaaagatc tctttgtgga cacgtagtgc   960
ggcgccatta ataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggtttcga acttggagaa agattgttaa gcttctgtat attctgccca aatttgtcgg   1260
gcccatggcg agagggagca gatcagtggg tagcagcagc agcaaatgga ggtactgcaa   1320
cccttcctat tacttgaagc gcccaaagcg tcttgctctg ctcttcatcg ttttcgtttg   1380
tgtctctttc gttttctggt gtgtctcttt cgttttctgg accgtcaaa ctctcgtcag    1440
agagcaccag gttgaaattt ctgagctgca gaaagaagtg actgatttga aaatttggt    1500
ggatgattta aataacaaac aaggtggtac ctctgggaag actgacttgg ggagaaaagc   1560
taccaagtcc agtaaagacg tcagtaaagg agaagaactt ttcactggag ttgtcccaat   1620
tcttgttgaa ttagatggtg atgttaatgg gcacaaattt tctgtcagtg gagagggtga   1680
aggtgatgca acatacggaa aacttaccct taaatttatt tgcactactg gaaaactacc   1740
tgttccatgg ccaacacttg tcactacttt ctccttatggt gttcaatgct tttcaagata   1800
cccagatcat atgaaacggc atgacttttt caagagtgcc atgcccgaag ttatgtaca    1860
ggaaagaact atatttttca agatgacgg gaactacaag acacgtgctg aagtcaagtt   1920
tgaaggtgat acccttgtta atagaatcga gttaaaaggt attgatttta agatgatgg   1980
aaacattctt ggacacaaat tggaatacaa ctataacgag cacttggtgt acatcatggc   2040
agacaaacaa aagaatggta ccaaagctat ctttcaagtt caccacaaca ttgaagatgg   2100
aggcgttcaa ctagcagacc attatcaaca aaatactcca attggcgatg ccctgtcct    2160
```

```
tttaccagac aaccattacc tgcacacaca atctgcccct tcgaaagatc ccaacgaaaa    2220
gagagaccac atggtccttc ttgagtttgt aacagctgct gggattacac atggcatgga    2280
tgaactatac aaataaaggc ctatttctt tagtttgaat ttactgttat tcggtgtgca     2340
tttctatgtt tggtgagcgg ttttctgtgc tcagagtgtg tttattttat gtaatttaat    2400
ttctttgtga gctcctgttt agcaggtcgt cccttcagca aggacacaaa aagatttaa     2460 ttttattaaa aaaaaaaaaa aaaagaccg ggaattcgat atcaagctta tcgacctgca     2520
gatcgttcaa acatttggca ataaagtttc ttaagattga atcctgttgc cggtcttgcg    2580
atgattatca tataatttct gttgaattac gttaagcatg taataattaa catgtaatgc    2640
atgacgttat ttatgagatg ggtttttatg attagagtcc cgcaattata catttaatac    2700
gcgatagaaa acaaaatata gcgcgcaaac taggataaat tatcgcgcgc ggtgtcatct    2760
atgttactag at                                                        2772
```

<210> SEQ ID NO 83
<211> LENGTH: 343
<212> TYPE: PRT
<213> ORGANISM: Artificial Sequence
<220> FEATURE:
<223> OTHER INFORMATION: Amino acid sequence of Man99TMD23/pHluorin

<400> SEQUENCE: 83

```
Met Ala Arg Gly Ser Arg Ser Val Gly Ser Ser Ser Lys Trp Arg
1               5                   10                  15

Tyr Cys Asn Pro Ser Tyr Tyr Leu Lys Arg Pro Lys Arg Leu Ala Leu
                20                  25                  30

Leu Phe Ile Val Phe Val Cys Val Ser Phe Val Phe Trp Cys Val Ser
            35                  40                  45

Phe Val Phe Trp Asp Arg Gln Thr Leu Val Arg Glu His Gln Val Glu
        50                  55                  60

Ile Ser Glu Leu Gln Lys Glu Val Thr Asp Leu Lys Asn Leu Val Asp
65                  70                  75                  80

Asp Leu Asn Asn Lys Gln Gly Gly Thr Ser Gly Lys Thr Asp Leu Gly
                85                  90                  95

Arg Lys Ala Thr Lys Ser Ser Lys Asp Val Ser Lys Gly Glu Glu Leu
            100                 105                 110

Phe Thr Gly Val Val Pro Ile Leu Val Glu Leu Asp Gly Asp Val Asn
        115                 120                 125

Gly His Lys Phe Ser Val Ser Gly Glu Gly Glu Gly Asp Ala Thr Tyr
    130                 135                 140

Gly Lys Leu Thr Leu Lys Phe Ile Cys Thr Thr Gly Lys Leu Pro Val
145                 150                 155                 160

Pro Trp Pro Thr Leu Val Thr Thr Phe Ser Tyr Gly Val Gln Cys Phe
                165                 170                 175

Ser Arg Tyr Pro Asp His Met Lys Arg His Asp Phe Phe Lys Ser Ala
            180                 185                 190

Met Pro Glu Gly Tyr Val Gln Glu Arg Thr Ile Phe Phe Lys Asp Asp
        195                 200                 205

Gly Asn Tyr Lys Thr Arg Ala Glu Val Lys Phe Glu Gly Asp Thr Leu
    210                 215                 220

Val Asn Arg Ile Glu Leu Lys Gly Ile Asp Phe Lys Asp Asp Gly Asn
225                 230                 235                 240

Ile Leu Gly His Lys Leu Glu Tyr Asn Tyr Asn Glu His Leu Val Tyr
                245                 250                 255
```

-continued

```
Ile Met Ala Asp Lys Gln Lys Asn Gly Thr Lys Ala Ile Phe Gln Val
            260                 265                 270

His His Asn Ile Glu Asp Gly Gly Val Gln Leu Ala Asp His Tyr Gln
        275                 280                 285

Gln Asn Thr Pro Ile Gly Asp Gly Pro Val Leu Leu Pro Asp Asn His
    290                 295                 300

Tyr Leu His Thr Gln Ser Ala Leu Ser Lys Asp Pro Asn Glu Lys Arg
305                 310                 315                 320

Asp His Met Val Leu Leu Glu Phe Val Thr Ala Ala Gly Ile Thr His
                325                 330                 335

Gly Met Asp Glu Leu Tyr Lys
            340

<210> SEQ ID NO 84
<211> LENGTH: 20
<212> TYPE: DNA
<213> ORGANISM: Artificial Sequence
<220> FEATURE:
<223> OTHER INFORMATION: pHluorin-F,5 prime

<400> SEQUENCE: 84
cattgaagat ggaggcgttc                                                 20

<210> SEQ ID NO 85
<211> LENGTH: 20
<212> TYPE: DNA
<213> ORGANISM: Artificial Sequence
<220> FEATURE:
<223> OTHER INFORMATION: pHluorin-R,5 prime

<400> SEQUENCE: 85
gaaagggcag attgtgtgtg                                                 20

<210> SEQ ID NO 86
<211> LENGTH: 34
<212> TYPE: PRT
<213> ORGANISM: H1 New Cal influenza

<400> SEQUENCE: 86

Val Arg Ser Ala Lys Leu Arg Met Val Thr Gly Leu Arg Asn Ile Pro
1

<213> ORGANISM: H1 Sol Islands Infleunza

<400> SEQUENCE: 88

Val Arg Ser Ala Lys Leu Arg Met Val Thr Gly Leu Arg Asn Ile Pro
1               5                   10                  15

Ser Ile Gln Ser Arg Gly Leu Phe Gly Ala Ile Ala Gly Phe Ile Glu
            20                  25                  30

Gly Gly

<210> SEQ ID NO 89
<211> LENGTH: 34
<212> TYPE: PRT
<213> ORGANISM: H2 A Singapore Influenza

<400> SEQUENCE: 89

Val Lys Ser Glu Lys Leu Val Leu Ala Thr Gly Leu Arg Asn Val Pro
1               5                   10                  15

Gln Ile Glu Ser Arg Gly Leu Phe Gly Ala Ile Ala Gly Phe Ile Glu
            20                  25                  30

Gly Gly

<210> SEQ ID NO 90
<211> LENGTH: 34
<212> TYPE: PRT
<213> ORGANISM: H3 A Brisbane Influenza

<400> SEQUENCE: 90

Val Lys Gln Asn Thr Leu Lys Leu Ala Thr Gly Met Arg Asn Val Pro
1               5                   10                  15

Glu Lys Gln Thr Arg Gly Ile Phe Gly Ala Ile Ala Gly Phe Ile Glu
            20                  25                  30

Asn Gly

<210> SEQ ID NO 91
<211> LENGTH: 34
<212> TYPE: PRT
<213> ORGANISM: H3 A WCN Influenza

<400> SEQUENCE: 91

Val Lys Gln Asn Thr Leu Lys Leu Ala Thr Gly Met Arg Asn Val Pro
1               5                   10                  15

Glu Lys Gln Thr Arg Gly Ile Phe Gly Ala Ile Ala Gly Phe Ile Glu
            20                  25                  30

Asn Gly

<210> SEQ ID NO 92
<211> LENGTH: 37
<212> TYPE: PRT
<213> ORGANISM: H5 Anhui Influenza

<400> SEQUENCE: 92

Val Lys Ser Asn Lys Leu Val Leu Ala Thr Gly Leu Arg Asn Ser Pro
1               5                   10                  15

Leu Arg Glu Arg Arg Lys Arg Gly Leu Phe Gly Ala Ile Ala Gly
            20                  25                  30

Phe Ile Glu Gly Gly
            35

<210> SEQ ID NO 93

-continued

```
<211> LENGTH: 38
<212> TYPE: PRT
<213> ORGANISM: H5 Indo Influenza

<400> SEQUENCE: 93

Val Lys Ser Asn Arg Leu Val Leu Ala Thr Gly Leu Arg Asn Ser Pro
1               5                   10                  15

Gln Arg Glu Ser Arg Arg Lys Lys Arg Gly Leu Phe Gly Ala Ile Ala
            20                  25                  30

Gly Phe Ile Glu Gly Gly
        35

<210> SEQ ID NO 94
<211> LENGTH: 38
<212> TYPE: PRT
<213> ORGANISM: H5 Viet Nam Influenza

<400> SEQUENCE: 94

Val Lys Ser Asn Arg Leu Val Leu Ala Thr Gly Leu Arg Asn Ser Pro
1               5                   10                  15

Gln Arg Glu Arg Arg Arg Lys Lys Arg Gly Leu Phe Gly Ala Ile Ala
            20                  25                  30

Gly Phe Ile Glu Gly Gly
        35

<210> SEQ ID NO 95
<211> LENGTH: 34
<212> TYPE: PRT
<213> ORGANISM: H6 Teal HK Influenza

<400> SEQUENCE: 95

Val Lys Ser Glu Ser Leu Arg Leu Ala Thr Gly Leu Arg Asn Val Pro
1               5                   10                  15

Gln Ile Glu Thr Arg Gly Leu Phe Gly Ala Ile Ala Gly Phe Ile Glu
            20                  25                  30

Gly Gly

<210> SEQ ID NO 96
<211> LENGTH: 45
<212> TYPE: PRT
<213> ORGANISM: H6 Eq Prague Influenza

<400> SEQUENCE: 96

Val Lys Gln Lys Ser Leu Met Leu Ala Thr Gly Met Lys Asn Val Pro
1               5                   10                  15

Glu Ala Pro Ala His Lys Gln Leu Thr His His Met Arg Lys Lys Arg
            20                  25                  30

Gly Leu Phe Gly Ala Ile Ala Gly Phe Ile Glu Asn Gly
        35                  40                  45

<210> SEQ ID NO 97
<211> LENGTH: 34
<212> TYPE: PRT
<213> ORGANISM: H9A HK Influenza

<400> SEQUENCE: 97

Val Arg Val Asn Ser Leu Lys Leu Ala Val Gly Leu Arg Asn Val Pro
1               5                   10                  15

Ala Arg Ser Ser Arg Gly Leu Phe Gly Ala Ile Ala Gly Phe Ile Glu
            20                  25                  30
```

Gly Gly

```
<210> SEQ ID NO 98
<211> LENGTH: 46
<212> TYPE: PRT
<213> ORGANISM: B Florida Influenza

<400> SEQUENCE: 98
```

Ala Lys Ala Ile Gly Asn Cys Pro Ile Trp Val Lys Thr Pro Leu Lys
1               5                   10                  15

Leu Ala Asn Gly Thr Lys Tyr Arg Pro Pro Ala Lys Leu Leu Lys Glu
            20                  25                  30

Arg Gly Phe Phe Gly Ala Ile Ala Gly Phe Leu Glu Gly Gly
        35                  40                  45

```
<210> SEQ ID NO 99
<211> LENGTH: 46
<212> TYPE: PRT
<213> ORGANISM: B Malaysia Influenza

<400> SEQUENCE: 99
```

Ala Lys Ala Ile Gly Asn Cys Pro Ile Trp Val Lys Thr Pro Leu Lys
1               5                   10                  15

Leu Ala Asn Gly Thr Lys Tyr Arg Pro Pro Ala Lys Leu Leu Lys Glu
            20                  25                  30

Arg Gly Phe Phe Gly Ala Ile Ala Gly Phe Leu Glu Gly Gly
        35                  40                  45

```
<210> SEQ ID NO 100
<211> LENGTH: 9
<212> TYPE: PRT
<213> ORGANISM: Artificial Sequence
<220> FEATURE:
<223> OTHER INFORMATION: Polybasic cleavage of H5

<400> SEQUENCE: 100
```

Arg Glu Arg Arg Arg Lys Lys Arg Gly
1               5

```
<210> SEQ ID NO 101
<211> LENGTH: 4
<212> TYPE: PRT
<213> ORGANISM: Artificial Sequence
<220> FEATURE:
<223> OTHER INFORMATION: First 4 charged amino acids deleted from
      polybasic cleavage site of H5

<400> SEQUENCE: 101
```

Arg Glu Arg Arg
1

```
<210> SEQ ID NO 102
<211> LENGTH: 4
<212> TYPE: PRT
<213> ORGANISM: Artificial Sequence
<220> FEATURE:
<223> OTHER INFORMATION: Polybasic cleavage site of H5

<400> SEQUENCE: 102
```

Arg Lys Lys Arg
1

```
<210> SEQ ID NO 103
<211> LENGTH: 4
```

```
<212> TYPE: PRT
<213> ORGANISM: Artificial Sequence
<220> FEATURE:
<223> OTHER INFORMATION: Modification of polybasic cleavage site of H5

<400> SEQUENCE: 103

Thr Glu Thr Arg
1

<210> SEQ ID NO 104
<211> LENGTH: 9
<212> TYPE: PRT
<213> ORGANISM: Artificial Sequence
<220> FEATURE:
<223> OTHER INFORMATION: Polybasic site

<400> SEQUENCE: 104

Gly Glu Arg Arg Arg Lys Lys Arg Gly
1               5

<210> SEQ ID NO 105
<211> LENGTH: 4
<212> TYPE: PRT
<213> ORGANISM: Artificial Sequence
<220> FEATURE:
<223> OTHER INFORMATION: Replacement to polybasic site

<400> SEQUENCE: 105

Arg Glu Thr Arg
1

<210> SEQ ID NO 106
<211> LENGTH: 4
<212> TYPE: PRT
<213> ORGANISM: Artificial Sequence
<220> FEATURE:
<223> OTHER INFORMATION: Replacement amino acids to polybasic site

<400> SEQUENCE: 106

Ile Glu Thr Arg
1

<210> SEQ ID NO 107
<211> LENGTH: 5
<212> TYPE: PRT
<213> ORGANISM: Artificial Sequence
<220> FEATURE:
<223> OTHER INFORMATION: Monobasic site of H6

<400> SEQUENCE: 107

Ile Glu Thr Arg Gly
1               5

<210> SEQ ID NO 108
<211> LENGTH: 8
<212> TYPE: PRT
<213> ORGANISM: Artificial Sequence
<220> FEATURE:
<223> OTHER INFORMATION: Deletion sequence at C-terminus of HA1

<400> SEQUENCE: 108

Ala Leu Lys Leu Leu Lys Glu Arg
1               5

<210> SEQ ID NO 109
<211> LENGTH: 12
<212> TYPE: PRT
```

-continued

```
<213> ORGANISM: Artificial Sequence
<220> FEATURE:
<223> OTHER INFORMATION: Deletion sequence of N-terminus of HA2

<400> SEQUENCE: 109

Gly Phe Phe Gly Ala Ile Ala Gly Phe Leu Glu Gly
1               5                   10

<210> SEQ ID NO 110
<211> LENGTH: 16
<212> TYPE: PRT
<213> ORGANISM: Artificial Sequence
<220> FEATURE:
<223> OTHER INFORMATION: Acid susceptible ridig linker

<400> SEQUENCE: 110

Asn Glu Ala Ala Ala Lys Glu Ala Ala Ala Lys Glu Ala Ala Ala Lys
1               5                   10                  15
```

US 11,390,878 B2

INCREASING PROTEIN YIELD IN PLANTS

FIELD OF INVENTION

The present invention relates to producing proteins in plants. More specifically, the present invention relates to increasing protein production in plants.

BACKGROUND OF THE INVENTION

Influenza is caused by an RNA virus of the orthomyxoviridae family. There are three types of these viruses and they cause three different types of influenza: type A, B and C. Influenza virus type A viruses infect mammals (humans, pigs, ferrets, horses) and birds. This is very important to mankind, as this is the type of virus that has caused worldwide pandemics. Influenza virus type B (also known simply as influenza B) infects only humans. It occasionally causes local outbreaks of flu. Influenza C viruses also infect only humans. They infect most people when they are young and rarely causes serious illness.

Vaccination provides protection against disease caused by a like agent by inducing a subject to mount a defense prior to infection. Conventionally, this has been accomplished through the use of live attenuated or whole inactivated forms of the infectious agents as immunogens. To avoid the danger of using the whole virus (such as killed or attenuated viruses) as a vaccine, recombinant viral proteins, for example subunits, have been pursued as vaccines. Both peptide and subunit vaccines are subject to a number of potential limitations. Subunit vaccines may exhibit poor immunogenicity, owing to incorrect folding or poor antigen presentation. A major problem is the difficulty of ensuring that the conformation of the engineered proteins mimics that of the antigens in their natural environment. Suitable adjuvants and, in the case of peptides, carrier proteins, must be used to boost the immune response. In addition these vaccines elicit primarily humoral responses, and thus may fail to evoke effective immunity. Subunit vaccines are often ineffective for diseases in which whole inactivated virus can be demonstrated to provide protection.

Virus-like particles (VLPs) are potential candidates for inclusion in immunogenic compositions. VLPs closely resemble mature virions, but they do not contain viral genomic material. Therefore, VLPs are nonreplicative in nature, which make them safe for administration as a vaccine. In addition, VLPs can be engineered to express viral glycoproteins on the surface of the VLP, which is their most native physiological configuration. Moreover, since VLPs resemble intact virions and are multivalent particulate structures, VLPs may be more effective in inducing neutralizing antibodies to the glycoprotein than soluble envelope protein antigens.

VLPs have been produced in plants (WO2009/009876; WO 2009/076778; WO 2010/003225; WO 2010/003235; WO 2011/03522; WO 2010/148511; which are incorporated herein by reference), and in insect and mammalian systems (Noad, R. and Roy, P., 2003, Trends Microbiol 11: 438-44; Neumann et al., 2000, J. Virol., 74, 547-551). Latham and Galarza (2001, J. Virol., 75, 6154-6165) reported the formation of influenza VLPs in insect cells infected with recombinant baculovirus co-expressing hemagglutinin (HA), neuramindase (NA), M1, and M2 genes. This study demonstrated that influenza virion proteins self-assemble upon co-expression in eukaryotic cells and that the M1 matrix protein was required for VLP production. However, Gomez-Puertas et al., (1999, J. Gen. Virol, 80, 1635-1645) also showed that overexpression of M2 completely blocked CAT RNA transmission to MDCK cultures.

The secretory pathway presents a particularly complex milieu for the maturation and modification of recombinant proteins, including heterogeneous redox environments and proton concentrations between subcellular compartments. pH variations can induce significant conformational changes in protein structures (Wu et al., 2009, J Chromatogr B Analyt Technol Biomed Life Sci, 877(31), 4015-4021) and aggregation status (Wang et al., 2010, Int J Pharm, 390(2), 89-99). Such variations can also compromise proper glycosylation of maturing proteins (Hassinen et al., 2011, J Biol Chem, 286(44), 38329-38340) or slow down molecular traffic along the secretory pathway (Henkel and Weisz, 1998, J Biol Chem, 273(11), 6518-6524). Proteins destined for secretion are synthesized in the endoplasmic reticulum (ER) with near neutral pH, while downstream compartments become progressively more acidic (Casey et al., 2010, Nat Rev Mol Cell Biol, 11(1), 50-61).

M2 functions as an ion channel protein and it has been shown that, when this protein is overexpressed, the intracellular transport of co-expressed HA is inhibited and the accumulation of heamaglutinin (HA) at the plasma membrane is reduced by 75-80% (Henkel & Weisz, 1998, J Biol Chem, 273(11), 6518-6524). Furthermore, by overexpressing M2, the accumulation of virus membrane proteins at the plasma membrane is reduced and hence there is a drastic reduction in the number of functional VLPs produced.

The M2 protein is abundantly expressed at the cell surface of influenza A infected cells (Lamb et al., 1985, Cell, 40, 627 to 633). The protein is also found in the membrane of the virus particle itself, but in much smaller quantities, 14 to 68 molecules of M2 per virion (Zebedee and Lamb, 1988, J. Virol. 62, 2762 to 72). The M2 protein is posttranslationally modified by the addition of a palmitic acid on cysteine at position 50 (Sugrue et al., 1990, Virology 179, 51 to 56).

The M2 protein is a homotetramer composed of two disulfide-linked dimers, which are held together by noncovalent interactions (Sugrue and Hay, 1991, Virology 180, 617 to 624). By site-directed mutagenesis, Holsinger and Lamb, (1991, Virology 183, 32 to 43), demonstrated that the cysteine residues at positions 17 and 19 are involved in disulfide bridge formation. Only the cysteine at position 17 is present in all viruses analyzed. In the virus strains where cysteine 19 is also present, it is not known whether a second disulfide bridge is formed in the same dimer (already linked by Cys 17-Cys 17) or with the other dimer.

Smith et al. (US Patent Application 2010/0143393) and Song et al. (Plos ONE 2011 6(1):e14538) describe vaccines and VLPs that comprise influenza M2 protein. The VLPs comprise at least a viral core protein such as M1. This core protein drives budding and release of the particles from the insect host cells.

Szecsi et al. (Virology Journal, 2006, 3:70) assembled VLPs on replication-defective core particles derived from murine leukaemia virus (MLV). The engineered influenza VLP are derived by transiently co-expressing cells surface (HA, NA, M2) and internal viral components (Gag, GFP marker genome) and harbour at their surface HA, HA and either NA or M2, or all three proteins derived from the H7N1 or H5N1 virus. According to Szecsi et al. the expression of M2 during Flu-VLP production did not influence the incorporation of HA or NA onto viral particles (page 2, right column, second paragraph in Szecsi et al.).

SUMMARY OF THE INVENTION

The present invention relates to producing viral proteins in plants. More specifically, the present invention relates to producing and increasing virus-like particles production in plants.

It is an object of the invention to provide an improved method to increase virus like particle production in plants.

According to the present invention there is provided a method (A) of producing a virus like particle (VLP) in a plant comprising,
 a) introducing a first nucleic acid comprising a first regulatory region active in the plant and operatively linked to a nucleotide sequence encoding a structural virus protein into the plant, or portion of the plant,
 b) introducing a second nucleic acid comprising a second regulatory region active in the plant and operatively linked to a nucleotide sequence encoding a channel protein
 c) incubating the plant or portion of the plant under conditions that permit the expression of the nucleic acids, thereby producing the VLP.

The first regulatory region active in the plant, and the second regulatory region active in the plant may be the same or different.

The channel protein of the method (A) described above may be a proton channel protein. The proton channel protein may be selected from M2 or BM2. Furthermore, the proton channel protein may comprise the proton channel signature sequence HXXXW. The M2 protein may be an M2 protein obtained from influenza A/Puerto Rico/8/1934 (SEQ ID NO:14) or from influenza A/New Caledonia/20/1999 (SEQ ID NO:11).

The present invention also provides the method (A) as described above, wherein the structural virus protein comprises a trimerization domain. Furthermore, the nucleotide sequence encoding the structural virus protein comprises a chimeric nucleotide sequence encoding, in series, an antigenic viral protein or fragment thereof, an influenza transmembrane domain, and a cytoplasmic tail. The structural virus protein may comprise an influenza HA protein. Furthermore one or more proteolytic loop of the influenza HA protein may be deleted.

The present invention provides the method (A) as described above wherein, the nucleotide sequence encoding the structural virus protein may be selected from the group consisting of B HA, C, HA, H2, H3, H4, H6, H7, H8, H9, H10, H11, H12, H13, H14, H15, and H16. For example, the nucleotide sequence encoding the structural virus protein may be Type B HA or H3. The nucleotide sequence encoding the structural virus protein may be for example HA from influenza B/Brisbane/60/2008, B/Malaysia/2506/2004 or B/Wisconsin/1/2010, or H3 from influenza A/Perth/16/2009 or A/Victoria/361/2011. Furthermore, the nucleotide sequence encoding a structural virus protein has at least 70% sequence identity to SEQ ID NO: 23, 28, 43, 46, 51, 57 or 61. The sequence of the structural virus protein may also be comprise the sequence of SEQ ID NO:25, 30, 41, 48, 54, 58 or 64.

The present invention also includes the method (A) as described above, wherein the first nucleic acid sequence comprises the first regulatory region operatively linked with a one or more than one comovirus enhancer, the nucleotide sequence encoding the structural virus protein, and one or more than one geminivirus amplification element, and a third nucleic acid encoding a geminivirus replicase is introduced into the plant or portion of the plant. The one or more than one comovirus enhancer may be a comovirus UTR, for example, a Cowpea Mosaic Virus hyperanslatable (CPMV-HT) UTR such as the CPMV-HT 5' and/or 3'UTR. The one or more than one geminivirus amplification element may be selected from a Bean Yellow Dwarf Virus long intergenic region (BeYDV LIR), and a BeYDV short intergenic region (BeYDV SIR). Furthermore, the nucleotide sequence encoding the structural virus protein may be Type B HA or H3, for example, the nucleotide sequence encoding a structural virus protein may have at least 70% sequence identity to SEQ ID NO: 23, 28, 43, 46, 51, 57 or 61. The sequence of the structural virus protein may also be comprise the sequence of SEQ ID NO:25, 30, 41, 48, 54, 58 or 64.

The method as described above (Method A) may also involving introducing another nucleic acid sequence encoding a suppressor of silencing, for example HcPro or p19.

The present invention also includes the method (A) as described above, wherein in the step of introducing (step a), the nucleic acid is transiently expressed in the plant. Alternatively, in the step of introducing (step a), the nucleic acid is stably expressed in the plant.

The method (A) as described above may further comprising a step of:
 d) harvesting the plant and purifying the VLPs.

The present invention also includes the method (A) as described above, wherein the VLP does not contain a viral matrix or a core protein.

The present invention provides a VLP produced by the method (A) as described above. The VLP may further comprising one or more than one lipid derived from a plant. The VLP may also be characterized by not containing the channel protein. Furthermore, the structural virus protein of the VLP may be an HA0 protein. The one or more virus protein comprises of the VLP may comprise plant-specific N-glycans, or modified N-glycans. The present invention also provides a polyclonal antibody prepared using the VLP.

The present invention includes a composition comprising an effective dose of the VLP as just described for inducing an immune response, and a pharmaceutically acceptable carrier.

The present invention also includes a method of inducing immunity to an influenza virus infection in a subject, comprising administering the VLP as just described to the subject. The VLP may be administered to a subject orally, intradermally, intranasally, intramusclarly, intraperitoneally, intravenously, or subcutaneously.

The present invention also provides plant matter comprising a VLP produced by the method (A) described above. The plant matter may be used in inducing immunity to an influenza virus infection in a subject. The plant matter may also be admixed as a food supplement.

The present invention also provides a method (B) of producing a virus like particle (VLP) comprising,
 a) providing a plant or portion of the plant comprising a first nucleic acid comprising a first regulatory region active in the plant and operatively linked to a nucleotide sequence encoding a structural virus protein into the plant, or portion of the plant, and a second nucleic acid comprising a second regulatory region active in the plant and operatively linked to a nucleotide sequence encoding a channel protein
 b) incubating the plant or portion of the plant under conditions that permit the expression of the nucleic acids, thereby producing the VLP.

The first regulatory region active in the plant, and the second regulatory region active in the plant may be the same or different.

The channel protein of the method (B) described above may be a proton channel protein. The proton channel protein may be selected from M2 or BM2. Furthermore, the proton channel protein may comprise the proton channel signature sequence HXXXW.

The present invention also provides the method (B) as described above, wherein the structural virus protein comprises a trimerization domain. Furthermore, the nucleotide sequence encoding the structural virus protein comprises a chimeric nucleotide sequence encoding, in series, an antigenic viral protein or fragment thereof, an influenza transmembrane domain, and a cytoplasmic tail. The structural virus protein may comprise an influenza HA protein. Furthermore one or more proteolytic loop of the influenza HA protein may be deleted.

The present invention provides the method (B) as described above wherein, the nucleotide sequence encoding the structural virus protein may be selected from the group consisting of B HA, C, HA, H2, H3, H4, H6, H7, H8, H9, H10, H11, H12, H13, H14, H15, and H16. For example, the nucleotide sequence encoding the structural virus protein may be Type B HA or H3. The nucleotide sequence encoding the structural virus protein may be for example HA from influenza B/Brisbane/60/2008, B/Malaysia/2506/2004 or B/Wisconsin/1/2010, or H3 from influenza A/Perth/16/2009 or A/Victoria/361/2011.

The Present invention also includes the method (B) as described above, wherein the first nucleic acid sequence comprises the first regulatory region operatively linked with a one or more than one comovirus enhancer, the nucleotide sequence encoding the structural virus protein, and one or more than one geminivirus amplification element, and a third nucleic acid encoding a geminivirus replicase is introduced into the plant or portion of the plant. The one or more than one comovirus enhancer may be a comovirus UTR, for example, a Cowpea Mosaic Virus hyperanslatable (CPMV-HT) UTR such as the CPMV-HT 5' and/or 3'UTR. Additionally, the one or more than one geminivirus amplification element may be selected from a Bean Yellow Dwarf Virus long intergenic region (BeYDV LIR), and a BeYDV short intergenic region (BeYDV SIR).

The method as described above (Method B) may also involving introducing another nucleic acid sequence encoding a suppressor of silencing, for example HcPro or p19.

The present invention also includes the method (B) as described above, wherein in the step of introducing (step a), the nucleic acid is transiently expressed in the plant. Alternatively, in the step of introducing (step a), the nucleic acid is stably expressed in the plant.

The method (B) as described above may further comprising a step of:
d) harvesting the plant and purifying the VLPs.

The present invention also includes the method (B) as described above, wherein the VLP does not contain a viral matrix or a core protein.

The present invention provides a VLP produced by the method (B) as described above. The VLP may further comprising one or more than one lipid derived from a plant. The VLP may also be characterized by not containing the channel protein. Furthermore, the structural virus protein of the VLP may be an HA0 protein. The, one or more virus protein comprises of the VLP may comprise plant-specific N-glycans, or modified N-glycans. The present invention also provides a polyclonal antibody prepared using the VLP.

The present invention includes a composition comprising an effective dose of the VLP made by the method (B) as just described, for inducing an immune response, and a pharmaceutically acceptable carrier.

The present invention also includes a method of inducing immunity to an influenza virus infection in a subject, comprising administering the VLP as just described, to the subject. The VLP may be administered to a subject orally, intradermally, intranasally, intramusclarly, intraperitoneally, intravenously, or subcutaneously.

The present invention also provides plant matter comprising a VLP produced by the method (B) described above. The plant matter may be used in inducing immunity to an influenza virus infection in a subject. The plant matter may also be admixed as a food supplement.

The present invention provides a polypeptide comprising the amino acid sequence of SEQ ID NO:41 (PDISP/HA from influenza B/Brisbane/60/2008 with deleted proteolytic loop), and a nucleic acid sequence encoding the polypeptide of SEQ ID NO:41. The nucleic acid sequence may comprises the nucleotide sequence of SEQ ID NO:43. The present invention provides a VLP comprising the polypeptide comprising the amino acid sequence of SEQ ID NO:41. The VLP may further comprising one or more than one lipid derived from a plant. The VLP may also be characterized by not containing the channel protein. The VLP may comprise plant-specific N-glycans, or modified N-glycans. The present invention provides a composition comprising an effective dose of the VLP comprising the amino acid sequence of SEQ ID NO:41, for inducing an immune response, and a pharmaceutically acceptable carrier. The present invention also includes a method of inducing immunity to an influenza virus infection in a subject, comprising administering the VLP comprising the amino acid sequence of SEQ ID NO:41, to the subject. The VLP may be administered to a subject orally, intradermally, intranasally, intramuscularly, intraperitoneally, intravenously, or subcutaneously. The present invention also provides plant matter comprising a VLP comprising the amino acid sequence of SEQ ID NO:41. The plant matter may be used in inducing immunity to an influenza virus infection in a subject. The plant matter may also be admixed as a food supplement.

According to the present invention there is provided a method (C) of increase the yield, stability, or both the yield and stability of an acid sensitive protein in a plant comprising,
  a) introducing a first nucleic acid comprising a first regulatory region active in the plant and operatively linked to a nucleotide sequence encoding the acid sensitive protein into the plant, or portion of the plant,
  b) introducing a second nucleic acid comprising a second regulatory region active in the plant and operatively linked to a nucleotide sequence encoding a proton channel protein
  c) incubating the plant or portion of the plant under conditions that permit the expression of the nucleic acids, thereby producing and increasing the yield of the acid sensitive protein, when compared to the yield of the acid sensitive protein produced in the plant or portion of the plant produced under the same conditions but in the absence of the proton channel protein.

The first regulatory region active in the plant, and the second regulatory region active in the plant may be the same or different.

The channel protein of the method (C) described above may be selected from M2 or BM2. Furthermore, the proton channel protein may comprise the proton channel signature sequence HXXXW. The M2 protein may be an M2 protein obtained from influenza A/Puerto Rico/8/1934 (SEQ ID NO:14) or from influenza A/New Caledonia/20/1999 (SEQ ID NO:11).

The present invention also provides a method (D) of increasing yield of an acid sensitive protein comprising,
   a) providing a plant or portion of the plant comprising a first nucleic acid comprising a first regulatory region active in the plant and operatively linked to a nucleotide sequence encoding the acid sensitive protein into the plant, or portion of the plant, and a second nucleic acid comprising a second regulatory region active in the plant and operatively linked to a nucleotide sequence encoding a proton channel protein
   b) incubating the plant or portion of the plant under conditions that permit the expression of the nucleic acids, thereby increasing the yield of the acid sensitive protein when compared to the yield of the acid sensitive protein produced in the plant or portion of the plant produced under the same conditions, and in the absence of the proton channel protein.

The first regulatory region active in the plant, and the second regulatory region active in the plant may be the same or different.

The channel protein of the method (D) described above may be selected from M2 or BM2. Furthermore, the proton channel protein may comprise the proton channel signature sequence HXXXW.

The method (C) as described above, where the acid sensitive protein is selected from the group of proteins that undergo pH-dependent conformation change, protein folding, protein stability, increase protein degradation within an acid environment, or a combination thereof.

By co-expressing a structural virus protein along with a channel protein, for example but not limited to a proton channel protein, increased yield of the structural virus protein and VLPs are observed. HA's are known to undergo pH-dependant conformation change. Without wishing to bound by theory, the pH within the Golgi apparatus of the HA producing cells during maturation and migration may influence HA folding, effects stability and increase degradation, or a combination thereof, of the HA. By co-expressing a channel protein, for example but not limited to a proton channel protein, along with an HA, the pH within the Golgi apparatus may increase, and result in an increase in stability, reduction of degradation, or a combination thereof, and increase HA yield.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A shows primer IF-H5A-I-05.s1+3c (SEQ ID NO: 2). FIG. 1B shows primer IF-H5dTm.r (SEQ ID NO: 3). FIG. 1C shows a schematic representation of construct 1191. FIG. 1D shows Construct 1191 (SEQ ID NO 4). FIG. 1E shows expression cassette number 489 (SEQ ID NO 5). FIG. 1F shows amino acid sequence of H5 from influenza A/Indonesia/5/2005 (H5N1) (SEQ ID NO: 6). FIG. 1G shows a nucleotide sequence encoding H5 from influenza A/Indonesia/5/2005 (H5N1) (SEQ ID NO: 42).

FIG. 2A shows primer IF-S1-M1+M2ANC.c (SEQ ID NO:7). FIG. 2B shows primer IF-S1-4-M2ANC.r (SEQ ID NO: 8). FIG. 2C shows the nucleotide sequence for the synthesized M2 gene (corresponding to nt 1-26 joined to 715-982 from Genbank accession number DQ508860) (SEQ ID NO: 9). FIG. 2D shows the expression cassette number 1261 from 2X35 S promoter to NOS terminator. M2 from influenza A/New Caledonia/20/1999 (H1N1) is underlined. (SEQ ID NO: 10). FIG. 2E shows the amino acid sequence of M2 from influenza A/New Caledonia/20/1999 (H1N1) (SEQ ID NO: 11).

FIG. 3A shows the nucleotide sequence of the synthesized M2 gene (corresponding to nt 26-51 joined to nt 740-1007 from Genbank accession number EF467824) (SEQ ID NO: 12). FIG. 3B shows the expression cassette number 859 from 2X35 S promoter to NOS terminator. M2 from Influenza A/Puerto Rico/8/1934 (H1N1) is underlined. (SEQ ID NO: 13). FIG. 3C shows the amino acid sequence of M2 from influenza A/Puerto Rico/8/1934 (H1N1) (SEQ ID NO:14).

FIG. 4A shows primer IF-H1A-C-09.s2+4c (SEQ ID NO: 15). FIG. 4B shows primer IF-H1A-C-09.s1-4r (SEQ ID NO: 16). FIG. 4C shows the nucleotide sequence of the synthesized H1 gene (Genbank accession number FJ966974) (SEQ ID NO: 17). FIG. 4D shows a schematic representation of construct 1192. SacII and StuI restriction enzyme sites used for plasmid linearization are annotated on the representation. FIG. 4E shows construct 1192 from left to right t-DNA borders (underlined). 2X35 S/CPMV-HT/PDISP/NOS with Plastocyanine-P19-Plastocyanine silencing inhibitor expression cassette (SEQ ID NO: 18). FIG. 4F shows expression cassette number 484 from 2X35 S promoter to NOS terminator. PDISP/H1 from influenza A/California/7/2009 (H1N1) is underlined. (SEQ ID NO: 19). FIG. 4G shows amino acid sequence of PDISP-H1 from influenza A/California/7/2009 (H1N1) (SEQ ID NO: 20).

FIG. 5A shows primer IF-S2+S4-H3 Per.c (SEQ ID NO: 21). FIG. 5B shows primer IF-S1a4-H3 Per.r (SEQ ID NO: 22). FIG. 5C shows the nucleotide sequence of the synthesized H3 gene (corresponding to nt 26-1726 from Genbank accession number GQ293081) (SEQ ID NO: 23). FIG. 5D shows the expression cassette number 1019 from 2X35 S promoter to NOS terminator. PDISP/H3 from influenza A/Perth/16/2009 (H3N2) is underlined. (SEQ ID NO: 24). FIG. 5E shows the amino acid sequence of PDISP/H3 from influenza A/Perth/16/2009 (H3N2) (SEQ ID NO: 25).

FIG. 6A shows primer IF-S2+S4-B Bris.c (SEQ ID NO: 26). FIG. 6B shows primer IF-S1a4-B Bris.r (SEQ ID NO: 27). FIG. 6C shows the nucleotide sequence of synthesized HA B Brisbane gene (corresponding to nt 34-1791 from Genbank accession number FJ766840) (SEQ ID NO: 28). FIG. 6D shows the nucleotide sequence of expression cassette number 1029 from 2X35 S promoter to NOS terminator. PDISP/HA from influenza B/Brisbane/60/2008 is underlined. (SEQ ID NO: 29). FIG. 6E shows the amino acid sequence of PDISP/HA from influenza B/Brisbane/60/2008 (SEQ ID NO: 30). FIG. 6F shows a schematic representation of construct 1194. SacII and StuI restriction enzyme sites used for plasmid linearization are annotated on the representation. FIG. 6G shows construct 1194 from left to right t-DNA borders (underlined). 2X35 S/CPMV-HT/PDISP/NOS into BeYDV+Replicase amplification system with Plastocyanine-P19-Plastocyanine silencing inhibitor expression cassette (SEQ ID NO: 31). FIG. 6H shows expression cassette number 1008 from BeYDV left LIR to BeYDV right LIR. PDISP/HA from influenza B/Brisbane/60/2008 is underlined. (SEQ ID NO: 32).

FIG. 7A shows primer dTmH5I-B Bris.r (SEQ ID NO: 33). FIG. 7B shows primer B Bris-dTmH5I.c (SEQ ID NO: 34). FIG. 7C shows primer IF-S1aS4-dTmH5I.r (SEQ ID NO: 35). FIG. 7D shows expression cassette number 1009 from BeYDV left LIR to BeYDV right LIR. PDISP/HA B Brisbane/H5Indo TMCT is underlined. (SEQ ID NO:36). FIG. 7E shows amino acid sequence of PDISP/HA B Brisbane/H5Indo TMCT (SEQ ID NO: 37).

FIG. 8A shows primer 1039+1059.r (SEQ ID NO: 38). FIG. 8B shows primer 1039+1059.c (SEQ ID NO: 39). FIG. 8C shows expression cassette number 1059 from BeYDV left LIR to BeYDV right LIR. PDISP/HA from influenza B/Brisbane/60/2008 with deleted proteolytic loop is underlined. (SEQ ID NO: 40). FIG. 8D shows amino acid sequence of PDISP/HA from influenza B/Brisbane/60/2008 with deleted proteolytic loop (SEQ ID NO: 41). FIG. 8E shows nucleotide sequence of PDISP/HA from influenza B/Brisbane/60/2008 with deleted proteolytic loop (SEQ ID NO: 43).

FIG. 9 shows the plasmid map of construct number 1008. Construct number 1008 directs the expression of wild-type HA from influenza strain B/Brisbane/60/2008. This construct comprises BeYDV-derived elements for DNA amplification.

FIG. 10 shows the plasmid map of construct number 1009. Construct number 1009 directs the expression of a chimeric HA from influenza strain B/Brisbane/60/2008 in which the transmembrane domain and cytosolic tail are replaced with those of H5 from influenza A/Indonesia/05/2005. This construct comprises BeYDV-derived elements for DNA amplification.

FIG. 23B shows a Western blot analysis of HA protein expression in agroinfiltrated *Nicotiana benthamiana* leaves: "1019": expression of wild-type HA from A/Perth/16/2009 (H3N2); "1019+1261": co-expression of wild-type HA from A/Perth/16/2009 (H3N2) with M2 from A/New Caledonia/20/99; "1019+859": co-expression of wild-type HA from A/Perth/16/2009 (H3N2) with M2 from A/Puerto Rico/8/34. Ratios indicate the proportion of *Agrobacterium* cultures used in co-expression experiments.

FIG. 24 shows the sequence alignment of HAs from several strains of influenza. The cleavage site of the precursor HA0 is indicated by an arrow.

FIG. 25A shows primer IF-H3V36111.S2+4c (SEQ ID NO: 44). FIG. 25B shows primer IF-H3V36111.s1-4r (SEQ ID NO: 45). FIG. 25C shows the nucleotide sequence of synthesized H3 gene (corresponding to nt 25 to 1725 from GISAID isolate number EPI_ISL_101506 HA sequence) (SEQ ID NO: 46). FIG. 25D shows the nucleotide sequence of expression cassette number 1391 from 2X35 S promoter to NOS terminator. PDISP/H3 from influenza A/Victoria/361/2011 (H3N2) is underlined. (SEQ ID NO: 47). FIG. 25E shows the amino acid sequence of PDISP-H3 from influenza A/Victoria/361/2011 (H3N2) (SEQ ID NO: 48). FIG. 25F shows a schematic representation of construct 1391.

FIG. 26A shows primer IF-HAB110.S1+3c (SEQ ID NO: 49). FIG. 26B shows primer IF-HAB110.s1-4r (SEQ ID NO: 50). FIG. 26C shows the nucleotide sequence of synthesized HA B Wisconsin (Genbank accession number JN993010) (SEQ ID NO: 51). FIG. 26D shows a schematic representation of construct 193. FIG. 26E shows construct 193 from left to right t-DNA borders (underlined). 2X35 S/CPMV-HT/NOS into BeYDV(m)+Replicase amplification system with Plastocyanine-P19-Plastocyanine silencing inhibitor expression cassette (SEQ ID NO: 52). FIG. 26F shows the nucleotide sequence of expression cassette number 1462 from 2X35 S promoter to NOS terminator. HA from influenza B/Wisconsin/1/2010 is underlined (SEQ ID NO: 53). FIG. 26G shows the amino acid sequence of HA from influenza B/Wisconsin/1/2010 (SEQ ID NO: 54). FIG. 26H shows a schematic representation of construct 1462.

FIG. 27A shows primer HAB110(PrL-).r (SEQ ID NO: 55). FIG. 27B shows primer HAB110(PrL-).c (SEQ ID NO: 56). FIG. 27C shows the nucleotide sequence of expression cassette number 1467 from 2X35 S promoter to NOS terminator. HA from influenza B/Wisconsin/1/2010 with deleted proteolytic loop is underlined (SEQ ID NO: 57). FIG. 27D shows the amino acid sequence of influenza B/Wisconsin/1/2010 with deleted proteolytic loop (SEQ ID NO: 58). FIG. 27E shows a schematic representation of construct 1467.

Figure 28H:
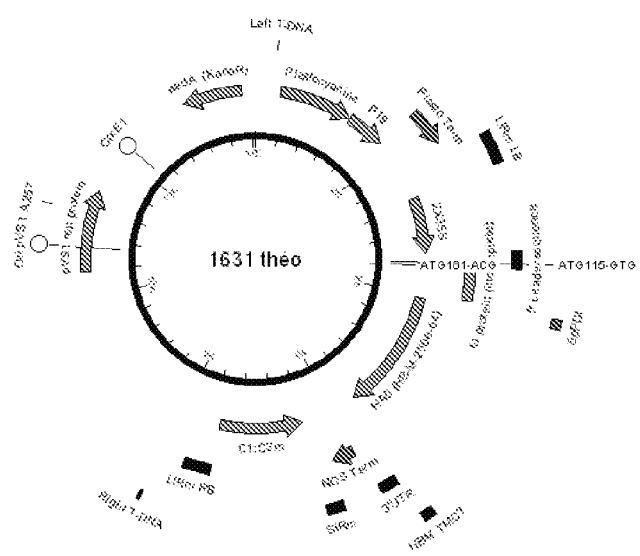

FIG. 28A shows primer IF-HB-M-04.s2+4c (SEQ ID NO: 59). FIG. 28B shows primer IF-HB-M-04.s1-4r (SEQ ID NO: 60). FIG. 28C shows the nucleotide sequence of synthesized HA B Malaysia (corresponding to nt 31-1743 from Genbank accession number EU124275) with T759C and C888G mutations being underlined. (SEQ ID NO: 61). FIG. 28D shows a schematic representation of construct 194, with SacII and StuI restriction enzyme sites used for plasmid linearization being annotated on the representation. FIG. 28E shows construct 194 from left to right t-DNA borders (underlined). 2X35 S/CPMV-HT/NOS into BeYDV (m)+Replicase amplification system with Plastocyanine-P19-Plastocyanine silencing inhibitor expression cassette (SEQ ID NO: 62). FIG. 28F shows the nucleotide sequence of expression cassette number 1631 from 2X35 S promoter to NOS terminator. PDISP-HA from influenza B/Malaysia/2506/2004 is underlined. (SEQ ID NO: 63). FIG. 28G shows the amino acid sequence of PDISP-HA from influenza B/Malaysia/2506/2004 (SEQ ID NO: 64). FIG. 28H shows a schematic representation of construct 1631.

Figure 32:
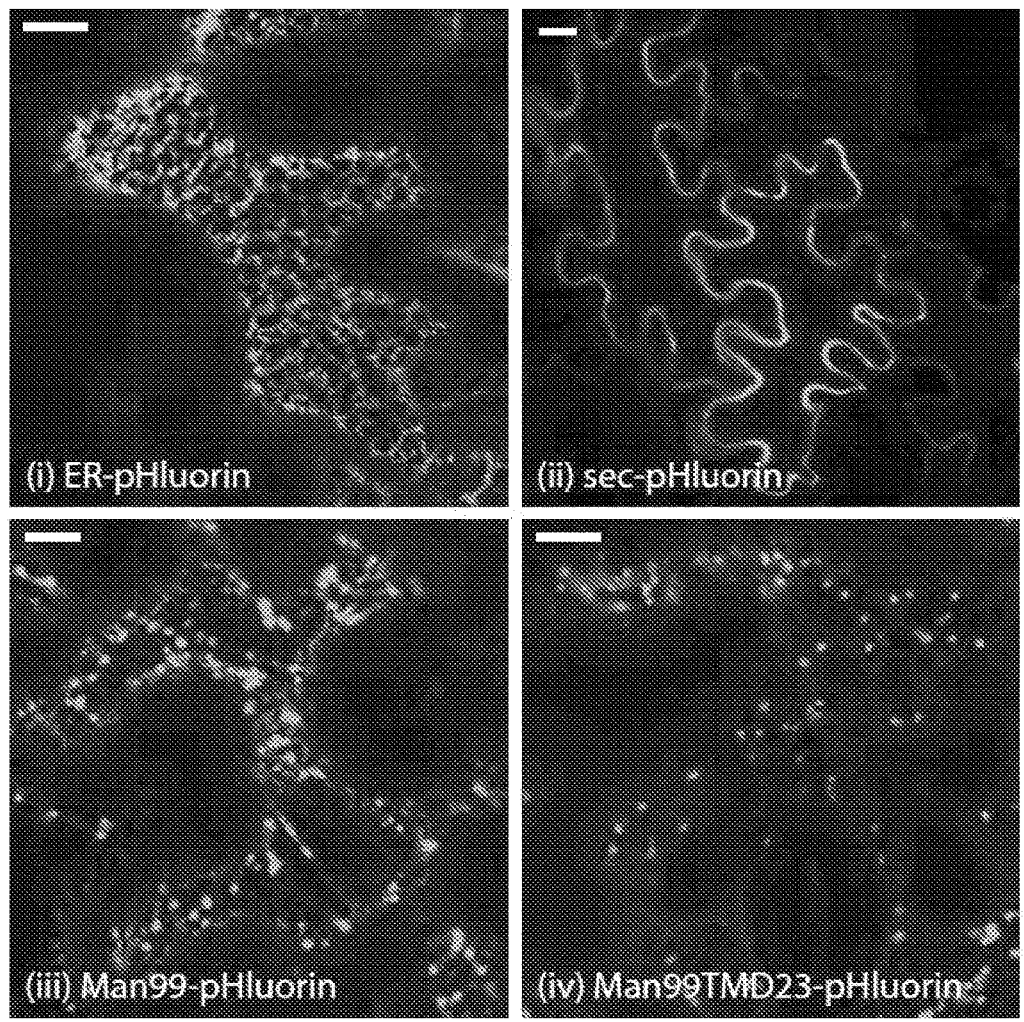

FIG. 29 shows a Western blot analysis of HA protein expression in agroinfiltrated *Nicotiana benthamiana* leaves. HA from B/Malaysia/2506/2004 is co-expressed with M2 from A/New Caledonia/20/99. Twenty micrograms of protein extract were loaded per lane. "C+": positive control, semi-purified B/Malaysia/2506/2004 virus from the National Institute for Biological Standards and Control, United Kingdom; "1631": expression of wild-type HA from B/Malaysia/2506/2004 in the presence of amplification elements (BeYDV); "1631+1261": co-expression of wild-type HA from B/Malaysia/2506/2004 in the presence of amplification elements (BeYDV) with M2. Ratios indicate the proportion of *Agrobacterium* cultures used in co-expression experiments.

FIG. 30A shows a Western blot analysis of HA protein expression in agroinfiltrated *Nicotiana benthamiana* leaves. HA from B/Wisconsin/1/2010 is co-expressed with M2 from A/New Caledonia/20/99. Ten micrograms of protein extract were loaded per lane. "C+": positive control, semi-purified B/Wisconsin/1/2010 virus from the National Institute for Biological Standards and Control, United Kingdom; "1462": expression of wild-type HA from B/Wisconsin/1/2010 in the presence of amplification elements (BeYDV); "1467": expression of the mutant HA from B/Wisconsin/1/2010 in the presence of amplification elements (BeYDV); "1462+1261": co-expression of wild-type HA from B/Wisconsin/1/2010 in the presence of amplification elements (BeYDV) with M2; "1467+1261": co-expression of the mutant HA from B/Wisconsin/1/2010 in the presence of amplification elements (BeYDV) with M2. Ratios indicate the optical density for each *Agrobacterium* culture used in expression and co-expression experiments. FIG. 30B shows a comparison of hemagglutination capacity of crude protein extracts from plants transformed with AGL1/1462, AGL1/1467, AGL1/1462+AGL1/1261 and AGL1/1467+AGL1/1261.

FIG. 31 shows a Western blot analysis of HA protein expression in agroinfiltrated *Nicotiana benthamiana* leaves. HA from H3/Victoria/361/2011 is co-expressed with M2 from A/New Caledonia/20/99. Twenty micrograms of protein extract were loaded per lane. "C+": positive control, semi-purified H3/Wisconsin/15/2009 virus from the Therapeutic Goods Administration, Australia; "1391": expression of wild-type HA from H3/Victoria/361/2011; "1391+1261": co-expression of wild-type HA from H3/Victoria/361/2011 with M2. Ratios indicate the optical density for each *Agrobacterium* culture used in expression and co-expression experiments.

FIG. 32A shows a schematic representation of ratiometric-pHluorin constructs. ER-pHluorin (see SEQ ID NO: 75; construct No: 1872; FIGS. 38B and 38D) comprises an N-terminal signal peptide from protein disulfide isomerase (PDI) and a C-terminal (SEKDEL) ER-retention sequence. sec-pHluorin (also termed PDISP/pHIuorin; see SEQ ID NO's: 71, 72, 73; construct No: 1871) comprises a PDI signal peptide for transit through to the apoplast. Man99-pHluorin (see, SEQ ID NO's: 78, 79, 80; construct No: 1873) includes a Man99 targeting signal for localization in the cis-Golgi with a 16-amino acid transmembrane domain from Man99. Man99TMD23-pHluorin (see SEQ ID NO's: 81, 82, 83; construct No: 1874) includes a complete 23 amino acid transmembrane domain from Man99 for targeting the protein to the trans-Golgi. FIG. 32B shows confocal microscopy images of transient expression of pHluorin in living *N. benthamiana* leaves. (i) Cell expressing the ER-retained pHluorin, showing a typical interconnected network pattern. (ii) Apoplastic accumulation of PDI-pHluorin on the edges of the cell. (iii) Golgi stacks of the cis-Golgi highlighted by Man99-pHluorin. (iv) Late Golgi vesicles of the trans-Golgi network identified by Man99TMD23-pHluorin. Bars=10 μm. FIG. 32C shows excitation ratios of ratiometric pHluorin targeted to compartments of the plant secretory pathway. Ratios were calculated by comparing images from epidermal leaf cells expressing pHluorin, excited at 405 and 488 nm. Small diamonds represent average ratios; the boxes contain 95% of the data and bars represent the lowest and highest extreme values.

Figure 33:
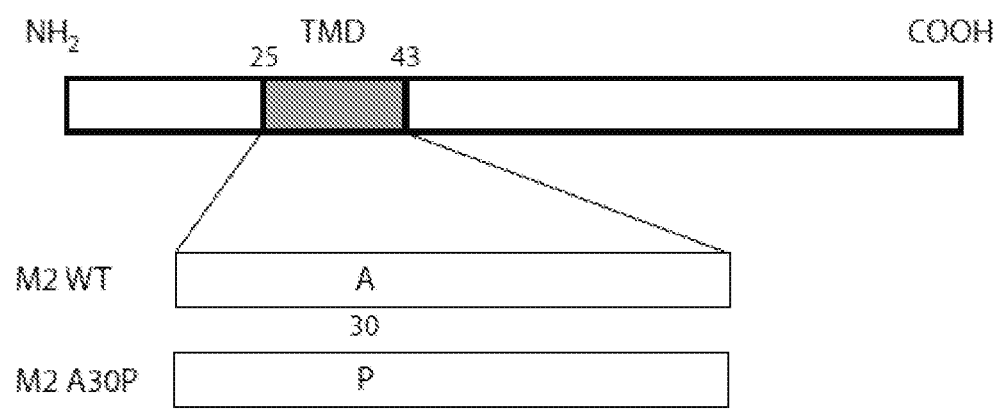
Figure 33:
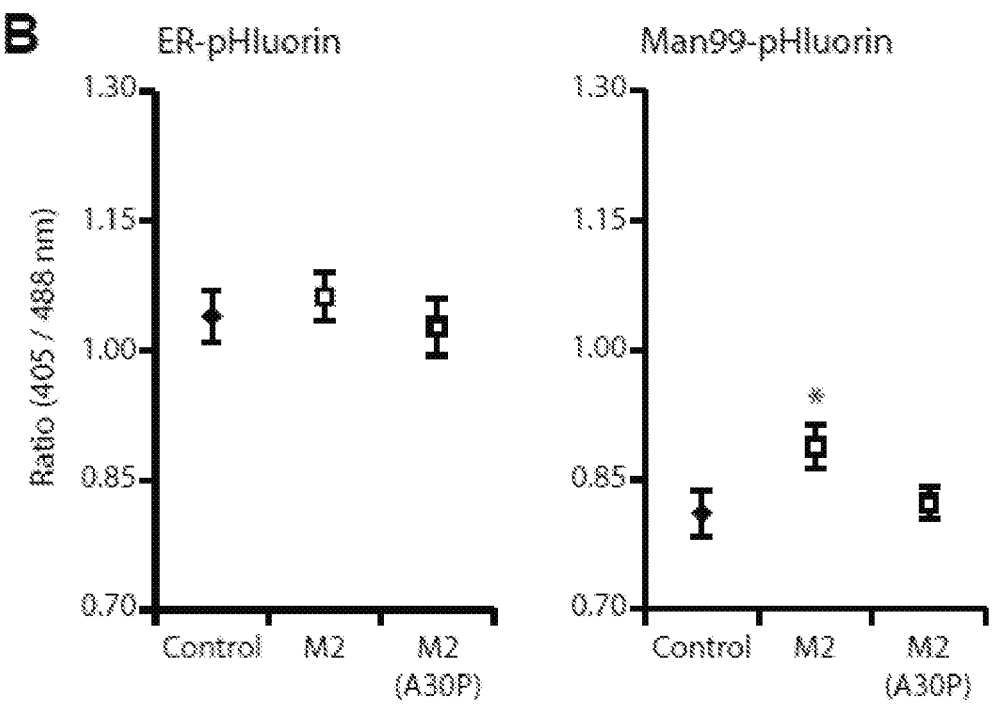
Figure 33B:
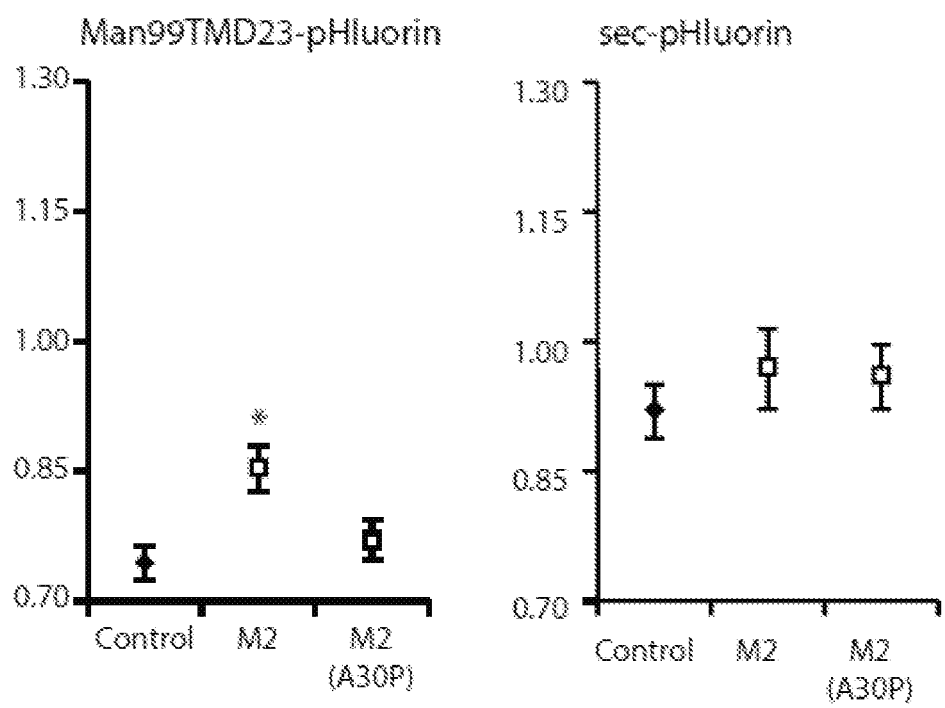

FIG. 33A shows schematic representation of the M2 ion channel constructs, M2WT (wild type M2; SEQ ID NO: 10; construct No: 1261); and an inactive M2 mutant, M2A30P (SEQ ID NO: 67; construct No: 1210). The transmembrane domain (TMD) is expanded to show the position of the A30P mutation that renders the channel inactive. FIG. 33B shows ratiometric fluorescence analysis of the pHluorin constructs of FIG. 32A targeted to different cell compartments (see text for details). Average ratios were calculated by comparing images from epidermal leaf cells expressing pHluorin, excited at 405 and 488 nm. Values are the mean of 15 replicates from three different plants±SE. Asterisks indicate significantly different values (P<0.05).

Figure 34A:
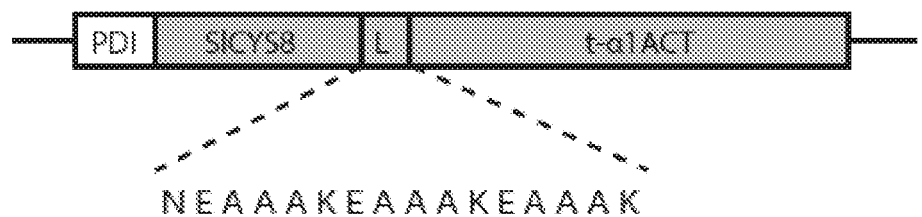
Figure 34B:
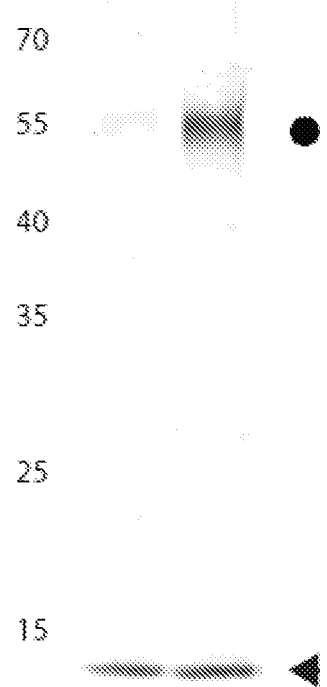
Figure 34C:
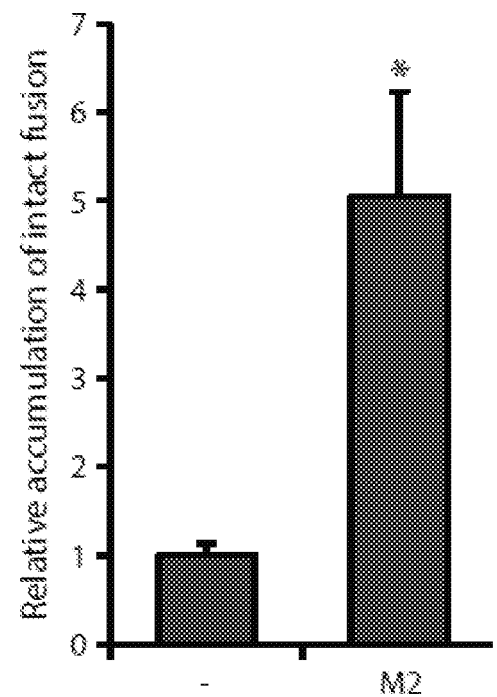
Figure 34:
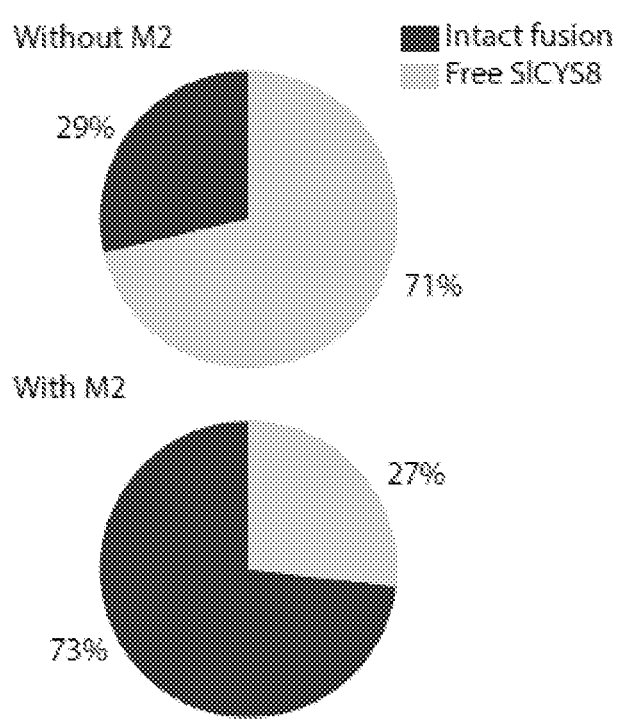

FIG. 34A shows a schematic diagram of SlCYS8-α1ACT fusion protein linked by an acid-susceptible rigid linker (N[EAAAK]3). PDI, signal peptide from protein disulphide isomerase; t-α1ACT, N-terminally truncated α1ACT; L, linker. FIG. 34B shows SlCYS8-α1ACT fusion protein co-expressed with (right hand lane) or without (left hand lane) M2. Soluble protein extracts were separated by 12% (w/v) reducing SDS-PAGE followed by Western blotting for SlCYS8. The position of molecular size markers is given on the left. The arrowhead points to the position of free SlCYS8 and the closed circle to intact fusion. FIG. 34C shows relative accumulation of the intact SlCYS8-α1ACT fusion co-expressed with M2 (right hand bar) compared to the fusion expressed alone (left hand bar; value set at 1). Each bar is the mean of three independent values±SD. The asterisk indicates a significant difference (P<0.05). FIG. 34D shows percentage of intact fusion (dark region) compared to free SlCYS8 (light grey region), determined using densitometric analysis of Western blots; Upper circle: SlCYS8-α1ACT fusion expressed alone; lower circle: SlCYS8-α1ACT fusion expressed along with M2.

Figure 35:
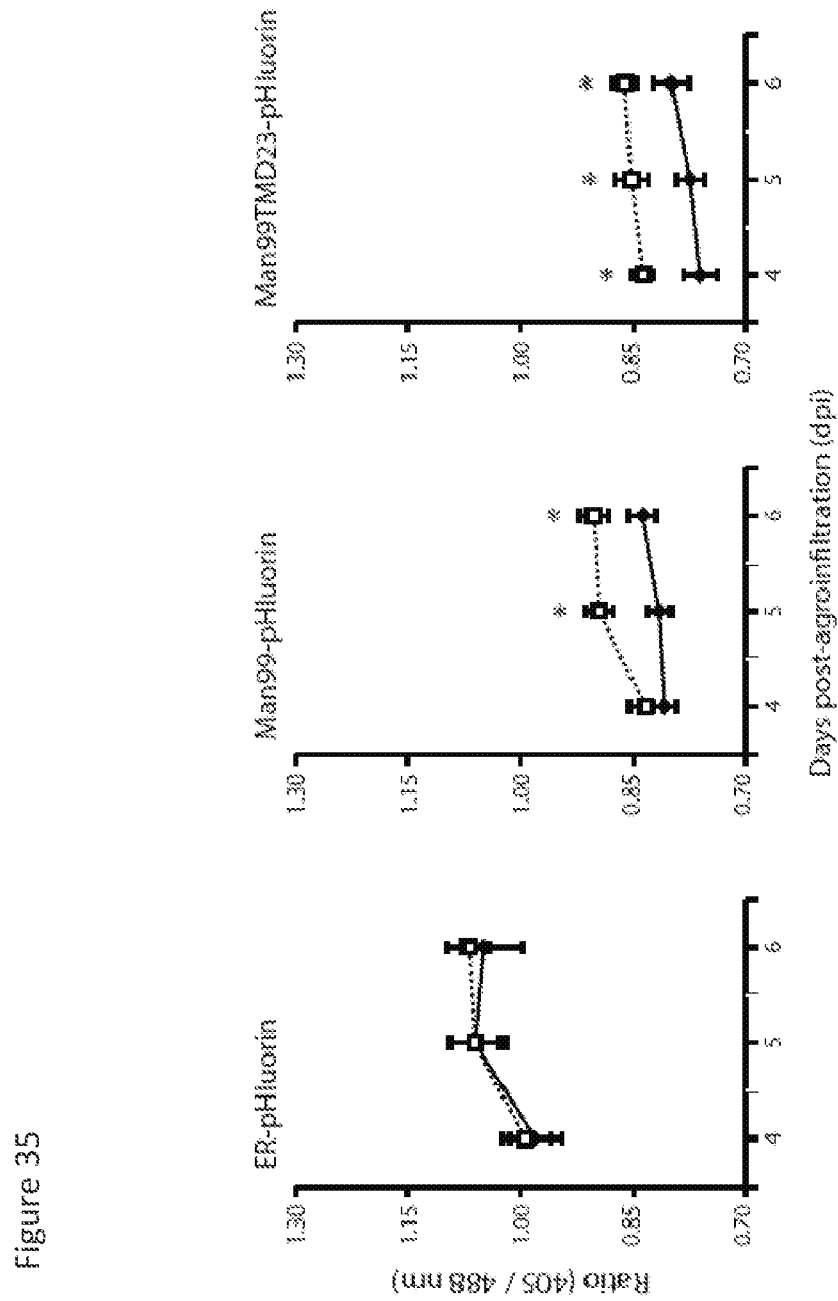

FIG. 35 shows a time course of M2 expression on the pH in subcellular compartments of the secretory pathway when co-expressed with the constructs outlined in FIG. 32A. Left hand panel: ER-pHluorin; middle panel: Man99-pHluorin; Right hand panel: Man99TMD23-pHluorin. Average ratios were calculated by comparing images from epidermal leaf cells expressing pHluorin, excited at 405 and 488 nm. Values are the mean of 15 replicates from three different plants±SE. Asterisks indicate significantly different values (P<0.05).

FIG. 36A shows primer "M2ANC2099(A30P).r" (SEQ ID NO:65). FIG. 36B shows primer M2ANC2099(A30P).c (SEQ ID NO:66). FIG. 36C shows the nucleotide sequence of expression cassette number 1210 (2X35 S promoter to NOS terminator. M2 from influenza A/New Caledonia/20/1999 (H1N1); M2 A30P is underlined; SEQ ID NO:67). FIG. 36D shows the amino acid sequence of M2 from influenza A/New Caledonia/20/1999 (H1N1) with mutation A30P. FIG. 36E shows the schematic representation of construct number 1210.

FIG. 37A shows primer "IF-PDI.S1+3c" (SEQ ID NO:69). FIG. 37B shows primer IF-pHluorin_primer6.r (SEQ ID NO: 70). FIG. 37C shows the nucleotide sequence of PDISP/pHluorin (SEQ ID NO:71). FIG. 37D shows the nucleotide sequence of expression cassette number 1871 (2X35 S promoter to NOS terminator. PDISP/pHluorin is underlined); SEQ ID NO:72. FIG. 37E shows the amino acid sequence of PDISP/pHluorin (SEQ ID NO:73). FIG. 37F shows the schematic representation of construct number 1871.

FIG. 38A shows primer "IF-pHluorin_primer2.r" (SEQ ID NO: 74). FIG. 38B shows the nucleic acid sequence of the expression cassette number 1872 (2X35 S promoter to NOS terminator. PDISP/pHluorin/SEKDEL is underlined; SEQ ID NO:75). FIG. 38C shows the amino acid sequence of PDISP/pHluorin/SEKDEL (SEQ ID NO:76). FIG. 38D shows the schematic representation of construct number 1872.

Figure 39E:
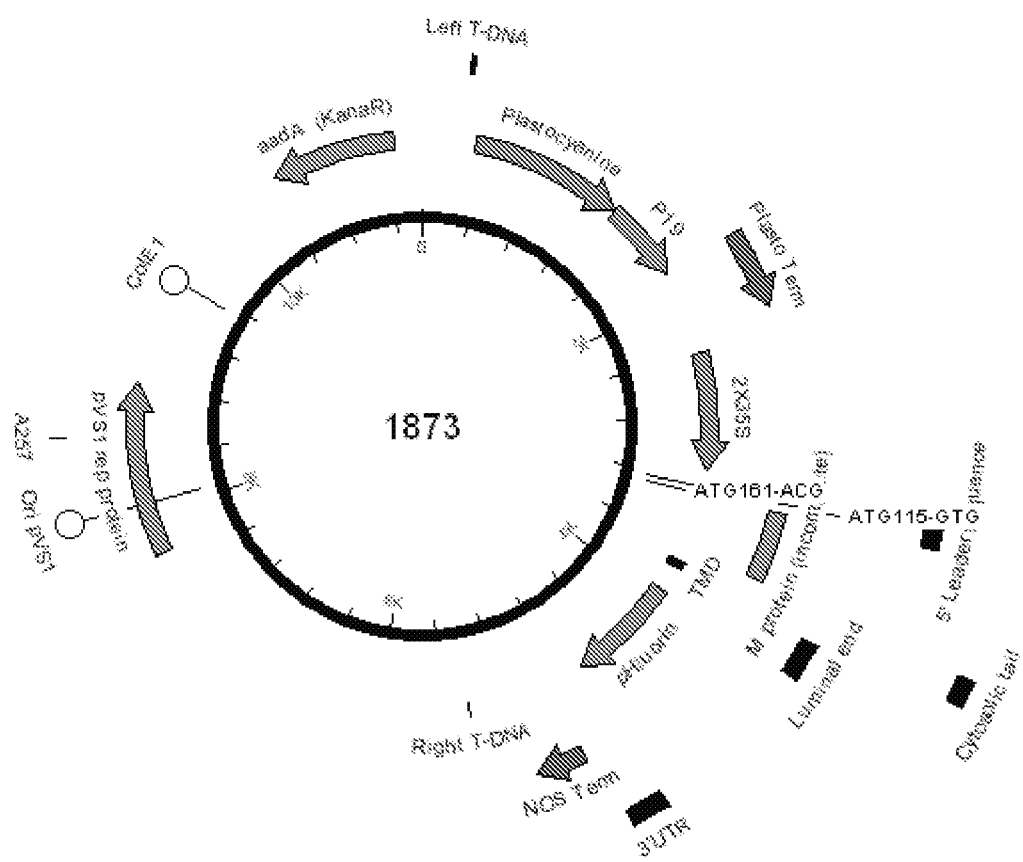

FIG. 39A shows primer "IF-pHluorin_primer3.c" (SEQ ID NO:77). FIG. 39B shows the nucleotide sequence of Man99/pHluorin (SEQ ID NO:78). FIG. 39C shows the nucleotide sequence of expression cassette number 1873 (2X35 S promoter to NOS terminator. Man99/pHluorin is underlined; SEQ ID NO:79). FIG. 39D shows the amino acid sequence of Man99/pHluorin (SEQ ID NO:80). FIG. 39E shows the schematic representation of construct number 1873.

Figure 40D:
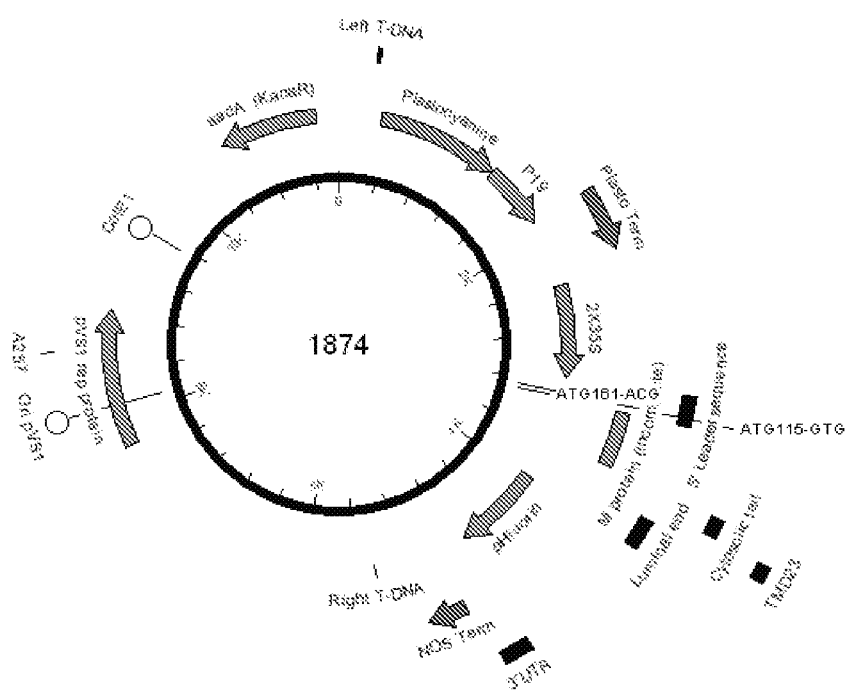

FIG. 40A shows nucleotide sequence of Man99TMD23/pHluorin (SEQ ID NO:81). FIG. 40B shows the expression cassette number 1874 from 2X35 S promoter to NOS terminator. Man99TMD23/pHluorin is underlined (SEQ ID NO:82). FIG. 40C shows the amino acid sequence of Man99TMD23/pHluorin (SEQ ID NO:83). FIG. 40D shows the schematic representation of construct number 1874.

DETAILED DESCRIPTION

The following description is of a preferred embodiment.

The present invention relates to methods of producing and increasing protein yield and production in plants.

The present invention provides, in part, a method of producing a virus like particle (VLP) in a plant, or portion of the plant. The method involves introducing a first nucleic acid and a second nucleic acid into the plant. The first nucleic acid comprises a first regulatory region active in the plant or portion of the plant, and operatively linked to a nucleotide sequence encoding a structural virus protein. The second nucleic acid comprising a second regulatory region active in the plant and operatively linked to a nucleotide sequence encoding a channel protein, for example but not limited to a proton channel protein. The first regulatory region and the second regulatory region may be the same or different. The plant or portion of the plant is incubated under conditions that permit the expression of the nucleic acids, thereby producing the VLP. If desired, the plant or portion of the plant may be harvested and the VLP purified. Preferably, the VLP does not contain M1, a viral matrix or a core protein. The present invention also provides a VLP produced by this method. The VLP may comprise one or more than one lipid derived from a plant. The VLP may be used to prepare a composition comprising an effective dose of the VLP for inducing an immune response, and a pharmaceutically acceptable carrier.

The present invention also provides plant matter comprising the VLP produced by expressing the first and second nucleic acids described above. The plant matter may be used in inducing immunity to an influenza virus infection in a subject. The plant matter may also be admixed as a food supplement.

The VLP of the present invention may also be produced by providing a plant or portion of the plant comprising a first nucleic acid and second nucleic acid as defined above, and incubating the plant or portion of the plant under conditions that permit the expression of the first and second nucleic acids, thereby producing the VLP. The VLP may comprise one or more than one lipid derived from a plant. The VLP may be used to prepare a composition comprising an effective dose of the VLP for inducing an immune response, and a pharmaceutically acceptable carrier. The present invention also provides plant matter comprising the VLP produced by expressing the first and second nucleic acids. The plant matter may be used in inducing immunity to an influenza virus infection in a subject. The plant matter may also be admixed as a food supplement.

The VLPs of the present invention comprise one or more virus proteins. For example, which is not to be considered limiting, the one or more virus protein may be a structural viral protein such as influenza hemagglutinin (HA) or a channel protein, for example but not limited to a proton channel protein, such as for example M2. The HA may be any HA, for example an H2, H3, H4, H6, H7, H8, H9, H10, H11, H12, H13, H14, H15, H16 or type B HA as described in WO 2009/009876; WO 2009/076778; WO 2010/003225; WO 2010/003235; WO 2011/03522; which are incorporated herein by reference).

As described in more detail below, VLPs may be produced in a plant by co-expressing a first nucleic acid encoding a virus protein with a second nucleic acid encoding a channel protein, for example but not limited to a proton channel protein. The first and second nucleic acids may be introduced to the plant in the same step, or they may be introduced to the plant sequentially. The first and second nucleic acids may be introduced in the plant in a transient manner, or in a stably manner. Furthermore, a plant that expresses a first nucleic acid encoding a viral protein may transformed with a channel protein, for example but not limited to a proton channel protein, (second nucleic acid) so that both the first and the second nucleic acids are co-expressed in the plant. Alternatively, a plant that expresses a channel protein, for example but not limited to a proton channel protein, (second nucleic acid) may transformed with a first nucleic acid encoding a viral protein so that both the first and the second nucleic acids are co-expressed in the plant. Additionally, a first plant expressing the first nucleic acid encoding a viral protein, may be crossed with a second plant expressing the second nucleic acid encoding the channel protein for example but not limited to a proton channel protein, to produce a progeny plant that co-expresses the first and second nucleic acids encoding the viral protein and the channel protein, for example but not limited to a proton channel protein, respectively.

The present invention also provides a method of increasing expression and yield of a virus protein in plant by co-expressing a first nucleic acid encoding a virus protein with a second nucleic acid encoding a channel protein, for example but not limited to a proton channel protein. The first and second nucleic acids may be introduced to the plant in the same step, or they may be introduced to the plant sequentially. The first and second nucleic acids may be introduced in the plant in a transient manner, or in a stably manner. Furthermore, a plant that expresses a first nucleic acid encoding a viral protein may transformed with a channel protein, for example but not limited to a proton channel protein (second nucleic acid) so that both the first and the second nucleic acids are co-expressed in the plant. Alternatively, a plant that expresses a channel protein, for example but not limited to a proton channel protein (second nucleic acid) may transformed with a first nucleic acid encoding a viral protein so that both the first and the second nucleic acids are co-expressed in the plant. Additionally, a first plant expressing the first nucleic acid encoding a viral protein, may be crossed with a second plant expressing the second nucleic acid encoding the channel protein, for example but not limited to a proton channel protein, to produce a progeny plant that co-expresses the first and second nucleic acids encoding the viral protein and the channel protein for example but not limited to a proton channel protein, respectively.

The present invention also provides a method of increasing yield, stability, or both yield and stability of an acid sensitive protein. The method involves introducing into a plant or portion of the plant a first nucleic acid comprising a first regulatory region active in the plant and operatively linked to a nucleotide sequence encoding the acid sensitive protein, and a second nucleic acid comprising a second regulatory region active in the plant and operatively linked to a nucleotide sequence encoding a proton channel protein. The plant or portion of the plant is then incubated under conditions that permit the expression of the first and second nucleic acids, thereby increasing the yield of the acid sensitive protein when compared to the yield of the acid sensitive protein produced in the plant or portion of the plant produced under the same conditions, and in the absence of the proton channel protein.

By "acid sensitive protein" (may also be referred to as acid-labile) it is meant a protein that changes confirmation, is inactivated, self-cleaved, denatured, unfolded, improperly folds or that is degraded within an acidic environment of less than pH 6.8, for example pH 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.8, 3.6, 3.4, 3.2, 3.0, 2.8, 2.6, 2.4, 2.2, 2.0, 1.8, 1.6, 1.4, 1.2, 1.0, 0.8, 0.6, 0.4, 0.2, or any pH therebetween. An acid sensitive protein may be selected from the group of proteins that undergo pH-dependent conformation change, protein folding, protein stability, or a combination thereof. An acid sensitive protein may also include an acid sensitive recombinant protein, an acid sensitive fusion protein, a fusion protein comprising an acid sensitive linker. Non-limiting examples of acid sensitive proteins include a structural virus protein comprising a trimerization domain, an HA, an insulin-like growth factor binding protein acid sensitive subunit, P19 (pH sensitive RNAi binding activity).

Channel Protein

By "channel protein" it is meant a protein that is capable of forming a channel across a phospholipid membrane that allows for the crossing of ions and/or small molecules through the membrane. Channel proteins may be selective for size and/or charge of the ions and/or small molecules. Non limiting examples of channel proteins are non-specific channel protein that alter permeability of membranes to low molecular weight compounds and ion channel protein, such as for example chloride channel, potassium channel, sodium channel, calcium channel and proton channel.

By "proton channel protein" it is meant a protein that is capable of forming a proton selective channel across a phospholipid bilayer. The proton channel protein may be a single pass membrane protein with a transmembrane (TM) domain flanked by hydrophobic domains. The (TM) of the proton channel may comprise the sequence HXXXW (SEQ ID NO. 1).

Following cleavage of HA0, HA becomes sensitive to pH, undergoing irreversible conformational change at the pH of endosome (<pH 6.0). The conformation of the precursor HA0 is stable at low pH, but the cleaved HA1-HA2 form, is metastable (Bullough P A et. al., 1994, Nature. Vol 371:37-43). Studies on the pH threshold that induce conformational changes in different HAs, show that this threshold is approx pH 5.8-5.9 for the B strains, whereas it is more acidic (pH 5.1 to 5.3) for type A HAs (Beyer W E P et al, 1986, Archives Virol, vol 90: 173). During extraction of the plant biomass (between pH 5-6), a conformational change of HA1-HA2 may also take place with type B HA.

Without wishing to be bound by theory, the pH of a cellular compartment comprising HA, including the Golgi apparatus, may therefore be important for the folding, stability and/or proteolysis of HA. Proton channel proteins, such as for example influenza M2 and BM2 protein may regulate the pH in cellular compartments. For example, M2 regulates the potentiation of membrane fusion by buffering intracellular compartments both in late and early stages of influenza viral replication. Early in infection of new cells after endocytic uptake of viral particles, activation of M2 proton channel activity leads to acidification of the interior of the virion during the uncoating process. Late in infection during virus production, M2 acts to raise the pH during transit through the trans-Golgi network and prevents the low pH-induced inactivation of co-transported proteins, such as HA in the case of influenza. By co-expressing a structural virus protein along with a channel protein, for example but not limited to a proton channel protein, increased yield of the structural virus protein and VLPs are observed. HA's are known to undergo pH-dependent conformation change. Without wishing to bound by theory, the pH within the Golgi apparatus of the HA producing cells during maturation and migration may influence HA folding, affect stability and increase degradation, or a combination thereof, of the HA. By co-expressing a channel protein, for example but not limited to a proton channel protein, along with an HA, the pH within the Golgi apparatus may increase, and result in an increase in stability, reduction of degradation, or a combination thereof, and increase expression levels and yield of HA and/or VLPs.

By co-expressing a structural virus protein along with a channel protein, for example but not limited to a proton channel protein, in a plant, increased yield of the structural virus protein and/or VLPs are observed, when compared to a plant that expressed the structural virus protein without co-expression of the channel protein, for example but not limited to a proton channel protein.

Furthermore, by co-expressing a structural virus protein such as HA with a channel protein, for example but not limited to a proton channel protein, in a plant, the HA protein may exhibits an increased activity as shown by a greater hemagglutination capacity, when compared to a HA protein that is not co-expressed with a channel protein, for example but not limited to a proton channel protein. By an increase in activity, it is meant an increase in hemagglutination capacity by about 2% to about 100%, or any amount therebetween as determined using standard techniques in the art, for example, from about 10% to about 50% or any value therebetween for example about 2, 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, or 100%, when compared to the activity of the same HA protein produced in the absence of a channel protein, for example but not limited to a proton channel protein.

As used herein, the terms "M2," "M2 protein," "M2 sequence" and "M2 domain" refer to all or a portion of an M2 protein sequence isolated from, based upon or present in any naturally occurring or artificially produced influenza virus strain or isolate. Thus, the term M2 and the like include naturally occurring M2 sequence variants produced by mutation during the virus life-cycle or produced in response to a selective pressure (e.g., drug therapy, expansion of host cell tropism or infectivity, etc.), as well as recombinantly or synthetically produced M2 sequences. Examples of channel proteins that may be used include, but are not limited to proton channel proteins for example those listed in Table 1. Non-limiting example of sequences that may be used with the present invention include M2 from A/Puerto Rico/8/1934 and M2 from A/New Caledonia/20/1999. An exemplary M2 protein consists of the amino acid sequence as shown in SEQ ID NO: 11 or 14.

As used herein, the terms "BM2," "BM2 protein," "BM2 sequence" and "BM2 domain" refer to all or a portion of a BM2 protein sequence isolated from, based upon or present in any naturally occurring or artificially produced influenza virus strain or isolate. Thus, the term BM2 and the like include naturally occurring BM2 sequence variants produced by mutation during the virus life-cycle or produced in response to a selective pressure (e.g., drug therapy, expansion of host cell tropism or infectivity, etc.), as well as recombinantly or synthetically produced BM2 sequences. Examples of channel proteins that may be used include, but are not limited to proton channel proteins those listed in Table 2.

Additional exemplary proton channel protein sequences consist of the sequences deposited under the GenBank accession numbers shown in Table 1 and Table 2.

TABLE 1

Accession numbers for amino acids sequences M2 proton channel proteins

| GenBank accession number | GenBank accession number | GenBank accession number | GenBank accession number | GenBank accession number |
| --- | --- | --- | --- | --- |
| ABA42438.1 | ABB54697.1 | ABI36079.1 | ADM95491.1 | ADM29632.1 |
| ABA42436.1 | AAA43253.1 | ABI36077.1 | ADM95489.1 | ADM29566.1 |
| ABA42434.1 | BAB19809.1 | ABI36075.1 | ADM95487.1 | ADM29555.1 |
| AAD51268.1 | ABD59884.1 | ABI36073.1 | ADM95485.1 | ADM29544.1 |
| AAD51264.1 | ABD59882.1 | ABI36071.1 | ADM95483.1 | ADM29533.1 |
| AAC60735.1 | ABD59880.1 | ABI36069.1 | ADM95481.1 | ADM29445.1 |
| BAI77393.1 | BAD89348.1 | ABI36067.1 | ADM95479.1 | ADM29434.1 |
| BAI77450.1 | BAD89338.1 | ABI36065.1 | ADM95477.1 | ADM29423.1 |
| CAP58009.1 | BAD89328.1 | ABI36063.1 | ADM95475.1 | ADM29412.1 |
| CAP58007.1 | BAE47133.1 | ABI36061.1 | ADM95473.1 | ADM29401.1 |
| CAP58005.1 | ABD59890.1 | ABI36059.1 | ADM95471.1 | ADM29379.1 |
| BAH84754.1 | ABD59888.1 | ABI36037.1 | BAF37390.1 | ADM29368.1 |
| BAH86619.1 | ABD59886.1 | ABI36027.1 | ADG59188.1 | ADM29357.1 |
| BAH86616.1 | ABD59900.1 | ABI36016.1 | ADG59186.1 | ADM29313.1 |
| BAH84985.1 | ABD59898.1 | ABI36005.1 | ADG59184.1 | ADM29302.1 |
| YP_308853.1 | ABD59896.1 | AAY87447.1 | ADG59182.1 | ADM29291.1 |
| AAD49092.1 | ABD59894.1 | AAY87431.1 | ADG59180.1 | ADM29280.1 |
| AAD49090.1 | ABD59892.1 | AAV32647.1 | ADG59178.1 | ADM29269.1 |
| AAD49088.1 | AAC79578.1 | AAV32639.1 | ADG59176.1 | ADM29258.1 |
| ABQ12378.1 | ABB51968.1 | AAU00829.1 | ADG59174.1 | ADM29698.1 |
| AAO33518.1 | ABY75105.1 | AAU00827.1 | ADG59172.1 | ADM29687.1 |
| AAO33516.1 | ABY75039.1 | AAA91324.1 | ADG59170.1 | ADM29676.1 |
| AAO33514.1 | ABY75037.1 | ABG75620.1 | ADG59168.1 | ADM29665.1 |
| AAO33512.1 | AAL60446.1 | ACR09361.1 | ADG59166.1 | ADM29654.1 |
| AAO33510.1 | ABB00351.1 | ACR09359.1 | ADG59164.1 | ADM29621.1 |
| AAO33508.1 | AAA43312.1 | ACR09355.1 | ADG59162.1 | ADM29610.1 |
| AAO33506.1 | ABB00339.1 | ACR09353.1 | ADG59160.1 | ADM29599.1 |
| AAO33504.1 | ABW38094.1 | ACQ99604.1 | ADG59158.1 | ADM29522.1 |
| AAO33502.1 | AAM09299.1 | ACQ99602.1 | ADG59156.1 | ADM29511.1 |
| ABS52607.1 | AAM09297.1 | ACQ99600.1 | ADG59154.1 | ADM29500.1 |
| ABS52597.1 | ABS00915.1 | ACQ99592.1 | ADG59152.1 | ADM29489.1 |
| ABS52587.1 | ABS00914.1 | ACQ99590.1 | ADG59150.1 | ADM29478.1 |
| ABM21873.1 | ABS00913.1 | ACQ99588.1 | ADG59148.1 | ADM29467.1 |
| ABM21871.1 | ABS00912.1 | ACQ99586.1 | ADG59146.1 | ADM29456.1 |

TABLE 1-continued

Accession numbers for amino acids sequences M2 proton channel proteins

| GenBank accession number | GenBank accession number | GenBank accession number | GenBank accession number | GenBank accession number |
|---|---|---|---|---|
| ABM21869.1 | ABS00911.1 | ACP41965.1 | ADG59144.1 | ADM29390.1 |
| ABM21867.1 | ABS00910.1 | ACP41955.1 | ADG59142.1 | ADM29346.1 |
| ABM21865.1 | ABS00909.1 | ACP41951.1 | ADG59140.1 | ADM29335.1 |
| ABM21863.1 | ABS00908.1 | ACP41946.1 | ADG59138.1 | ADM29324.1 |
| ABM21861.1 | ABS00907.1 | ACR49258.1 | ADG59136.1 | ADM29247.1 |
| AAO33500.1 | ABS00906.1 | ACR49256.1 | ADG59134.1 | AEE73588.1 |
| AAD49094.1 | ABS00905.1 | ACR49254.1 | ADG59132.1 | AEB89880.1 |
| AAD49086.1 | ABS00904.1 | ACR49252.1 | ADG59130.1 | AEB89869.1 |
| AAD49084.1 | ABS00903.1 | ACR49250.1 | ADG59128.1 | AEB89858.1 |
| AAD49082.1 | ABS00902.1 | ACR49248.1 | ADG59126.1 | AEA74023.1 |
| AAD49080.1 | ABB51974.1 | ACR49246.1 | ADG59124.1 | AEA74013.1 |
| AAD49078.1 | ABB51972.1 | ACR49244.1 | ADG59122.1 | ADF42731.1 |
| AAD49076.1 | ABB51970.1 | ACR38840.1 | ADG59120.1 | ADF42721.1 |
| AAD49074.1 | AAD00150.1 | ACR38838.1 | ADG59118.1 | ADF28007.1 |
| AAD49072.1 | AAD00148.1 | ACR38836.1 | ADG59116.1 | ADF27997.1 |
| AAD49070.1 | AAD00146.1 | ACR38834.1 | ADG59114.1 | ADF27987.1 |
| AAD49068.1 | AAD00144.1 | ACR38832.1 | ADG59112.1 | ADF27977.1 |
| ACA25333.1 | AAD00142.1 | ACR18965.1 | ADG59110.1 | ADF27967.1 |
| ACA25323.1 | AAD00140.1 | ACR18963.1 | ADG59108.1 | ADF27957.1 |
| ACA25313.1 | AAD00138.1 | ACR18958.1 | ADG59106.1 | ADF27947.1 |
| CAJ12148.1 | AAD00136.1 | ACR18957.1 | ADG59104.1 | ADF27937.1 |
| CAJ12154.1 | AAD00134.1 | ACR18953.1 | ADG59102.1 | ADF27927.1 |
| CAJ12152.1 | AAD00132.1 | ACR18949.1 | ADG59100.1 | ADF27917.1 |
| CAJ12150.1 | AAD00130.1 | ACR18946.1 | ADG59098.1 | ADF27907.1 |
| ACP41109.1 | AAC80168.1 | ACR18945.1 | ADG59096.1 | ADF27897.1 |
| ADG59536.1 | AAC80166.1 | ACR18943.1 | ADG59094.1 | ADF27887.1 |
| AAK14988.1 | AAC80164.1 | ACR08560.1 | AB021713.1 | ACS87931.1 |
| AAK14984.1 | AAC80162.1 | ACR08556.1 | ADG59717.1 | ACU44926.1 |
| ACR67209.1 | AAC80160.1 | NP_040979.2 | ADG59706.1 | ACU44922.1 |
| ACP41929.2 | AAC80158.1 | ABZ91697.1 | AAF74335.1 | ACU44920.1 |
| ACR18961.1 | AAC80156.1 | ABZ91685.1 | AAF74333.1 | ACU44918.1 |
| ACR18955.1 | ABY75159.1 | ACB54711.1 | ADF56637.1 | ACU44916.1 |
| ACR18941.1 | ABY75157.1 | ABM90504.1 | ADF56636.1 | ACU44914.1 |
| ACR08564.1 | ABY75155.1 | ABM90493.1 | ADF56635.1 | ACU44912.1 |
| ACR08562.1 | ABY75153.1 | ABM90482.1 | ADF29921.1 | ACU44910.1 |
| ACR08558.1 | ABY75151.1 | ABM90471.1 | ADE75385.1 | ACU44908.1 |
| ACQ99594.1 | ABY75149.1 | ABM90460.1 | ADE75374.1 | ACU44906.1 |
| ACQ83308.1 | ABY75147.1 | ABM90449.1 | ADE75365.1 | ACU44904.1 |
| ACQ76400.1 | ABY75145.1 | ABM90438.1 | ADE75354.1 | ACU44902.1 |
| ACQ76382.1 | ABY75143.1 | ABI49411.1 | ADE75344.1 | ACU44900.1 |
| ACQ76375.1 | ABY75141.1 | ABI49400.1 | ADE75327.1 | ACU44898.1 |
| ACQ76369.1 | ABY75139.1 | AB031433.1 | ADE75298.1 | ACU44896.1 |
| ACQ76361.1 | ABY75137.1 | ABM90548.1 | ADE75287.1 | ACU44894.1 |
| ACQ76355.1 | ABY75135.1 | ABM90537.1 | ADE75276.1 | ACU44892.1 |
| ACQ76346.1 | ABY75133.1 | ABM90526.1 | ADE75265.1 | ACU44890.1 |
| ACQ76332.1 | ABY75131.1 | ABM90515.1 | ADE75254.1 | ACU44888.1 |
| ACQ76325.1 | ABY75129.1 | ABL31784.1 | ADE75244.1 | ACU44886.1 |
| ACQ76313.1 | ABY75127.1 | ABL31770.1 | ADE75235.1 | ACU44883.1 |
| ACQ76303.1 | ABY75125.1 | ABL31759.1 | ADE75228.1 | ACU44881.1 |
| ACQ76293.1 | ABY75123.1 | ABL31748.1 | ADE75218.1 | ACU44879.1 |
| ACQ63288.1 | ABY75121.1 | ABI49419.1 | ADE75207.1 | ACU44877.1 |
| ACQ63259.1 | ABY75119.1 | ABL07034.1 | ADE75196.1 | ACU44875.1 |
| ACQ63250.1 | ABY75117.1 | ABL07023.1 | ADE75187.1 | ACU44873.1 |
| ACQ63217.1 | ABY75115.1 | ABL07012.1 | ADE75178.1 | ACU44871.1 |
| ACQ63211.1 | ABY75113.1 | ACC55276.2 | ADE75170.1 | ACU44869.1 |
| ACQ55364.1 | ABY75111.1 | ABV53559.1 | ADE75152.1 | ACU44867.1 |
| ACQ55353.1 | ABY75109.1 | AEB71385.1 | ADE75143.1 | ACU44865.1 |
| ACP44171.1 | ABY75107.1 | AEB66897.1 | ADE75134.1 | ACU44863.1 |
| ACP44160.1 | ABY75103.1 | AEB40208.1 | ADE75124.1 | ACU44861.1 |
| ACP44153.1 | ABY75101.1 | ADX36111.1 | ADE75115.1 | ACU44859.1 |
| ACP44149.1 | ABY75099.1 | ADX21100.1 | ADE75095.1 | ACU44857.1 |
| ACR18951.2 | ABY75097.1 | ADX21090.1 | ADE75085.1 | ACU44855.1 |
| AAY87421.1 | ABY75095.1 | ADX21080.1 | ADE75075.1 | ACU44853.1 |
| AAY87413.1 | ABY75093.1 | ADW93762.1 | ADE75057.1 | ACU44851.1 |
| ACQ63284.1 | ABY75091.1 | ADW82270.1 | ADE75046.1 | ACU44849.1 |
| ACQ63275.1 | ABY75089.1 | ADW82260.1 | ADE75030.1 | ACU44847.1 |
| ACQ63266.1 | ABY75087.1 | ADW82250.1 | ACL11961.1 | ACU44845.1 |
| ACQ63255.1 | ABY75085.1 | ADW82240.1 | ABY40439.1 | ACU44843.1 |
| ACP44185.1 | ABY75083.1 | ADW82230.1 | ABY40432.1 | ACU44841.1 |
| ACP44178.1 | ABY75081.1 | ADW82220.1 | AAD25212.1 | ACU44839.1 |
| ACA28776.1 | ABY75079.1 | ADW82210.1 | AAD25206.1 | ACU44837.1 |
| ACA28772.1 | ABY75077.1 | ADW82200.1 | AAD25172.1 | ACU44835.1 |
| ACA28768.1 | ABY75075.1 | ADW82190.1 | BAF36962.1 | ACU44833.1 |
| ACR49240.1 | ABY75073.1 | ADW82179.1 | ABI94583.1 | ACU44831.1 |
| ACQ84453.1 | ABY75071.1 | ADW82168.1 | ACT21522.1 | ACU44829.1 |
| ACU00946.2 | ABY75069.1 | ADW82157.1 | ABY81638.1 | ACU44827.1 |
| ACR46665.1 | ABY75067.1 | ADW82148.1 | ACF40971.1 | ACU44825.1 |
| ACZ81655.1 | ABY75065.1 | ADW82137.1 | ACD88518.1 | ACU44823.1 |
| ACZ81651.1 | ABY75063.1 | ADW82126.1 | ACD88507.1 | ACU44821.1 |
| ACR46675.1 | ABY75061.1 | ADV19021.1 | ABW97453.1 | ACU44819.1 |
| ACU00956.1 | ABY75059.1 | ADL41167.1 | ACZ81646.1 | ACU44817.1 |
| ACU00936.1 | ABY75057.1 | AAF74337.1 | YP_308670.1 | ACU44815.1 |
| ACT21587.1 | ABY75055.1 | ACS92616.1 | AAA56808.1 | ACU44813.1 |
| ACT21581.1 | ABY75053.1 | ACC94117.1 | AAA56806.1 | ACU44811.1 |
| ACT21576.1 | ABY75051.1 | ACC94089.1 | ABS00311.1 | ACU44809.1 |
| ACR19302.2 | ABY75049.1 | ACC94087.1 | ABS00320.1 | ACU44807.1 |
| ACR19300.2 | ABY75047.1 | ACC94085.1 | ACR08491.1 | ACU44805.1 |
| ACR19298.2 | ABY75045.1 | ACC94071.1 | ACR01010.1 | ACU44803.1 |
| ACR19296.2 | ABY75043.1 | ACC94067.1 | ACR01006.1 | ACU44801.1 |
| ABX10529.1 | ABY75041.1 | ACC94065.1 | ACG80612.1 | ACU44799.1 |
| ABJ90284.2 | ABY75035.1 | ACC94059.1 | ABG78553.1 | ACU44797.1 |
| ABJ90273.2 | ABY75033.1 | ACC94057.1 | ABG78550.1 | ACU44795.1 |
| ABJ90230.1 | ABY75031.1 | ACC94051.1 | ACD37773.1 | ACU44793.1 |
| ADD21567.1 | ABY75029.1 | ACC94041.1 | ACD37763.1 | ACU44791.1 |
| ACU44924.1 | ABY75027.1 | ACC94033.1 | ACA64013.1 | ACU44789.1 |
| ACU44779.1 | ABY75025.1 | ABW97496.1 | ABX10519.1 | ACU44787.1 |
| ACU44773.1 | ABY75023.1 | ACA28780.1 | ABW95953.1 | ACU44785.1 |
| ADE48138.1 | ABY75021.1 | ACA28778.1 | ABW95942.1 | ACU44783.1 |
| ACG80349.1 | ABY75019.1 | ACA28774.1 | ABJ90263.1 | ACU44781.1 |
| ADN34731.1 | ABY75017.1 | ACA28770.1 | ABJ90251.1 | ACU44777.1 |
| ADN34711.1 | ABY75015.1 | ACA28766.1 | ABJ90241.1 | ACU44775.1 |
| ADG59534.1 | ABY75013.1 | ACZ81636.1 | BAF38386.1 | ACU44771.1 |
| ADG59532.1 | ABY75011.1 | ACU27045.1 | BAF37824.1 | ACU44769.1 |
| ADG59530.1 | ABY75009.1 | ACR54040.1 | BAF33431.1 | ACU44767.1 |
| ACX43975.1 | ABY75007.1 | ACH68522.1 | BAF33417.1 | ACU44765.1 |
| ACX43973.1 | ABY75005.1 | ACF04730.1 | BAF33412.1 | ACU44763.1 |
| ABG91471.1 | ABY75003.1 | ACF04728.1 | BAF33401.1 | ACU44761.1 |
| ABG91467.1 | ABY75001.1 | ACF04726.1 | ACN22341.1 | ACU44759.1 |
| ABF21313.1 | ABY74999.1 | ACF04724.1 | ACV49525.1 | ACU44757.1 |
| ABF21301.1 | ABY74997.1 | ACF04722.1 | ACV49503.1 | ACU44755.1 |
| ABF21299.1 | ABY74995.1 | ACC69091.1 | ACU79906.1 | AEA92622.1 |
| ABF21297.1 | ABY74993.1 | ABV53579.1 | ACU79895.1 | AEA35548.1 |
| ABQ57382.1 | ABY74991.1 | ABV53569.1 | ACU79884.1 | ADM29588.1 |
| ACR09357.1 | ABY74989.1 | ABV53549.1 | ACU79873.1 | ADM29577.1 |
| ACQ99606.1 | ABY74987.1 | ABV53539.1 | ACI25792.1 | BAK08628.1 |
| ACQ99598.1 | ABY74985.1 | ABV53529.1 | ACI25781.1 | BAK08626.1 |
| ACQ99596.1 | ABY74983.1 | ABV53519.1 | ACI25770.1 | ADZ75331.1 |
| ACU43624.2 | ABV45404.1 | ABV53509.1 | ACI25759.1 | ADZ75320.1 |
| ACR67240.1 | AAC63486.1 | ABV53499.1 | ACI25748.1 | ADP07242.1 |
| ACR67238.1 | AAC63484.1 | ABV53489.1 | ACF54468.1 | ACZ54004.1 |
| ACR67235.1 | AAC63482.1 | ABV53479.1 | ACF54457.1 | ACX93288.1 |
| ACR67234.1 | AAC63480.1 | ABV53470.1 | ACF54446.1 | ACX93222.1 |
| ACR67232.1 | ABB00355.1 | ADP37370.1 | ACF54435.1 | ACD65198.1 |
| ACR67230.1 | ABB00353.1 | ADG21464.1 | ACF54424.1 | ACD65196.1 |
| ACR67228.1 | ABB00349.1 | ADG21457.1 | ACF54413.1 | ACD65194.1 |
| ACR67226.1 | ABB00347.1 | ACF17953.1 | ACF54402.1 | ACD65191.1 |
| ACR67224.1 | ABB00345.1 | ACF17943.1 | ACF41825.1 | ACD65189.1 |
| ACR67222.1 | ABB00343.1 | ADM95569.1 | ACF41814.1 | ACX93277.1 |
| ACR67220.1 | ABB00341.1 | ADM95567.1 | ACF41803.1 | ACX93269.1 |
| ACR67218.1 | ABB00337.1 | ADM95565.1 | ACF41792.1 | ABD79034.1 |
| ACR67216.1 | ABB00335.1 | ADM95563.1 | ACF41781.1 | ABJ16853.1 |
| ACR67214.1 | ABB00333.1 | ADM95561.1 | ACF41770.1 | ABJ16842.1 |
| ACR67212.1 | CAA30889.1 | ADM95559.1 | ACF41759.1 | ADI99547.1 |
| ACR67208.1 | CAA30887.1 | ADM95557.1 | ACF41748.1 | ADI99536.1 |
| ACR67206.1 | CAA30885.1 | ADM95555.1 | ACF41737.1 | ADI34045.1 |
| ACR54054.1 | CAA30893.1 | ADM95553.1 | ACF22399.1 | ADD21471.1 |
| ACR09363.1 | CAA30891.1 | ADM95551.1 | ACF22388.1 | ADD21461.1 |
| ACP41961.1 | AAA43091.1 | ADM95549.1 | ACF22377.1 | ADD21451.1 |
| ACP41938.1 | AAA43577.1 | ADM95547.1 | ACF22366.1 | ACZ48112.1 |
| ABI36484.1 | BAB19808.1 | ADM95545.1 | ACF22355.1 | ACF25678.1 |
| ABI36475.1 | CAA30883.1 | ADM95543.1 | ACF22344.1 | ACF25466.1 |
| ABI36464.1 | AAD51929.1 | ADM95541.1 | ACF22333.1 | ACF25466.1 |
| ABI36456.1 | BAA99398.1 | ADM95539.1 | ACF22322.1 | ACF25065.1 |
| ABI36445.1 | AAF99673.1 | ADM95537.1 | ACF22311.1 | ACF25057.1 |
| ABI36434.1 | AAF99671.1 | ADM95535.1 | ACF22300.1 | ACF24971.1 |
| ABI36425.1 | ABH04389.1 | ADM95533.1 | ACF22278.1 | ACV74288.1 |

TABLE 1-continued

Accession numbers for amino acids sequences M2 proton channel proteins

| GenBank accession number | GenBank accession number | GenBank accession number | GenBank accession number | GenBank accession number |
|---|---|---|---|---|
| ABI36412.1 | ABB90274.1 | ADM95531.1 | ACF22256.1 | ACV74286.1 |
| ABI36401.1 | AAD51270.1 | ADM95529.1 | ACF22245.1 | ABV56243.1 |
| ABI36390.1 | AAM70004.1 | ADM95527.1 | ACF22234.1 | ACI25712.1 |
| ABI36379.1 | AAB19772.1 | ADM95525.1 | ACF22223.1 | ACI25710.1 |
| ABI36368.1 | AAD51266.1 | ADM95523.1 | ACF22212.1 | ADA81213.1 |
| ABI36357.1 | ABD59885.1 | ADM95521.1 | ACF22201.1 | ACZ56084.1 |
| ABI36346.1 | AAM70001.1 | ADM95519.1 | ACF22190.1 | ACZ45024.1 |
| ABI36335.1 | AAM69992.1 | ADM95517.1 | ACF22172.1 | ACV91683.1 |
| ABI36324.1 | AAM69982.1 | ADM95515.1 | ADL41185.1 | ACV91679.1 |
| ABI36313.1 | AAM69972.1 | ADM95513.1 | ADM07115.1 | ACV91675.1 |
| ABI36297.1 | AAM69961.1 | ADM95511.1 | ADM07104.1 | ACV72405.1 |
| ABI36277.1 | AAZ38741.1 | ADM95509.1 | ADM07093.1 | ACV72403.1 |
| ABI36202.1 | AAZ38739.1 | ADM95507.1 | ADM07082.1 | ACV72401.1 |
| ABI36191.1 | AAZ38737.1 | ADM95505.1 | ADM07071.1 | ACV72399.1 |
| ABI36181.1 | AAZ38735.1 | ADM95503.1 | ADM07060.1 | ACV72397.1 |
| ABI36170.1 | AAZ38733.1 | ADM95501.1 | ADE62289.1 | ACV72395.1 |
| ABI36159.1 | AAZ38731.1 | ADM95499.1 | AEG65177.1 | ACV72393.1 |
| ABI36148.1 | AAZ38729.1 | ADM95497.1 | AEC46386.1 | ACV72391.1 |
| ABI36083.1 | ABA42442.1 | ADM95495.1 | ADR78653.1 | ACV72389.1 |
| ABI36081.1 | ABA42440.1 | ADM95493.1 | ADM29643.1 | ACV72349.1 |

TABLE 2

Accession numbers for amino acids sequences BM2 proton channel proteins

| GenBank accession number | GenBank accession number | GenBank accession number | GenBank accession number |
|---|---|---|---|
| AAU01002.1 | ACR15701.1 | ACA96576.1 | ABN50549.1 |
| BAC54010.1 | ACR15690.1 | ACA96565.1 | ABN50538.1 |
| BAC53999.1 | ACR15679.1 | ACA96554.1 | ABN50527.1 |
| P0COX4.1 | ACR15668.1 | ACA65099.1 | ABN50516.1 |
| P03493.2 | ACR15657.1 | ACA65088.1 | ABN50505.1 |
| P08383.2 | ACR15646.1 | ACA65077.1 | ABN50494.1 |
| P13882.2 | ACR15635.1 | ACA65066.1 | ABN50483.1 |
| P13881.2 | ACR15624.1 | ACA65055.1 | ABN50472.1 |
| Q8ODN6.1 | AC094663.1 | ACA65044.1 | ABN50450.1 |
| ABF21319.1 | AC006025.1 | ACA65033.1 | ABN50439.1 |
| ABN50461.1 | AC006014.1 | ACA65022.1 | ABN50428.1 |
| YP419283.1 | AC006003.1 | ACA65011.1 | ABN50417.1 |
| ACN32784.1 | AC005992.1 | ACA65000.1 | ABN50406.1 |
| ACN32773.1 | AC005981.1 | ACA64989.1 | ABN50395.1 |
| ACN32719.1 | AC005970.1 | ACA64978.1 | ABN50384.1 |
| ACN32613.1 | AC005959.1 | ACA64967.1 | ABL77389.1 |
| ACN32602.1 | AC005937.1 | ACA64956.1 | ABL77378.1 |
| ACN32591.1 | AC005926.1 | ACA64945.1 | ABL77367.1 |
| ACN32580.1 | ACF54369.1 | ACA64934.1 | ABL77356.1 |
| ACN32569.1 | ACF54358.1 | ACA64923.1 | ABL77345.1 |
| ACN32558.1 | ACF54347.1 | ACA64912.1 | ABL77334.1 |
| ABL77103.1 | ACF54336.1 | ACA64901.1 | ABL77323.1 |
| ABN50725.1 | ACF54325.1 | ABR16019.1 | ABL77312.1 |
| ABX71689.1 | ACF54314.1 | ABR16008.1 | ABL77301.1 |
| ABF21321.1 | ACF54303.1 | ABR15997.1 | ABL77290.1 |
| AAD29209.1 | ACF54292.1 | ABR15986.1 | ABL77279.1 |
| AAD29207.1 | ACF54281.1 | ABR15975.1 | ABL77268.1 |
| AAD29205.1 | ACF54270.1 | AB072379.1 | ABL77257.1 |
| AAD29203.1 | ACF54259.1 | ABN50637.1 | ABL77246.1 |
| AAD29201.1 | ACF54248.1 | ABN59447.1 | ABL77235.1 |
| AAD29199.1 | ACF54226.1 | ABN58663.1 | ABL77224.1 |
| AAD29197.1 | ACF54215.1 | ABN51197.1 | ABL77213.1 |
| AAD29195.1 | ACF54204.1 | ABN51186.1 | ABL77202.1 |
| AAD29193.1 | ACF54182.1 | ABN50747.1 | ABL77191.1 |
| AAD29191.1 | ACF54160.1 | ABN50736.1 | ABL77180.1 |
| AAD29189.1 | ACF54149.1 | ABN50714.1 | ABL77169.1 |
| AAD29185.1 | ACF54138.1 | ABN50703.1 | ABL77158.1 |
| AAD29183.1 | ACF41660.1 | ABN50692.1 | ABL77147.1 |
| AAD29181.1 | ACD56579.1 | ABN50681.1 | ABL77136.1 |
| AAD29179.1 | ACD56568.1 | ABN50670.1 | ABL77125.1 |

TABLE 2-continued

Accession numbers for amino acids sequences BM2 proton channel proteins

| GenBank accession number | GenBank accession number | GenBank accession number | GenBank accession number |
|---|---|---|---|
| AAD29177.1 | ACB06477.1 | ABN50659.1 | ABL77114.1 |
| AAD29175.1 | ACA96664.1 | ABN50648.1 | ABL77092.1 |
| AAD29173.1 | ACA96653.1 | ABN50626.1 | ABL77081.1 |
| AAT69452.1 | ACA96642.1 | ABN50615.1 | ABL77070.1 |
| AAT69441.1 | ACA96631.1 | ABN50604.1 | ABL77059.1 |
| AAT69430.1 | ACA96620.1 | ABN50593.1 | ABL77048.1 |
| ACR39338.1 | ACA96609.1 | ABN50582.1 | ABL77037.1 |
| ACR15734.1 | ACA96598.1 | ABN50571.1 | ABL77026.1 |
| ACR15723.1 | ACA96587.1 | ABN50560.1 | ABL77015.1 |
| ACR15712.1 | ACA96576.1 | ABN50549.1 | ABL77004.1 |

Structural Virus Protein

The structural virus protein (also referred to as structural viral protein) may be a viral antigenic protein or fragment thereof, for example but not limited to a virus glycoprotein or virus envelop protein. The structural virus protein may be a chimeric virus protein. The viral protein may exist as a monomer, a dimer, a trimer, or a combination thereof. A trimer is a macromolecular complex formed by three, usually non-covalently bound proteins. Without wishing to be bound by theory, the trimerization domain of a protein may be important for the formation such trimers. Therefore the structural viral protein or fragment thereof may comprise a trimerization domain. A non-limiting example of a structural virus protein is influenza hemagglutinin (HA), or a fragment of HA. Non-limiting examples of HA, or fragments of HA that may be used according to the present invention include those described in WO2009/009876, WO 2009/076778; WO 2010/003225, WO 2010/003235, WO 2011/03522, WO 2010/006452, WO 2010/148511, WO 2011/035422 (which are incorporated herein by reference).

Furthermore the structural virus protein may be the unprocessed precursor protein of HA. HA protein is synthesized as a precursor protein (HA0) of about 75 kDa, which assembles at the surface into an elongated trimeric protein. The precursor protein is cleaved at a conserved activation cleavage site into 2 polypeptide chains, HA1 and HA2 (comprising the transmembrane region), linked by a disulfide bond.

Proteolytic Loop (Cleavage Site) Modification

The structural virus protein may be an influenza B hemagglutinin or Influenza A hemagglutinin protein with a deletion or modification of the proteolytic loop (cleavage site) within the hemagglutinin protein. Deletion or modification of the proteolytic loop ensures that the HA molecule is mostly maintained as HA0 precursor.

HA is synthesized as a precursor protein HA0, which undergoes proteolytic processing into two subunits (HA1 and HA2) linked together by a disulfide bridge. Mammalian and apathogenic avian influenza virus strains cause anatomically localized infections as a result of the restricted range of cells secreting a protease that can cleave the HA0 precursor extracellularly (Chen J, et. al. 1998, Cell. Vol 95:409-417). The proteases responsible for cleavage of HA0 in influenza infections of humans, are secreted by cells of the respiratory tract, or by coinfecting bacteria or mycoplasma, or they may be produced in inflammatory responses to infections. A major protease candidate is the tryptase Clara, which is produced by Clara cells of the bronchiolar epithelium, and has limited tissue distribution (upper respiratory tract). The protease is specific for the monobasic sequence Q/E-X-R found at the cleavage site of the H1, H2, H3, and H6. HA from H9 and B strains show a slightly different monobasic cleavage site with SSR and KER sequence respectively (see FIG. 24). No protease has been identified for the majority of influenza viruses that cause enteric and respiratory infection seen in aquatic birds. In the laboratory, most cell lines do not support multi-cycle replication unless exogenous protease (usually trypsin) is added.

Highly pathogenic avian strains, however, are cleaved by a family of more widespread intracellular proteases, resulting in systemic infections. This difference in pathogenicity correlates with structural differences at the HA0 cleavage site. Pathogenic strains have inserts of polybasic amino acids within, or next to, the monobasic site. Cleavage in this case occurs intracellularly and the proteases involved have been identified as furin, and other subtilisin-like enzymes, found in the Golgi and involved in the post-translational processing of hormone and growth factor precursors. The furin recognition sequence R-X-R/K-R is a frequent insertion amino acid at the HA0 cleavage sites of H5 and H7 (see FIG. 24). The wide tissue distribution of the enzyme, and the efficiency of intracellular cleavage, contribute to the widespread and virulent systemic infection caused by these viruses.

Horimoto T, et. al. (2006, Vaccine, Vol 24: 3669-3676) describes the abolition of the polybasic cleavage site of H5 (RERRRKKR↓G) (SEQ ID NO: 100) in H5. Selected mutants were submitted to immunogenicity study in mice, including a mutant with a deletion of the 4 first charged amino acids (RERR) (SEQ ID NO: 101) and a modification to inactivate the polybasic cleavage site (RKKR (SEQ ID NO: 102) with TETR (SEQ ID NO: 103)). Abolition of the cleavage site did not affect the immunogenic properties of the mutant H5. Abolition the polybasic site (GERRRKKR↓G (SEQ ID NO: 104) replaced by RETR (SEQ ID NO: 105)) to produce mutant NIBSC 05/240 NIBSC influenza reference virus NIBG-23, has also been reported. Hoffman et. al. (2002, 2002, Vaccine, Vol 20:3165-3170) replaced the polybasic cleavage site of a H5 HA with the monobasic site of H6 in order to boost the expression in eggs. The first 4 residues were deleted and replaced the four last amino acids of the polybasic site by IETR (SEQ ID NO: 106) (replacement of RERRRKKR↓G with IETR↓G) (SEQ ID NO: 107). This mutant H5 showed a high expression level, potential proteolysis and conformational change at low pH, immunogenicity data were not reported. These studies show that modification of the cleavage site can be employed to diminishes the virulence of the viral particle (in cases where the true viruses is replicated, allowing the virus to replicate without killing the host egg. Without such mutations, viruses kill the egg before reaching high titers.

During the folding of HA and secretion thorough the Golgi, the hemagglutinin precursor cleavage site, which is located on a loop at the surface of HA, is well accessible for proteolysis by proteases. Without wishing to be bound by theory, if proteolysis of precursor HA0 occurs at the mono or the polybasic site during folding of the HA in the ER, a conformational change of the protein may take place in the Golgi apparatus during secretion, because the pH environment inside the Golgi of the plant and in the apoplast is slightly acidic. A low-pH conformation HA may be produced, decreasing both the level of expression and intrinsic stability of the particle. Thus, mostly uncleaved HA0 precursor protein would be budding from plasma membrane.

By "proteolytic loop" or "cleavage site" is meant the consensus sequence of the proteolytic site that is involved in precursor HA0 cleavage. "Consensus" or "consensus sequence" as used herein means a sequence (either amino acid or nucleotide sequence) that comprises the sequence variability of related sequences based on analysis of alignment of multiple sequences, for example, subtypes of a particular influenza HA0 sequence. Consensus sequence of the influenza HA0 cleavage site may include influenza A consensus hemagglutinin amino acid sequences, including for example consensus H1, consensus H3, or influenza B consensus hemagglutinin amino acid sequences. Non limiting examples of consensus sequences are shown in FIG. 24.

In the amino acid sequence of the HA the proteolytic loop is located, before the fusion peptide that consist of the 20 first amino acids of the HA2 part. The crystal structure of HA0 from A/Hong Kong/68 has been determined (Chen, J., 1998. Cell 95:409-417; incorporated herein by reference). Residues that are exposed to solvent are generally thought of being part of the cleavage site which forms an extended, highly exposed surface loop. From this specific peptide sequence, the consensus sequence may be determined in this chosen region (Bianchi et al., 2005, Journal of Virology, 79:7380-7388; incorporated herein by reference).

In order to abolish the proteolytic loop, the structure of a B HA was examined Deletion of only the proteolytic cleavage site of the HA would have left the C-terminal of HA1 and N-terminal of HA2 left apart and a long linker would have needed to be designed. However deleting part of the fusion peptide along with the proteotic cleave site allowed to remove the complete proteolytic loop and join the remaining HA1 and HA2 sequence by a minimal peptide linker of 2 amino acids. In summary, the B variant contains a deletion of sequence ALKLLKER (SEQ ID NO: 108) at the C-terminus of HA1 in addition of deletion of the N-terminus amino acids GFFGAIAGFLEG (SEQ ID NO: 109) of HA2. The shortened HA1-HA2 were linked together by a GG linker.

Figures 22A, 22B:
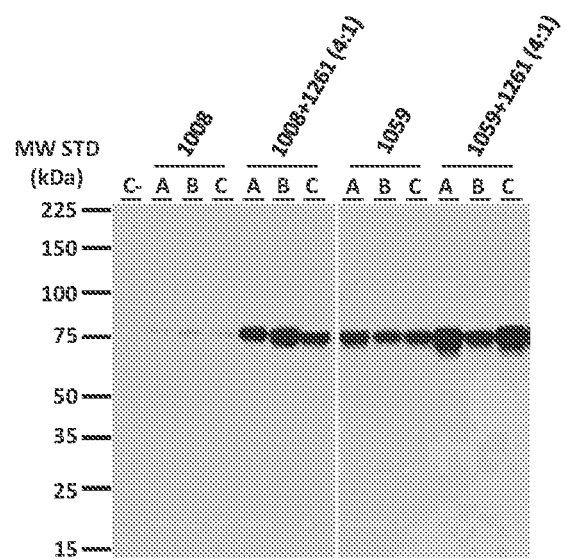
FIG. 22A shows a Western blot analysis of HA protein expression in agroinfiltrated *Nicotiana benthamiana* leaves. "1008": expression of wild-type HA from B/Brisbane/60/2008 in the presence of amplification elements (BeYDV); "1008+1261": co-expression of wild-type HA from B/Brisbane/60/2008 in the presence of amplification elements (BeYDV) with M2 from A/New Caledonia/20/99; "1059": expression of mutant HA from B/Brisbane/60/2008 in the presence of amplification elements (BeYDV); "1059+1261": co-expression of mutant HA from B/Brisbane/60/2008 in the presence of amplification elements (BeYDV) with M2 from A/New Caledonia/20/99. Plants from three separate infiltrations were analyzed (A, B and C). Ratios indicate the proportion of *Agrobacterium* cultures used in co-expression experiments.
FIG. 22B shows a comparison of hemagglutination capacity of crude protein extracts from HA-producing plants.

As show in FIG. 22B, by deleting the proteolytic loop of HA0, the resultant HA0 protein exhibits an increased activity as shown by a greater hemagglutination capacity, when compared to a HA protein that does not have its proteolytic loop removed. By an increase in activity, it is meant an increase in hemagglutination capacity by about 2% to about 100%, or any amount therebetween as determined using standard techniques in the art, for example, from about 10% to about 50% or any value therebetween for example about 2, 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, or 100%, when compared to the activity of the same HA protein that does not have its proteolytic loop removed.

By "chimeric virus protein" or "chimeric virus polypeptide", also referred to as "chimeric protein" or "chimeric polypeptide", it is meant a protein or polypeptide that comprises amino acid sequences from two or more than two sources, for example but not limited to, two or more influenza types or subtypes, or influenza's of a different origin, that are fused as a single polypeptide. The chimeric protein or polypeptide may include a signal peptide that is the same as, or heterologous with, the remainder of the polypeptide or protein. The chimeric protein or chimeric polypeptide may be produced as a transcript from a chimeric nucleotide sequence, and the chimeric protein or chimeric polypeptide cleaved following synthesis, and as required, associated to form a multimeric protein. Therefore, a chimeric protein or a chimeric polypeptide also includes a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide. A chimeric virus protein may also comprises an antigenic protein or a fragment thereof of a first influenza virus, and a transmembrane domain complex (TDC) from an second virus influenza HA, including a transmembrane domain and cytosolic tail domains (TM/CT). The polypeptide may be hemagglutinin (HA), and each of the two or more than two amino acid sequences that make up the polypeptide may be obtained from different HA's to produce a chimeric HA, or chimeric influenza HA. A chimeric HA may also include an amino acid sequence comprising heterologous signal peptide (a chimeric HA preprotein) that is cleaved after or during protein synthesis. Preferably, the chimeric polypeptide, or chimeric influenza HA is not naturally occurring. A nucleic acid encoding a chimeric polypeptide may be described as a "chimeric nucleic acid", or a "chimeric nucleotide sequence". A virus-like particle comprised of chimeric HA may be described as a "chimeric VLP".

The chimeric protein or polypeptide may include a signal peptide that is the same as, or heterologous with, the remainder of the polypeptide or protein. The term "signal peptide" is well known in the art and refers generally to a short (about 5-30 amino acids) sequence of amino acids, found generally at the N-terminus of a polypeptide that may direct translocation of the newly-translated polypeptide to a particular organelle, or aid in positioning of specific domains of the polypeptide chain relative to others. As a non-limiting example, the signal peptide may target the translocation of the protein into the endoplasmic reticulum and/or aid in positioning of the N-terminus proximal domain relative to a membrane-anchor domain of the nascent polypeptide to aid in cleavage and folding of the mature protein, for example which is not to be considered limiting, a mature HA protein.

Non limiting examples of chimeric virus proteins or chimeric virus nucleic acids that may be used according to the present invention are described in, WO 2009/076778, WO 2010/003235, or WO 2010/148511 (which are incorporated herein by reference).

Signal Peptide

A signal peptide (SP) may be native to the antigenic protein or virus protein, or a signal peptide may be heterologous with respect to the primary sequence of the antigenic protein or virus protein being expressed. A antigenic protein or virus protein may comprise a signal peptide from a first influenza type, subtype or strain with the balance of the HA from one or more than one different influenza type, subtype or strain. For example the native signal peptide of HA subtypes H1, H2, H3, H5, H6, H7, H9 or influenza type B may be used to express the chimeric virus protein in a plant system. In some embodiments of the invention, the SP may be of an influenza type B, H1, H3 or H5; or of the subtype H1/Bri, H1/NC, H5/Indo, H3/Bri or B/Flo.

A signal peptide may also be non-native, for example, from a antigenic protein, viral protein or hemagglutinin of a virus other than virus protein, or from a plant, animal or bacterial polypeptide. A non limiting example of a signal peptide that may be used is that of alfalfa protein disulfide isomerase ("PDISP"; nucleotides 32-103 of Accession No. Z11499; also see WO 2009/076778; WO 2010/148511, or WO 2010/003235, which are incorporated herein by reference). The present invention therefore provides for a chimeric virus protein comprising a native, or a non-native signal peptide, and nucleic acids encoding such chimeric virus proteins.

The present invention therefore also provides for a method of producing chimeric VLP in a plant, wherein a first nucleic acid encoding a chimeric virus protein is co-expressed with a second nucleic acid encoding a channel protein, for example but not limited to a proton channel protein. The first and second nucleic acids may be introduced to the plant in the same step, or may be introduced to the plant sequentially.

HA

With reference to influenza virus, the term "hemagglutinin" or "HA" as used herein refers to a glycoprotein found on the outside of influenza viral particles. HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available—see, for example, the BioDefence Public Health base (Influenza Virus; see URL: biohealthbase.org) or National Center for Biotechnology Information (see URL: ncbi.nlm.nih.gov), both of which are incorporated herein by reference.

The term "homotrimer" or "homotrimeric" indicates that an oligomer is formed by three HA protein molecules. Without wishing to be bound by theory, HA protein is synthesized as monomeric precursor protein (HA0) of about 75 kDa in animal cells, which assembles at the surface into an elongated trimeric protein. Before trimerization occurs, the precursor protein is cleaved at a conserved activation cleavage site (also referred to as fusion peptide) into 2 polypeptide chains, HA1 and HA2 (comprising the transmembrane region), linked by a disulfide bond. The HA1 segment may be 328 amino acids in length, and the HA2 segment may be 221 amino acids in length. Although this cleavage may be important for virus infectivity, it may not be essential for the trimerization of the protein. Insertion of HA within the endoplasmic reticulum (ER) membrane of the host cell, signal peptide cleavage and protein glycosylation are co-translational events. Correct refolding of HA requires glycosylation of the protein and formation of 6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains. It has also been established that HA undergoes major conformational changes during the infection process, which requires the precursor HA0 to be cleaved into the 2 polypeptide chains HA1 and HA2. The HA protein may be processed (i.e., comprise HA1 and HA2 domains), or may be unprocessed (i.e. comprise the HA0 domain). The HA protein may be used in the production or formation of VLPs using a plant, or plant cell, expression system.

The HA of the present invention may be obtained from any subtype. For example, the HA may be of subtype H2, H3, H4, H6, H7, H8, H9, H10, H11, H12, H13, H14, H15, H16, or influenza type B HA. The recombinant HA of the present invention may also comprise an amino acid sequence based on the sequence any hemagglutinin known in the art—see, for example, the BioDefence Public Health base (Influenza Virus; see URL: biohealthbase.org) or National Center for Biotechnology Information (see URL: ncbi.nlm.nih.gov). Furthermore, the HA may be based on the sequence of a hemagglutinin that is isolated from one or more emerging or newly-identified influenza viruses.

Non-limiting examples of HA, or fragments of HA that may be used according to the present invention include those described in WO2009/009876, WO 2009/076778; WO 2010/003225, WO 2010/003235, WO 2010/006452, WO 2011/035422 or WO 2010/148511 (which are incorporated herein by reference).

Figure 18:
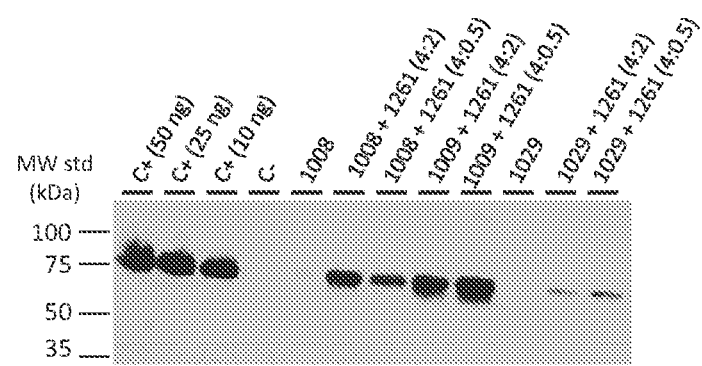
FIG. 18 shows Western blot analysis of HA protein expression in agroinfiltrated *Nicotiana benthamiana* leaves. HA from B/Brisbane/60/2008 is co-expressed with M2 from A/New Caledonia/20/99. "C+": positive control, semi-purified B/Brisbane/60/2008 virus from the Therapeutic Goods Administration, Australia; "C-": negative control, mock-infiltrated plants; "1008": expression of wild-type HA from B/Brisbane/60/2008 in the presence of amplification elements (BeYDV); "1008+1261": co-expression of wild-type HA from B/Brisbane/60/2008 in the presence of amplification elements (BeYDV) with M2; "1009+1261": co-expression of chimeric HA from B/Brisbane/60/2008 in the presence of amplification elements (BeYDV) with M2; "1029": expression of wild-type HA from B/Brisbane/60/2008 in the absence of amplification elements (BeYDV); "1029+1261": co-expression of wild-type HA from B/Brisbane/60/2008 in the absence of amplification elements (BeYDV) with M2 from A/New Caledonia/20/99. Ratios indicate the proportion of *Agrobacterium* cultures used in co-expression experiments.

As shown in FIG. 18, HA from B/Brisbane/60/2008 is poorly expressed in agroinfiltrated *Nicotiana benthamiana* leaves (see lanes "1008” or “1029”). However, co-expression of HA-type B with M2 from A/New Caledonia/20/99, results in a significant increase in HA expression (see lanes “1008+1261”; “1009+1261” and 1029+1261”). The increase in HA expression was observed in with both native type B HA or a chimeric HA type B. HA expression was observed in the presence or absence of amplification elements (BeYDV), and across various dilutions of *Agrobacterium*. A similar increase in H3 expression was observed when H3 from A/Perth/16/2009 was co-expressed with M2 from A/New Caledonia/20/99 (FIG. 19; compare lane “1019” H3 alone, with “1019+1261” H3 co-expressed with M2).

VLP

The term “virus like particle” (VLP), or “virus-like particles” or “VLPs” refers to structures that self-assemble and comprise virus proteins for example a structural viral protein such as influenza HA protein or a channel protein, for example but not limited to a proton channel protein, such as M2 or a combination of those proteins. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence. VLPs may be produced in suitable host cells including plant and insect host cells. Following extraction from the host cell and upon isolation and further purification under suitable conditions, VLPs may be purified as intact structures.

Furthermore, VLPs may be produced that comprise a combination of HA subtypes. For example, VLPs may comprise one or more than one HA from the subtype H2, H3, H4, H6, H7, H8, H9, H10, H11, H12, H13, H14, H15, H16, subtype B HA or a combination thereof. Selection of the combination of HAs may be determined by the intended use of the vaccine prepared from the VLP. For example a vaccine for use in inoculating birds may comprise any combination of HA subtypes, while VLPs useful for inoculating humans may comprise subtypes one or more than one of subtypes H2, H3, H4, H6, H7, H8, H9, H10, H11, H12, H13, H14, H15, H16, subtype B HA. However, other HA subtype combinations may be prepared depending upon the use of the VLP. In order to produce VLPs comprising combinations of HA subtypes, the desired HA subtype may be co-expressed within the same cell, for example a plant cell.

As described in more detail below, the expression of a type B HA or H3 from B/Brisbane/60/2008 in agroinfiltrated *Nicotiana benthamiana* leaves is increased when co-expressed M2 from A/New Caledonia/20/99 (see FIGS. 18 and 19). A similar increase is not observed when H1 or H5 is co-expressed with M2, as high levels of H1 or H5 expression are observed in the presence or absence of M2 (FIGS. 20 and 21 respectively). HA are known to be processed in a pH-dependent manner (see Reed M. L. et. al. Journal of Virology, February 2010, p. 1527-1535, Vol. 84, No. 3), and to undergo pH-dependent confirmation change (Skehel J. J. et. al. 1982, PNAS 79: 968-972). H1 and H5 exhibit a conformational change at a pH lower than that observed with either H3 and type B HA. Without wishing to be bound by theory, the pH within the Golgi Apparatus during maturation and migration may not have an effect on H1 or H5 folding, however, a low pH within the Golgi Apparatus may effect H3 and type B HA folding. By co-expressing a channel protein, for example but not limited to a proton channel protein, long with H3 or Type B HA, the pH within the Golgi Apparatus may increase and result in HA folding leading to increased HA yield. Furthermore, H1 and H5 may be more stable at lower pH, than H3 and Type B HA. Therefore, by co-expressing a channel protein, for example but not limited to a proton channel protein, along with H3 or Type B HA, less HA is degraded within the Golgi apparatus.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

The VLPs produced as described herein do not typically comprise neuramindase (NA). However, NA may be co-expressed with HA should VLPs comprising HA and NA be desired.

The invention also includes, but is not limited to, virus derived VLPs that obtain a lipid envelope from the plasma membrane of the cell in which the VLP proteins are expressed. For example, if the VLP is expressed in a plant-based system, the VLP may obtain a lipid envelope from the plasma membrane of the cell.

Generally, the term “lipid” refers to a fat-soluble (lipophilic), naturally-occurring molecules. The term is also used more specifically to refer to fatty-acids and their derivatives (including tri-, di-, and monoglycerides and phospholipids), as well as other fat-soluble sterol-containing metabolites or sterols. Phospholipids are a major component of all biological membranes, along with glycolipids, sterols and proteins. Examples of phospholipids include phosphatidylethanolamine, phosphatidylcholine, phosphatidylinositol, phosphatidylserine, and the like. Examples of sterols include zoosterols (e.g., cholesterol) and phytosterols. Over 200 phytosterols have been identified in various plant species, the most common being campesterol, stigmasterol, ergosterol, brassicasterol, delta-7-stigmasterol, delta-7-avenasterol, daunosterol, sitosterol, 24-methylcholesterol, cholesterol or beta-sitosterol. As one of skill in the art would understand, the lipid composition of the plasma membrane of a cell may vary with the culture or growth conditions of the cell or organism from which the cell is obtained.

Cell membranes generally comprise lipid bilayers, as well as proteins for various functions. Localized concentrations of particular lipids may be found in the lipid bilayer, referred to as ‘lipid rafts’. Without wishing to be bound by theory, lipid rafts may have significant roles in endo- and exocytosis, entry or egress of viruses or other infectious agents, inter-cell signal transduction, interaction with other structural components of the cell or organism, such as intracellular and extracellular matrices.

In plants, influenza VLPs bud from the plasma membrane therefore the lipid composition of the VLPs reflects their origin. The VLPs produced according to the present invention comprise HA of one or more than one type or subtype of influenza, complexed with plant derived lipids. Plant lipids can stimulate specific immune cells and enhance the immune response induced. Plant membranes are made of lipids, phosphatidylcholine (PC) and phosphatidyletha-nolamine (PE), and also contain glycosphingolipids, saponins, and phytosterols. Additionally, lipid rafts are also found in plant plasma membranes—these microdomains are enriched in sphingolipids and sterols. In plants, a variety of phytosterols are known to occur, including stigmasterol, sitosterol, 24-methylcholesterol and cholesterol (Mongrand et al., 2004).

PC and PE, as well as glycosphingolipids can bind to CD1 molecules expressed by mammalian immune cells such as antigen-presenting cells (APCs) like dendritic cells and macrophages and other cells including B and T lymphocytes in the thymus and liver (Tsuji M., 2006). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

A variety of phytosterols may be found in a plasma membrane—the specific complement may vary depending on the species, growth conditions, nutrient resources or pathogen state, to name a few factors. Generally, beta-sitosterol is the most abundant phytosterol.

The phytosterols present in an influenza VLP complexed with a lipid bilayer, such as an plasma-membrane derived envelope may provide for an advantageous vaccine composition. Without wishing to be bound by theory, plant-made VLPs complexed with a lipid bilayer, such as a plasma-membrane derived envelope, may induce a stronger immune reaction than VLPs made in other expression systems, and may be similar to the immune reaction induced by live or attenuated whole virus vaccines.

Therefore, in some embodiments, the invention provides for a VLP complexed with a plant-derived lipid bilayer. In some embodiments the plant-derived lipid bilayer may comprise the envelope of the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a ‘plant lipid’. Examples of phytosterols are known in the art, and include, for example, stigmasterol, sitosterol, 24-methylcholesterol and cholesterol—see, for example, Mongrand et al., 2004.

VLPs may be assessed for structure and size by, for example, hemagglutination assay, electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Precipitation with PEG may be used. The soluble protein is quantified, and the extract passed through a size exclusion matrix, for example but not limited to Sephacryl™. Following chromatography, fractions may be further analyzed by immunoblot to determine the protein complement of the fraction.

Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (see also Ito T. et al, 1997, Virology, vol 227, p 493-499; and Medeiros R et al, 2001, Virology, vol 289 p. 74-85).

Folding (Chaperon)

Correct folding of the expressed virus protein may be important for stability of the protein, formation of multimers, formation of VLPs, function of the virus protein and recognition of the virus protein by an antibody, among other characteristics. Folding and accumulation of a protein may be influenced by one or more factors, including, but not limited to, the sequence of the protein, the relative abundance of the protein, the degree of intracellular crowding, the pH in a cell compartment, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases (see, for example, Macario, A. J. L., *Cold Spring Harbor Laboratory Res.* 25:59-70. 1995; Parsell, D. A. & Lindquist, S. *Ann. Rev. Genet.* 27:437-496 (1993); U.S. Pat. No. 5,232,833). As described herein, chaperone proteins, for example but not limited to Hsp40 and Hsp70 may be used to ensure folding of a virus protein.

Examples of Hsp70 include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71). DnaK from *Escherichia coli*, yeast and other prokaryotes, and BiP and Grp78 from eukaryotes, such as *A. thaliana* (Lin et al. 2001 (Cell Stress and Chaperones 6:201-208). A particular example of an Hsp70 is *A. thaliana* Hsp70 (encoded by Genbank ref: AY120747.1). Hsp70 is capable of specifically binding ATP as well as unfolded polypeptides and peptides, thereby participating in protein folding and unfolding as well as in the assembly and disassembly of protein complexes.

Examples of Hsp40 include DnaJ from prokaryotes such as *E. coli* and mycobacteria and HSJ1, HDJ1 and Hsp40 from eukaryotes, such as alfalfa (Frugis et al., 1999. Plant Molecular Biology 40:397-408). A particular example of an Hsp40 is *M. sativa* MsJ1 (Genbank ref: AJ000995.1). Hsp40 plays a role as a molecular chaperone in protein folding, thermotolerance and DNA replication, among other cellular activities.

Among Hsps, Hsp70 and its co-chaperone, Hsp40, are involved in the stabilization of translating and newly synthesized polypeptides before the synthesis is complete. Without wishing to be bound by theory, Hsp40 binds to the hydrophobic patches of unfolded (nascent or newly transferred) polypeptides, thus facilitating the interaction of Hsp70-ATP complex with the polypeptide. ATP hydrolysis leads to the formation of a stable complex between the polypeptide, Hsp70 and ADP, and release of Hsp40. The association of Hsp70-ADP complex with the hydrophobic patches of the polypeptide prevents their interaction with other hydrophobic patches, preventing the incorrect folding and the formation of aggregates with other proteins (reviewed in Hartl, F U. 1996. Nature 381:571-579).

Native chaperone proteins may be able to facilitate correct folding of low levels of recombinant protein, but as the expression levels increase, the abundance of native chaperones may become a limiting factor. High levels of expression of virus protein in the agroinfiltrated leaves may lead to the accumulation of virus protein in the cytosol, and co-expression of one or more than one chaperone proteins such as Hsp70, Hsp40 or both Hsp70 and Hsp40 may reduce the level of misfolded or aggregated proteins, and increase the number of proteins exhibiting tertiary and quaternary structural characteristics that allow for formation of virus-like particles.

Therefore, the present invention also provides for a method of producing virus protein VLPs in a plant, wherein a first nucleic acid encoding a virus protein is co-expressed with a second nucleic acid encoding a channel protein, for example but not limited to a proton channel protein, and a third nucleic acid encoding a chaperone. The first, second and third nucleic acids may be introduced to the plant in the same step, or may be introduced to the plant sequentially.

N-Glycans

The VLP produced within a plant may induce an virus protein comprising plant-specific N-glycans. Therefore, this invention also provides for a VLP comprising virus protein having plant specific N-glycans.

Furthermore, modification of N-glycan in plants is known (see for example WO 2008/151440; WO 2010/006452; or U.S. 60/944,344; which are incorporated herein by reference) and virus protein having modified N-glycans may be produced. Virus protein comprising a modified glycosylation pattern, for example with reduced fucosylated, xylosylated, or both, fucosylated and xylosylated, N-glycans may be obtained, or virus protein having a modified glycosylation pattern may be obtained, wherein the protein lacks fucosylation, xylosylation, or both, and comprises increased galactosylation. Furthermore, modulation of post-translational modifications, for example, the addition of terminal galactose may result in a reduction of fucosylation and xylosylation of the expressed virus protein when compared to a wild-type plant expressing virus protein.

For example, which is not to be considered limiting, the synthesis of virus protein having a modified glycosylation pattern may be achieved by co-expressing the protein of interest along with a nucleotide sequence encoding beta-1.4galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with virus protein. The virus protein may also be co-expressed along with a nucleotide sequence encoding N-acetylglucosaminyltransferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also includes VLP's comprising one or more virus protein having modified N-glycans.

pH within the Secretory Pathway

The secretory pathway presents a complex milieu for the maturation and modification of recombinant proteins, including heterogeneous redox environments and proton concentrations between subcellular compartments. pH gradient across compartments has a central role in secretory function (Paroutis et al., 2004), however, pH variations can induce significant conformational changes in protein structures (Wu et al., 2009; Harrison et al., 2013) and aggregation status (Wang et al., 2010). Such variations can also compromise proper glycosylation of maturing proteins (Hassinen et al., 2011) or slow down molecular traffic along the secretory pathway (Henkel and Weisz, 1998). Proteins destined for secretion are synthesized in the endoplasmic reticulum (ER) with near neutral pH, while downstream compartments become progressively more acidic (Casey et al., 2010). Variations in pH within the secretory pathway impacts protein maturation and stability.

As described herein, regulating pH in the plant secretory pathway improves protein processing and stabilization of certain acid-labile or acid sensitive proteins, including recombinant polypeptides. The M2 protein from Orthomyxoviridae forms a tetrameric pH-activated proton-selective ion channel (Holsinger et al., 1994) and maintains a high pH in the trans-Golgi network of infected cells. The high pH has been suggested to prevent premature conformational change of hemagglutinin (Cady et al., 2009). The M2 protein contains a 20-residue transmembrane domain helix (Schnell and Chou, 2008) that is destabilized by low pH resulting in opening and activation of the channel (Holsinger et al., 1994).

Ratiometric pHluorin (Miesenböck et al., 1998, Nature, 394(6689), 192-195) was used to measure in situ pH variations in the secretory pathway of transiently transformed plant cells (see Example 3). To measure pH variations along the secretory pathway, constructs that target pHluorin to the ER, to the cis-Golgi (Man99-pHluorin; construct No, 1873; SEQ ID NO:79; see FIGS. 32A, 39B, 39C, 39D and 39E), to the trans-Golgi network (Man99TMD23-pHlurion; construct No. 1874; SEQ ID NO:82; see FIGS. 32A, 40A, 40B, 40C and 40D) or to the apoplast (sec-pHluorin; construct No. 1871; SEQ ID NO:72; see FIGS. 32A, 37C, 37D, 37E and 37F) were used. ER and apoplast pHluorin constructs were targeted to the secretory pathway by the addition of a heterologous signal peptide. Cis- and trans-Golgi pHluorin constructs were fused with the modified N-terminus of α-1,2 mannosidase I, a membrane-bound enzyme of the secretory pathway. The Man99 membrane targeting signal has been reported to partially target to the ER, with most targeting in the cis-Golgi of N. benthamiana leaf cells (Saint-Jore-Dupas et. Alo. 2006, Plant Cell, 18(11), 3182-3200.). The addition of 7 amino acids in the transmembrane domain of Man99, yielding Man99TMD23, changed the localization of the protein to almost exclusively the trans-Golgi (Saint-Jore-Dupas et al., 2006).

Transient agroinfiltrated, pHluorin constructs (see Example 3) were expressed in different subcellular compartments of N. benthamiana leaves, (FIG. 32B) and that fluorescence was sufficient at both excitation wavelengths for ratiometric analysis (FIG. 32B). Epidermal cells expressing the ER marker protein "ER-pHluorin"-(comprising SEKDEL) showed a typical interconnected network pattern of the cortical ER (FIG. 32B, upper left hand panel) while secreted pHluorin (sec-pHluorin; FIG. 32B, upper right hand panel) accumulated on the edges of the cell in the apoplast.

The excitation spectrum of pHluorin is bimodal and shows a reversible switch between the two excitation maxima at pH 7.5 and 5.5 (Mahon, 2011, Adv Biosci Biotechnol, 2(3), 132-137.). pHluorin can therefore function as a pH indicator with ratiometric responsiveness within pH ranges that characterize the plant secretory pathway (Schulte et al., 2006, *Plant Methods*, 2, 7). While emission remains constant at 515 nm, excitation is strongest at 488 nm in acidic conditions whereas at pH closer to neutral the excitation maxima switch to 405 nm. Therefore, a low 405/488 nm ratio is indicative of acidic pH environment whereas a higher ratio indicates a more basic pH. Calibration of pHluorin in vitro shows a direct correlation between excitation ratios and pH values.

Using transiently expressed pHluorin, pH variations between discrete compartments of the plant secretory pathway may be detected (FIG. 32C). The ratio in the ER was the highest indicating a more neutral pH, and a lower ratio was observed in the trans-Golgi, revealing an acidic pH. The pH of the secretory pathway in agroinfiltrated *N. benthamiana* tissue varies from near neutral in the ER, to an estimated pH of approximately 5.5 in the trans-Golgi.

Effect of M2 on pH Along the Secretory Pathway

During synthesis, M2 is co-translationally inserted into the ER membrane and transported along the secretory pathway to the plasma membrane (Henkel and Weisz, 1998, *J Biol Chem*, 273(11), 6518-6524). M2 is activated when reaching a cell compartment below pH 6.2 (Cady et al., 2009, *Biochemistry*, 48(31), 7356-7364).

To determine whether a transiently expressed proton channel can be used to modulate the pH of the secretory pathway of plants, *N. benthamiana* leaves were co-agroinfiltrated with Influenzavirus A M2 (M2WT; construct No. 1261; SEQ ID NO:10; see FIG. 33A) and the pHluorin constructs ER-pHluorin and sec-pHluorin (FIG. 32A; Example 3). The inactive M2 mutant, M2(A30P); (construct No. 1210; SEQ ID NO:67; see FIGS. 33A, 36C, 36D and 36E), co-expressed with ER-pHluorin and sec-pHluorin, was used as a control. The alanine 30 to proline (A30P) mutation of M2(A30P) eliminates ion channel activity without affecting the tertiary structure or transport to the plasma membrane (Holsinger et al., 1994, *J Virol*, 68(3), 1551-1563).

Ratiometric fluorescence analysis at 5 dpi confirmed that functional ion channel co-expression specifically modified the pH of the plant secretory pathway (FIG. 33B). No discernible pH change was observed in the ER in the presence of M2 (FIG. 33B; see ER-pHluorin and sec-pHluorin). Since the pH of the ER lumen is close to neutral, and above the pH at which M2 is activated, this result is expected. There was also no impact of the mutant (A30P) M2 on pH of the Golgi when M2(A30P) was co-expressed with Man99-pHluorin or Man99TMD23-pHluorin (FIG. 33B). However, a significant increase in the pH of both regions of the Golgi apparatus was seen with wild-type M2 when co-expressed with either Man99-pHluorin (cis Golgi) and Man99TMD23-pHluorin (trans Golgi). The highest increase was observed in the trans-Golgi (M2WT co-expressed with Man99TMD23-pHluorin; FIG. 33B). Higher fluorescence ratios in the presence of M2 indicated that the ion channel was activated by the low pH of these organelles and that this activation resulted in a discernible change in pH.

Time course analysis of pHluorin excitation ratios as a result of varied M2 expression showed the protein to be detectable after 3 dpi and reach a maximum at 5 dpi, before finally decreasing (FIG. 36). No significant differences between ratios were observed for ER-targeted pHluorin (ER-pHluorin) in the presence of M2 at any time point. However, M2 expression increased pH of the cis-Golgi (determined using Man99-pHluorin) and trans-Golgi (determined Man99TMD23-pHluorin) and was detectable from 5 dpi to 6 dpi (FIG. 36). These results show that it is possible to modulate the pH of the plant Golgi apparatus through the transient co-expression of the M2 ion channel.

M2 Co-Expression Stabilizes an Acid-Susceptible Peptide Linker

Fusion of a protein of interest to a stabilizing protein domain may be used to increase the accumulation of recombinant proteins. The rigid linker $(EAAAK)_n$ (where n=1, 2, 3, 4, 5, 6, 7, 8, 9, 10 or more, as required; SEQ ID NO:110) can been used to separate each protein within the fusion, and may be used to reduce steric interference between the attached domains (Arai et al., 2001, *Protein Eng*, 14(8), 529-532.; Wriggers et al., 2005, *Biopolymers*, 80(6), 736-746.). This linker is known to be susceptible to autoproteolytic cleavage at or below pH 6.0 (Wu et al., 2009, J Chromatogr B Analyt Technol Biomed Life Sci, 877(31), 4015-4021), and is susceptible to cleavage in yeast (Zhao et al., 2008, *Protein Expr Purif*, 61(1), 73-77) and plants (Sainsbury et al., 2013, *Plant Biotechnol J*, 11(9), 1058-1068). The Golgi apparatus is known to be approx. of pH 6.0 (Casey et al., 2010, *Nat Rev Mol Cell Biol*, 11(1), 50-61).

As determined herein, a pH range of 5.5 to 6.5 is observed along the cis- and trans-Golgi route in plants. To investigate the impact of increasing pH in the secretory pathway (by co-expressing M2) on the stability of the (EAAAK). linker (SEQ ID NO:110), a secreted fusion protein comprising this linker was prepared and tested. The fusion protein consisted of tomato cystatin SlCYS8 and a truncated version of human alpha-1-antichymotrypsin (α1ACT), separated by a $(EAAAK)_3$ peptide linker (SlCYS8-α1ACT fusion protein; described in Sainsbury et al. (2013, Plant Biotechnol J 11: 1058-1068).

The SlCYS8-α1ACT fusion protein was not stable in the plant secretory pathway as the detection of free SlCYS8 (10.7 kDa) showed that the two domains were separated (FIG. 35B; left hand lane). Increasing the pH in the Golgi apparatus by co-expressing M2 resulted in stabilization of the 55 kDa SlCYS8-α1ACT fusion protein containing the rigid linker $(EAAAK)_3$ (SEQ ID NO:110; FIG. 34B, right hand lane), and an enhanced accumulation (5 fold increase) of the intact fusion protein when compared to expression of the fusion protein in the absence of M2 (FIG. 34C).

Densitometric analysis of the Western blott (FIG. 35B) indicated that in the absence of M2, over 70% of the SlCYS8 was detected in the free form, and that the majority of the fusion was protein was cleaved. In contrast, co-expression or M2 along with SlCYS8-α1ACT fusion protein resulted in over 70% of the fusion protein remaining intact (FIG. 35D).

These results show that modulation of pH can have a positive impact on the accumulation of recombinant proteins that are sensitive to acid environments. Furthermore, peptide sequences or proteins of interest can be stabilized by increasing the pH along the secretory pathway by co-expressing a nucleotide sequence encoding M2 along with a nucleotide sequence encoding the acid sensitive protein of interest.

These data demonstrate that modulated the pH of the plant secretory pathway may be modulated through the expression of an Orthomyxovirus M2 ion channel. Co-expression of functional M2 resulted in a significant pH increase in the Golgi apparatus. The increase in pH within this compartment may be used to assist in the accumulation of acid-sensitive or acid-labile proteins of interest.

Examples of acid-sensitive proteins of interest that may be co-expressed in the presence of M2 include a protein that changes confirmation, is inactivated, self-cleaved, denatured, unfolded, improperly folds or that is degraded within an acidic environment of the natural pH of the Golgi sub-compartments. The acid sensitive protein may be selected from the group of proteins that undergo pH-dependent conformation change, protein folding, protein stability, or a combination thereof. An acid sensitive protein may also include an acid sensitive recombinant protein, an acid sensitive fusion protein, a fusion protein comprising an acid sensitive linker. Non-limiting examples of acid sensitive proteins include a structural virus protein comprising a trimerization domain, an HA, an insulin-like growth factor binding protein acid sensitive subunit, P19 (ph sensitive RNAi binding), chimeric proteins comprising the acid-cleavable linker: (EAAAK)$_n$, where n is from 1-25 (SEQ ID NO:110; Wu et al., 2009, *J Chromatogr B Analyt Technol Biomed Life Sci*, 877(31), 4015-4021).

Non-limiting example of sequences that may be used with the present invention include:

H2 protein encoded by the nucleic acid molecule may be from the A/Singapore/1/57 (H2N2) strain;

H3 protein encoded by the nucleic acid molecule may be from the A/Brisbane 10/2007 (H3N2), A/Wisconsin/67/2005 (H3N2) strain, A/Victoria/361/2011 (H3N2) or A/Perth/16/2009 (H3N2);

H6 protein encoded by the nucleic acid molecule may be from the A/Teal/HongKong/W312/97 (H6N1) strain;

H7 protein encoded by the nucleic acid molecule may also be from the A/Equine/Prague/56 (H7N7) strain;

H9 protein encoded by the nucleic acid molecule may be from the A/HongKong/1073/99 (H9N2) strain;

HA protein from B subtype encoded by the nucleic acid may be from the B/Florida/4/2006, B/Malaysia/2506/2004, B/Wisconsin/1/2010, or B/Brisbane/60/2008 strain.

Chimeric Proteins

Non-limiting example of sequences that may be used with the present invention also include those described in WO 2009/009876; WO 2009/076778; WO 2010/003225; WO 2010/148511; WO 2010/003235; WO 2010/006452 which are herein incorporated by reference). Examples of sequences of amino acid molecules encoding such HA proteins from H2, H3, H4, H6, H7, H8, H9, H10, H11, H12, H13, H14, H15, H16 and type B HA, which are known in the art. For example H3 or B subtypes include SEQ ID Nos: 25 or 30. The sequence encoding the structural virus protein may be for example HA from influenza B/Brisbane/60/2008, B/Malaysia/2506/2004 or B/Wisconsin/1/2010, or H3 from influenza A/Perth/16/2009 or A/Victoria/361/2011. Other examples include sequences of nucleic acid molecules that encode HA proteins wherein the proteolytic loop of the HA protein has been deleted such as for example, but not limited to the sequence defined by SEQ ID NO: 41.

The present invention also includes, but is not limited to, nucleotide sequences encoding HA from for example H2, H3, H4, H6, H7, H8, H9, H10, H11, H12, H13, H14, H15, H16 or type B HA. For example SEQ ID NO: 28, 43, 23, encoding an HA from B, B with deleted proteolytic loop or H3. respectively, a nucleotide sequence that hybridizes under stringent hybridisation conditions to SEQ ID NO: 28, 43, 23, or a nucleotide sequence that hybridizes under stringent hybridisation conditions to a compliment of SEQ ID NO: 28, 43, 23, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA from B or H3. The VLP, when administered to a subject, induces an immune response. The nucleotide sequence may also be co-expressed with a second nucleotide sequence encoding a channel protein, for example but not limited to, nucleotide sequences SEQ ID NO: 9, 12, a nucleotide sequence that hybridizes under stringent hybridisation conditions to SEQ ID NO: 9, 12, or a nucleotide sequence that hybridizes under stringent hybridisation conditions to a compliment of SEQ ID NO: 9, 12, wherein the second nucleotide sequence encodes a proton channel protein forms a VLP. Preferably, the VLP induces the production of an antibody and the VLP, when administered to a subject, induces an immune response.

For example, expression of the nucleotide sequence within a plant cell forms a VLP, and the VLP may be used to produce an antibody that is capable of binding a virus protein such for example HA, including but not limited to HA0, HA0 protein with its proteolytic loop deleted or modified, HA1 or HA2 of one or more influenza types or subtypes, such for example but not limited to subtypes H2, H3, H4, H6, H7, H8, H9, H10, H11, H12, H13, H14, H15, H16, subtype B HA. The VLP, when administered to a subject, induces an immune response.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M NaPO$_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93, 94, 95, 96, 97, 98, 99, 100% or any amount therebetween, sequence identity, or sequence similarity, with the nucleotide sequence encoding HA from B (SEQ ID NO: 28), B with deleted or modified proteolytic loop (SEQ ID NO: 43), H3 (SEQ ID NO:23), or an HA encoded by any one or more of SEQ ID NO:23, 28, 43, 46, 51, 57, or 61, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including unprocessed and/or mature HA from B or H3, or unprocessed and/or mature HA wherein the proteolytic loop has been deleted. The VLP, when administered to a subject, induces an immune response.

The present invention also includes nucleotide sequences that are characterized as having about 70, 75, 80, 85, 87, 90, 91, 92, 93, 94, 95, 96, 97, 98, 99, 100% or any amount therebetween, sequence identity, or sequence similarity, with the nucleotide sequence encoding M2 (SEQ ID NO: 9, 12), wherein the nucleotide sequence encodes a channel protein, for example but not limited to a proton channel protein, that when co-expressed with a structural virus protein forms a VLP. Preferably, the VLP induces the production of an antibody and the VLP, when administered to a subject, induces an immune response.

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST), or by manual alignment and visual inspection. An example of sequence alignment of HAs from different strains of influenza can be found in FIG. 24.

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cross-reactivity HAI titres may also be used to demonstrate the efficacy of an immune response to other strains of virus related to the vaccine subtype. For example, serum from a subject immunized with a vaccine composition of a first strain (e.g. VLPs of A/Indonesia 5/05) may be used in an HAI assay with a second strain of whole virus or virus particles (e.g. A/Vietnam/1194/2004), and the HAI titer determined.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be obtained several ways, including: 1) enumeration of lysis plaques (plaque assay) following crystal violet fixation/coloration of cells; 2) microscopic observation of cell lysis in culture; 3) ELISA and spectrophotometric detection of NP virus protein (correlate with virus infection of host cells).

Constructs

The present invention is further directed to a gene construct comprising a nucleic acid encoding a channel protein, for example but not limited to a proton channel protein or a structural virus protein, as described above, operatively linked to a regulatory element that is operative in a plant. Examples of regulatory elements operative in a plant cell and that may be used in accordance with the present invention include but are not limited to a plastocyanin regulatory region (U.S. Pat. No. 7,125,978; which is incorporated herein by reference), or a regulatory region of Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS 1 (associated with the oxygen-evolving complex of photosystem II and described by Stockhaus et al. 1987, 1989; which is incorporated herein by reference).

Regulatory Elements

The use of the terms "regulatory region", "regulatory element" or "promoter" in the present application is meant to reflect a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" may includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, may also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, LR. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. BioI. 48,89-108; which is incorporated by reference), steroid inducible promoter (Aoyama. T. and Chua, N. H., 1997, Plant 1. 2, 397-404; which is incorporated by reference) and ethanol-inducible promoter (Salter, M. G., et al, 1998, Plant 10urnal 16, 127-132; Caddick, M. X., et al, 1998, Nature Biotech. 16, 177-180, which are incorporated by reference) cytokinin inducible IB6 and CKI 1 genes (Brandstatter, I. and Kieber, 1.1., 1998, Plant Cell 10, 1009-1019; Kakimoto, T., 1996, Science 274,982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript (Odell et al., 1985, Nature, 313: 810-812), the rice actin 1 (Zhang et al, 1991, Plant Cell, 3: 1155-1165), actin 2 (An et al., 1996, *Plant J.*, 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995, Plant Mol. Biol. 29: 995-1004).

The term "constitutive" as used herein does not necessarily indicate that a gene under control of the constitutive regulatory region is expressed at the same level in all cell types, but that the gene is expressed in a wide range of cell types even though variation in abundance is often observed. Constitutive regulatory elements may be coupled with other sequences to further enhance the transcription and/or translation of the nucleotide sequence to which they are operatively linked. For example, the CPMV-HT system is derived from the untranslated regions of the Cowpea mosaic virus (CPMV) and demonstrates enhanced translation of the associated coding sequence. By "native" it is meant that the nucleic acid or amino acid sequence is naturally occurring, or "wild type". By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The one or more virus protein such as a structural virus protein or channel protein, for example but not limited to a proton channel protein may be expressed in an expression system comprising a viral based, DNA or RNA, expression system, for example but not limited to, a comovirus-based expression cassette and geminivirus-based amplification element.

The expression system as described herein may comprise an expression cassette based on a bipartite virus, or a virus with a bipartite genome. For example, the bipartite viruses may be of the Comoviridae family. Genera of the Comoviridae family include Comovirus, Nepovirus, Fabavirus, Cheravirus and Sadwavirus. Comoviruses include Cowpea mosaic virus (CPMV), Cowpea severe mosaic virus (CPSMV), Squash mosaic virus (SqMV), Red clover mottle virus (RCMV), Bean pod mottle virus (BPMV), Turnip ringspot virus (TuRSV), Broad bean true mosaic virus (BBtMV), Broad bean stain virus (BBSV), Radish mosaic virus (RaMV). Examples of comovirus RNA-2 sequences comprising enhancer elements that may be useful for various aspects of the invention include, but are not limited to: CPMV RNA-2 (GenBank Accession No. NC_003550), RCMV RNA-2 (GenBank Accession No. NC_003738), BPMV RNA-2 (GenBank Accession No. NC_003495), CPSMV RNA-2 (GenBank Accession No. NC_003544), SqMV RNA-2 (GenBank Accession No. NC_003800), TuRSV RNA-2 (GenBank Accession No. NC_013219.1). BBtMV RNA-2 (GenBank Accession No. GU810904), BBSV RNA2 (GenBank Accession No. FJ028650), RaMV (GenBank Accession No. NC_003800)

Segments of the bipartite comoviral RNA genome are referred to as RNA-1 and RNA-2. RNA-1 encodes the proteins involved in replication while RNA-2 encodes the proteins necessary for cell-to-cell movement and the two capsid proteins. Any suitable comovirus-based cassette may be used including CPMV, CPSMV, SqMV, RCMV, or BPMV, for example, the expression cassette may be based on CPMV.

"Expression cassette" refers to a nucleotide sequence comprising a nucleic acid of interest under the control of, and operably (or operatively) linked to, an appropriate promoter or other regulatory elements for transcription of the nucleic acid of interest in a host cell.

It has been shown that transformation of Nicotiana benthamiana with full-length, replication-competent cDNA copies of both genomic RNAs of CPMV can result in a productive infection (Liu et al., 2004, Virology 323, 37-48, herein incorporated by reference). Examples of CPMV-based expression cassettes are described in WO2007/135480; WO2009/087391; and Sainsbury F. et al., (2008, Plant Physiology; 148: 1212-1218; Sainsbury F. et al., (2008, Plant Biotechnology Journal; 6: 82-92; Sainsbury F. et al., 2009, Plant Biotechnology Journal; 7: 682-693; which documents are herein incorporated by reference). As an example, which is not to be considered limiting, the untranslated regions (UTRs) obtained from the genomic RNA 2 of the cowpea mosaic virus (CPMV) in which the two first translation initiation codons found in the 5'leader sequence have been deleted, may be used as described in WO 2009/087391. When combined to the CaMV 35S promoter and the nopaline synthase (NOS) terminator, the modified CPMV UTRs enhanced translation of the flanking coding region. The CPMV-based expression system was named CPMV-HT (hyperanslatable). Expression cassettes, expression constructs and expression systems of the invention may therefore also comprise a CPMV-based expression system such as for example an CPMV-HT expression system.

As described herein, an expression enhancer sequence, which sequence is derived from (or shares homology with) the RNA-2 genome segment of a bipartite RNA virus, such as a comovirus, in which a target initiation site has been mutated, may be used for expressing a nucleic acid sequence of interest. The present invention further provides processes for increasing the expression, or translational enhancing activity, of a sequence derived from an RNA-2 genome segment of a bipartite virus, which processes comprise mutating a target initiation site therein.

"Enhancer" sequences (or enhancer elements), include sequences derived from (or sharing homology with) the RNA-2 genome segment of a bipartite RNA virus, such as a comovirus, in which a target initiation site has been mutated. Such sequences can enhance downstream expression of a heterologous ORF to which they are attached. Without limitation, it is believed that such sequences when present in transcribed RNA, can enhance translation of a heterologous ORF to which they are attached.

The expression systems may also comprise amplification elements from a geminivirus for example, an amplification element from the bean yellow dwarf virus (BeYDV). BeYDV belongs to the Mastreviruses genus adapted to dicotyledonous plants. BeYDV is monopartite having a single-strand circular DNA genome and can replicate to very high copy numbers by a rolling circle mechanism. BeYDV-derived DNA replicon vector systems have been used for rapid high-yield protein production in plants.

As used herein, the phrase "amplification elements" refers to a nucleic acid segment comprising at least a portion of one or more long intergenic regions (LIR) of a geminivirus genome. As used herein, "long intergenic region" refers to a region of a long intergenic region that contains a rep binding site capable of mediating excision and replication by a geminivirus Rep protein. In some aspects, the nucleic acid segment comprising one or more LIRs may further comprises a short intergenic region (SIR) of a geminivirus genome. As used herein, "short intergenic region" refers to the complementary strand (the short IR (SIR) of a Mastreviruses). Any suitable geminivirus-derived amplification element may be used herein. See, for example, WO2000/20557; WO2010/025285; Zhang X. et al. (2005, Biotechnology and Bioengineering, Vol. 93, 271-279), Huang Z. et al. (2009, Biotechnology and Bioengineering, Vol. 103, 706-714), Huang Z. et al. (2009, Biotechnology and Bioengineering, Vol. 106, 9-17); which are herein incorporated by reference). If more than one LIR is used in the construct, for example two LIRs, then the promoter, CMPV-HT regions and the nucleic acid sequence of interest and the terminator are bracketed by each of the two LIRs.

As described herein, co-delivery of bean yellow dwarf virus (BeYDV)-derived vector and a Rep/RepA-supplying vector, by agroinfiltration of Nicotiana benthamiana leaves results in efficient replicon amplification and robust protein production.

A comovirus-based expression cassette and a geminivirus-derived amplification element may be comprised in respective, first and second vectors, or the component parts may be included in one vector. If two vectors are used, the first and second vectors may be introduced into a plant cell simultaneously or separately.

A viral replicase may also be included in the expression system as described herein to increase expression of the nucleic acid of interest. A non-limiting example of a replicase is a BeYDV replicase (pREP 110) encoding BeYDV Rep and RepA (C2/C1; Huang et al., 2009, Biotechnol. Bioeng. 103, 706-714; which is incorporated herein by reference).

Post-transcriptional gene silencing (PTGS) may be involved in limiting expression of transgenes in plants, and co-expression of a suppressor of silencing from the p19 of Tomato bushy stunt virus (TBSV p19) or potato virus Y (HcPro) may be used to counteract the specific degradation of transgene mRNAs (Brigneti et al., 1998).

Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristexa virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

By "co-expressed" it is meant that two, or more than two, nucleotide sequences are expressed at about the same time within the plant, and within the same tissue of the plant. However, the nucleotide sequences need not be expressed at exactly the same time. Rather, the two or more nucleotide sequences are expressed in a manner such that the encoded products have a chance to interact. For example, the protein that modifies glycosylation of the protein of interest may be expressed either before or during the period when the protein of interest is expressed so that modification of the glycosylation of the protein of interest takes place. The two or more than two nucleotide sequences can be co-expressed using a transient expression system, where the two or more sequences are introduced within the plant at about the same time under conditions that both sequences are expressed. Alternatively, a platform plant comprising one of the nucleotide sequences, for example the sequence encoding the protein that modifies the glycosylation profile of the protein of interest, may be transformed, either transiently or in a stable manner, with an additional sequence encoding the protein of interest. In this case, the sequence encoding the protein that modifies the glycosylation profile of the protein of interest may be expressed within a desired tissue, during a desired stage of development, or its expression may be induced using an inducible promoter, and the additional sequence encoding the protein of interest may be expressed under similar conditions and in the same tissue, to ensure that the nucleotide sequences are co-expressed.

The one or more virus protein may be produced as a transcript from a nucleotide sequence, and the protein cleaved following synthesis, and as required, associated to form a multimeric protein. Therefore, the one or more virus protein also includes a protein or polypeptide comprising subunits that are associated via disulphide bridges (i.e. a multimeric protein). For example, a protein comprising amino acid sequences from two or more than two sources may be processed into subunits, and the subunits associated via disulphide bridges to produce a protein.

The one or more nucleic acid sequences or genetic constructs of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, *Nicotiana* spp., potato, ginseng, pea, oat, rice, soybean, wheat, barley, sunflower, cotton and the like.

The one or more genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (NOS) gene, plant genes such as the soybean storage protein genes, the small subunit of the ribulose-I, 5-bisphosphate carboxylase gene (ssRUBISCO; U.S. Pat. No. 4,962,028; which is incorporated herein by reference), the promoter used in regulating plastocyanin expression, described in U.S. Pat. No. 7,125,978 (which is incorporated herein by reference).

One or more of the genetic constructs of the present invention may also include further enhancers, either translation or transcription enhancers, as may be required. Enhancers may be located 5' or 3' to the sequence being transcribed. Enhancer regions are well known to persons skilled in the art, and may include an ATG initiation codon, adjacent sequences or the like. The initiation codon, if present, may be in phase with the reading frame ("in frame") of the coding sequence to provide for correct translation of the transcribed sequence.

By "transformation" it is meant the interspecific transfer of genetic information (nucleotide sequence) that is manifested genotypically, phenotypically or both. The interspecific transfer of genetic information from a construct to a host may be transient and the transfer of genetic information is not inheritable or the transfer may be heritable and the transfer of genetic information considered stable.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J Virol Meth, 105:343-348, 2002), U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

As described below, transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al., 1997, which is incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacteria* infect and transfer t-DNA copies into the cells. The t-DNA is episomally transcribed and the mRNA translated, leading to the production of the protein of interest in infected cells, however, the passage of t-DNA inside the nucleus is transient.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

It is contemplated that a plant comprising the protein of interest, or expressing the VLP comprising the protein of interest may be administered to a subject or target organism, in a variety of ways depending upon the need and the situation. For example, the protein of interest obtained from the plant may be extracted prior to its use in either a crude, partially purified, or purified form. If the protein is to be purified, then it may be produced in either edible or non-edible plants. Furthermore, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to a subject or an animal with little or no further processing it is preferred that the plant tissue being administered is edible.

The VLP's produced according to the present invention may be purified, partially purified from a plant, portion of a plant or plant matter, or may be administered as an oral vaccine, using methods as know to one of skill in the art. Purification may include production of an apoplast fraction as described in WO 2011/035422 (which is incorporated herein by reference). For preparative size exclusion chromatography, a preparation comprising VLPs may be obtained and insoluble material removed by centrifugation. Precipitation with PEG may also be used. The recovered protein may be quantified using conventional methods (for example, Bradford Assay, BCA), and the extract passed through a size exclusion column, using for example SEPHACRYL™, SEPHADEX™, or similar medium, and the fractions collected. Blue Dextran 2000 or a suitable protein, may be used as a calibration standard. The extract may also be passed through a cation exchange column and active fractions collected. Following chromatography, fractions may be further analyzed by protein electrophoresis, immunoblot, or both, to confirm the presence of VLPs and the protein complement of the fraction.

Also considered part of this invention are transgenic plants, plant cells, seeds or any fraction thereof containing the nucleotide sequences of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

As shown in FIG. 18, HA from B/Brisbane/60/2008 is poorly expressed in agroinfiltrated *Nicotiana benthamiana* leaves (see lanes "1008" or "1029"). However, co-expression of HA-type B with M2 from A/New Caledonia/20/99, results in a significant increase in HA expression (see lanes "1008+1261"; "1009+1261" and 1029+1261"). The increase in HA expression was observed with native type B HA, or a chimeric HA type B. HA expression was observed in the presence or absence of amplification elements (BeYDV), and across various dilutions of *Agrobacterium*. A similar increase in H3 expression was observed when H3 from A/Perth/16/2009 was co-expressed with M2 from A/New Caledonia/20/99 (FIG. 19; compare lane "1019" H3 alone, with "1019+1261" H3 co-expressed with M2).

The present invention includes nucleotide sequences as set forth in Table 3:

TABLE 3

List of Sequence Identification numbers.

| SEQ ID NO: | Description | FIGURE |
|---|---|---|
| 1 | proton channel signature sequence HXXXW | |
| 2 | primer IF-HSA-I-05.s1 + 3c | FIG. 1A |
| 3 | primer IF-H5dTm.r | FIG. 1B |
| 4 | Construct 1191 | FIG. 1D |

TABLE 3-continued

List of Sequence Identification numbers.

| SEQ ID NO: | Description | FIGURE |
|---|---|---|
| 5 | Expression cassette number 489 | FIG. 1E |
| 6 | Amino acid sequence of H5 from influenza A/Indonesia/5/2005 (H5N1) | FIG. 1F |
| 7 | primer IF-S1-M1 + M2ANC.c | FIG. 2A |
| 8 | primer IF-S1-4-M2ANC.r | FIG. 2B |
| 9 | nucleotide sequence of synthesized M2 gene (DQ508860) | FIG. 2C |
| 10 | Expression cassette number 1261 | FIG. 2D |
| 11 | Amino acid sequence of M2 from influenza A/New Caledonia/20/1999 (H1N1) | FIG. 2E |
| 12 | nucleotide sequence of synthesized M2 gene | FIG. 3A |
| 13 | Expression cassette number 859 | FIG. 3B |
| 14 | Amino acid sequence of M2 from influenza A/Puerto Rico/8/1934 (H1N1) | FIG. 3C |
| 15 | primer IF-H1A-C-09.s2 + 4c | FIG. 4A |
| 16 | primer IF-H1A-C-09.s1 – 4r | FIG. 4B |
| 17 | nucleotide sequence of synthesized H1 gene | FIG. 4C |
| 18 | Construct 1192 | FIG. 4E |
| 19 | Expression cassette number 484 | FIG. 4F |
| 20 | Amino acid sequence of PDISP-H1 from influenza A/California/7/2009 (H1N1) | FIG. 4G |
| 21 | primer IF-S2 + S4-H3 Per.c | FIG. 5A |
| 22 | primer IF-S1a4-H3 Per.r | FIG. 5B |
| 23 | nucleotide sequence of synthesized H3 gene | FIG. 5C |
| 24 | Expression cassette number 1019 | FIG. 5D |
| 25 | Amino acid sequence of PDISP/H3 from influenza A/Perth/16/2009 (H3N2) | FIG. 5E |
| 26 | primer IF-S2 + S4-B Bris.c | FIG. 6A |
| 27 | primer IF-S1a4-B Bris.r | FIG. 6B |
| 28 | nucleotide sequence of synthesized HA B Brisbane gene | FIG. 6C |
| 29 | Expression cassette number 1029 | FIG. 6D |
| 30 | Amino acid sequence of PDISP/HA from influenza B/Brisbane/60/2008 | FIG. 6E |
| 31 | Construct 1194 | FIG. 6G |
| 32 | Expression cassette number 1008 | FIG. 6H |
| 33 | primer dTmH5I-B Bris.r | FIG. 7A |
| 34 | primer B Bris-dTmH5I.c | FIG. 7B |
| 35 | primer IF-S1aS4-dTmH5I.r | FIG. 7C |
| 36 | Expression cassette number 1009 | FIG. 7D |
| 37 | Amino acid sequence of PDISP/HA B Brisbane/H5Indo TMCT | FIG. 7E |
| 38 | primer 1039 + 1059.r | FIG. 8A |
| 39 | primer 1039 + 1059.c | FIG. 8B |
| 40 | Expression cassette number 1059 from BeYDV left LIR to BeYDV right LIR. PDISP/HA from influenza B/Brisbane/60/2008 with deleted proteolytic loop | FIG. 8C |
| 41 | Amino acid sequence of PDISP/HA from influenza B/Brisbane/60/2008 with deleted proteolytic loop | FIG. 8D |
| 42 | nucleotide sequence encoding H5 from influenza A/Indonesia/5/2005 (H5N1) | FIG. 1G |
| 43 | nucleotide sequence of PDISP/HA from influenza B/Brisbane/60/2008 with deleted proteolytic loop | FIG. 8E |
| 44 | primer IF-H3V36111.S2 + 4c | FIG. 25A |
| 45 | primer IF-H3V36111.s1-4r | FIG. 25B |
| 46 | nucleotide sequence of synthesized H3 gene | FIG. 25C |
| 47 | expression cassette number 1391 | FIG. 25D |
| 48 | Amino acid sequence of PDISP-H3 from influenza A/Victoria/361/2011 | FIG. 25E |
| 49 | primer IF-HAB110.S1 + 3c | FIG. 26A |
| 50 | primer IF-HAB110.s1-4r | FIG. 26B |
| 51 | nucleotide sequence of synthesized HA B/Wisconin (JN993010) | FIG. 26C |
| 52 | Construct 193 | FIG. 26E |
| 53 | Expression cassette number 1462 | FIG. 26F |
| 54 | Amino acid sequence of HA from influenza B/Wisconsin/1/2010 | FIG. 26G |
| 55 | primer HAB110(PrL-).r | FIG. 27A |
| 56 | primer HAB110(PrL-).c | FIG. 27B |
| 57 | Expression cassette number 1467 | FIG. 27C |
| 58 | Amino acid sequence of HA from influenza B/Wisconsin/1/2010 with deleted proteolytic loop | FIG. 27D |
| 59 | primer IF-HB-M-04.s2 + 4c | FIG. 28A |
| 60 | primer IF-HB-M-04.s1-4r | FIG. 28B |
| 61 | nucleotide sequence of synthesized HA B Malaysia | FIG. 28C |
| 62 | Construct 194 | FIG. 28E |
| 63 | Expression cassette number 1631 | FIG. 28F |
| 64 | Amino acid sequence of PDISP-HA from influenza B/Malaysia/2506/2004 | FIG. 28G |
| 65 | Primer M2ANC2099(A30P).r | FIG. 36A |
| 66 | Primer M2ANC2099(A30P).c | FIG. 36B |
| 67 | Construct 1210 | FIG. 36C |
| 68 | Amino acid sequence of M2 A30P | FIG. 36D |
| 69 | Primer IF-PDI.S1 + 3c | FIG. 37A |
| 70 | Primer IF-pHluorin_primer6.r | FIG. 37B |
| 71 | Nucleotide sequence of PDISP/pHluorin | FIG. 37C |
| 72 | Construct 1871 | FIG. 37D |
| 73 | Amino acid sequence of PDISP/pHluorin | FIG. 37E |
| 74 | Primer IF-pHluorin_primer2.r | FIG. 38A |
| 75 | Construct 1872 | FIG. 38B |
| 76 | Amino acid sequence of PDISP/pHluorin/SEKDEL | FIG. 38C |
| 77 | Primer IF-pHluorin_primer3.c | FIG. 39A |
| 78 | Nucleotide sequence of Man99/pHluorin | FIG. 39B |
| 79 | Construct 1873 | FIG. 39C |
| 80 | Amino acid sequence of Man99/pHluorin | FIG. 39D |
| 81 | Nucleotide sequence of Man99TMD23/pHluorin | FIG. 40A |
| 82 | Construct 1874 | FIG. 40B |
| 83 | Amino acid sequence of Man99TMD23/pHluorin | FIG. 40C |
| 84 | pHluorin-F, 5' | — |
| 85 | pHluorin-R, 5' | — |

The present invention will be further illustrated in the following examples.

EXAMPLES

Material and Methods: Assembly of Expression Cassettes with Influenza Protein

A-2X35 S/CPMV-HT/H5 Indonesia/NOS (Construct Number 489)

Figure 15:
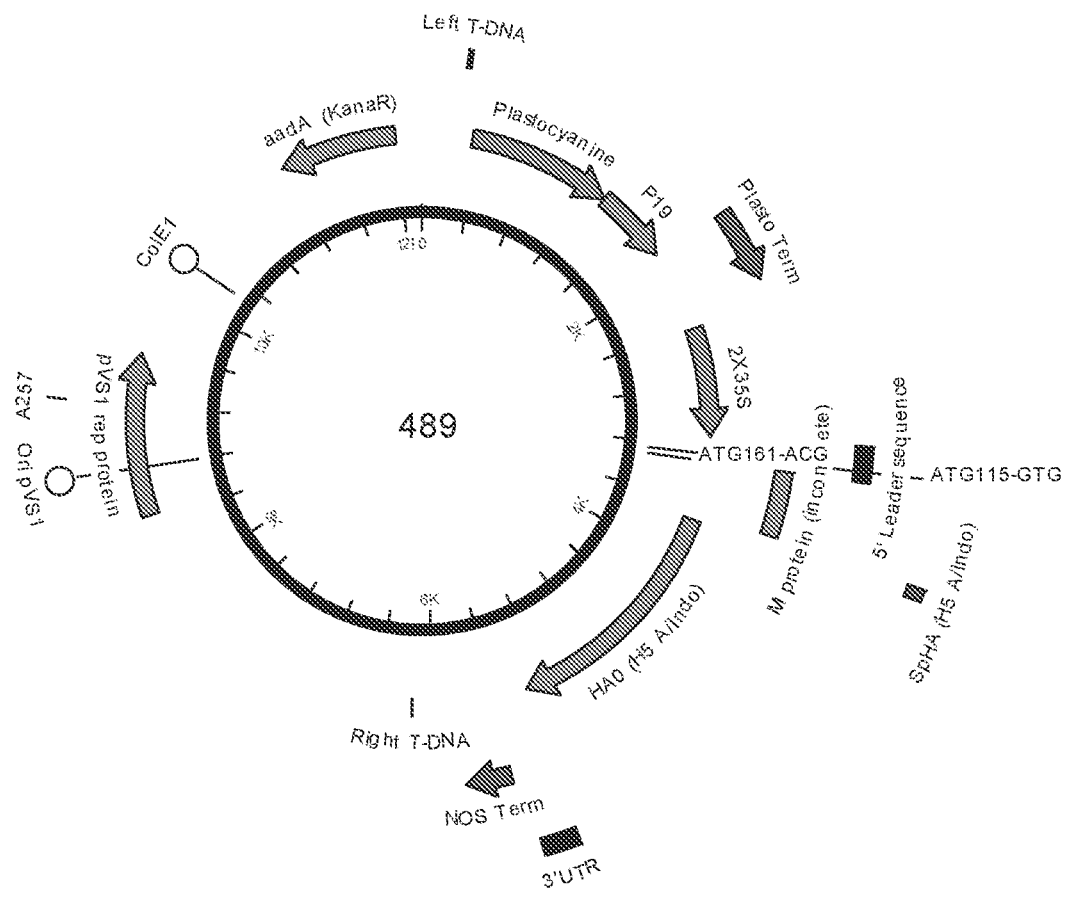
FIG. 15 shows the plasmid map of construct number 489. Construct number 489 directs the expression of wild-type H5 from influenza strain A/Indonesia/05/2005 (H5N1).

A sequence encoding H5 from influenza A/Indonesia/5/2005 (H5N1) was cloned into 2X35 S/CPMV-HT/NOS expression system in a plasmid containing Plasto_pro/P19/Plasto_ter expression cassette using the following PCR-based method. A fragment containing the complete H5 coding sequence was amplified using primers IF-HSA-I-05.s1+3c (FIG. 1A, SEQ ID NO: 2) and IF-H5dTm.r (FIG. 1B, SEQ ID NO: 3) using construct number 972 (see FIG. 94, SEQ ID NO: 134 of WO 2010/003225, which is incorporated herein by reference, for the sequence of construct number 972) as template. The PCR product was cloned in 2X35 S/CPMV-HT/NOS expression system using In-Fusion cloning system (Clontech, Mountain View, Calif.). Construct 1191 (FIG. 1D, SEQ ID NO: 4) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 489 (FIG. 1E, SEQ ID NO: 5). The amino acid sequence of H5 from influenza A/Indonesia/5/2005 (H5N1) is presented in FIG. 1F (SEQ ID NO: 6). A representation of plasmid 489 is presented in FIG. 15.

B-2X35 S/CPMV-HT/M2 New Caledonia/NOS (Construct Number 1261)

Figure 16:
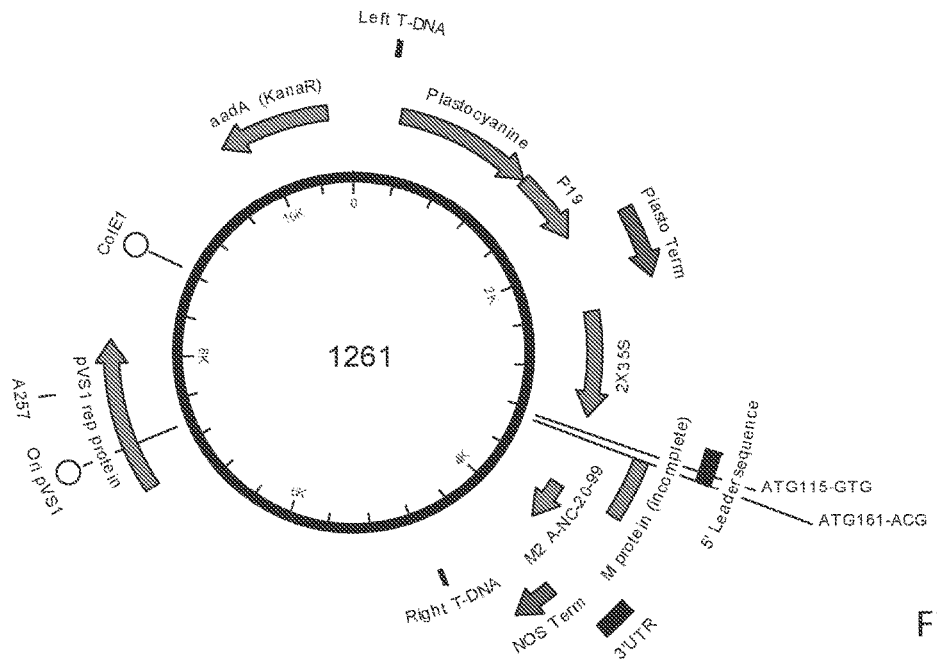
FIG. 16 shows the plasmid map of construct number 1261. Construct number 1261 directs the expression of wild-type M2 from influenza strain A/New Caledonia/20/99 (H1N1).

A sequence encoding M2 from influenza A/New Caledonia/20/1999 (H1N1) was cloned into 2X35 S/CPMV-HT/NOS expression system in a plasmid containing Plasto_pro/P19/Plasto_ter expression cassette using the following PCR-based method. A fragment containing the complete M2 coding sequence was amplified using primers IF-S1-M1+M2ANC.c (FIG. 2A, SEQ ID NO: 7) and IF-S1-4-M2ANC.r (FIG. 2B, SEQ ID NO: 8) using synthesized M2 gene (corresponding to nt 1-26 joined to nt 715-982 from GenBank accession number DQ508860) (FIG. 2C, SEQ ID NO: 9) as template. The PCR product was cloned in 2X35 S/CPMV-HT/NOS expression system using In-Fusion cloning system (Clontech, Mountain View, Calif.). Construct 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 1261 (FIG. 2D, SEQ ID NO: 10). The amino acid sequence of M2 from influenza A/New Caledonia/20/1999 (H1N1) is presented in FIG. 2E (SEQ ID NO: 11). A representation of plasmid 1261 is presented in FIG. 16.

C-2X35 S/CPMV-HT/M2 Puerto Rico/NOS (Construct Number 859)

Figure 17:
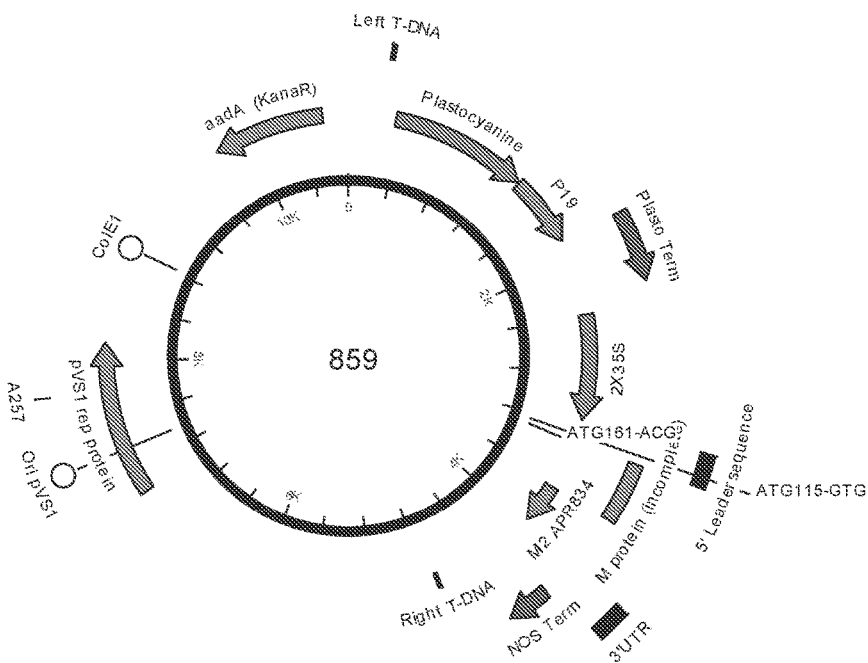
FIG. 17 shows the plasmid map of construct number 859. Construct number 859 directs the expression of wild-type M2 from influenza strain A/Puerto Rico/8/34 (H1N1).

A sequence encoding M2 from influenza A/Puerto Rico/8/1934 (H1N1) was cloned into 2X35 S/CPMV-HT/NOS expression system in a plasmid containing Plasto_pro/P19/Plasto_ter expression cassette using the following PCR-based method. A fragment containing the complete M2 coding sequence was amplified using primers IF-S1-M1+M2ANC.c (FIG. 2A, SEQ ID NO: 7) and IF-S1-4-M2ANC.r (FIG. 2B, SEQ ID NO: 8), using synthesized M2 gene (corresponding to nt 26-51 joined to nt 740-1007 from Genbank accession number EF467824) (FIG. 3A, SEQ ID NO: 12) as template. The PCR product was cloned in 2X35 S/CPMV-HT/NOS expression system using In-Fusion cloning system (Clontech, Mountain View, Calif.). Construct 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The vector is a pCAMBIA binary plasmid and the sequence from left to right t-DNA borders is presented in FIG. 1D (SEQ ID NO: 4). The resulting construct was given number 859 (FIG. 3B, SEQ ID NO: 13). The amino acid sequence of M2 from influenza A/Puerto Rico/8/1934 (H1N1) is presented in FIG. 3C (SEQ ID NO: 14). A representation of plasmid 859 is presented in FIG. 17.

D-2X35 S/CPMV-HT/PDISP/H1 California/NOS (Construct Number 484)

Figure 14:
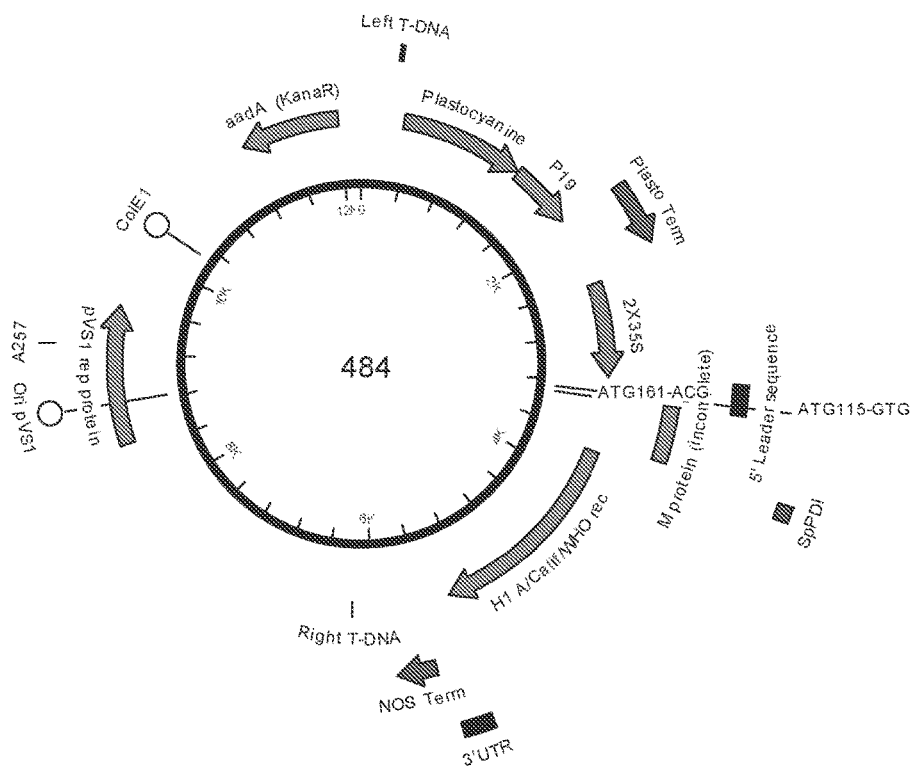
FIG. 14 shows the plasmid map of construct number 484. Construct number 484 directs the expression of wild-type H1 from influenza strain A/California/07/2009 (H1N1).

A sequence encoding H1 from influenza A/California/7/2009 (H1N1) was cloned into 2X35 S-CPMV-HT-PDISP-NOS expression system in a plasmid containing Plasto_pro/P19/Plasto_ter expression cassette using the following PCR-based method. A fragment containing the H1 coding sequence without his wild type signal peptide was amplified using primers IF-H1A-C-09.s2+4c (FIG. 4A, SEQ ID NO: 15) and IF-H1A-C-09.s1-4r (FIG. 4B, SEQ ID NO: 16), using synthesized H1 gene (Genbank accession number FJ966974) (FIG. 4C, SEQ ID NO: 17) as template. The PCR product was cloned in-frame with alfalfa PDI signal peptide in 2X35 S/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 484 (FIG. 4F, SEQ ID NO: 19). The amino acid sequence of PDISP/H1 from influenza A/California/7/2009 (H1N1) is presented in FIG. 4G (SEQ ID NO: 20). A representation of plasmid 484 is presented in FIG. 14.

E-2X35 S/CPMV-HT/PDISP/H3 Perth/NOS (Construct Number 1019)

Figure 13:
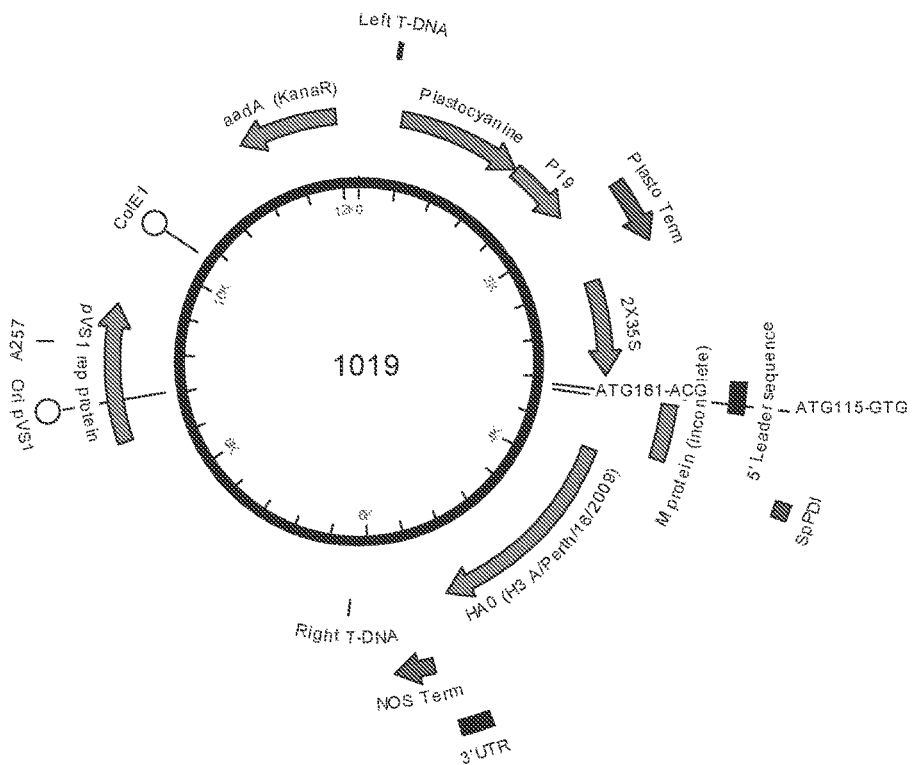
FIG. 13 shows the plasmid map of construct number 1019. Construct number 1019 directs the expression of wild-type H3 from influenza strain A/Perth/16/2009 (H3N2).

A sequence encoding H3 from influenza A/Perth/16/2009 (H3N2) was cloned into 2X35 S/CPMV-HT/PDISP/NOS expression system in a plasmid containing Plasto_pro/P19/Plasto_ter expression cassette using the following PCR-based method. A fragment containing the H3 coding sequence without his wild type signal peptide was amplified using primers IF-S2+S4-H3 Per.c (FIG. 5A, SEQ ID NO: 21) and IF-S1a4-H3 Per.r (FIG. 5B, SEQ ID NO: 22), using synthesized H3 gene (corresponding to nt 26-1726 from Genbank accession number GQ293081) (FIG. 5C, SEQ ID NO: 23) as template. The PCR product was cloned in-frame with alfalfa PDI signal peptide in 2X35 S/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 1019 (FIG. 5D, SEQ ID NO: 24). The amino acid sequence of PDISP/H3 from influenza A/Perth/16/2009 (H3N2) is presented in FIG. 5E (SEQ ID NO: 25). A representation of plasmid 1019 is presented in FIG. 13.

F-2X35 S/CPMV-HT/PDISP/HA B Brisbane/NOS (Construct Number 1029)

Figure 11:
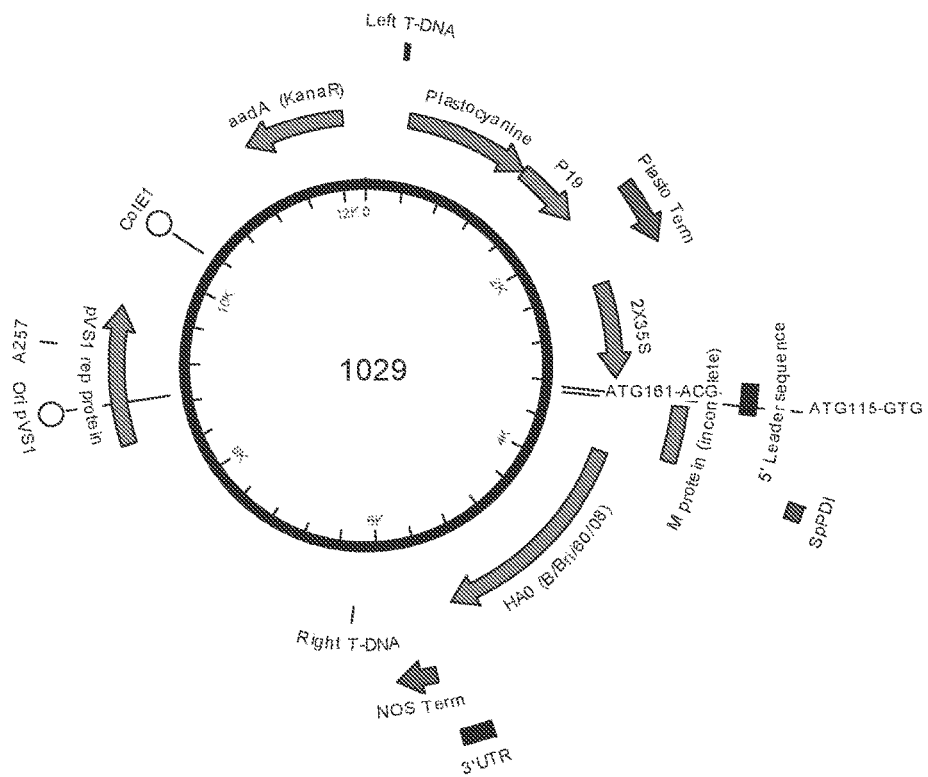
FIG. 11 shows the plasmid map of construct number 1029. Construct number 1029 directs the expression of wild-type HA from influenza strain B/Brisbane/60/2008.

A sequence encoding HA from influenza B/Brisbane/60/2008 was cloned into 2X35 S/CPMV-HT/PDISP/NOS expression system in a plasmid containing Plasto_pro/P19/Plasto_ter expression cassette using the following PCR-based method. A fragment containing HA B Brisbane coding sequence without his wild type signal peptide was amplified using primers IF-S2+S4-B Bris.c (FIG. 6A, SEQ ID NO: 26) and IF-S1a4-B Bris.r (FIG. 6B, SEQ ID NO: 27), using synthesized HA B Brisbane gene (corresponding to nt 34-1791 from Genbank accession number FJ766840) (FIG. 6C, SEQ ID NO: 28) as template. The PCR product was cloned in-frame with alfalfa PDI signal peptide in 2X35 S/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 1029 (FIG. 6D, SEQ ID NO: 29). The amino acid sequence of PDISP/HA from influenza B/Brisbane/60/2008 is presented in FIG. 6E (SEQ ID NO: 30). A representation of plasmid 1029 is presented in FIG. 11.

G-2X35 S/CPMV-HT/PDISP/HA B Brisbane/NOS into BeYDV+Replicase Amplification System (Construct Number 1008)

A sequence encoding HA from influenza B/Brisbane/60/2008 was cloned into 2X35 S/CPMV-HT/PDISP/NOS comprising the BeYDV+replicase amplification system in a plasmid containing Plasto pro/P19/Plasto ter expression cassette using the following PCR-based method. A fragment containing HA B Brisbane coding sequence without his wild type signal peptide was amplified using primers IF-S2+S4-B Bris.c (FIG. 6A, SEQ ID NO: 26) and IF-S1a4-B Bris.r (FIG. 6B, SEQ ID NO: 27), using synthesized HA B Brisbane gene (corresponding to nt 34-1791 from Genbank accession number FJ766840) (FIG. 6C, SEQ ID NO: 28) as template. The PCR product was cloned in-frame with alfalfa PDI signal peptide in 2X35 S/CPMV-HT/NOS expression cassette into the BeYDV amplification system using In-Fusion cloning system (Clontech, Mountain View, Calif.). Construct 1194 (see FIGS. 6F and 6G) was digested with SacII and StuI restriction enzyme and the linearized plasmid was used for the In-Fusion assembly reaction. Construct number 1194 is an acceptor plasmid intended for "In Fusion" cloning of genes of interest in frame with an alfalfa PDI signal peptide in a CPMV-HT-based expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6G (SEQ ID NO: 31). The resulting construct was given number 1008 (FIG. 6H SEQ ID NO: 32). The amino acid sequence of Influenza PDISP/HA from B/Brisbane/60/08 is presented in FIG. 6E (SEQ ID NO: 30). A representation of plasmid 1008 is presented in FIG. 9.

H-2X35 S/CPMV-HT/PDISP/HA B Brisbane/H5 Indonesia Transmembrane Domain and Cytoplasmic Tail (H5Indo TMCT)/NOS into BeYDV+Replicase Amplification System (Construct number 1009)

A sequence encoding HA from influenza B/Brisbane/60/2008 ectodomain fused to the transmembrane and cytosolic domains of H5 from A/Indonesia/5/2005 (H5N1) was cloned into 2X35 S/CPMV-HT/PDISP/NOS comprising the BeYDV+replicase amplification system in a plasmid containing Plasto_pro/P19/Plasto_ter expression cassette as follows using the PCR-based ligation method presented by Darveau et al. (Methods in Neuroscience 26: 77-85 (1995)). In a first round of PCR, a fragment containing HA B Brisbane ectodomain coding sequence without the native signal peptide, transmembrane and cytoplasmic domains was amplified using primers IF-S2+S4-B Bris.c (FIG. 6A, SEQ ID NO: 26) and dTmH5I-B Bris.r (FIG. 7A, SEQ ID NO: 33), using synthesized HA B Brisbane gene (corresponding to nt 34-1791 from Genbank accession number FJ766840) (FIG. 6C, SEQ ID NO: 28) as template. A second fragment containing the transmembrane and cytoplasmic domains of H5 Indonesia was amplified using primers B Bris-dTmH5I.c (FIG. 7B, SEQ ID NO: 34) and IF-S1aS4-dTmH5I.r (FIG. 7C, SEQ ID NO: 35), using construct number 489 (see FIG. 1E, SEQ ID NO: 5) as template. The PCR products from both amplifications were then mixed and used as template for a second round of amplification using IF-S2+S4-B Bris.c (FIG. 6A, SEQ ID NO: 26) and IF-HSdTm.r (FIG. 7C, SEQ ID NO: 34) as primers. The resulting fragment was cloned in-frame with alfalfa PDI signal peptide in 2X35 S/CPMV-HT/NOS expression cassette into the BeYDV amplification system using In-Fusion cloning system (Clontech, Mountain View, Calif.). Construct 1194 (FIGS. 6F and 6G) was digested with SacII and StuI restriction enzyme and the linearized plasmid was used for the In-Fusion assembly reaction. Construct number 1194 is an acceptor plasmid intended for "In Fusion" cloning of genes of interest in frame with an alfalfa PDI signal peptide in a CPMV HT-based expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6G (SEQ ID NO: 31). The resulting construct was given number 1009 (FIG. 7D, SEQ ID NO: 36). The amino acid sequence of PDISP/HA B Brisbane/H5indo TMCT is presented in FIG. 7E (SEQ ID NO: 37). A representation of plasmid 1009 is presented in FIG. 10.

I-2X35 S/CPMV-HT/PDISP-HA B Brisbane with Deleted Proteolytic Loop into BeYDV+Replicase Amplification System (Construct Number 1059)

Figure 12:
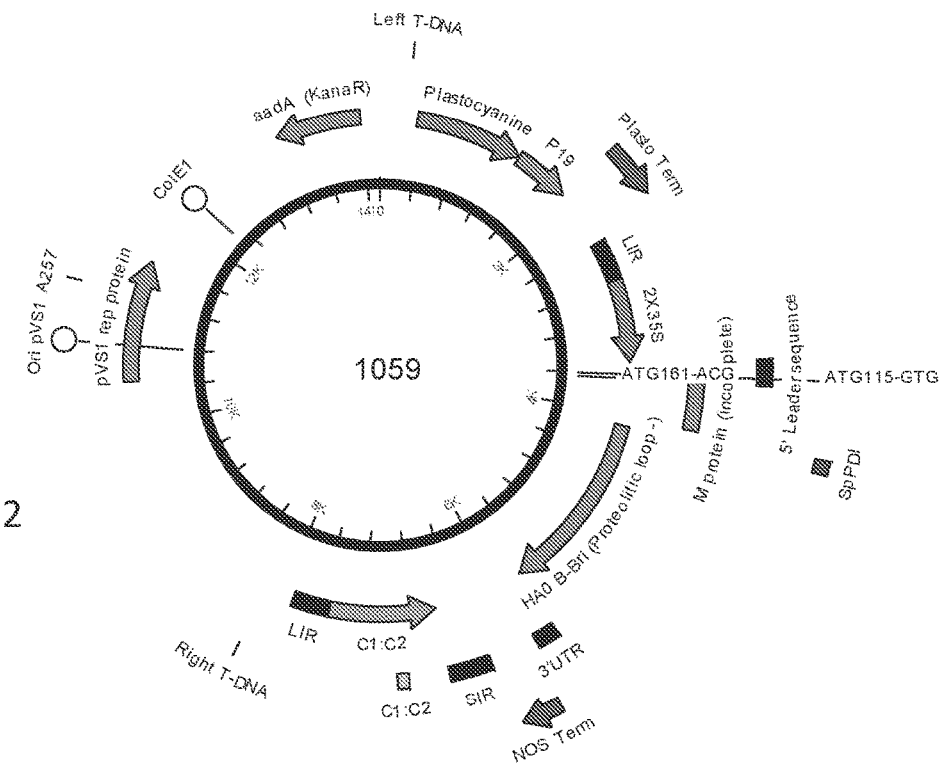
FIG. 12 shows the plasmid map of construct number 1059. Construct number 1059 directs the expression of a mutant HA from influenza strain B/Brisbane/60/2008 with deleted proteolytic loop. This construct comprises BeYDV-derived elements for DNA amplification.

A sequence encoding HA from influenza B/Brisbane/60/2008 with deleted proteolytic loop was cloned into 2X35 S/CPMV-HT/PDISP/NOS comprising the BeYDV+replicase amplification system in a plasmid containing Plasto_pro/P19/Plasto_ter expression cassette using the following PCR-based ligation method presented by Darveau et al. (Methods in Neuroscience 26: 77-85 (1995)). In a first round of PCR, a fragment containing HA B Brisbane coding sequence from nt 46 to nt 1065 was amplified using primers IF-S2+S4-B Bris.c (FIG. 6A, SEQ ID NO: 26) and 1039+1059.r (FIG. 8A, SEQ ID NO: 38), using synthesized HA B Brisbane gene (corresponding to nt 34-1791 from Genebank accession number FJ766840) (FIG. 6C, SEQ ID NO: 28) as template. A second fragment, containing HA B Brisbane coding sequence from nt 1123 to nt 1758, was amplified using primers 1039+1059.c (FIG. 8B, SEQ ID NO: 39) and IF-S1a4-B Bris.r (FIG. 6B, SEQ ID NO: 27), using synthesized HA B Brisbane gene (corresponding to nt 34-1791 from Genbank accession number FJ766840) (FIG. 6C, SEQ ID NO: 28) as template. The PCR products from both amplifications were then mixed and used as template for a second round of amplification using IF-S2+S4-B Bris.c (FIG. 6A, SEQ ID NO: 26) and IF-HSdTm.r IF-S1a4-B Bris.r (FIG. 6B, SEQ ID NO: 27) as primers. The resulting fragment (encoding HA B/Brisbane/60/2008 Δa.a. 356-374 with a GG linker between fragments) was cloned in-frame with alfalfa PDI signal peptide in 2X35 S/CPMV-HT/NOS expression cassette comprising the BeYDV amplification system using In-Fusion cloning system (Clontech, Mountain View, Calif.). Construct 1194 (FIGS. 6F and 6G) was digested with SacII and StuI restriction enzyme and the linearized plasmid was used for the In-Fusion assembly reaction. Construct number 1194 is an acceptor plasmid intended for "In Fusion" cloning of genes of interest in frame with an alfalfa PDI signal peptide in a CPMV-HT-based expression cassette into the BeYDV amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6G (SEQ ID NO: 31). The resulting construct was given number 1059 (FIG. 8C, SEQ ID NO: 40). The amino acid sequence of PDISP-HA B/Brisbane/60/2008 with deleted proteolytic loop is presented in FIG. 8D (SEQ ID NO: 41). A representation of plasmid 1059 is presented in FIG. 12.

A-2X35 S/CPMV-HT/PDISP/H3 Victoria/NOS (Construct Number 1391)

A sequence encoding H3 from influenza A/Victoria/361/2011 (H3N2) was cloned into 2X35 S-CPMV-HT-PDISP-NOS expression system in a plasmid containing Plasto_pro/P19/Plasto_ter expression cassette using the following PCR-based method. A fragment containing the H3 coding sequence without his wild type signal peptide was amplified using primers IF-H3V36111.S2+4c (FIG. 25A, SEQ ID NO: 44) and IF-H3V36111.s1-4r (FIG. 25B, SEQ ID NO: 45), using synthesized H3 gene (corresponding to nt 25 to 1725 from GISAID EPI_ISL_101506 isolate HA sequence) (FIG. 25C, SEQ ID NO: 46) as template. The PCR product was cloned in-frame with alfalfa PDI signal peptide in 2X35 S/CPMV-HT/NOS expression system using In-Fusion cloning system (Clontech, Mountain View, Calif.). Construct 1192 (FIG. 4D) was digested with SacII and StuI restriction enzyme and the linearized plasmid was used for the In-Fusion assembly reaction. Construct number 1192 is an acceptor plasmid intended for "In Fusion" cloning of genes of interest in frame with an alfalfa PDI signal peptide in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 4E (SEQ ID NO: 18). The resulting construct was given number 1391 (FIG. 25D, SEQ ID NO: 47). The amino acid sequence of PDISP/H3 from Influenza A/Victoria/361/2011 (H3N2) is presented in FIG. 25E (SEQ ID NO: 48). A representation of plasmid 1391 is presented in FIG. 25F.

B-2X35 S/CPMV-HT/HA B Wisconsin/NOS into BeYDV (m)+Replicase Amplification System (Construct Number 1462)

A sequence encoding HA from influenza B/Wisconsin/1/2010 was cloned into 2X35 S/CPMV-HT/NOS comprising the BeYDV(m)+replicase amplification system in a plasmid containing Plasto_pro/P19/Plasto_ter expression cassette using the following PCR-based method. A fragment containing the complete HA B Wisconsin coding sequence was amplified using primers IF-HAB110.S1+3c (FIG. 26A, SEQ ID NO: 49) and IF-HAB110.s1-4r (FIG. 26B, SEQ ID NO: 50), using synthesized HA B Wisconsin gene (Genbank accession number JN993010) (FIG. 26C, SEQ ID NO: 51) as template. The PCR product was cloned in 2X35 S/CPMV-HT/NOS expression cassette into the BeYDV(m) amplification system using In-Fusion cloning system (Clontech, Mountain View, Calif.). Construct 193 (FIG. 26D) was digested with SacII and StuI restriction enzyme and the linearized plasmid was used for the In-Fusion assembly reaction. Construct number 193 is an acceptor plasmid intended for "In Fusion" cloning of genes of interest in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 26E (SEQ ID NO: 52). The resulting construct was given number 1462 (FIG. 26F, SEQ ID NO: 53). The amino acid sequence of PDISP/HA from Influenza B/Wisconsin/1/2010 is presented in FIG. 26G (SEQ ID NO: 54). A representation of plasmid 1462 is presented in FIG. 26H.

C-2X35 S/CPMV-HT/HA B Wisconsin with Deleted Proteolytic Loop into BeYDV(m)+Replicase Amplification System (Construct Number 1467)

A sequence encoding HA from influenza B/Wisconsin/1/2010 with deleted proteolytic loop was cloned into 2X35 S/CPMV-HT/NOS comprising the BeYDV(m)+replicase amplification system in a plasmid containing Plasto_pro/P19/Plasto_ter expression cassette using the following PCR-based ligation method presented by Darveau et al. (Methods in Neuroscience 26: 77-85 (1995)). In a first round of PCR, a fragment containing HA B Wisconsin coding sequence from nt 1 to nt 1062 was amplified using primers IF-HAB110.S1+3c (FIG. 26A, SEQ ID NO: 49) and HAB110(PrL-).r (FIG. 27A, SEQ ID NO: 55), using synthesized HA B Wisconsin gene (Genbank accession number JN1993010) (FIG. 26C, SEQ ID NO: 51) as template. A second fragment, containing HA B Wisconsin coding sequence from nt 1120 to nt 1755, was amplified using primers HAB110(PrL-).c (FIG. 27B, SEQ ID NO: 56) and IF-HAB110.s1-4r (FIG. 26B, SEQ ID NO: 50), using synthesized HA B Wisconsin gene (Genbank accession number JN993010) (FIG. 26C, SEQ ID NO: 51) as template. The PCR products from both amplifications were then mixed and used as template for a second round of amplification using IF-HAB110.S1+3c (FIG. 26A, SEQ ID NO: 49) and IF-HAB110.s1-4r (FIG. 26B, SEQ ID NO: 50) as primers. The resulting fragment (encoding HA B/Wisconsin/1/2010 Δa.a. 340-358 with a GG linker between fragments) was cloned in 2X35 S/CPMV-HT/NOS expression cassette comprising the BeYDV(m) amplification system using In-Fusion cloning system (Clontech, Mountain View, Calif.). Construct 193 (FIG. 26D) was digested with SacII and StuI restriction enzyme and the linearized plasmid was used for the In-Fusion assembly reaction. Construct number 193 is an acceptor plasmid intended for "In Fusion" cloning of genes of interest in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 26E (SEQ ID NO: 52). The resulting construct was given number 1467 (FIG. 27C, SEQ ID NO: 57). The amino acid sequence of HA from Influenza B/Wisconsin/1/2010 with deleted proteolytic loop is presented in FIG. 27D (SEQ ID NO: 58). A representation of plasmid 1467 is presented in FIG. 27E.

D-2X35 S/CPMV-HT/PDISP/HA B Malaysia/NOS into BeYDV(m)+Replicase Amplification System (Construct Number 1631)

A sequence encoding HA from influenza B/Malaysia/2506/2004 was cloned into 2X35 S/CPMV-HT/PDISP/NOS comprising the BeYDV(m)+replicase amplification system in a plasmid containing Plasto_pro/P19/Plasto_ter expression cassette using the following PCR-based method. A fragment containing HA B Malaysia coding sequence without his wild type signal peptide was amplified using primers IF-HB-M-04.s2+4c (FIG. 28A, SEQ ID NO: 59) and IF-HB-M-04.s1-4r (FIG. 28B, SEQ ID NO: 60), using synthesized HA B Malaysia gene (corresponding to nt 31-1743 from Genbank accession number EU124275. Silent mutations T759C and C888G were inserted in synthesized sequence in order to modify DraIII and BamHI restriction enzyme recognition sites) (FIG. 28C, SEQ ID NO: 61) as template. The PCR product was cloned in-frame with alfalfa PDI signal peptide in 2X35 S/CPMV-HT/NOS expression cassette into the BeYDV(m) amplification system using In-Fusion cloning system (Clontech, Mountain View, Calif.). Construct 194 (FIG. 28D) was digested with SacII and StuI restriction enzyme and the linearized plasmid was used for the In-Fusion assembly reaction. Construct number 194 is an acceptor plasmid intended for "In Fusion" cloning of genes of interest in frame with an alfalfa PDI signal peptide in a CPMV-HT-based expression cassette into the BeYDV(m) amplification system. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 28E (SEQ ID NO: 62). The resulting construct was given number 1631 (FIG. 28F, SEQ ID NO: 63). The amino acid sequence of PDISP/HA from Influenza B/Malaysia/2506/2004 is presented in FIG. 28G (SEQ ID NO: 64). A representation of plasmid 1631 is presented in FIG. 28H.

B-2X35 S/CPMV-HT/M2 New Caledonia (A30P)/NOS (Construct Number 1210)

A sequence encoding M2 from influenza A/New Caledonia/20/1999 (H1N1) with mutation A30P was cloned into 2X35 S/CPMV-HT/NOS expression system in a plasmid containing Plasto pro/P19/Plasto ter expression cassette using the following PCR-based ligation method presented by Darveau et al. (Methods in Neuroscience 26: 77-85 (1995)). In a first round of PCR, a fragment containing M2 from influenza A/New Caledonia/20/1999 (H1N1) including A30P mutation coding sequence from nt 1 to nt 105 was amplified with primers IF-S1-M1+M2ANC.c (FIG. 2A, SEQ ID NO:7) and M2ANC2099(A30P).r (FIG. 37A, SEQ ID NO:65), using synthesized M2 gene (corresponding to nt 1-26 joined to nt 715-982 from GenBank accession number DQ508860) (FIG. 2C, SEQ ID NO:9) as template. A second fragment, containing M2 from influenza A/New Caledonia/20/1999 (H1N1) including A30P mutation coding sequence from nt 80 to nt 294, was amplified with primers M2ANC2099(A30P).c (FIG. 37B, SEQ ID NO:66) and IF-S1-4-M2ANC.r (FIG. 2B, SEQ ID NO:8) using synthesized M2 gene (corresponding to nt 1-26 joined to nt 715-982 from GenBank accession number DQ508860) (FIG. 2C, SEQ ID NO:9) as template. The PCR products from both amplifications were then mixed and used as template for a second round of amplification using IF-S1-M1+M2ANC.c (FIG. 2A, SEQ ID NO:7) and IF-S1-4-M2ANC.r (FIG. 2B, SEQ ID NO:8) as primers. The PCR product (comprising M2 from influenza A/New Caledonia/20/1999 (H1N1) with mutation A30P) was cloned in 2X35 S/CPMV-HT/NOS expression system using In-Fusion cloning system (Clontech, Mountain View, Calif.). Construct number 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO:4). The resulting construct was given number 1210 (FIG. 37C, SEQ ID NO:67). The amino acid sequence of M2 from influenza A/New Caledonia/20/1999 (H1N1) with mutation A30P is presented in FIG. 37D (SEQ ID NO:68). A representation of plasmid 1210 is presented in FIG. 37E.

Sec-pHluorin: C-2X35 S/CPMV-HT/PDISP/pHluorin/NOS (Construct Number 1871)

A sequence encoding the pHluorin (GenBank accession AF058694) fused to the plant signal peptide of alfalfa protein disulfide isomerase for the localisation to the plant apoplast (PDISP/pHluorin) was cloned into 2X35 S/CPMV-HT/NOS expression system in a plasmid containing Plasto pro/P19/Plasto ter expression cassette using the following PCR-based method. A fragment containing PDISP/pHluorin coding sequence was amplified using primers IF-PDI.S1+3c (FIG. 37A, SEQ ID NO:69) and IF-pHluorin_primer6.r (FIG. 37B, SEQ ID NO:70) using synthesized PDISP/pHluorin (FIG. 37C, SEQ ID NO:71) as template. The PCR product was cloned in 2X35 S/CPMV-HT/NOS expression system using In-Fusion cloning system (Clontech, Mountain View, Calif.). Construct number 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO: 4). The resulting construct was given number 1871 (FIG. 37D, SEQ ID NO: 72). The amino acid sequence of PDISP/pHluorin is presented in FIG. 37E (SEQ ID NO: 73). A representation of plasmid 1871 is presented in FIG. 38F and schematically presented in FIG. 32A (sec-pHluorin).

ER-pHluorin: D-2X35 S/CPMV-HT/PDISP/pHluorin/SEKDEL/NOS (Construct number 1872)

A sequence encoding the pHluorin (GenBank accession AF058694) fused to the plant signal peptide of alfalfa protein disulfide isomerase for the localisation to the plant endoplasmic reticulum (PDISP/pHluorin/SEKDEL) was cloned into 2X35 S/CPMV-HT/NOS expression system in a plasmid containing Plasto pro/P19/Plasto ter expression cassette using the following PCR-based method. A fragment containing PDISP/pHluorin/SEKDEL coding sequence was amplified using primers IF-PDI.S1+3c (FIG. 37A, SEQ ID NO:69) and IF-pHluorin_primer2.r (FIG. 38A, SEQ ID NO:74) using synthesized PDISP/pHluorin (FIG. 37C, SEQ ID NO:71) as template. The PCR product was cloned in 2X35 S/CPMV-HT/NOS expression system using In-Fusion cloning system (Clontech, Mountain View, Calif.). Construct number 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO:4). The resulting construct was given number 1872 (FIG. 38B, SEQ ID NO:75). The amino acid sequence of PDISP/pHluorin/SEKDEL is presented in FIG. 38C (SEQ ID NO:76). A representation of plasmid 1872 is presented in FIG. 38D, and schematically presented in FIG. 32A (ER-pHluorin).

E-2X35 S/CPMV-HT/Man99/pHluorin/NOS (Construct number 1873)

A sequence encoding the pHluorin (GenBank accession AF058694) fused to the cytosolic tail, the transmembrane domain and the luminal end of the α-mannosidase I from *Glycine max* for the localisation to the plant cys-Golgi network (Man99/pHluorin) was cloned into 2X35 S/CPMV-HT/NOS expression system in a plasmid containing Plasto pro/P19/Plasto ter expression cassette using the following PCR-based method. A fragment containing Man99/pHluorin coding sequence was amplified using primers IF-pHluorin_primer3.c (FIG. 39A, SEQ ID NO:77) and IF-pHluorin_primer6.r (FIG. 37B, SEQ ID NO:70) using synthesized Man99/pHluorin (FIG. 39B, SEQ ID NO:78; having the ATG changed by the cytosolic tail, the transmembrane domain and the luminal end of the α-mannosidase I coding sequence (nt 1 to nt 297 from GenBank accession number AF126550)) as template. The PCR product was cloned in 2X35 S/CPMV-HT/NOS expression system using In-Fusion cloning system (Clontech, Mountain View, Calif.). Construct number 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO:10). The resulting construct was given number 1873 (FIG. 39C, SEQ ID NO:79). The amino acid sequence of Man99/pHluorin is presented in FIG. 39D (SEQ ID NO:80). A representation of plasmid 1873 is presented in FIG. 39E.

F-2X35 S/CPMV-HT/PDISP/Man99TMD23/pHluorin/NOS (Construct Number 1874)

A sequence encoding the pHluorin (GenBank accession AF058694) fused to the cytosolic tail, a modified transmembrane domain and the luminal end of the α-mannosidase I from *Glycine max* for the localisation to the plant trans-Golgi network (Man99TMD23/pHluorin) was cloned into 2X35 S/CPMV-HT/NOS expression system in a plasmid containing Plasto pro/P19/Plasto ter expression cassette using the following PCR-based method. A fragment containing Man99TMD23/pHluorin coding sequence was amplified using primers IF-pHluorin_primer3.c (FIG. 39A, SEQ ID NO:77) and IF-pHluorin_primer6.r (FIG. 38B, SEQ ID NO:70) using synthesized Man99TMD23/pHluorin (FIG. 40A, SEQ ID NO:81; having the ATG changed by the cytosolic tail, a 23 amino acid transmembrane domain and the luminal end of the α-mannosidase I coding sequence (nt 1 to nt 297 from GenBank accession number AF126550 with a 21 bases insertion between nt 135 and 136)) as template. The PCR product was cloned in 2X35 S/CPMV-HT/NOS expression system using In-Fusion cloning system (Clontech, Mountain View, Calif.). Construct number 1191 (FIG. 1C) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 1D (SEQ ID NO:4). The resulting construct was given number 1874 (FIG. 40B, SEQ ID NO:82). The amino acid sequence of Man99TMD23/pHluorin is presented in FIG. 40C (SEQ ID NO:83). A representation of plasmid 1873 is presented in FIG. 40D.

*Agrobacterium* Transfection

*Agrobacterium* strain AGL1 was transfected by electroporation with the DNA constructs using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

The terms "biomass" and "plant matter" as used herein are meant to reflect any material derived from a plant. Biomass or plant matter may comprise an entire plant, tissue, cells, or any fraction thereof. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

*Agrobacteria* transfected with each construct were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 2-6 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 3 volumes of cold 50 mM Tris pH 8.0, 0.15 M NaCl, 0.1% Triton X-100 and 1 mM phenylmethanesulfonyl fluoride. After homogenization, the slurries were centrifuged at 10,000 g for 10 min at 4° C. and these clarified crude extracts (supernatant) kept for analyses.

Protein Analysis and Immunoblotting

The total protein content of clarified crude extracts was determined by the Bradford assay (Bio-Rad, Hercules, Calif.) using bovine serum albumin as the reference standard. Proteins were separated by SDS-PAGE and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed with a first incubation with a primary antibody (Table 4 presents the antibodies and conditions used for the detection of each HA), in 2 µg/ml in 2% skim milk in TBS-Tween 20 0.1%. Secondary antibodies used for chemiluminescence detection were as indicated in Table 4, diluted as indicated in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

TABLE 4

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| B | B/Brisbane/60/2008 | Non-reducing | TGA, AS397 | 1:20000 | Rabbit anti-sheep (JIR 313-035-045) | 1:10 000 |
| B | B/Wisconsin/1/2010 | Non-reducing | NIBSC 07/356 | 1:2000 | Rabbit anti-sheep (JIR 313-035-045) | 1:10 000 |
| B | B/Malaysia/2506/2004 | Non-reducing | NIBSC 07/184 | 1:2000 | Rabbit anti-sheep (JIR 313-035-045) | 1:10 000 |
| H3 | A/Perth/16/2009 (H3N2) | Non-reducing | TGA, AS400 | 1:20000 | Rabbit anti-sheep (JIR 313-035-045) | 1:10 000 |
| H3 | A/Victoria/361/2011 | Non-reducing | TGA, AS400 | 1:20000 | Rabbit anti-sheep (JIR 313-035-045) | 1:10 000 |
| H1 | A/California/07/2009 (H1N1) | Reducing | Sino, 11055-MMO1 | 1 µg/ml | Goat anti-mouse (JIR 115-035-146) | 1:7 500 |
| H5 | A/Indonesia/05/2005 (H5N1) | Reducing | CBER, S-7858 | 1:4000 | Rabbit anti-sheep (JIR 313-035-045) | 1:10 000 |

JIR: Jackson ImmunoResearch, West Grove, PA, USA;
CBER: Center for Biologics Evaluation and Research, Rockville, MD, USA.
Sino: Sino Biological inc., Beijing, China.
TGA: Therapeutic Goods Administration, Australia.
NIBSC: National Institute for Biological Standards and Control, United Kingdom Hemagglutination Assay Hemagglutination assay was based on a method described by Nayak and Reichl (2004). Briefly, serial double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, Conn.) was diluted in PBS and run as a control on each plate.

Example 1

Effect of Influenza M2 Co-Expression on the Accumulation Level of B HA and H3

The effect of influenza M2 co-expression on the accumulation level of HA from different influenza strains was analyzed by co-transferring constructs driving expression of HA with a construct for the expression of M2 from influenza A/New Caledonia/20/1999 (H1N1) in the agroinfiltration-based transient transformation system.

Figure 19:
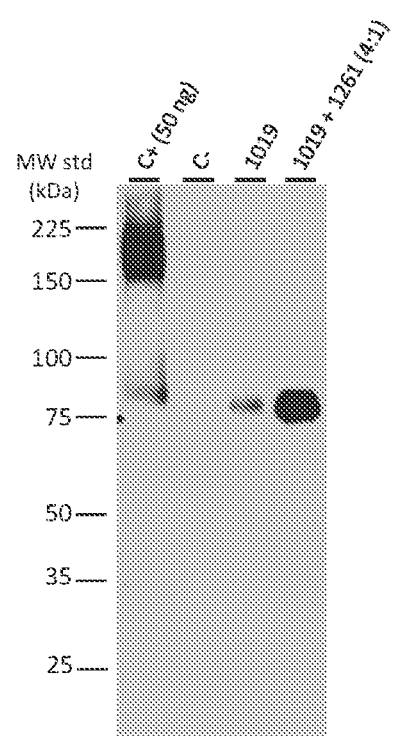
FIG. 19 shows a Western blot analysis of HA protein expression in agroinfiltrated *Nicotiana benthamiana* leaves. Lane "C+": Positive control, semi-purified A/Wisconsin/15/2009 (H3N2) virus from the Therapeutic Goods Administration, Australia; "C-": negative control, mock-infiltrated plants; "1019": expression of wild-type HA from A/Perth/16/2009 (H3N2); "1019+1261": co-expression of wild-type HA from A/Perth/16/2009 (H3N2) with M2 from A/New Caledonia/20/99. The ratio indicates the proportion of *Agrobacterium* cultures used in co-expression experiments.

Western blot analysis of protein extracts from plants transformed with gene constructs driving the expression of influenza B HA (from B/Brisbane/60/2008) (constructs no. 1008, 1009 and 1029) in the presence or absence of M2-expression construct (construct no. 1261) showed that M2 co-expression results in increased accumulation of influenza B HA (FIG. 18). Similarly, the co-expression of M2 with H3 from influenza A/Perth/16/2009 (construct no. 1019+1261) resulted in increased accumulation of H3 in transformed plants when compared to plants transformed with H3-expression construct only (construct no. 1019) as shown in FIG. 19.

Figure 20:
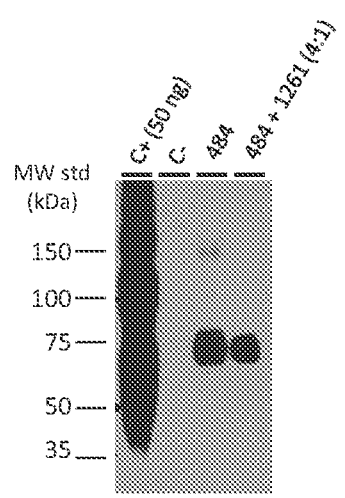
FIG. 20 shows a Western blot analysis of HA protein expression in agroinfiltrated *Nicotiana benthamiana* leaves. Lane "C+": Positive control, semi-purified A/California/7/2009 (H1N1) NYMC X-179A from NIBSC virus (NIBSC code 09/146); "C-": negative control, mock-infiltrated plants; "484": expression of wild-type HA from A/California/7/2009 (H1N1); "484+1261": co-expression of wild-type HA from A/California/7/2009 (H1N1) with M2 from A/New Caledonia/20/99. The ratio indicates the proportion of *Agrobacterium* cultures used in co-expression experiments.
Figure 21:
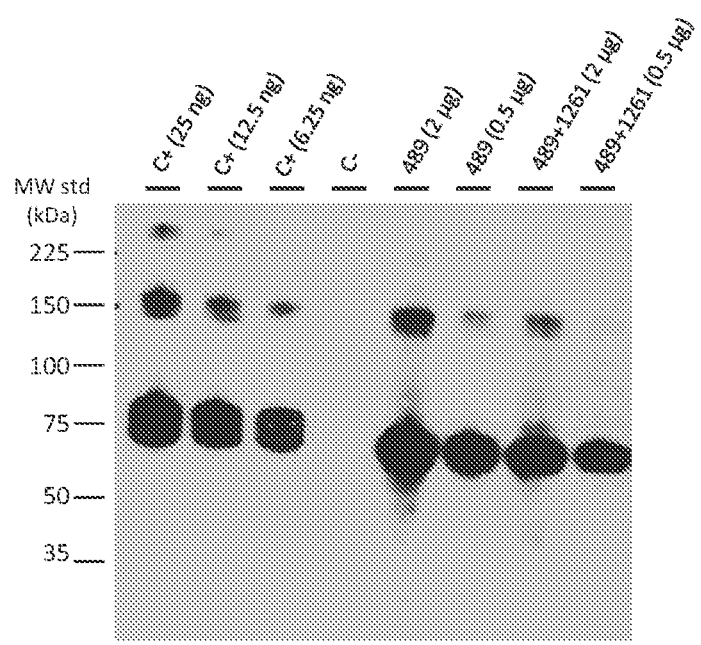
FIG. 21 shows a Western blot analysis of HA protein expression in agroinfiltrated *Nicotiana benthamiana* leaves. Lane "C+": Positive control, purified recombinant H5 from A/Indonesia/05/2005, Immune Technology Corporation (product no. IT-003-052p),"C-": negative control, mock-infiltrated plants; "489": expression of wild-type HA from A/Indonesia/5/05 (H5N1); "489+1261": co-expression of wild-type HA from A/Indonesia/5/05 (H5N1) with M2 from A/New Caledonia/20/99.

Western blot analysis of protein extracts from plants co-expressing M2 with H1 from influenza A/California/07/2009 showed that the co-expression of M2 with H1 resulted in a slight decrease in H1 accumulation level (FIG. 20, 484 vs 484+1261). The co-expression of M2 with H5 from influenza A/Indonesia/05/2005 also resulted in a reduced H5 accumulation when compared to H5 expressed alone (FIG. 21, 489 vs 489+1261).

The co-expression of M2 was further evaluated for its impact on the accumulation level of a modified influenza B HA. Construct no. 1059 encodes an influenza B HA in which the proteolytic loop is replaced by a 2 amino acid linker (GG in place of aa 341-359). The results from western blot analysis presented in FIG. 22A show that the removal of the proteolytic loop resulted in increased influenza B HA accumulation level (compare 1008 with 1059) and that the co-expression of M2 with the modified influenza B HA further increased HA accumulation level (FIG. 22A, 1059 vs 1059+1261). An analysis of hemagglutination activity on crude protein extracts from plants transformed with influenza B HA with or without modification and with or without co-expression of M2 confirmed the positive effect of M2 co-expression on the accumulation level of the native influenza B HA (FIG. 22B, 1008 vs 1008+1261) and the modified influenza B HA (FIG. 22B, 1059 vs 1059+1261).

Figure 23A:
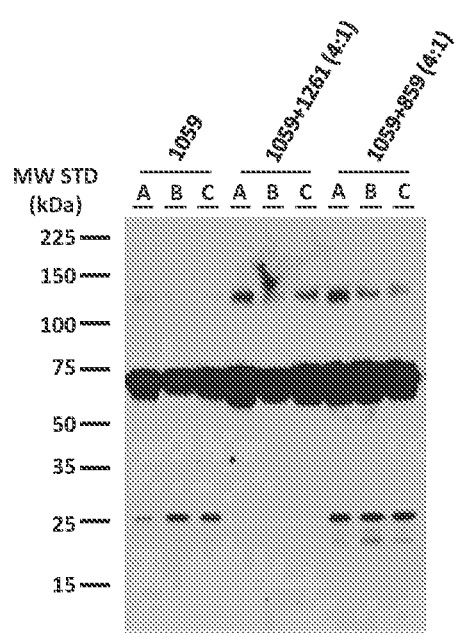
FIG. 23A shows a Western blot analysis of HA protein expression in agroinfiltrated *Nicotiana benthamiana* leaves: "1059": expression of mutant HA from B/Brisbane/60/2008 in the presence of amplification elements (BeYDV); "1059+1261": co-expression of mutant HA from B/Brisbane/60/2008 in the presence of amplification elements (BeYDV) with M2 from A/New Caledonia/20/99. "1059+859": co-expression of mutant HA from B/Brisbane/60/2008 in the presence of amplification elements (BeYDV) with M2 from A/Puerto Rico/8/34. Plants from three separate infiltrations were analyzed (A, B and C). Ratios indicate the proportion of *Agrobacterium* cultures used in co-expression experiments.
Figure 23B:
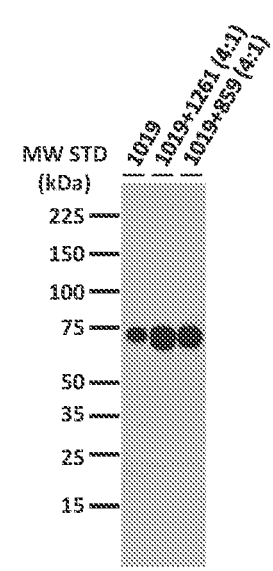

The efficacy of M2 from influenza A/Puerto Rico/8/1934 to increase accumulation of the modified influenza B HA and H3 was compared to that of M2 from influenza A/New Caledonia/20/1999. For the modified influenza B HA, the comparison was undertaken by western blot analysis of protein extracts from plants transformed with constructs 1059, 1059+1261 and 1059+859. For H3, a similar comparison was performed on protein extracts from plants transformed with 1019, 1019+1261 and 1019+859. The results obtained demonstrated that the co-expression of M2 from influenza A/Puerto Rico/8/1934 (encoded by construct no. 859) was as efficient as the co-expression of M2 from influenza A/New Caledonia/20/1999 (encoded by construct no. 1261) for increasing accumulation of both the modified influenza B HA (FIG. 23A) and H3 (FIG. 23B).

Example 2

Effect of Influenza M2 Co-Expression on the Accumulation Level of Different Strains of B HA and H3

Figure 29:
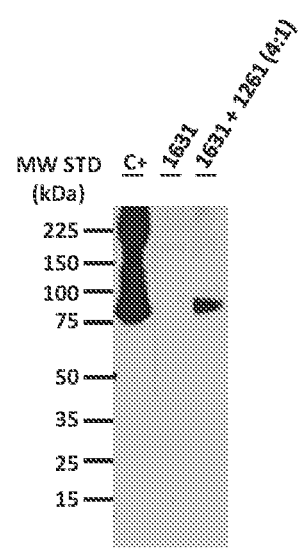

Western blot analysis of protein extracts from plants transformed with gene constructs driving the expression of influenza B HA (from B/Malaysia/2506/2004) (constructs no. 1631) in the presence or absence of M2-expression construct (construct no. 1261) showed that M2 co-expression results in increased accumulation of influenza B HA (FIG. 29).

Western blot analysis of protein extracts from plants transformed with gene constructs driving the expression of influenza B HA (from B/Wisconsin/1/2010) (constructs no. 1462) in the presence or absence of M2-expression construct (construct no. 1261) showed that M2 co-expression results in increased accumulation of influenza B HA (FIG. 30).

Figures 30A, 30B:
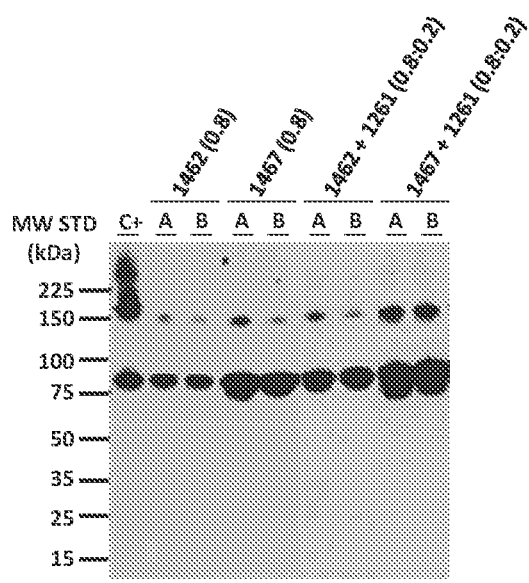

The co-expression of M2 was further evaluated for its impact on the accumulation level of a modified influenza B HA. Construct no. 1467 encodes an influenza B HA in which the proteolytic loop is replaced by a 2 amino acid linker (GG in place of aa 341-359). The results from western blot analysis presented in FIG. 30A show that the removal of the proteolytic loop resulted in increased influenza B HA accumulation level (compare 1462 with 1467) and that the co-expression of M2 with the modified influenza B HA further increased HA accumulation level (FIG. 30A, 1467 vs 1467+1261). An analysis of hemagglutination activity on crude protein extracts from plants transformed with influenza B HA with or without modification and with or without co-expression of M2 confirmed the positive effect of M2 co-expression on the accumulation level of the native influenza B HA (FIG. 30B, 1462 vs 1462+1261) and the modified influenza B HA (FIG. 26B, 1467 vs 1467+1261).

Figure 31:
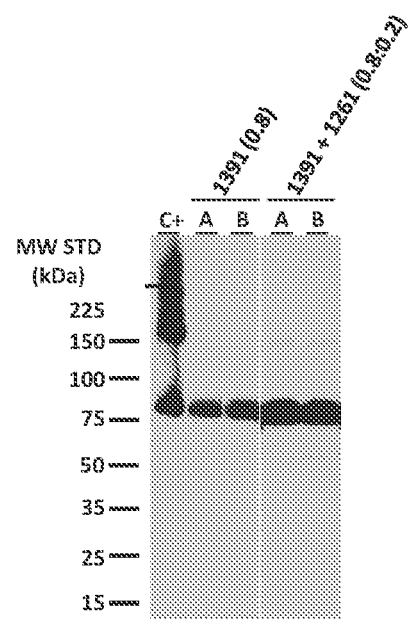

Western blot analysis of protein extracts from plants transformed with gene constructs driving the expression of influenza H3 (from H3/Victoria/361/2011) (constructs no. 1391) in the presence or absence of M2-expression construct (construct no. 1261) showed that M2 co-expression results in increased accumulation of influenza H3 (FIG. 31).

Example 3 Effect of M2 Expression on pH and Protein Stability

To measure pH variations along the secretory pathway, constructs that target pHluorin to the ER, to the cis-Golgi (Mann99-pHluorin), to the trans-Golgi (Mann99TMD23-pHluorin) network or to the apoplast (FIG. 32A) were used. ER and apoplast pHluorin constructs were targeted to the secretory pathway by the addition of a heterologous signal peptide. Cis- and trans-Golgi pHluorin constructs were fused with the modified N-terminus of α-1,2 mannosidase I, a membrane-bound enzyme of the secretory pathway. The Man99 membrane targeting signal has been reported to partially target to the ER, with most targeting in the cis- Golgi of *N benthamiana* leaf cells (Saint-Jore-Dupas et. al, 2006, *Plant Cell*, 18(11), 3182-3200.). The addition of 7 amino acids in the transmembrane domain of Man99, yielding Man99TMD23, changed the localization of the protein to almost exclusively the trans-Golgi (Saint-Jore-Dupas et al., 2006).

The coding sequences of ratiometric pHluorin (GenBank accession AF058694) and Influenza A/New Caledonia/20/1999(H1N1) M2 protein (GenBank accession HQ008884.1) were placed downstream of a double Cauliflower mosaic virus 35S promoter in the presence or absence of CPMV-HT, and followed by the nopaline synthase terminator as described above.

ER-pHluorin (35S/CPMV-HT/ER-pHluorin/NOS; Construct number 1872; FIGS. 38B and 38C; SEQ ID NOs:75 and 76) is shown schematically in FIGS. 32A and 38D. ER-pHluorin includes a protein disulfide isomerase signal peptide (Shorrosh and Dixon, 1991, *Proc Natl Acad Sci USA*, 88(23), 10941-10945). and a SEKDEL motif at the C terminus to retain the protein in the endoplasmic reticulum (ER).

Secreted pHluorin (sec-pHluorin; 35 S/CPMV-HT/sec-pHluorin/NOS (Construct number 1871; FIGS. 37C, 37D and 37E; SEQ ID NOs:71, 72 and 73) is shown schematically in FIGS. 32A and 37F. Sec-pHluorin includes a protein disulfide isomerase signal peptide (PDI).

For localization of pHluorin to the cis-Golgi, a construct comprising a modified N-terminus from the *Glycine max* α-1,2 mannosidase I, with seven amino acids removed from the transmembrane domain by PCR amplification and fused to pHluorin to make Man99-pHluorin (35S/CPMV-HT/Man99-pHluorin/NOS; Construct number 1873; FIGS. 39B, 39C and 39D; SEQ ID NOs:78, 79 and 80) was prepared as described above. A schematic of Mann99-pHluorin is shown in FIGS. 32A and 39E.

To localize pHluorin in the trans-Golgi, a construct comprising the N-terminus from the *Glycine max* α-1,2 mannosidase I, including the transmembrane domain, 29 residues of the cytoplasmic tail and 54 amino acids of the luminal stem region (Saint-Jore-Dupas et al., 2006, *Plant Cell*, 18(11), 3182-3200.) was fused to pHluorin to make the Man99TMD23-pHluorin construct (construct No. 1874; FIGS. 40A, 40B and 40C; SEQ ID NOs:81, 82 and 83; 35S/CPMV-HT/Man99TMD23-pHluorin/NOS) was prepared as described above. A schematic of Mann99TMD23-pHluorin is shown in FIGS. 32A and 40D.

M2 Constructs (FIG. 33):

Influenzavirus A M2 (synthesized by DNA 2.0, USA) comprised a native signal peptide and a wild type M2 sequence (M2 WT; construct No: 1261; SEQ ID NO:10; FIG. 2D). The construct was prepared as described above. A schematic of M2 WT is shown in FIG. 33A.

A mutant, inactive Influenzavirus A M2 (M2 A30P; construct No: 1210; FIGS. 36C and 36D; SEQ ID NOs:67 and 68) included a mutation that changed alanine at position 30 to a proline was prepared as described above. The alanine 30 to proline (A30P) mutation eliminates ion channel activity without affecting the tertiary structure or appropriate transport to the plasma membrane (Holsinger et al., 1994, *J Virol*, 68(3), 1551-1563). As M2A30P is inactive, it was used to confirm that effects on pH were specific to proton channel activity. A schematic of M2 A30P is shown in FIGS. 33A and 36E.

SlCYS8-α1ACT fusion protein (FIG. 34A) was prepared as described in Sainsbury et al. (2013, Plant Biotechnol J 11: 1058-1068; which is incorporated herein by reference). The SlCYS8-α1ACT fusion protein consists of a tomato cystatin SlCYS8 and a truncated version of human alpha-1-antichymotrypsin (a1ACT), separated by a (EAAAK)$_3$ peptide (SEQ ID NO:110).

Plant-Based Expression

The above constructs were transferred into the plant binary vector pCambia 2300 (CAMBIA, Canberra, Australia). pCambia vectors were maintained in the *Agrobacteria tumefaciens* strain, AGL1 (Lazo et al., 1991, *Biotechnology (NY)*, 9(10), 963-967), which was transformed by heat shock (u and Li. 2008, Plant Methods 4: 4-10). Bacterial cultures were grown to stable phase in Luria-Bertani medium supplemented with the appropriate antibiotics, and pelleted by gentle centrifugation. Following resuspension in infiltration medium (10 mM MES (2-[N-morpholino]ethanesulfonic acid), pH 5.6, 10 mM MgCl$_2$) to an OD$_{600}$ of 0.5, and a 2 to 4 h incubation at ambient temperature, suspensions were pressure infiltrated into *Nicotiana benthamiana* leaves using a needle-less syringe (D'Aoust et al., 2009, Methods in Mol Biol 483: 41-50). Co-agroinfiltration of pHluorin or fusion constructs with M2 was at a 4:1 ratio. Leaf tissue was harvested 5 days post infiltration (dpi) except where indicated otherwise.

Protein Extraction

Leaf discs (160 mg) obtained from infiltrated tissue were homogenized by disrupting tissue with ceramic beads in a Mini-Beadbeater apparatus (BioSpec, Bartlesville Okla., USA).

pHluorin (ER-pHluorin or sec-pHluorin) or SlCYS8-α1ACT fusion protein-expressing tissue was extracted in three volumes of phosphate-buffered saline (PBS), pH 7.3, containing 5 mM EDTA, 0.05% (v/v) Triton X-100, and complete protease inhibitor cocktail (Roche Diagnostics, Laval QC, Canada).

M2-(M2WT or M2A30P) expressing tissue was extracted in three volumes of 83 mM Tris buffer, pH 6.8, containing 8.3% (v/v) glycerol and 3.3% (w/v) SDS. Leaf lysates were clarified by centrifugation at 20,000 g for 20 min.

Western Blotting pHluorin (ER-pHluorin, or sec-pHluorin) and SlCYS8-α1ACT fusion protein were detected by Western blotting onto nitrocellulose membranes following electrotransfer of leaf proteins resolved by SDS-PAGE under reducing conditions. Non-specific binding sites were blocked by incubation in blocking solution (5% (w/v) skim milk powder in PBS, containing 0.025% (v/v) Tween-20), which also served as antibody dilution buffer.

pHluorin was detected with anti-GFP monoclonal antibodies (Clontech Laboratories, Mountain View Calif., USA), followed by goat anti-mouse alkaline phosphatase (AP)-conjugated secondary antibodies (Sigma-Aldrich).

SlCYS8 was detected with rabbit anti-SlCYS8 polyclonal antibodies (Robert et al., 2013, PLoS ONE 8: e70203, doi:10.1371/journal.pone.0070203) followed by incubation with AP-conjugated secondary antibodies raised in goat (Sigma-Aldrich, Oakville ON, Canada). Colorimetric signals were developed with 5-bromo-4-chloro-3-indolyl phosphate/Nitro blue tetrazolium (Sigma-Aldrich). Chemiluminescent signals were obtained using the ECL Advance Western blotting detection kit (GE Healthcare, Baie d'Urfé QC, Canada).

Imaging and Data Analysis

Transient expression of ratiometric pHluorin in fresh leaf tissue was imaged using a Nikon C1 confocal laser imaging microscope (Nikon, Melville N.Y., USA). Excitation scans were performed at 405 nm and 488 nm with the emission set at 515 nm using a 60X water-immersion lens. The power of each laser line and the gain were maintained at consistent levels between experiments so that the images were comparable. Image data were analyzed using the open source software ImageJ (available at: rsb.info.nih.gov/ij/) and background values, such as autofluorescence from chloroplasts, were subtracted from each image based on the average values of images acquired from uninfiltrated plants. Images or pixels with saturated intensities were eliminated or set to zero using a mask. Some pixels were excluded by masking if their intensity values fell below a cut-off threshold and ratio values were generated through pixel-by-pixel calculations of intensities. Each treatment was evaluated with more than 15 pairs of images coming from three different plants and from leaves of the same morphological age.

pHluorin and SlCYS8-α1ACT Fusion Protein Quantification

Ratiometric-pHluorin expression was determined by fluorescence measurements using a Fluostar Galaxy microplate fluorimeter (BMG, Offenburg, Germany; www.bmglabtech.com), with excitation and emission filters of 485 and 520 nm, respectively. Soluble protein extracts were diluted in 0.1 M $Na_2CO_3$ buffer, pH 10, and all dilutions were performed in a control extract from leaf tissue infiltrated with a mock inoculum so that any matrix effect was eliminated. Samples were loaded in triplicate onto a fluorescently neutral black 96-well plate (Costar) and six replicates from three different plants were used per assay. Extracts from ER-pHluorin-expressing leaf tissue was used to generate a linear response range, within which all measurements were taken. Densitometric analysis of the fusion protein signals was performed with the Phoretix 2D Expression software, v. 2005 (Non-Linear USA, Durham N.C., USA), on the Western blots digitalized with an Amersham Image Scanner (GE Healthcare). Densitometric analysis was performed on three independent biological replicates.

RNA Extraction and Quantitative PCR

Plants samples were harvested as two leaf discs representing 100 mg of fresh tissue. Leaf tissue was disrupted in a Mini-Beadbeater (OMNI International, Kennesaw Ga., USA) followed by two min on ice and clarified at 20,000 g for 20 min. RNA extractions were performed on supernatants using the RNeasy Plant Mini Kit (Qiagen, Mississauga ON, Canada) according to the manufacturer's instructions. RNA concentration and quality was determined using a Nanodrop® ND-1000 Spectrophotometer (NanoDrop Technologies, Wilmington Del., USA). cDNA was synthesized using the Omniscript Reverse Transcription kit (Qiagen). Relative quantification of pHluorin transcripts was determined by quantitative real-time PCR performed in duplicate using an ABI PRISM 7500 Fast real-time PCR system (Applied Biosystems, Burlington ON, Canada) and SYBR Green PCR Master Mix (Thermo Scientific, Ottawa ON, Canada). Target transcripts were detected with the following primers:

```
                                        (SEQ ID NO: 84)
    pHluorin-F,5'-CATTGAAGATGGAGGCGTTC-3'
    and (SEQ ID NO: 85)
    pHluorin-R,5'-GAAAGGGCAGATTGTGTGTG-3'.
```

Leaf extracts obtained from infiltrated tissue of five plants were assayed, and relative abundance of pHluorin RNA was calculated using a standard curve generated by amplifying dilutions of cDNA containing pHluorin transcripts.

Statistical Analysis

Statistical analyses were performed using SAS, version 9.1 (SAS Institute, Cary N.C., USA). Analysis of variance (ANOVA) using the General Linear Model (GLM) procedures was used to compare fluorescence ratios and yields of pHluorin expressed with or without M2. Contrast and LSD calculations were made when the ANOVA was significant at an alpha value threshold of 0.05. The relative abundance of intact fusions was compared using a mean comparison Student's t-test at $\alpha=0.05$ pH Changes Along the Cell Secretory Pathway pHluorin constructs were expressed in different subcellular compartments of *N. benthamiana* leaves (FIG. 32B). Epidermal cells expressing ER-pHluorin showed a typical interconnected network pattern of the cortical ER while secreted pHluorin (sec-pHluorin) accumulated on the edges of the cell in the apoplast.

pHluorin functions as a pH indicator with ratiometric responsiveness within pH ranges that characterize the plant secretory pathway (Schulte et al., 2006, Plant Methods, 2, 7). While emission remains constant at 515 nm, excitation is strongest at 488 nm in acidic conditions whereas at pH closer to neutral the excitation maxima switch to 405 nm. A low 405/488 nm ratio is indicative of acidic pH environment whereas a higher ratio indicates a more basic pH. Calibration of pHluorin in vitro shows a direct correlation between excitation ratios and pH values As shown in FIG. 32C, the ratio in the ER was the highest indicating a more neutral pH, and a lower ratio was observed in the trans-Golgi, revealing an acidic pH. The pH in agroinfiltrated *N. benthamiana* tissue varies from near neutral in the ER, to an estimated pH of approximately 5.5 in the trans-Golgi.

Impact of M2 on pH Along the Secretory Pathway

*N. benthamiana* leaves were co-agroinfiltrated with Influenzavirus A M2 and the pHluorin constructs. The inactive M2 mutant (A30P) was used as a control to confirm that effects on pH were specific to proton channel activity (FIG. 33A).

Ratiometric fluorescence analysis at 5 dpi confirmed that functional ion channel co-expression specifically modified the pH of the plant secretory pathway (FIG. 33B). No discernible pH change was observed in the ER in the presence of M2, since the pH of the ER lumen is close to neutral, and above the pH at which M2 is activated.

While M2 (A30P) had no effect on pH of the Golgi, a significant increase in the pH of both regions of the Golgi apparatus was seen with wild-type M2, with the highest increase observed in the trans-Golgi (FIG. 33B). Higher fluorescence ratios in the presence of M2 suggests that the ion channel was activated by the low pH of these organelles and that this activation resulted in a discernible change in pH.

pHluorin excitation ratios as a result of varied M2 expression showed the protein to be detectable after 3 dpi and reach a maximum at 5 dpi, before finally decreasing (FIG. 36). No significant differences between ratios were observed for ER-targeted pHluorin in the presence of M2. However, M2 expression increased pH of the cis-Golgi and trans-Golgi and was detectable at 5 dpi and 4 dpi, respectively, and was maintained to at least 6 days despite the apparent decrease in M2 expression (FIG. 36). These results show that it is possible to modulate the pH of the plant Golgi apparatus through the transient co-expression of the M2 ion channel.

M2 Co-Expression Stabilizes an Acid-Susceptible Peptide Linker

The rigid linker $(EAAAK)_n$ (where n=1, 2, 3, . . . ; SEQ ID NO:110) can been used to separate fusion partners and prevent steric interference between the attached domains This linker is also known to be susceptible to auto-proteolytic cleavage at or below pH 6.0 (Wu et al., 2009, *J Chromatogr B Analyt Technol Biomed Life Sci*, 877(31), 4015-4021). To investigate the effect of increasing the pH in the secretory pathway on this linker, a secreted fusion protein consisting of tomato cystatin SlCYS8 and a truncated version of human alpha-1-antichymotrypsin (α1ACT), separated by a (EAAAK)₃ peptide linker was used (FIG. 35A; described in Sainsbury et al. (2013, Plant Biotechnol J 11: 1058-1068).

M2-dependent pH increase in the Golgi apparatus had a significant impact on the stability of the SlCYS8-α1ACT fusion protein. Results from Western blotting show that the fusion protein was not stable in the plant secretory pathway as free SlCYS8 (10.7 kDa) was detected (FIG. 35B). Co-expression of the SlCYS8-α1ACT fusion protein and M2 resulted in stabilization of the 55 kDa fusion and an enhanced accumulation of the intact the SlCYS8-α1ACT fusion protein (FIG. 35B).

Densitometric analysis of the Western blot signal, indicates that in the absence of M2, over 70% of the S1CYS8 was detected in the free (cleaved) form. In contrast, co-expression of the SlCYS8-α1ACT fusion protein with M2 resulted in over 70% of the fusion remaining intact (FIG. 35D). In terms of the absolute accumulation of the intact fusion, a significant five-fold increase was observed in the presence of M2 (FIG. 35C). Together these results show that modulation of pH can have a positive impact on the stability, yield and accumulation of acid sensitive proteins and that specific peptide sequences can be stabilized against degradation through transient increases in pH along the secretory pathway.

These data demonstrate that modulated the pH of the plant secretory pathway may be modulated through the expression of an Orthomyxovirus M2 ion channel. Co-expression of functional M2 resulted in a significant pH increase in the Golgi apparatus, as detected by pHluorin co-expression, and in a concomitant increase in the accumulation of proteins, or recombinant proteins, susceptible or sensitive, to low pH environments. This data also suggest, that by co-expressing functional M2, the pH within the secretory pathway was maintained at or above 6.0.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of increasing accumulation of a fusion protein in a plant or a portion of the plant, the method comprising:

a) introducing a first nucleic acid comprising a first regulatory region active in the plant and operatively linked to a nucleotide sequence encoding the fusion protein into the plant, or portion of the plant, wherein the fusion protein comprises an $(EAAAK)_n$ linker, where n is 1 to 10, and undergoes irreversible conformational change at a pH within the Golgi apparatus of the plant;

b) introducing a second nucleic acid comprising a second regulatory region active in the plant and operatively linked to a nucleotide sequence encoding a proton channel protein, wherein the proton channel protein is M2 or BM2 and wherein the proton channel protein increases the pH within the Golgi apparatus of the plant; and c) incubating the plant or portion of the plant under conditions that permit the expression of the nucleic acids and accumulation of the fusion protein, wherein accumulation of the fusion protein is increased when compared to accumulation of the fusion protein produced in the plant or portion of the plant produced under the same conditions, and in the absence of the proton channel protein.

2. The method of claim 1, wherein the first nucleic acid sequence comprises the first regulatory region operatively linked with one or more than one comovirus enhancer, and the nucleotide sequence encoding the fusion protein.

3. The method of claim 2, wherein the first nucleic acid sequence additionally comprises one or more than one geminivirus amplification element, and wherein a third nucleic acid encoding a geminivirus replicase is introduced into the plant or portion of the plant.

4. The method of claim 2, wherein the one or more than one comovirus enhancer is a comovirus UTR.

5. The method of claim 4, wherein the comovirus UTR is a Cowpea Mosaic Virus (CPMV) UTR.

6. The method of claim 1, wherein the first nucleic acid is transiently expressed in the plant.

7. The method of claim 1, wherein the first nucleic acid is stably expressed in the plant.

8. The method of claim 1 further comprising a step of d) harvesting the plant and purifying the fusion protein.

9. The method of claim 1, wherein n is 2 to 5.

10. The method of claim 1, wherein the plant or portion of the plant is *Nicotiana benthamiana*.

* * * * *